United States Patent
Sadow et al.

(10) Patent No.: US 12,030,843 B2
(45) Date of Patent: Jul. 9, 2024

(54) CATALYTIC UPCYCLING OF POLYOLEFINS VIA VERSATILE ALKYLALUMINUMS

(71) Applicant: IOWA STATE UNIVERSITY RESEARCH FOUNDATION, INC., Ames, IA (US)

(72) Inventors: Aaron David Sadow, Ames, IA (US); Uddhav Kanbur, Ames, IA (US)

(73) Assignee: IOWA STATE UNIVERSITY RESEARCH FOUNDATION, INC., Ames, IA (US)

(*) Notice: Subject to any disclaimer, the term of this patent is extended or adjusted under 35 U.S.C. 154(b) by 0 days.

(21) Appl. No.: 17/554,666

(22) Filed: Dec. 17, 2021

(65) Prior Publication Data

US 2022/0213007 A1    Jul. 7, 2022

Related U.S. Application Data

(60) Provisional application No. 63/134,014, filed on Jan. 5, 2021.

(51) Int. Cl.
| | | |
|---|---|---|
| *C07C 4/06* | (2006.01) | |
| *B01J 21/12* | (2006.01) | |
| *B01J 31/14* | (2006.01) | |
| *B01J 31/16* | (2006.01) | |
| *C07C 17/06* | (2006.01) | |
| *C07C 29/50* | (2006.01) | |
| *C07C 41/01* | (2006.01) | |
| *C07C 45/45* | (2006.01) | |
| *C07C 51/15* | (2006.01) | |
| *C07C 67/24* | (2006.01) | |
| *C07C 231/02* | (2006.01) | |

(52) U.S. Cl.
CPC ................ *C07C 4/06* (2013.01); *B01J 21/12* (2013.01); *B01J 31/143* (2013.01); *B01J 31/1616* (2013.01); *C07C 17/06* (2013.01); *C07C 29/50* (2013.01); *C07C 41/01* (2013.01); *C07C 45/455* (2013.01); *C07C 51/15* (2013.01); *C07C 67/24* (2013.01); *C07C 231/02* (2013.01); *C07C 2521/12* (2013.01); *C07C 2531/16* (2013.01); *C07C 2531/22* (2013.01)

(58) Field of Classification Search
CPC ...... B01J 27/125; B01J 1/1616; Y02W 30/50; Y02W 30/62
See application file for complete search history.

(56) References Cited

U.S. PATENT DOCUMENTS

| | | | |
|---|---|---|---|
| 3,894,066 A * | 7/1975 | Buschhoff | C07F 7/2208 |
| | | | 556/102 |
| 5,446,188 A | 8/1995 | Gruber et al. | |
| 6,171,475 B1 | 1/2001 | Dufaud et al. | |
| 8,048,394 B2 | 11/2011 | Yano et al. | |
| 8,415,267 B2 | 4/2013 | Lee | |
| 8,449,856 B2 | 5/2013 | Yano et al. | |
| 8,883,308 B2 | 11/2014 | Polshettiwar et al. | |
| 9,283,545 B2 | 3/2016 | Asefa et al. | |
| 9,533,286 B2 | 1/2017 | Stamm Masias et al. | |
| 9,943,826 B2 | 4/2018 | Haynes et al. | |
| 9,956,545 B2 | 5/2018 | Calderone et al. | |
| 10,351,781 B2 | 7/2019 | Sinha et al. | |
| 11,053,598 B2 | 7/2021 | Chou | |
| 11,198,112 B2 | 12/2021 | Lu et al. | |
| 11,857,951 B2 | 1/2024 | Sadow et al. | |
| 2004/0210072 A1 * | 10/2004 | Citron | C07C 29/09 |
| | | | 556/187 |
| 2010/0056360 A1 | 3/2010 | Lee | |
| 2011/0250122 A1 | 10/2011 | Joo et al. | |
| 2011/0311635 A1 | 12/2011 | Stucky et al. | |
| 2012/0264599 A1 | 10/2012 | Komatsu et al. | |
| 2013/0318863 A1 | 12/2013 | Chang et al. | |
| 2018/0056277 A1 | 3/2018 | Lee et al. | |
| 2019/0126247 A1 | 5/2019 | Deeba | |
| 2019/0291092 A1 | 9/2019 | Cargnello et al. | |
| 2020/0122122 A1 | 4/2020 | Gong et al. | |
| 2021/0031176 A1 | 2/2021 | Suriye et al. | |
| 2021/0061971 A1 * | 3/2021 | Delferro | C08J 11/16 |
| 2021/0322961 A1 | 10/2021 | Wattanakit et al. | |
| 2022/0111356 A1 * | 4/2022 | Sadow | C08J 11/16 |
| 2023/0219870 A1 * | 7/2023 | Sadow | C07C 29/36 |
| | | | 568/840 |

OTHER PUBLICATIONS

Q. Hou et al., 2 Cell Reports Physical Science (2021) (Year: 2021).*
C. Jehano, 10 Polymer Chemistry, 172-186 (2019) (Year: 2019).*
J. Lee et al., 321 Journal of Cleaner Production (2021) (Year: 2021).*
J. Zheng et al., 19 Chemistry a European Journal, 541-548 (2013) (Year: 2013).*
F. Cannavacciuolo et al., 61 Angew. Chem. Int. Ed. (2022) (Year: 2022).*
V. Defaud et al., Angew. Chem. Int. Ed., 806-810 (1998) (Year: 1998).*
U. Kanbur et al., 7 Chem, 1347-1362 (2021) (Year: 2021).*
Y. Gu et al., 161 Polymer, 181-189 (2019) (Year: 2019).*
Y. Gu et al., 170 Polymer, 24-30 (2019) (Year: 2019).*
G. Coates et al., 5 Nature Reviews Materials, (2020) (Year: 2020).*
F. Zhang et al., Science, 437-441 (2020) (Year: 2020).*

(Continued)

*Primary Examiner* — Alexander R Pagano
(74) *Attorney, Agent, or Firm* — Troutman Pepper Hamilton Sanders LLP (Rochester)

(57) ABSTRACT

Disclosed herein is a process for the conversion of polymers, oligomers, or mixtures thereof into shorter alkanes, carboxylic acids, alcohols, alkyl halides or aldehydes. This process includes contacting the polymers, oligomers, or mixtures thereof with the compound of formula (I):

$$Al(R^1)_3 \qquad (I)$$

where $R^1$ is independently selected at each occurrence thereof from the group consisting of H, aryl, $C_1$-$C_8$ alkyl, and $C_1$-$C_8$ alkoxy, as a reaction mixture, in the presence of a catalyst selected from the group consisting of a transition metal catalyst, a lanthanide series metal catalyst, or combinations thereof.

20 Claims, 98 Drawing Sheets

(56) References Cited

OTHER PUBLICATIONS

Bae et al. "Catalytic Hydroxylation of Polypropylenes," J. Am. Chem. Soc. 127:767-776 (2005).
Bae et al., "Regiospecific Side-Chain Functionalization of Linear Low-Density Polyethylene with Polar Groups," Angew. Chem. Int. Ed. 44:6410-6413 (2005).
Boaen et al., "Selective and Mild Oxyfunctionalization of Model Polyolefins," Macromolecules 36:7027-7034 (2003).
Bunescu et al., "Catalytic Hydroxylation of Polyethylenes," ACS Cent. Sci. 3:895-903 (2017).
Diaz-Requejo et al., "Controlled, Copper-Catalyzed Functionalization of Polyolefins," Macromolecules 38:4966-4969 (2005).
Kondo et al., "Rhodium-Catalyzed, Regiospecific Functionalization of Polyolefins in the Melt," J. Am. Chem. Soc. 124:1164-1165 (2002).
Lewis et al., "Upcycling Aromatic Polymers through C—H Fluoroalkylation," Chem. Sci. 10:6270-6277 (2019).
Plummer et al., "Mild Halogenation of Polyolefins Using an N-Haloamide Reagent," Polym. Chem. 9:1309-1317 (2018).
Williamson et al., "Chemo- and Regioselective Functionalization of Isotactic Polypropylene: A Mechanistic and Structure-Property Study," J. Am. Chem. Soc. 141:12815-12823 (2019).
Williamson et al., "Regioselective C—H Xanthylation as a Platform for Polyolefin Functionalization," Angew. Chem. Int. Ed. 57:6261-6265 (2018).
Zhou et al., "Direct Amination of Polyethylene by Metal-Free Reaction," Macromolecules 50:3510-3515 (2017).
Chen et al., "Selective, Catalytic Oxidations of C—H Bonds in Polyethylenes Produce Functional Materials with Enhanced Adhesion," Chem. 7:137-145 (2021).
U.S. Appl. No. 17/983,165, filed Nov. 8, 2022, first named inventor Aaron D. Sadow.
Tennakoon et al., "Catalytic Upcycling of High-Density Polyethylene via a Processive Mechanism," Nat. Catal. 3:893-901 (2020).
Takei et al., "Anionic Surfactants: Lauric Products," JAOCS 62(2):341-347 (1985).
David B. Hatcher, "Fatty Alcohol Sulfates," The Journal of the American Oil Chemists' Society 34:175-178 (1957).
Backstrom et al., "Trash to Treasure: Microwave-Assisted Conversion of Polyethylene to Functional Chemicals," Industrial & Engineering Chemistry Research 56:14814-14821 (2017).
Zheng et al., "Controlled Chain-Scission of Polybutadiene by the Schwarts Hydrozirconation," Chem. Eur. J. 19:541-548 (2013).
Inoue et al., "Structural and Dynamical Studies of 13C-Labeled Polyethylene Adsorbed on the Surface of Silica Gel by High-Resolution Solid-State 13C Nmr Spectroscopy," Acta Polymer. 46:420-423 (1995).
Kanbur et al., "Catalytic Carbon-Carbon Bond Cleavage and Carbon-Element Bond Formation Give New Life for Polyolefins as Biodegradable Surfactants," Chem 7(5):1347-1362 (2021).
Xiao et al., "High-Temperature-Stable and Regenerable Catalysts: Platinum Nanoparticles in Aaligned Mesoporous Silica Wells," ChemSusChem. 6(10):1915-1922 (2013).
Flaherty et al., "Metal-Catalyzed C—C Bond Cleavage in Alkanes: Effects of Methyl Substitution on Transition-state Structures and Stability," J Am Chem Soc 136(27):9664-9676 (2014).
Dufaud et al., "Catalytic Hydrogenolysis at Low Temperature and Pressure of Polyethylene and Polypropylene to Diesels or Lower Alkanes by a Zirconium Hydride Supported on Silica-Alumina: A Step Toward Polyolefin Degradation by the Microscopic Reverse of Ziegler-Natta Polymerization," Angew Chem Int Ed Engl 37(6):806-810 (1998).
Dong et al., "In Situ Quantitative Single-Molecule Study of Dynamic Catalytic Processes in Nanoconfinement," Nature Catalysis 1:135-140 (2018).
Celik et al., "Upcycling Single-Use Polyethylene into High-Quality Liquid Products," ACS Cent. Sci. 5:1795-1803 (2019).
Schmidt-Rohr and Spiess, "Chain Diffusion Between Crystalline and Amorphous Regions in Polyethylene Detected by 2D Exchange 13C NMR," Macromolecules 24:5288-5293 (1991).
DOE Grant proposal (Jul. 1, 2020).
Office Action for U.S. Appl. No. 17/497,206 (Mar. 2, 2023).
U.S. Appl. No. 18/508,055, filed Nov. 13, 2023, first named inventor Aaron D. Sadow.

* cited by examiner

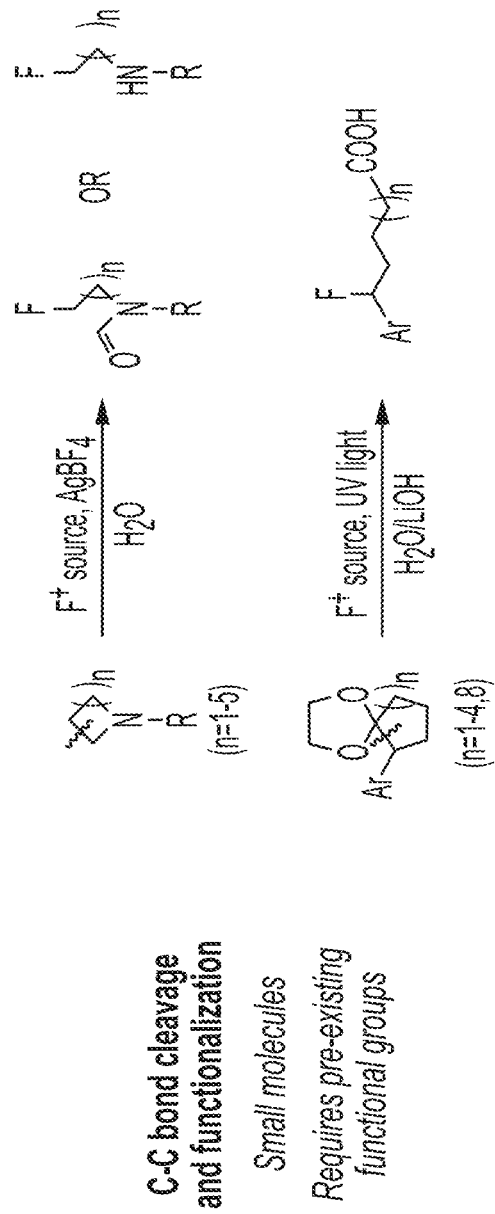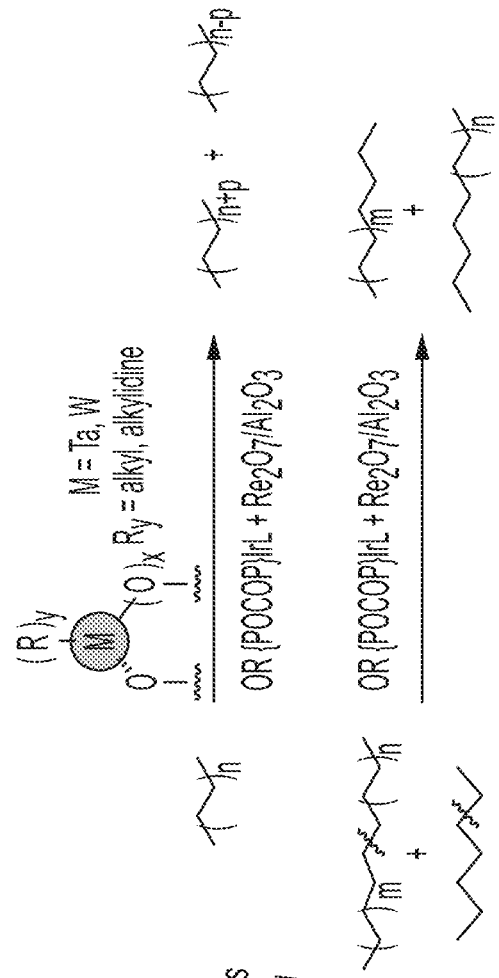
FIG. 1A
FIG. 1B

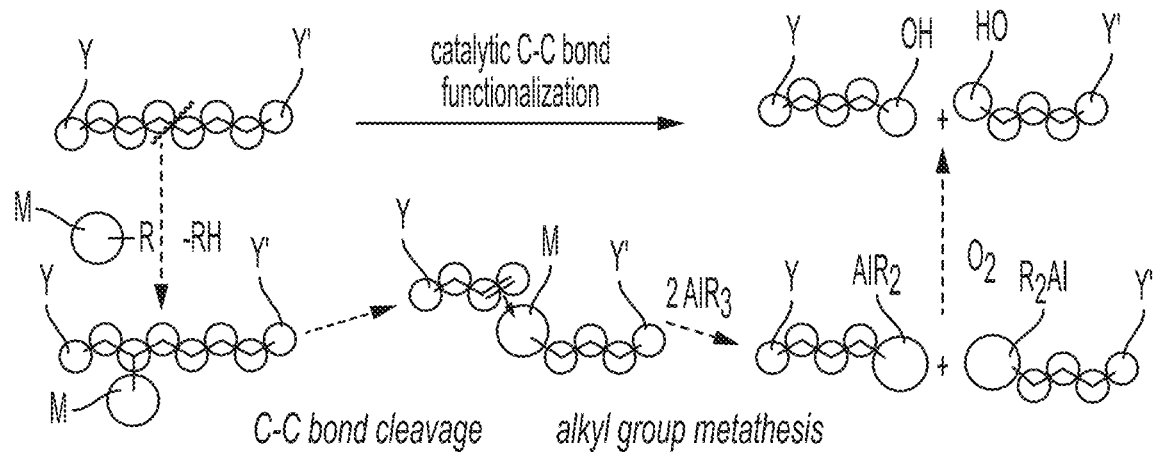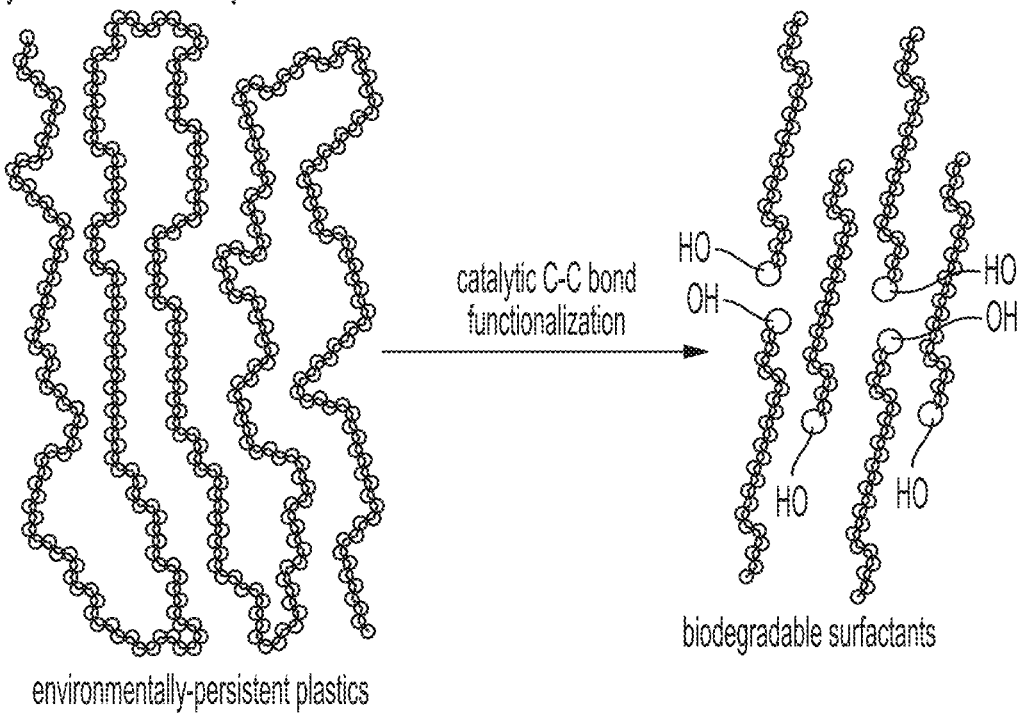
FIG. 2

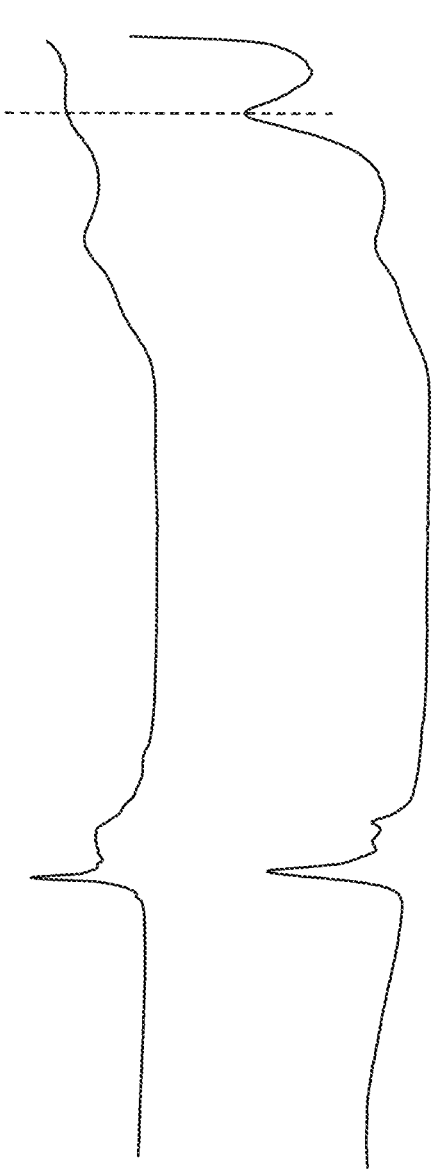
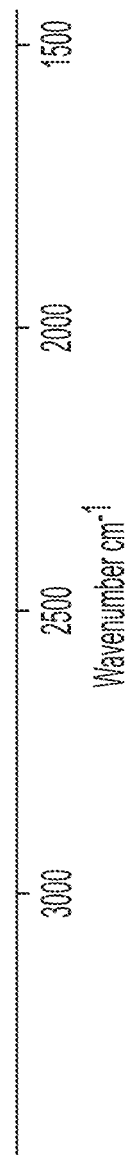
FIG. 93A
FIG. 93B
FIG. 93C

CATALYTIC UPCYCLING OF POLYOLEFINS VIA VERSATILE ALKYLALUMINUMS

CROSS-REFERENCE TO RELATED APPLICATIONS

This application claims the benefit of U.S. Provisional Application No. 63/134,014 filed Jan. 5, 2021. The disclosure of which is incorporated herein by reference.

This invention was made with government support under DE-AC-0207CH11358 awarded by the U.S. Department of Energy. The government has certain rights in the invention.

FIELD

The present application relates to catalytic upcycling of polyolefins via versatile alkylaluminums.

BACKGROUND

The widespread single-use applications of polyolefins derive from their numerous desirable attributes, including mechanical, thermal, and chemical resistance, hydrophobicity, and high strength-to-weight ratios. Polyethylene and polypropylene are inexpensively synthesized on tremendous scale, representing more than half of the entire plastics market (Geyer and Jambeck, "Law, Production, Use, and Fate of All Plastics Ever Made," *Sci. Adv.* 3:e1700782 (2017)) and allowing disposable containers, films, and laminates to be ubiquitous in packaging, storage, construction, military, and biomedical applications. These features, however, also have detrimental and persistent ecological consequences, generating concern for human and terrestrial health (Jambeck et al., "Plastic Waste Inputs from Land into the Ocean,"*Science* 347:768-771 (2015); Brahney et al., "Plastic Rain in Protected Areas of the United States,"*Science* 368: 1257-1260 (2020)). Furthermore, separation and recycling of low value polyolefin wastes is too expensive. These materials partially degrade during reprocessing for reuse and are not currently reclaimed as starting materials for chemical manufacturing.

Conversion of these materials into lower molecular weight species involves cleavage of some of the carbon-carbon bonds, either in pyrolysis or oxidative pyrolysis (Pifer and Sen, "Chemical Recycling of Plastics to Useful Organic Compounds by Oxidative Degradation," *Angew. Chem. Int. Ed.* 37:3306-3308 (1998); J. Scheirs, *Feedstock Recycling and Pyrolysis of Waste Plastics*, Scheirs Eds. Sussex, UK John Wiley & Sons, p 381-433 (2006)), cationic species in hydrocracking (Yanik and Karayildirim, Feedstock Recycling and Pyrolysis of Waste Plastics, Scheirs Eds. Sussex, UK John Wiley & Sons, p 209-224 (2006)), or organometallic species in hydrogenolysis (Celik et al., "Upcycling Single-Use Polyethylene into High-Quality Liquid Products," *ACS Cent. Sci.* 5:1795-1803 (2019)). β-Alkyl elimination, which involves organometallic intermediates, is an alternative approach for breaking aliphatic carbon-carbon bonds under mild conditions (Watson and Roe, "β-Alkyl Transfer in a Lanthanide Model for Chain Termination," *J. Am. Chem. Soc.* 104:6471-6473 (1982); Watson and Parshall, "Organolanthanides in Catalysis," *Acc. Chem. Res.* 18:51-56 (1985); Bunel et al., "Carbon Carbon Bond Activation Via Beta-Alkyl Elimination—Reversible Branching of 1,4-Pentadienes Catalyzed by Scandocene Hydride Derivatives," *J Am. Chem. Soc.* 110:976-978 (1988); O'Reilly et al., "β-Alkyl Elimination: Fundamental Principles and Some Applications," *Chem. Rev.* 116:8105-8145 (2016)). This step is the microscopic reverse of alkene insertion. The hydrogenolysis of polyethylene, catalyzed by hydridoziroconium species supported on silica-alumina, is proposed to involve mid-chain metalation by (—SiO)$_3$ZrH or (—SiO)$_2$ZrH$_2$, followed by the key 3-alkyl elimination step and subsequent alkyl group transfer from (—SiO)$_3$Zr—CH$_2$R species to hydrogen (Dufaud and Basset, "Catalytic Hydrogenolysis at Low Temperature and Pressure of Polyethylene and Polypropylene to Diesels or Lower Alkanes by a Zirconium Hydride Supported on Silica-Alumina: A Step Toward Polyolefin Degradation by the Microscopic Reverse of Ziegler-Natta Polymerization," *Angew. Chem. Int. Ed.* 37:806-810 (1998)). Unfortunately, this approach is limited by the extreme air and moisture sensitivity of the hydridozirconium catalyst, as well as the fact that plastics are deconstructed to lowest value, functional-group free hydrocarbons such as methane and ethane, rather than valuable chemical intermediates with catenated carbon chains (FIG. 1).

C—H bond metalations, in which a hydrogen atom is replaced by a metal center, have revolutionized syntheses by reducing or eliminating requirements for specific and limiting chemical functional groups (Kennedy et al., "Synergic Sedation of Sensitive Anions: Alkali-Mediated Zincation of Cyclic Ethers and Ethene," *Science* 326:706-708 (2009); Chen et al., "Thermal, Catalytic, Regiospecific Functionalization of Alkanes,"*Science* 287:1995-1997 (2000); Cho et al., "Remarkably Selective Iridium Catalysts for the Elaboration of Aromatic C—H Bonds,"*Science* 295:305-308 (2002)). In these reactions, the carbon-based molecular framework of the organic reactants is preserved in the functionalized products. An even wider range of starting materials could be leveraged by methods that concurrently alter the carbon-based skeleton of organic molecules and introduce new functional groups. With such transformations for example, natural resources that contain structural components of the desired products would become available for chemical manufacturing, or framework reconstructions could increase late-stage structural diversification during multistep syntheses. C—C bond metalations, in which a metal center replaces a specific hydrocarbyl moiety, would enable these framework functionalization reactions. Current methods that install a metal center while breaking a carbon-carbon bond, however, are limited to positions activated either by thermodynamically weakened bonds or directing functional groups (FIG. 1A) (Pitts et al., "Unstrained C—C Bond Activation and Directed Fluorination Through Photocatalytically-generated Radical Cations," *Chem. Sci.* 6:5225-5229 (2015); Roque et al., "Deconstructive Fluorination of Cyclic Amines by Carbon-carbon Cleavage," *Science* 361:171 (2018); Morcillo, S. P., "Radical-Promoted C—C Bond Cleavage: A Deconstructive Approach for Selective Functionalization," *Angew. Chem. Int. Ed.* 58:14044-14054 (2019); Gozin et al., "Activation of a Carbon-carbon Bond in Solution by Transition-metal Insertion," *Nature* 364:699-701 (1993)). On the other hand, established C—C bond cleavages involving only sp$^3$-hybridized carbon centers generally do not provide new carbon-heteroatom bonds. For example, alkane metathesis (FIG. 1B) alters chain lengths without introducing new functional groups (Basset et al., "Metathesis of Alkanes and Related Reactions," *Acc. Chem. Res.* 43:323-334 (2009); Haibach et al., "Alkane Metathesis by Tandem Alkane-Dehydrogenation-Olefin-Metathesis Catalysis and Related Chemistry," *Acc. Chem. Res.* 45:947-958 (2012)). Likewise, hydrogenolysis of carbon-carbon bonds in hydrocarbons (FIG. 1C), catalyzed by heterogeneous platinum group nanoparticles (Flaherty et al., "Metal-Catalyzed C—C Bond Cleavage in Alkanes: Effects of Methyl Substitution on Transition-State Structures and Stability," *J. Am. Chem. Soc.* 136:9664-9676 (2014); Flaherty and Iglesia, "Transition-State Enthalpy and Entropy Effects on Reactivity and Selectivity in Hydrogenolysis of n-Alkanes," *J Am. Chem. Soc.* 135:18586-18599 (2013)) or air-sensitive early transition metal hydrides (Lecuyer et al., "Surface Organometallic Chemistry on Oxides: Selective Catalytic Low-Temperature Hydrogenolysis of Alkanes by a Highly Electrophilic Zirconium Hydride Complex Supported on Silica," *Angew. Chem. Int. Ed Engl.* 30:1660-1661 (1991); Corker et al., "Catalytic Cleavage of the C—H and C—C Bonds of Alkanes by Surface Organometallic Chemistry: An EXAFS and IR Characterization of a Zr—H Catalyst,"*Science* 271: 966-969 (1996)), provide shorter, yet heteroatom-free, alkane products.

Molecular skeleton restructuring transformations could be useful, for instance, in the deconstruction of polymers for which there are growing environmental and socioeconomic concerns (Brahney et al., "Plastic Rrain in Protected Areas of the United States,"*Science* 368:1257-1260 (2020); Jambeck et al., "Plastic Waste Inputs from Land into the Ocean,"*Science* 347:768-771 (2015)). Conventional technologies, such as mechanical recycling through melt-processing, are insufficient to fully address this global problem (Lau et al., "Evaluating Scenarios Toward Zero Plastic Pollution," *Science* 369:1455 (2020); Borrelle et al., "Predicted Growth in Plastic Waste Exceeds Efforts to Mitigate Plastic Pollution,"*Science* 369:1515 (2020)). Chemical conversion of polymers has been proposed as an alternative strategy that could provide a second life for the catenated chains of used plastics (Vollmer et al., "Beyond Mechanical Recycling: Giving New Life to Plastic Waste," *Angew. Chem. Int. Ed.* 59:15402-15423 (2020); Rahimi and Garcia, "Chemical Recycling of Waste Plastics for New Materials Production," *Nat. Rev. Chem.* 1:0046 (2017)). For example, polyolefins may be transformed into liquid fuels by pyrolysis or hydrocracking (Scheirs, J., "Overview of Commercial Pyrolysis Processes for Waste Plastics," In *Feedstock Recycling and Pyrolysis of Waste Plastics*, J. Scheirs, and W. Kaminsky, eds. (Sussex, UK: John Wiley & Sons), pp. 381-433 (2006)), polyesters may be chemically recycled via monomers (George and Kurian, "Recent Developments in the Chemical Recycling of Postconsumer Poly(ethylene terephthalate) Waste," *Ind. Eng. Chem. Res.* 53:14185-14198 (2014)), plastic-to-plastic transformations can upcycle used materials into new (Jones et al., "Computational and Experimental Investigations of One-step Conversion of Poly(carbonate)s Into Value-added Poly(aryl ether sulfone)s," *Proc. Natl. Acad. Sci. U.S.A.* 113:7722 (2016); Blasco et al., "50th Anniversary Perspective: Polymer Functionalization," Macromolecules 50:5215-5252 (2017); Williamson et al., "Regioselective C—H Xanthylation as a Platform for Polyolefin Functionalization," *Angew. Chem. Int. Ed.* 57:6261-6265 (2018); Lewis et al., "Upcycling Aromatic Polymers Through C—H Fluoroalkylation," *Chem. Sci.* 10:6270-6277 (2019)), and discarded plastics can serve as feedstocks for value-added chemical products. Catalytic C—C bond metalation reactions, which provide versatile organometallic intermediates, could also benefit from catalyst-controlled selectivity.

The present application is directed to overcoming these and other deficiencies in the art.

SUMMARY

One aspect of the present application relates to a process including:
providing one or more polymers, oligomers, or mixtures thereof;
providing a compound of formula (I):

where
$R^1$ is independently selected at each occurrence thereof from the group consisting of H, aryl, $C_1$-$C_8$ alkyl, and $C_1$-$C_8$ alkoxy;
contacting the polymers, oligomers, or mixtures thereof with the compound of formula (I), as a reaction mixture, in the presence of a catalyst selected from the group consisting of a transition metal catalyst, a lanthanide series metal catalyst, or combinations thereof, under conditions effective to form alkanes, carboxylic acids, alcohols, alkyl halides or aldehydes, which are shorter than the polymers, the oligomers, or the mixtures thereof; and
recovering the formed shorter alkanes, carboxylic acids, alcohols, alkyl halides or aldehydes.

A second aspect of the present application relates to a process including:
providing one or more polymers, oligomers, or mixtures thereof;
providing a compound of formula (I):

where
$R^1$ is independently selected at each occurrence from the group consisting of H, aryl, $C_1$-$C_8$ alkyl, and $C_1$-$C_8$ alkoxy;
contacting the polymers, oligomers, or mixtures thereof with the compound of formula (I), as a reaction mixture, in the presence of a catalyst selected from the group consisting of a transition metal catalyst, a lanthanide series metal catalyst, or combinations thereof, under conditions effective to form an aluminum alkyl compound of formula (III)

where
$R^3$ is independently selected at each occurrence thereof from $C_{12}$-$C_{60}$ alkyls, which are shorter than the polymers, the oligomers, or the mixtures thereof; and
n is an integer ranging from one to three.

A third aspect of the present application relates to an alkyl aluminum of formula (III):

where
$R^1$ is independently selected at each occurrence thereof from the group consisting of H, aryl, $C_1$-$C_8$ alkyl, and $C_1$-$C_8$ alkoxy;
$R^3$ is independently selected at each occurrence thereof from $C_{12}$-$C_{60}$ alkyls; and
n is an integer ranging from one to three.

Fatty alcohols and fatty acids are high value chemicals. The technology of the present application involves conversion of waste polyolefins (e.g., high-, linear low-, or low-density polyethylene, polypropylene) into fatty alcohols or fatty acids by early metal or lanthanide-catalyzed chain cleavage and functionalization. The conditions are related to those of olefin polymerizations, in the absence of olefins, and the reactions occur solvent free (melted polyolefin), using alkylaluminum reagents. The zirconium precatalyst is active under catalytic conditions even after being exposed to air, and the alkylaluminum reagent 'dries' adventitious water in the plastic feedstock.

Catalytic methods that introduce functional groups via carbon-carbon bond cleavage steps have typically been limited to moieties activated by strain or by directing groups, with few transformations engaging the bonds of only $sp^3$-hybridized carbon atoms in saturated hydrocarbons. Herein is reported the conversion of catenated carbon chains in polyolefins, which currently represent >50% of discarded plastics, into shorter aliphatic alkylaluminum species via a sequence of zirconation via C—H bond activation, β-alkyl elimination for carbon-carbon bond cleavage, and heterobimetallic alkyl group exchange for carbon-aluminum bond formation. The versatility of aliphatic alkylaluminum species is exemplified by their subsequent conversion into high value fatty acids or alcohols, which have applications as biodegradable surfactants and detergents (FIG. 1D).

Upcycling processes, the conversion of wasted materials into higher value products (Rahimi and Garcia, "Chemical Recycling of Waste Plastics for New Materials Production," *Nat. Rev. Chem.* 1:0046 (2017), which is hereby incorporated by reference in its entirety) involving selective cleavage of carbon-carbon bonds in polymer chains, would also benefit from concurrent introduction of functional groups such as alcohols and acids to afford high value products. Higher value short chains could be accessed from polyolefins by utilizing the relationship between alkene coordinative-insertion and β-alkyl elimination. The insertion step is central to chain growth during olefin polymerizations; thus, mechanistic features and insight from polymerization could provide guidance for designing new catalytic deconstructions of polyolefins for chemical synthesis. Polymerizations are often performed in the presence of excess alkylaluminum species, which serve as alkylating agents to generate organometallic species, Lewis acid sites (in the case of methylaluminoxane) to activate the catalyst, chain transfer agents such as in the case of chain-shuttling (Arriola et al., "Catalytic Production of Olefin Block Copolymers via Chain Shuttling Polymerization,"*Science* 312:714-718 (2006), which is hereby incorporated by reference in its entirety), and air and moisture scavengers that inoculate sensitive catalytic sites from poisons. Based on these roles, it was envisioned that simultaneous deconstruction and functionalization of polyolefins, involving β-alkyl eliminations, could also be facilitated by the combination of an early metal catalytic site and alkylaluminum reagent. In fact, the deconstruction of the unsaturated polymer, polybutadiene, and its alumination is catalyzed by $Cp_2ZrHCl$ (Schwartz's reagent) in the presence of $AliBu_3$ via alkene insertion, a facile β-allyl elimination, and chain transfer to aluminum (Zheng et al., "Controlled Chain-Scission of Polybutadiene by the Schwartz Hydrozirconation," *Chem. Eur. J.* 19:541-548 (2013), which is hereby incorporated by reference in its entirety). Herein, surface-supported zirconium-catalyzed deconstruction/alumination of saturated polyolefins is reported to generate long chain alkyl aluminum intermediates, which are easily converted to valuable fatty alcohols (FIG. 2) and acids with applications as surfactants, plasticizers, lubricants, and cosmetics (Noweck, K., "Fatty Alcohols." *Ullmann's Encyclopedia of Industrial Chemistry* (2001); Ahmad, M. U., "Fatty Acids: Chemistry, Synthesis, and Applications," London, Academic Press, pp. xxii, 593 p. (2017), which is hereby incorporated by reference in its entirety).

The environmental, economic, and health impacts of the plastic waste crisis motivate the design and study of new chemistries that enable efficient upcycling of polymers into versatile, value-added intermediates. A new catalytic strategy for transforming single-use polyolefin waste via reactive hydrocarbylaluminum intermediates into functionalized aliphatic chains, such as fatty alcohols and acids is reported in the present application. Earth-abundant zirconium surface sites catalyze the deconstruction of polyolefins under mild (<200° C.), solvent-free conditions via C—H bond activation, β-alkyl elimination for carbon-carbon bond cleavage, and aluminum-carbon bond formation for functionalization. Catalytic efficiency and selectivity are governed by the activation of surface-supported zirconium precatalysts, which become most effective in the presence of aluminum reagents capable of generating zirconium hydrides.

BRIEF DESCRIPTION OF THE DRAWINGS

FIGS. 1A-1D show catalytic methods for carbon-carbon bond cleavage. FIG. 1A depicts the prior art carbon-carbon bond cleavage and functionalization reactions where the functional groups are added at thermodynamically activated or kinetically preferred positions. Saturated hydrocarbons in small molecules and polymers may be shorted by alkane metathesis (FIG. 1B) or nanoparticle or early-metal hydride-catalyzed hydrogenolysis (FIG. 1C) without introduction of new functionality. FIG. 1D depicts carbon-carbon bond cleavage and aluminum-carbon bond formation catalyzed by surface-supported organozirconium species as presented herein.

FIG. 2 is a graphical representation of the tandem carbon-carbon bond cleavage and carbon aluminum bond formation reaction of the present application.

Cross-peaks at 4.7-5.2 ppm correlate with methylene signals at 1.3-2.0 ppm, indicative of —$CH_2$—$CH_2$—OH moieties.

Figure 75:
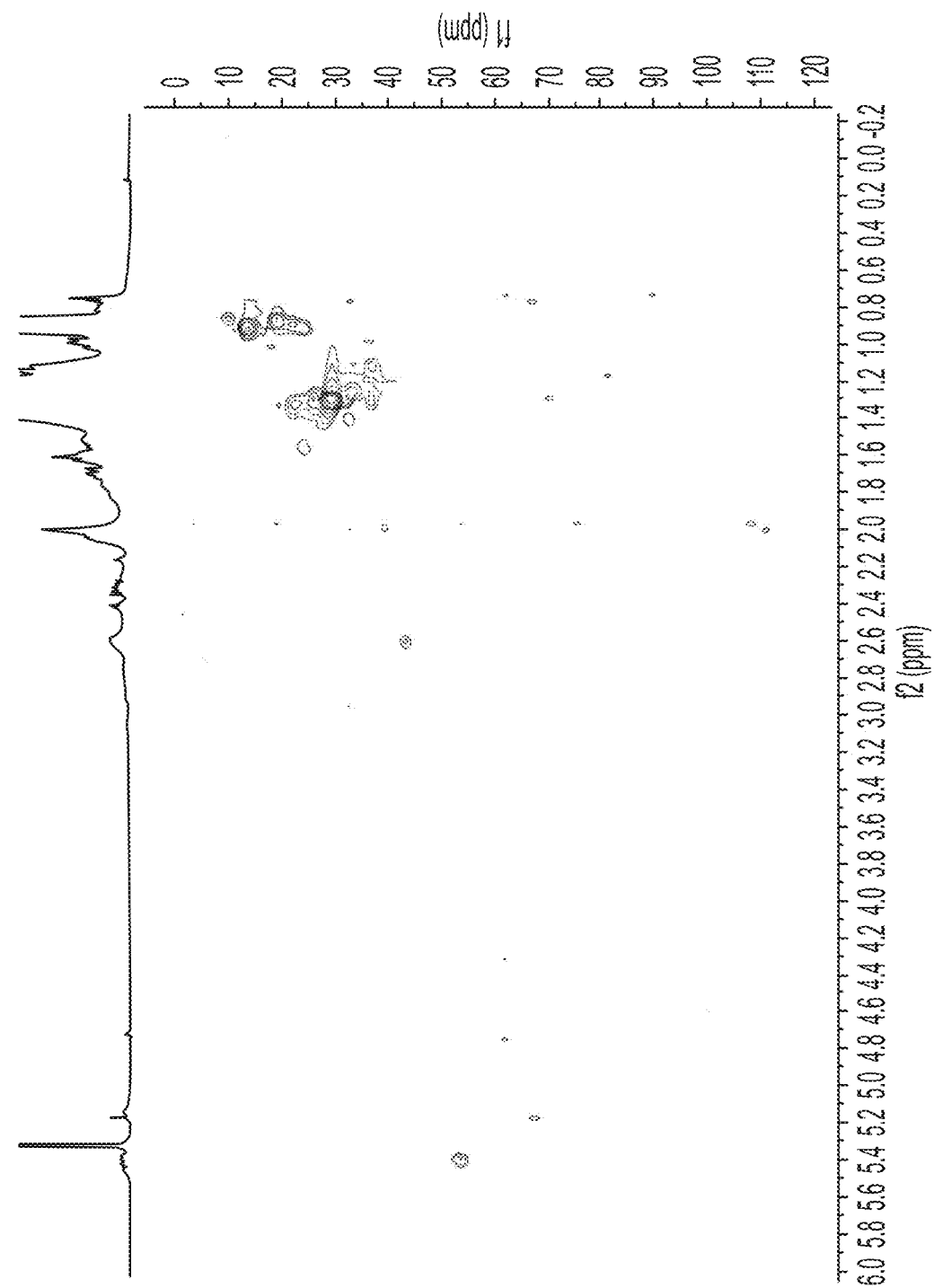

FIG. 75 is the phase sensitive $^1H$-$^{13}C$ HSQC spectrum of the oil isolated after reaction of HDPE and $AlEt_3$ in the presence of $Zr(CH_2CMe_3)_2$@$SiO_2$ at 200° C. for 12 h, quenched with $O_2$, and extracted with methylene chloride. The spectrum was acquired at room temperature in methylene chloride-$d_2$. Cross-peaks at $^{13}C$ 60-70 ppm have the same phase as methylene peaks at 30 ppm revealing the former are —$CH_2$—OH moieties.

Figure 76:
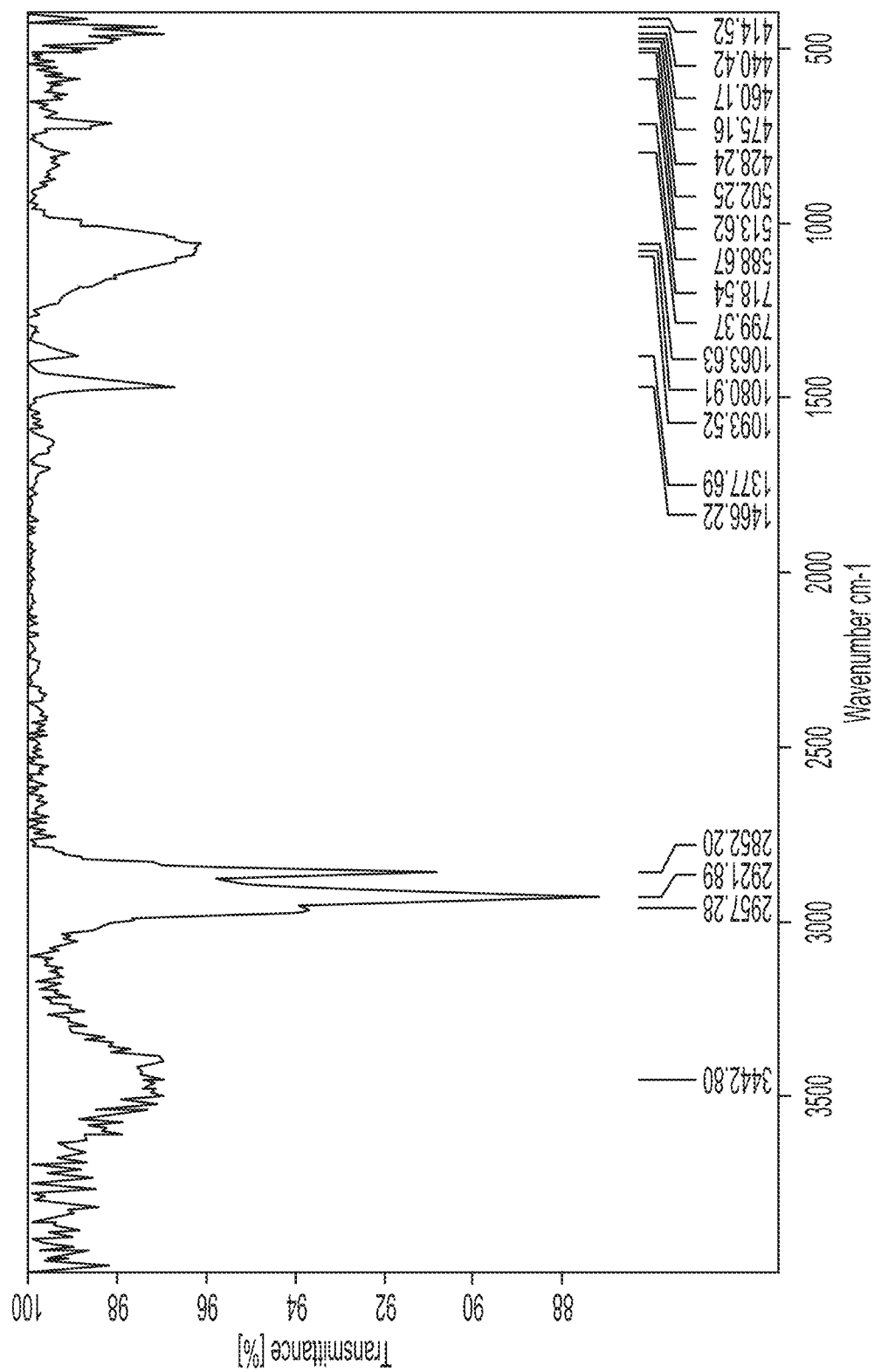

FIG. 76 is the FT-IR spectrum (KBr) of the oil isolated after reaction of HDPE and $AlEt_3$ in the presence of $Zr(CH_2CMe_3)_2$@$SiO_2$ at 200° C. for 12 h, quenched with $O_2$, and extracted with methylene chloride. The broad signal at 3442 $cm^{-1}$ corresponds to an O—H stretch.

Figure 77:
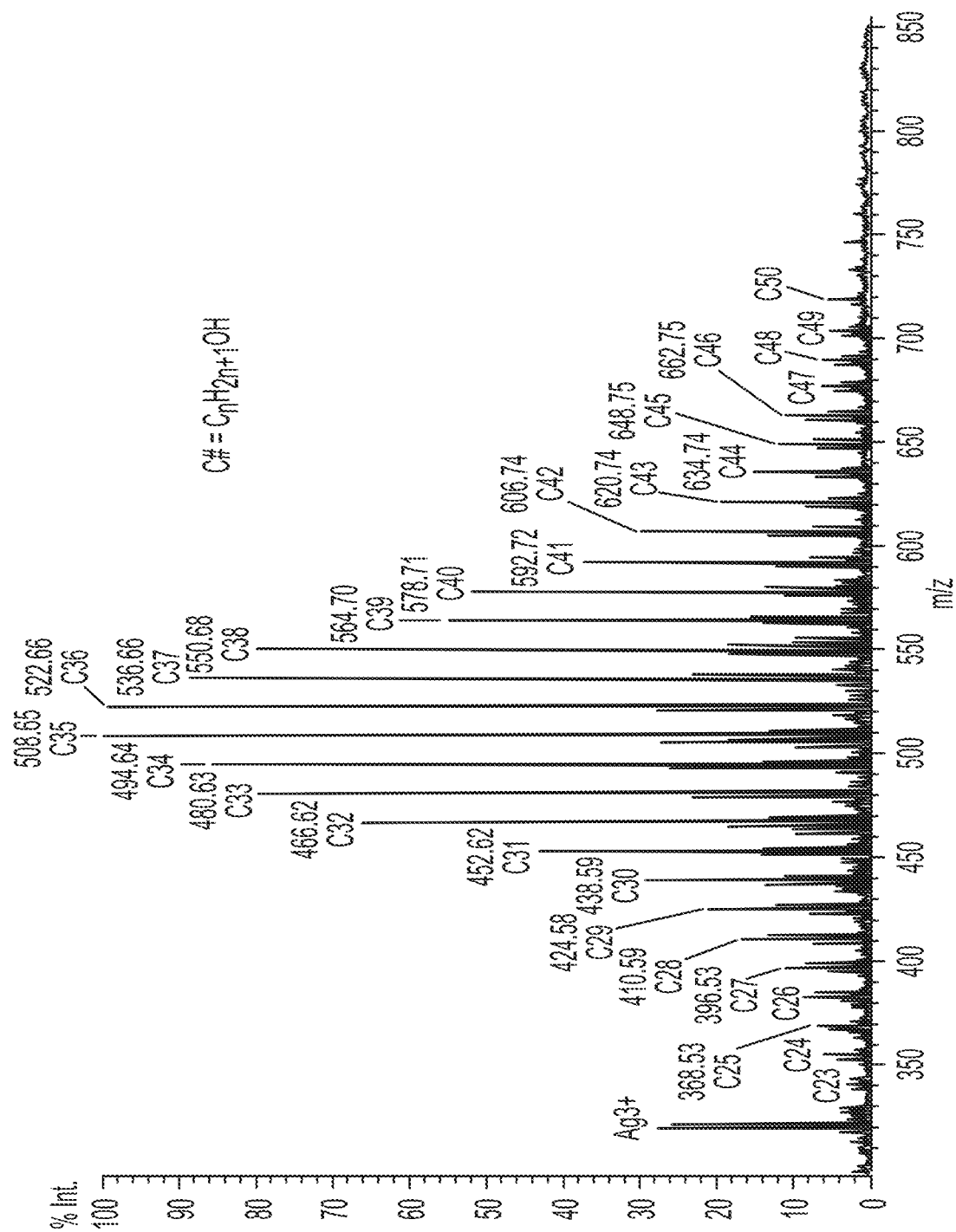

FIG. 77 is the MALDI-TOF-MS spectrum of the oil isolated after reaction of HDPE and $AlEt_3$ in the presence of $Zr(CH_2CMe_3)_2$@$SiO_2$ at 200° C. for 12 h, quenched with $O_2$, and extracted with methylene chloride. The spectrum was acquired in linear, positive mode with $AgNO_3$ (salt) and DHB (matrix).

Figure 78:
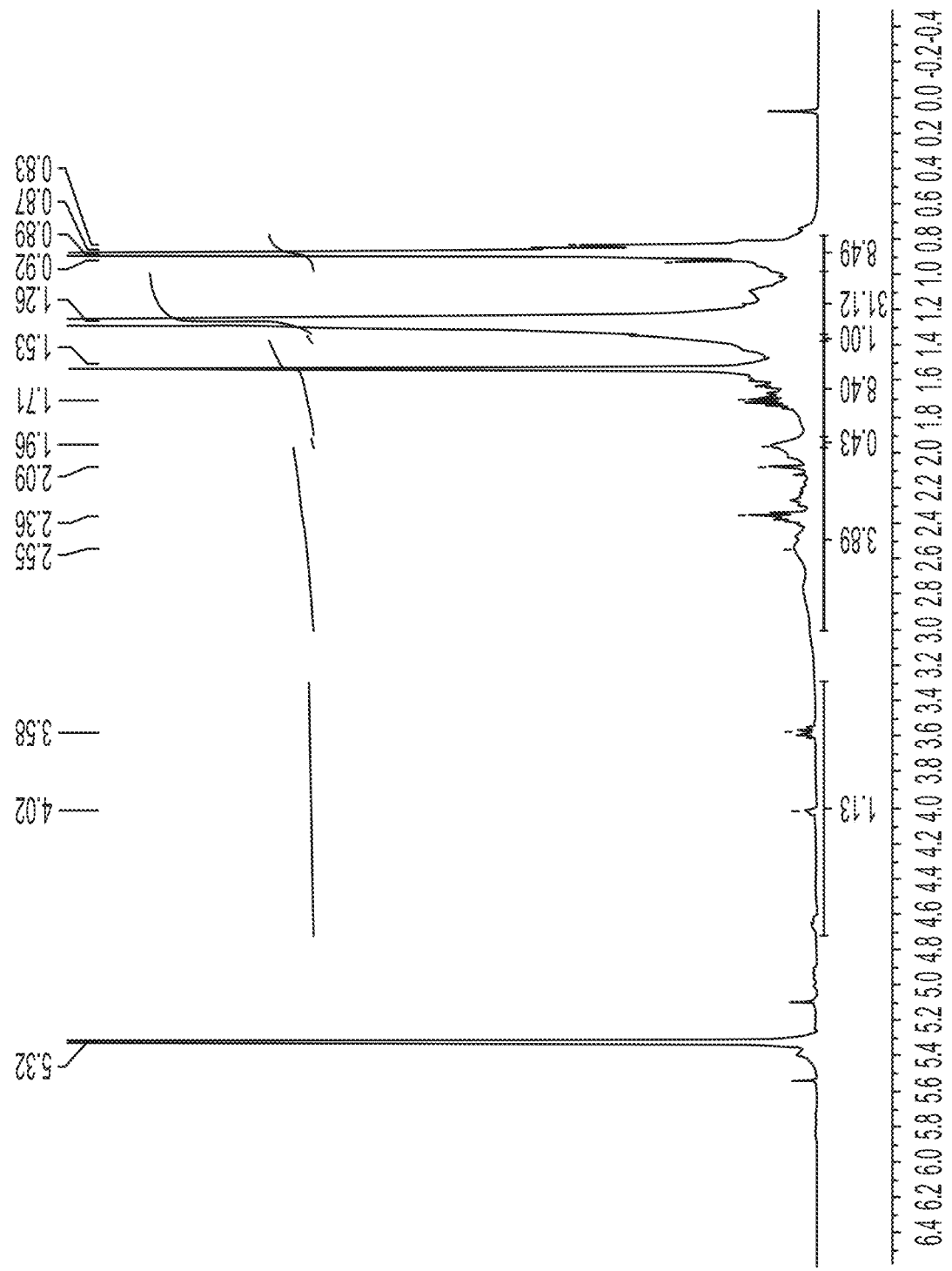

FIG. 78 is the $^1H$ NMR spectrum of the oil isolated after reaction of a post-consumer HDPE plastic grocery bag and $AliBu_3$ in the presence of $Zr(CH_2CMe_3)_2$@$SiAlO_x$ at 200° C. for 12 h, quenched with $O_2$, and extracted with methylene chloride. The spectrum was acquired at room temperature in methylene chloride-$d_2$ and assigned based on TOCSY and HSQC experiments in FIGS. 79 and 80. Signals at 0.7-1.0 ppm correspond to methyl groups, peaks at 1.0-1.3, 1.4-1.9, and 2.0-3.0 ppm are assigned to methylene groups, and those at 1.3-1.4 and 1.9-2.0 ppm correspond to methine groups. Peaks at 3.5-4.8 ppm are assigned to —$CH_2$—OH groups.

Figure 79:
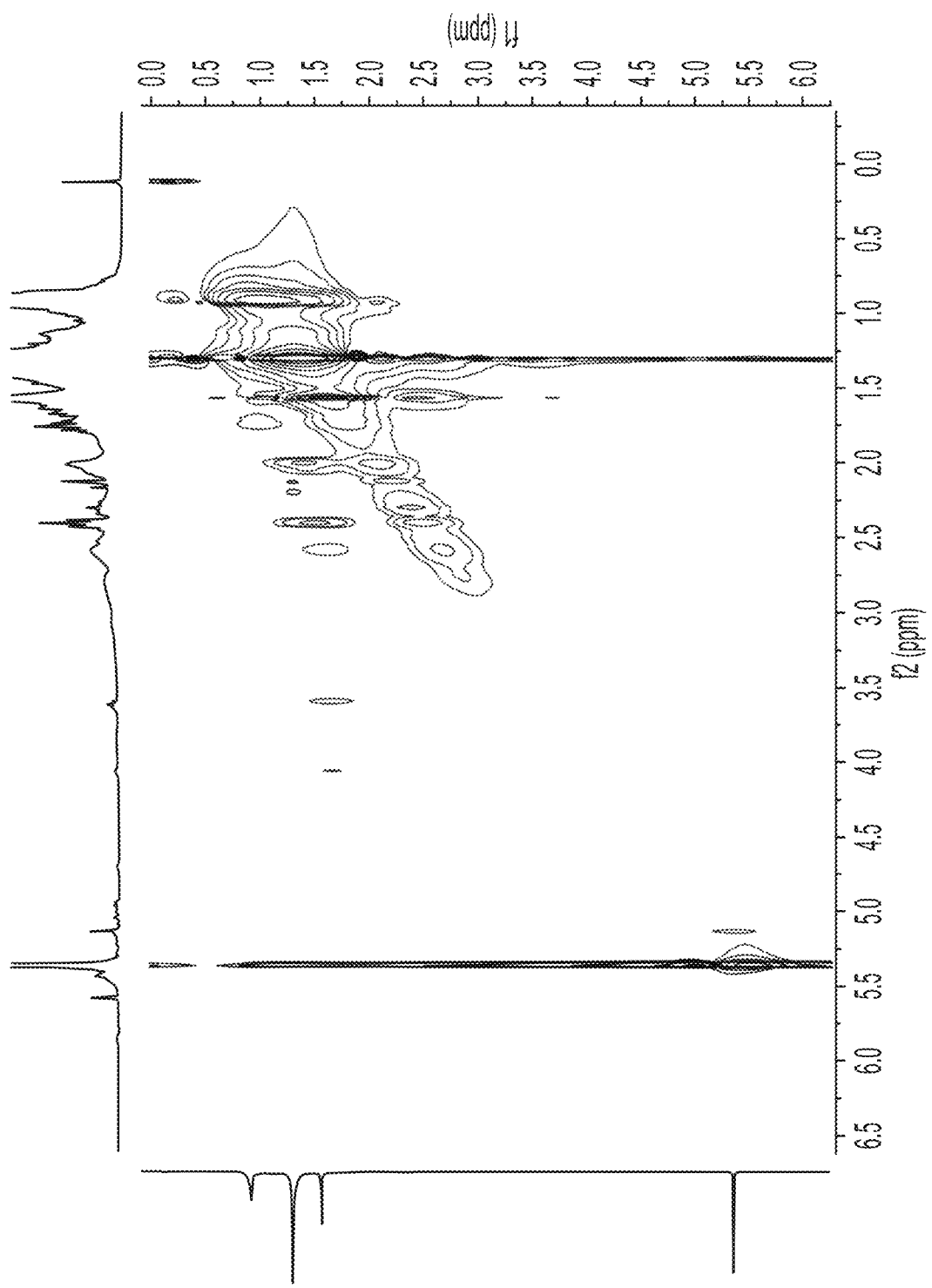

FIG. 79 is the TOCSY spectrum of the oil isolated after reaction of a post-consumer HDPE plastic grocery bag and $AliBu_3$ in the presence of $Zr(CH_2CMe_3)_2$@$SiAlO_x$ at 200° C. for 12 h, quenched with $O_2$, and extracted with methylene chloride. The spectrum was acquired at room temperature in methylene chloride-$d_2$. Cross-peaks at 3.6-4.0 ppm correlate with methylene signals at 1.6 ppm, which is indicative of —$CH_2$—$CH_2$—OH species.

Figure 80:
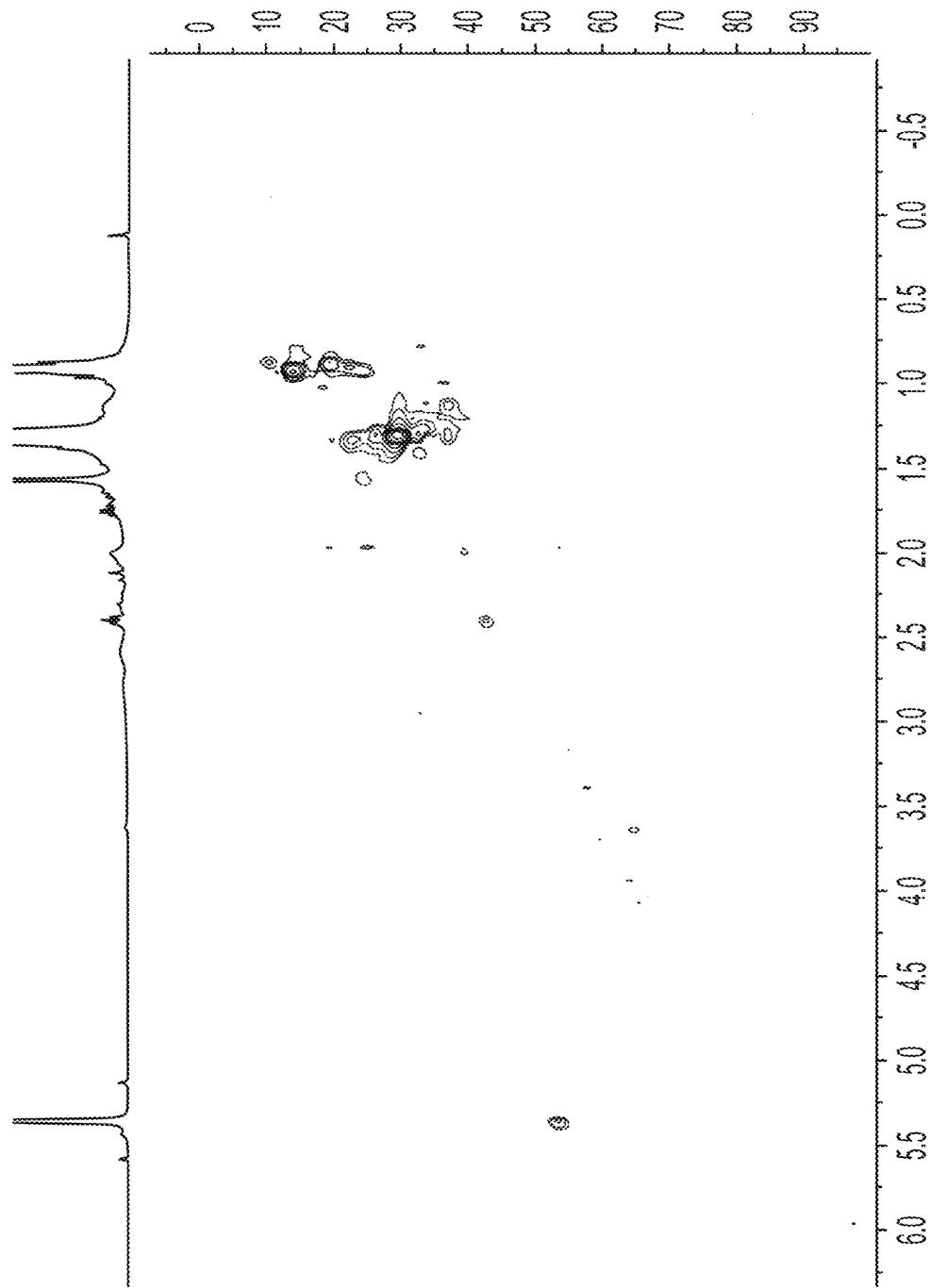

FIG. 80 is the phase sensitive $^1H$-$^{13}C$ HSQC spectrum of the oil isolated after reaction of a post-consumer HDPE plastic grocery bag and $AliBu_3$ in the presence of $Zr(CH_2CMe_3)_2$@$SiAlO_x$ at 200° C. for 12 h, quenched with $O_2$, and extracted with methylene chloride. The spectrum was acquired at room temperature in methylene chloride-$d_2$. Cross-peaks at $^{13}C$ 55-70 ppm have the same phase as methylene peaks at 30 ppm, revealing the former are —$CH_2$—OH moieties.

Figure 81:
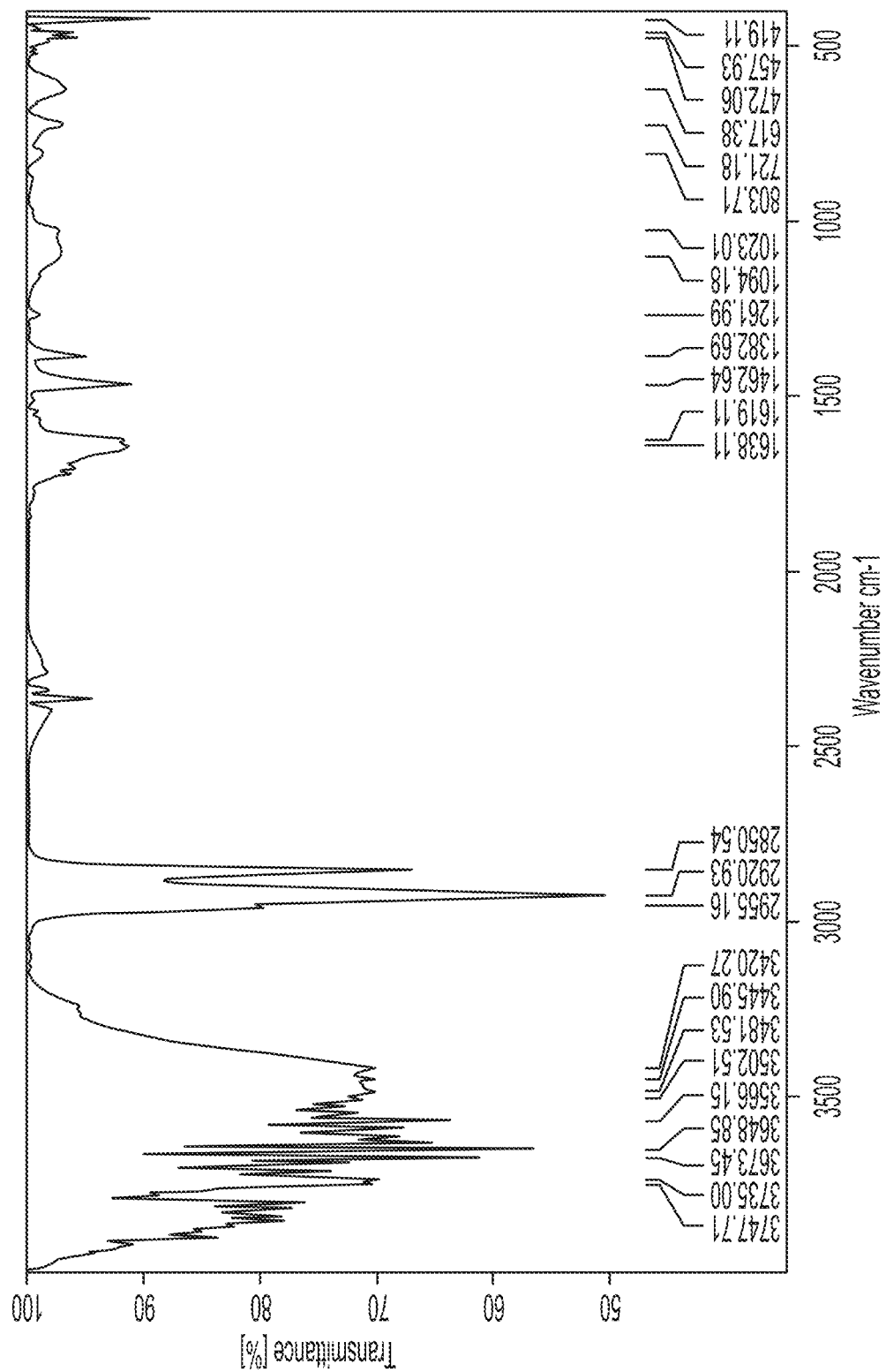

FIG. 81 is the FT-IR spectrum (KBr) of the oil isolated after reaction of a post-consumer HDPE plastic grocery bag and $AliBu_3$ in the presence of $Zr(CH_2CMe_3)_2$@$SiAlO_x$ at 200° C. for 12 h, quenched with $O_2$, and extracted with methylene chloride. Broad signals between 3200-3600 $cm^{-1}$ correspond to 0-H stretches.

Figure 82:
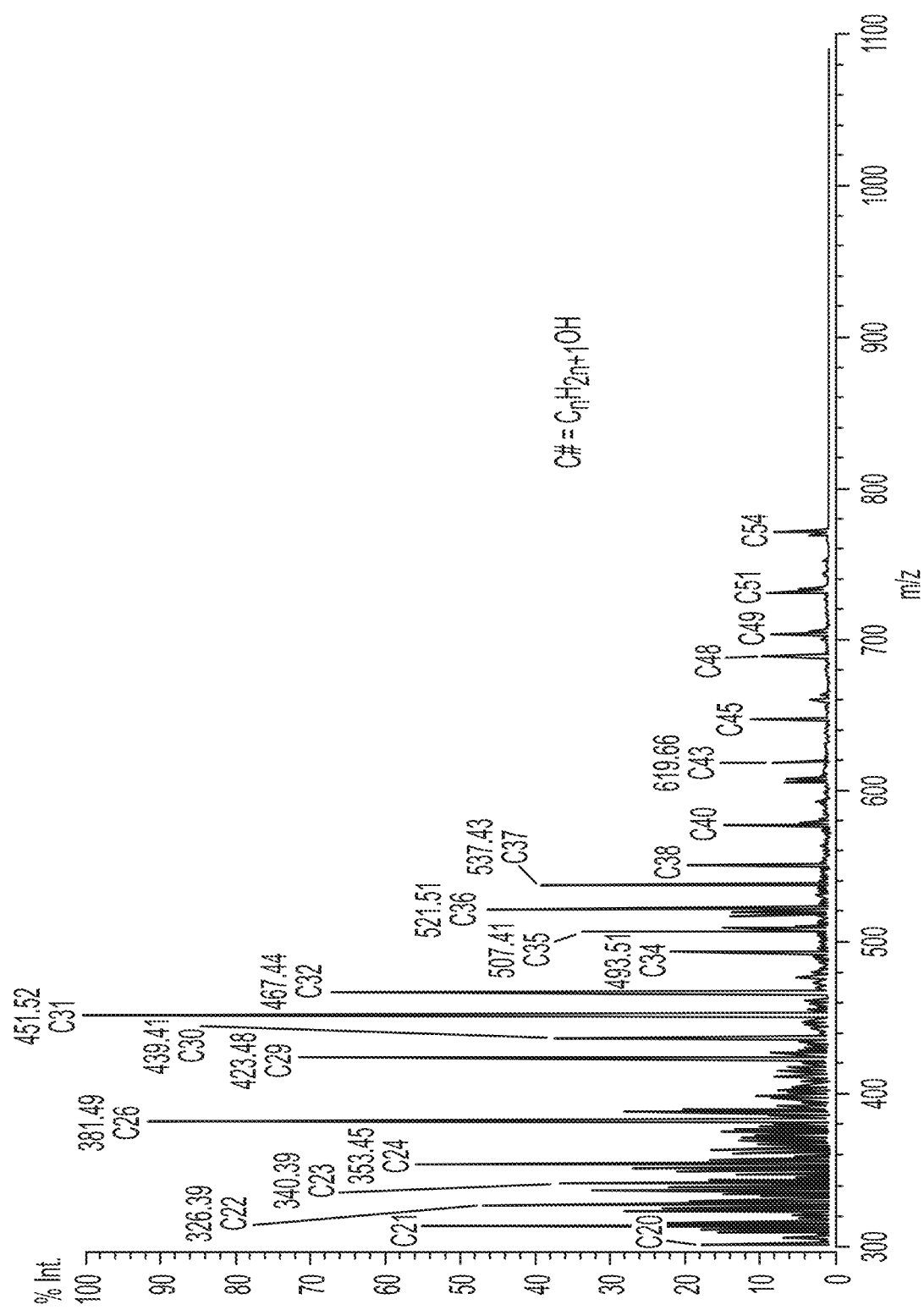

FIG. 82 is the MALDI-TOF-MS spectrum of the oil isolated after reaction of a post-consumer HDPE plastic grocery bag and $AliBu_3$ in the presence of $Zr(CH_2CMe_3)_2$@$SiAlO_x$ at 200° C. for 12 h, quenched with $O_2$, and extracted with methylene chloride. The spectrum was acquired in linear, positive mode with $AgNO_3$ (salt) and DHB (matrix).

Figure 83:
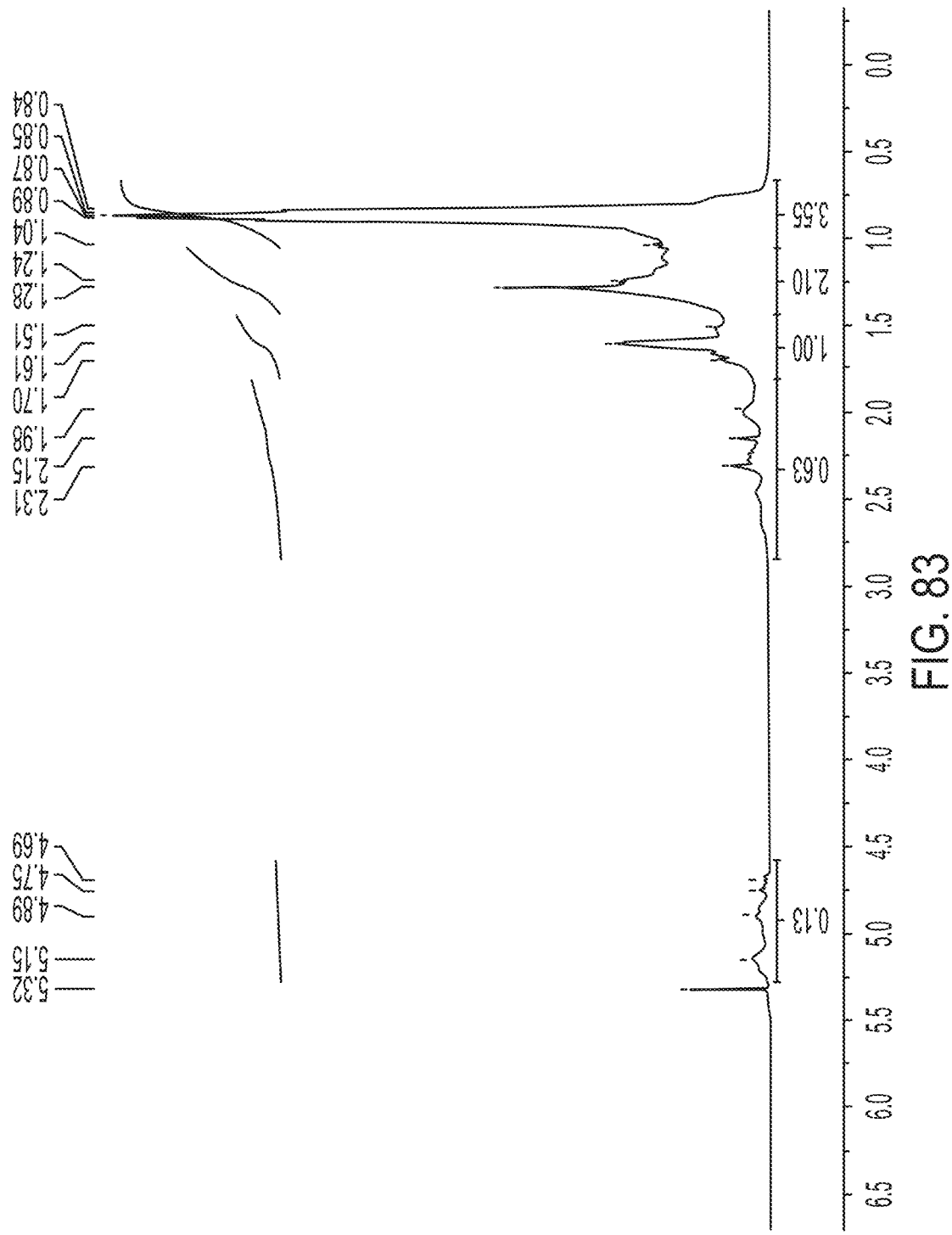

FIG. 83 is the $^1H$ NMR spectrum of the oil isolated after reaction of isotactic polypropylene and $AliBu_3$ in the presence of $Zr(CH_2CMe_3)_2$@$SiAlO_x$ at 200° C. for 12 h, quenched with $O_2$, and extracted with methylene chloride. The spectrum was acquired at room temperature in methylene chloride-$d_2$ and assigned based on COSY and HSQC experiments in FIGS. 84 and 85. Signals at 0.7-1.0 ppm are assigned to methyl groups, peaks at 1.0-1.5 ppm correspond to methylene groups, and those at 1.5-3.0 ppm are attributed to methine groups. Peaks at 4.6-5.2 ppm are assigned to —$CH_2$—OH groups.

Figure 84:
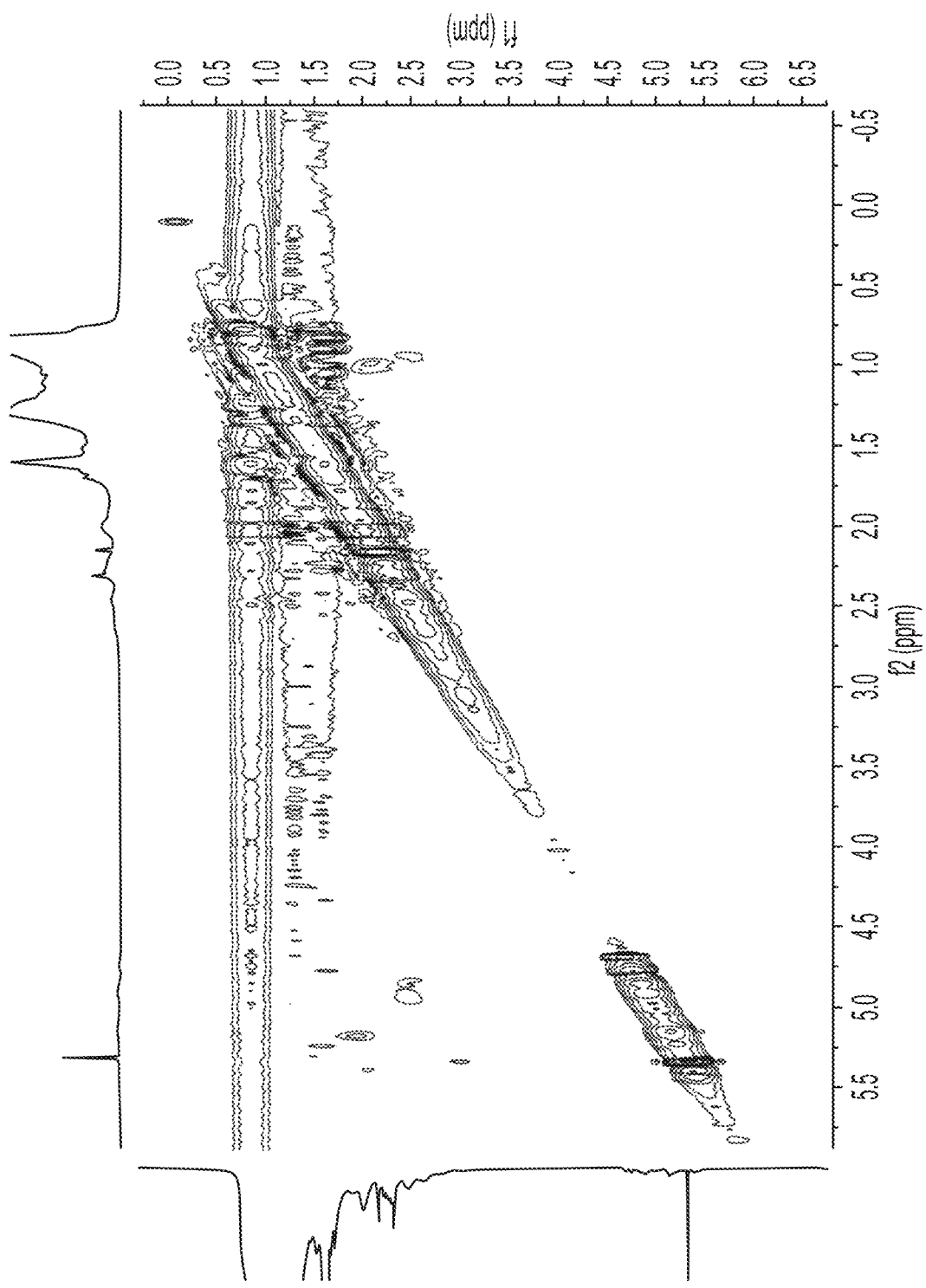

FIG. 84 is the COSY spectrum of the oil isolated after reaction of polypropylene and $AliBu_3$ in the presence of $Zr(CH_2CMe_3)_2$@$SiAlO_x$ at 200° C. for 12 h, quenched with $O_2$, and extracted with methylene chloride. The spectrum was acquired at room temperature in methylene chloride-$d_2$. Cross-peaks at 4.7-5.2 ppm correlate with methine signals at 1.6-2.5 ppm, which is indicative of —(R)CH—$CH_2$—OH species.

Figure 85:
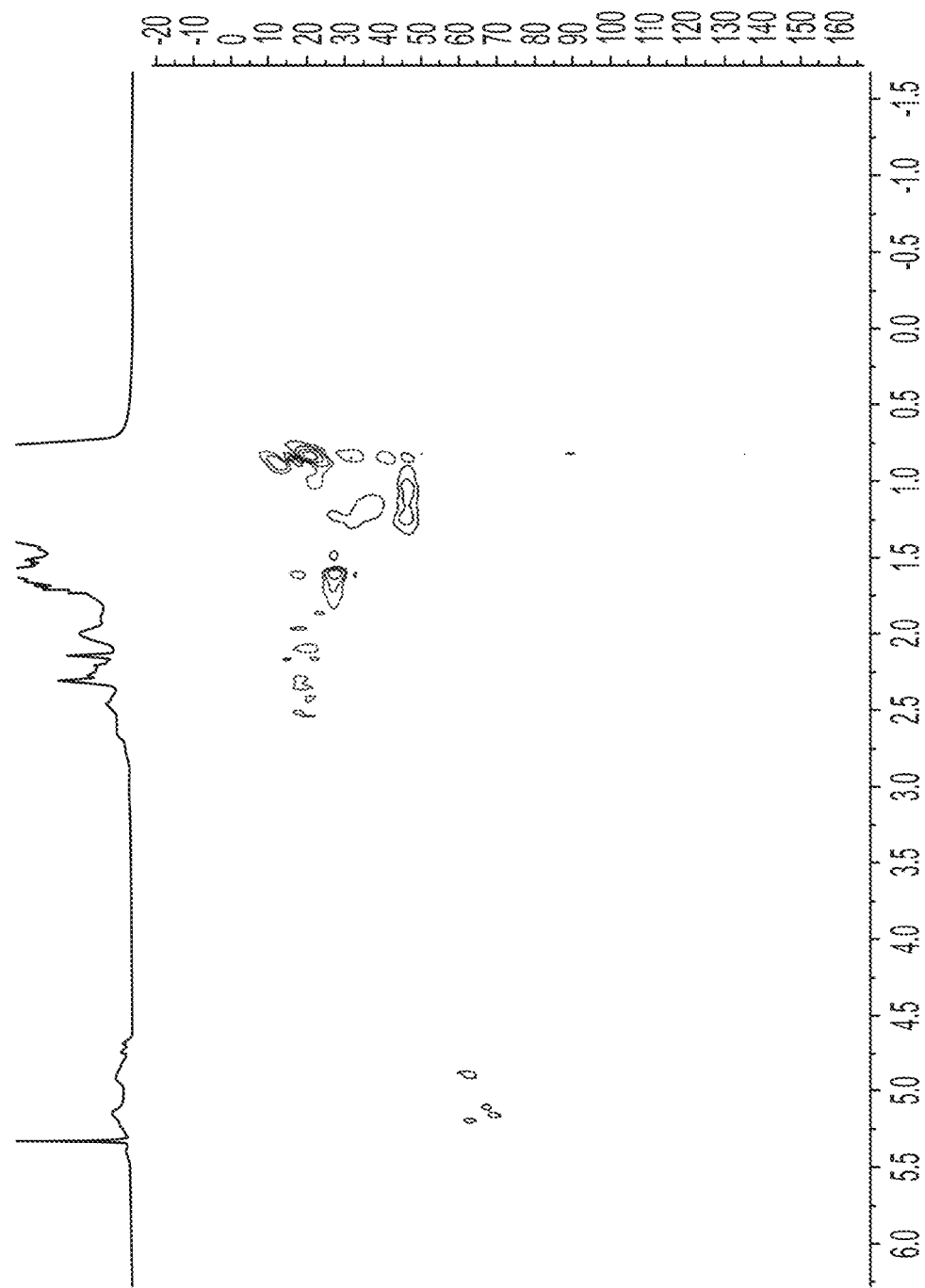

FIG. 85 is the phase sensitive $^1H$-$^{13}C$ HSQC spectrum of the oil isolated after reaction of polypropylene and $AliBu_3$ in the presence of $Zr(CH_2CMe_3)_2$@$SiAlO_x$ at 200° C. for 12 h, quenched with $O_2$, and extracted with methylene chloride. The spectrum was acquired at room temperature in methylene chloride-$d_2$. Cross-peaks at $^{13}C$ 60-70 ppm have the same phase as methylene peaks at 30 ppm, revealing the former are —$CH_2$—OH moieties.

Figure 86:
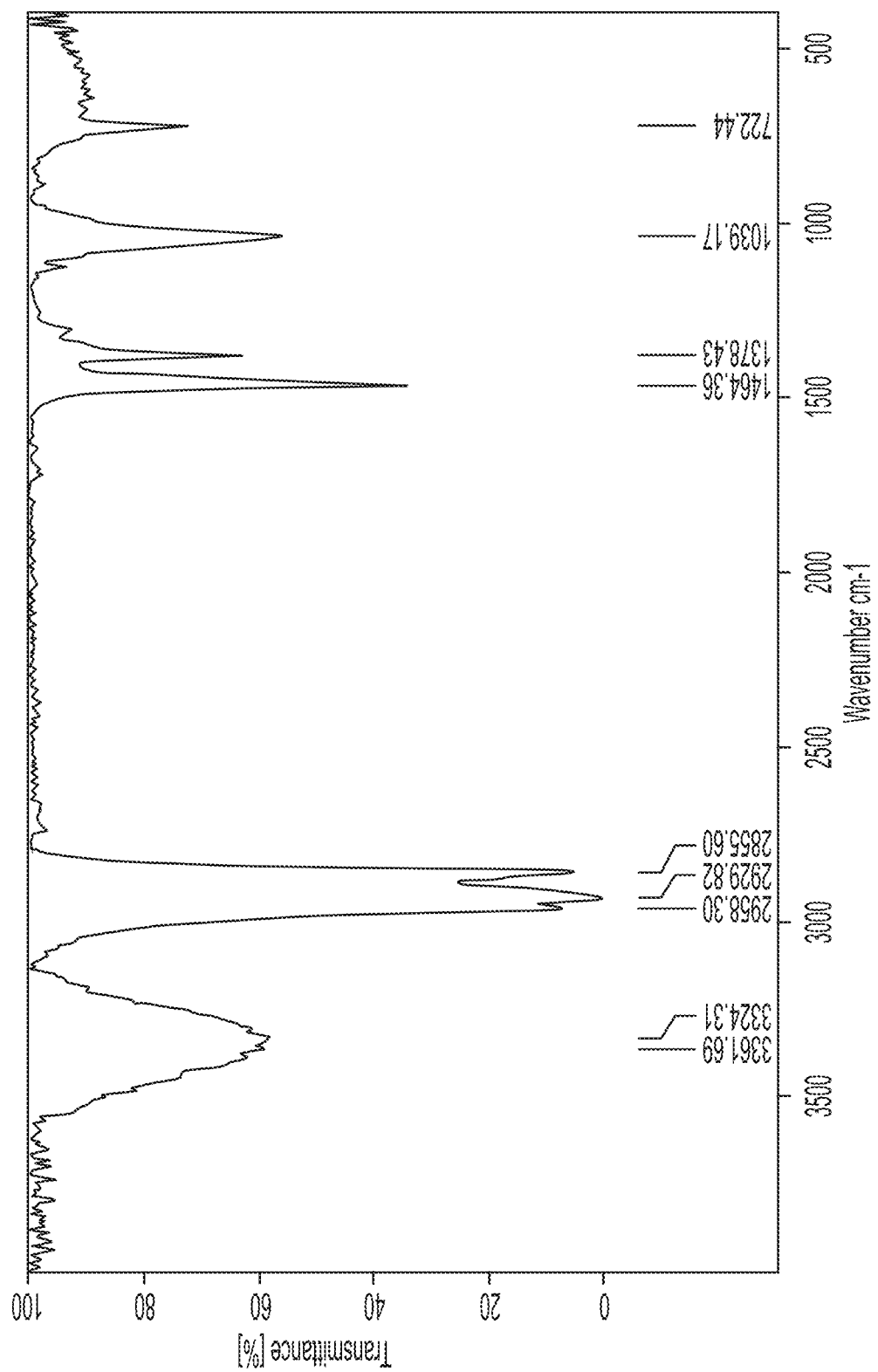

FIG. 86 is the FT-IR spectrum (KBr) of the oil isolated after reaction of polypropylene and $AliBu_3$ in the presence of $Zr(CH_2CMe_3)_2$@$SiAlO_x$ at 200° C. for 12 h, quenched with $O_2$, and extracted with methylene chloride. Broad signals between 3200-3600 $cm^{-1}$ correspond to O—H stretching modes.

Figure 87:
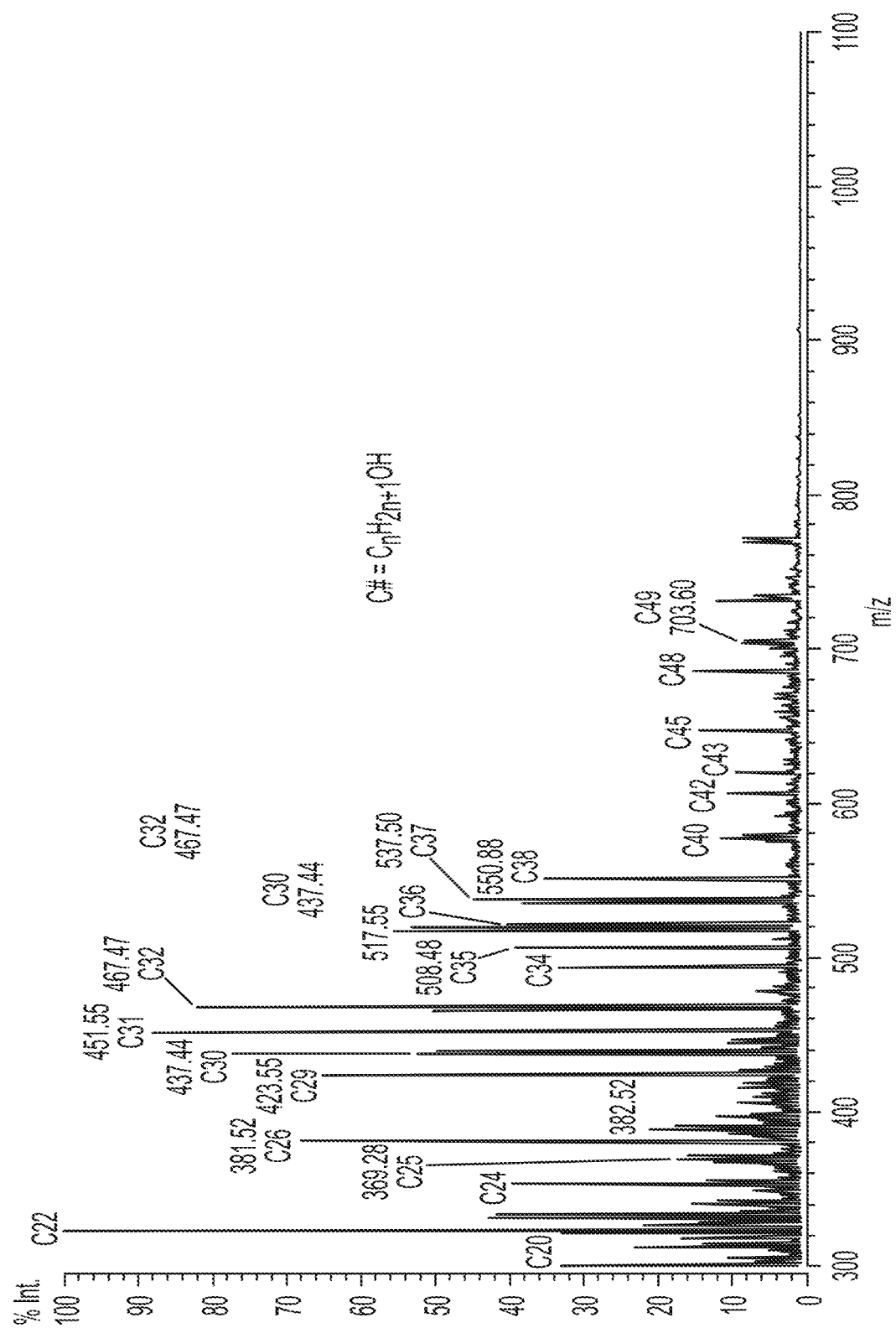

FIG. 87 is the MALDI-TOF-MS spectrum of the oil isolated after reaction of polypropylene and $AliBu_3$ in the presence of $Zr(CH_2CMe_3)_2$@$SiAlO_x$ at 200° C. for 12 h, quenched with $O_2$, and extracted with methylene chloride. The spectrum was acquired in linear, positive mode with $AgNO_3$ (salt) and DHB (matrix).

Figure 88:
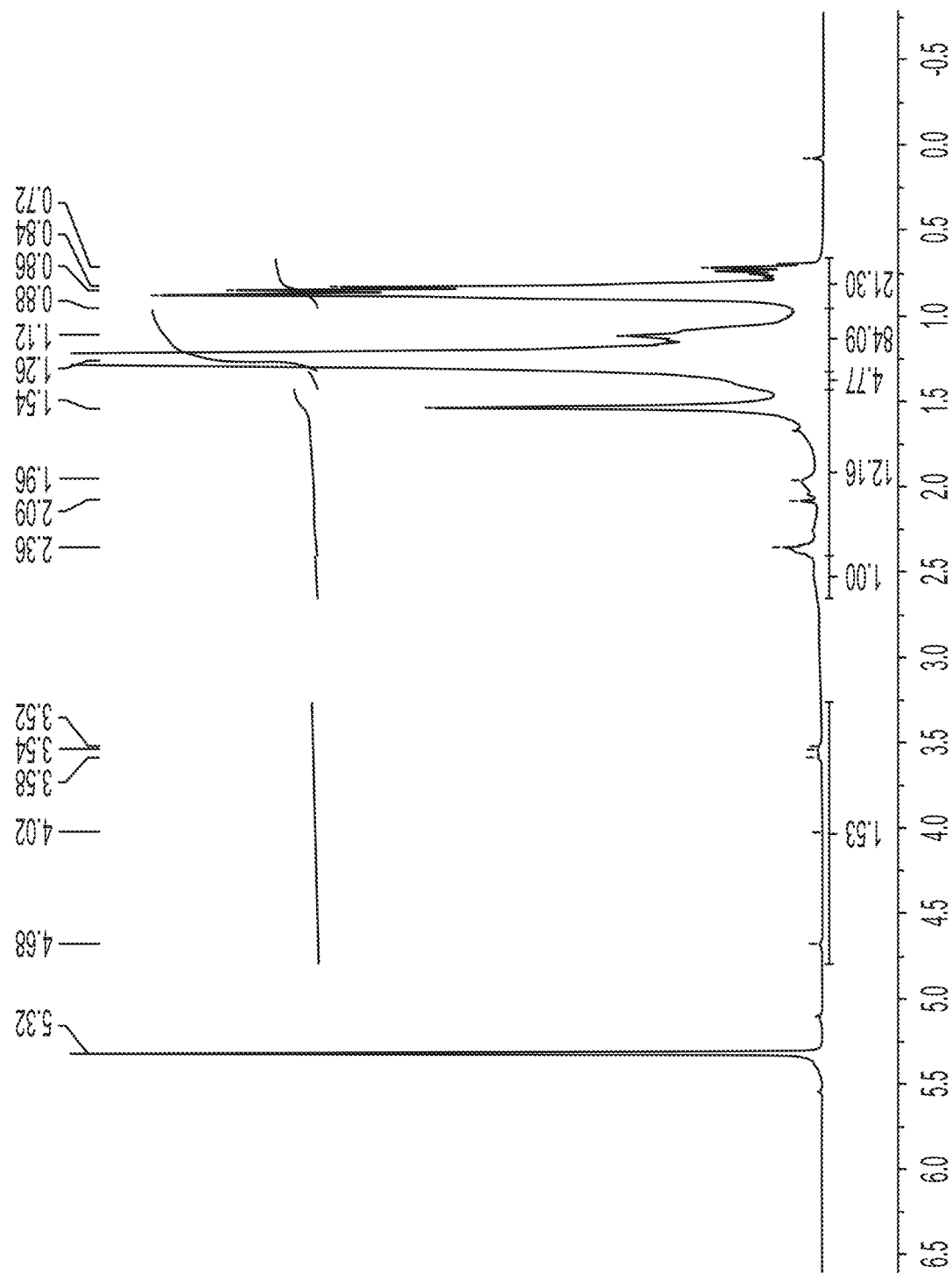

FIG. 88 is the $^1H$ NMR spectrum of the oil isolated after reaction of HDPE and $AlH_3$ in the presence of $Zr(OCH_2CMe_3)_2$@$SiAlO_x$ at 200° C. for 12 h under dynamic vacuum, quenched with $O_2$, and extracted with methylene chloride. The spectrum was acquired at room temperature in methylene chloride-$d_2$ and assigned based on TOCSY and HSQC experiments in FIGS. 89 and 90. Signals at 0.7-1.0 ppm correspond to methyl groups, peaks at 1.0-1.3 and 1.5-2.4 ppm are attributed to methylene groups, and those at 1.3-1.5 and 2.4-2.7 ppm correspond to methine groups. Peaks at 3.5-4.7 ppm are assigned to —$CH_2$—OH groups.

Figure 89:
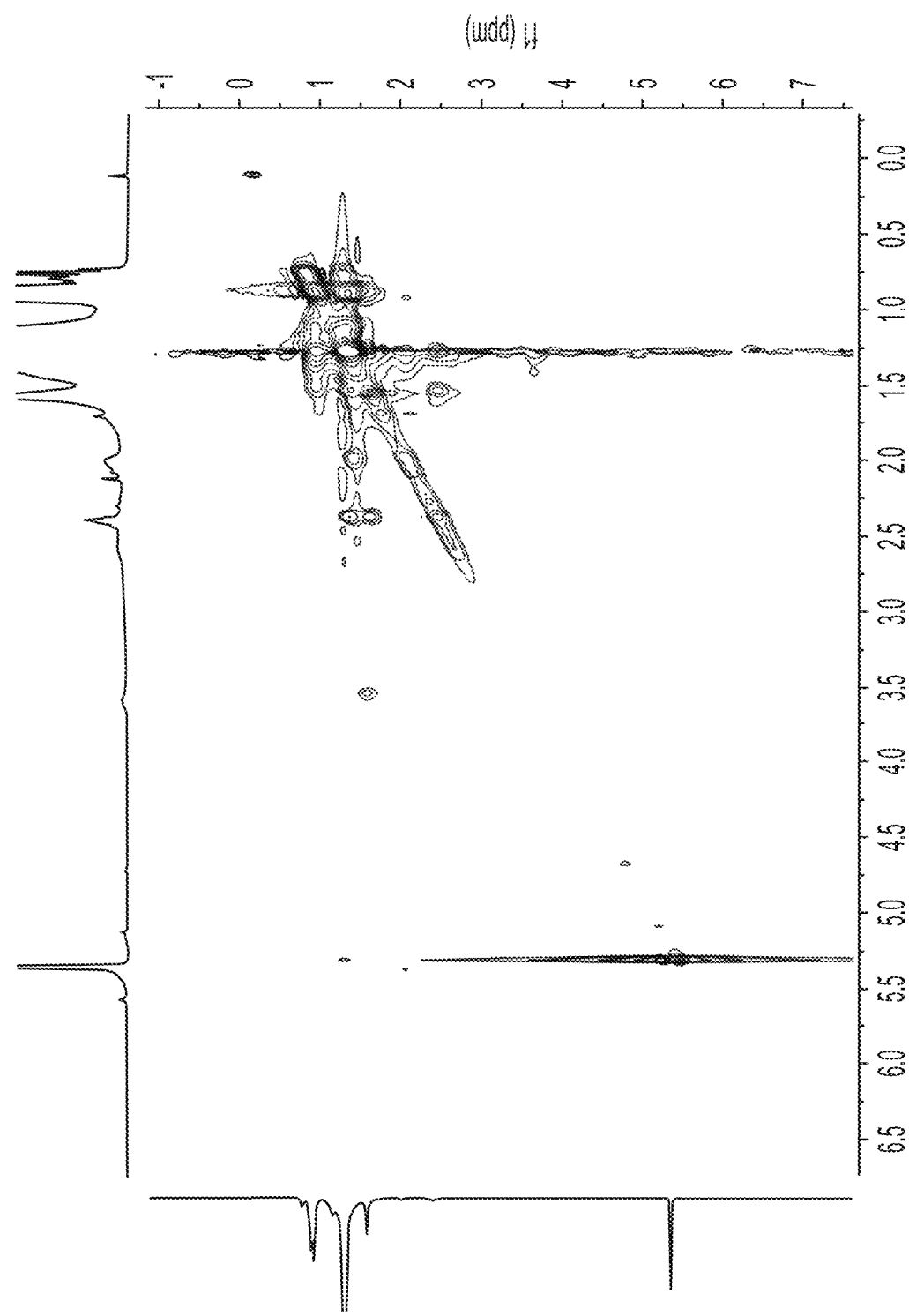

FIG. 89 is the COSY spectrum of the oil isolated after reaction of HDPE and $AlH_3$ in the presence of $Zr(CH_2CMe_3)_2$@$SiAlO_x$ at 200° C. for 12 h under dynamic vacuum, quenched with $O_2$, and extracted with methylene chloride. The spectrum was acquired at room temperature in methylene chloride-$d_2$. The cross-peak at 3.6 ppm correlates with methylene signals at 1.6 ppm, indicative of —$CH_2$—$CH_2$—OH species.

Figure 90:
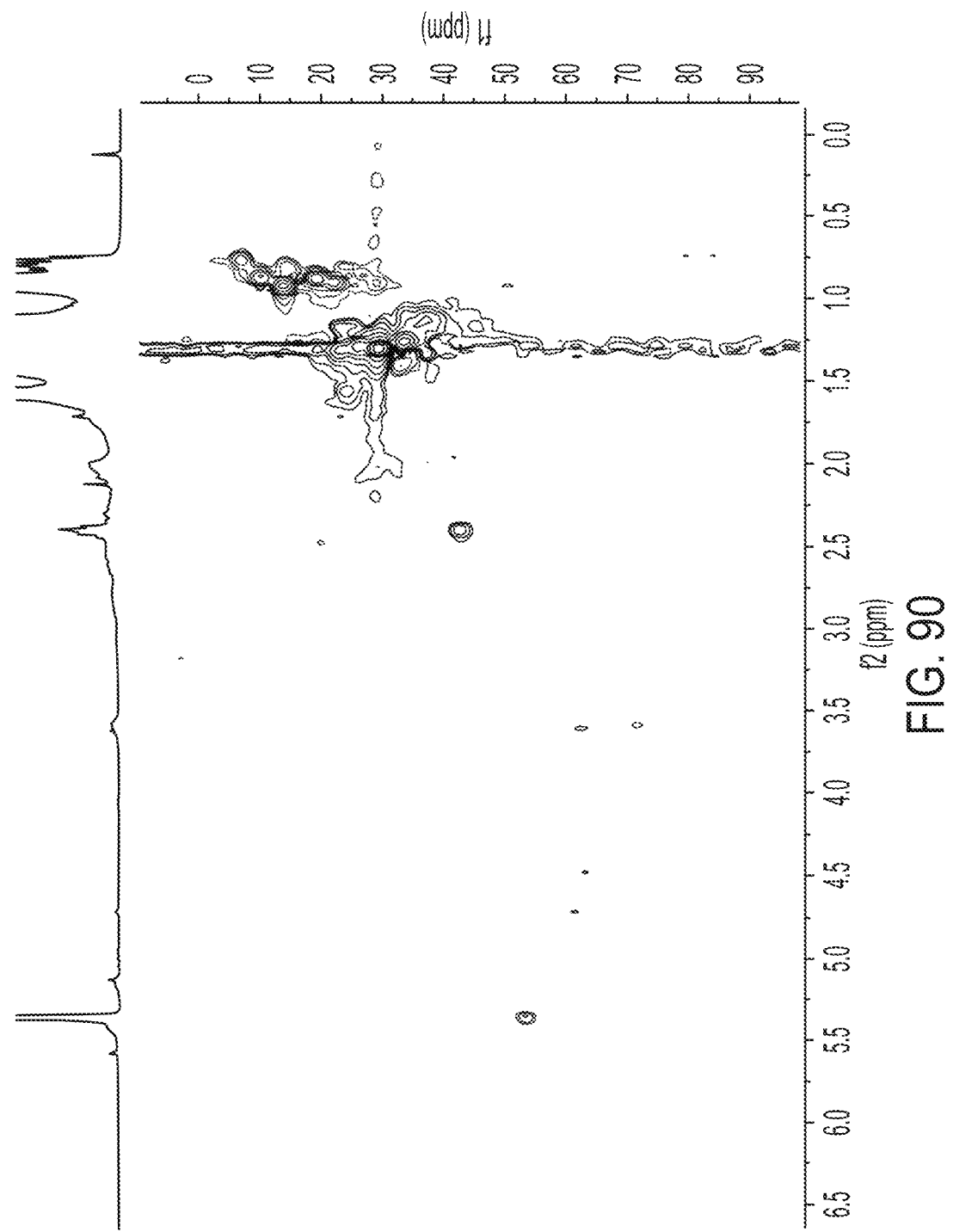

FIG. 90 is the phase sensitive $^1H$-$^{13}C$ HSQC spectrum of the oil isolated after reaction of HDPE and $AlH_3$ in the presence of $Zr(CH_2CMe_3)_2$@$SiAlO_x$ at 200° C. for 12 h under dynamic vacuum, quenched with $O_2$ and extracted with methylene chloride. The spectrum was acquired at room temperature in methylene chloride-$d_2$. Cross-peaks at $^{13}C$ 60-70 ppm have the same phase as methylene peaks at $^{13}C$ 30 ppm, revealing the former are —$CH_2$—OH moieties (primary alcohols), whereas the cross-peak at $^{13}C$ 72 ppm is attributed to an —(R)CH—OH species (i.e. a secondary alcohol).

Figure 91:
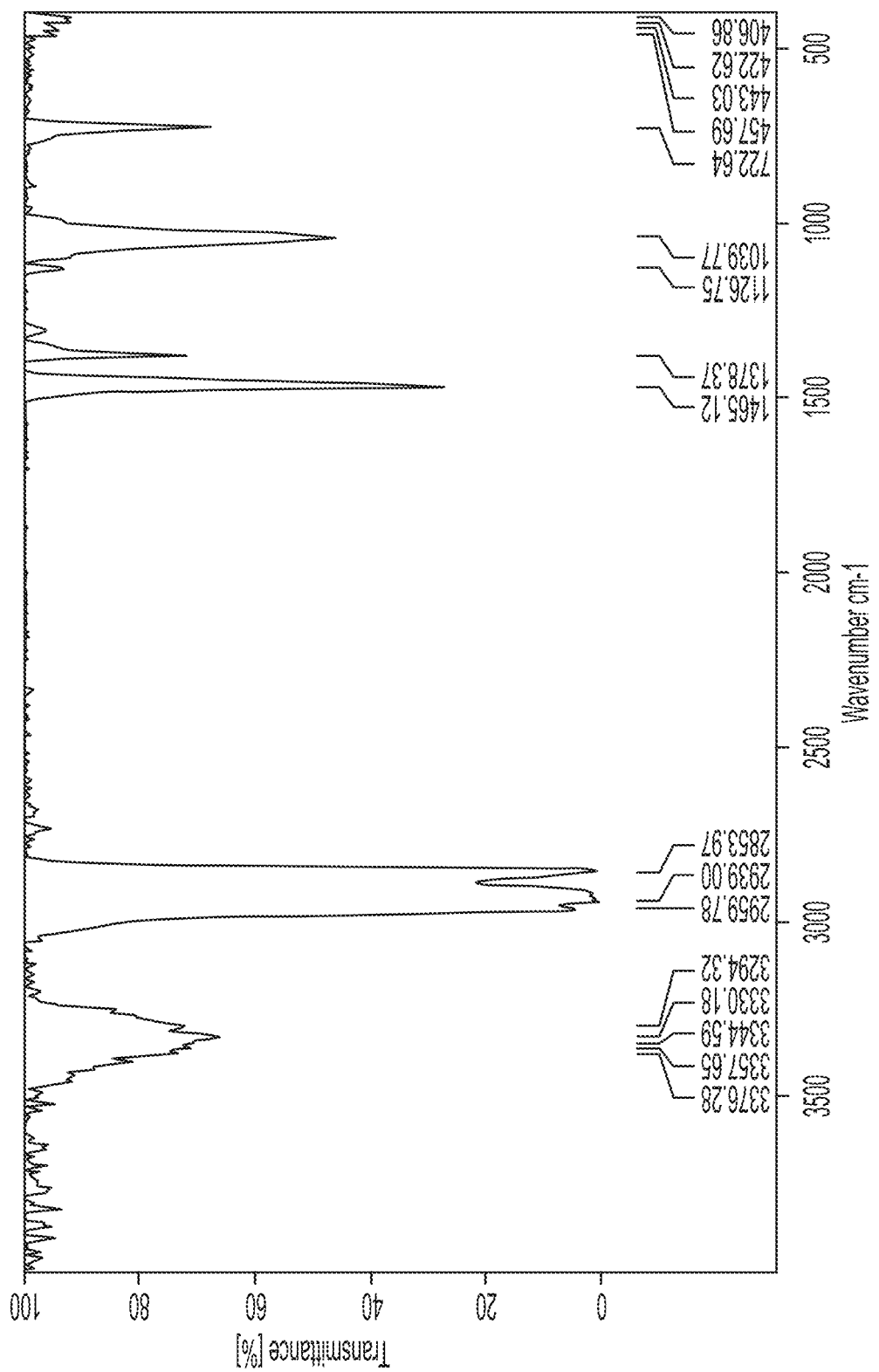

FIG. 91 is the FT-IR spectrum (KBr) of the oil isolated after reaction of HDPE and $AlH_3$ in the presence of Zr(CH$_2$CMe$_3$)$_2$@SiAlO$_x$ at 200° C. for 12 h under dynamic vacuum, quenched with O$_2$, and extracted with methylene chloride. Broad signals between 3200-3500 cm$^{-1}$ correspond to 0-H stretches.

Figure 92:
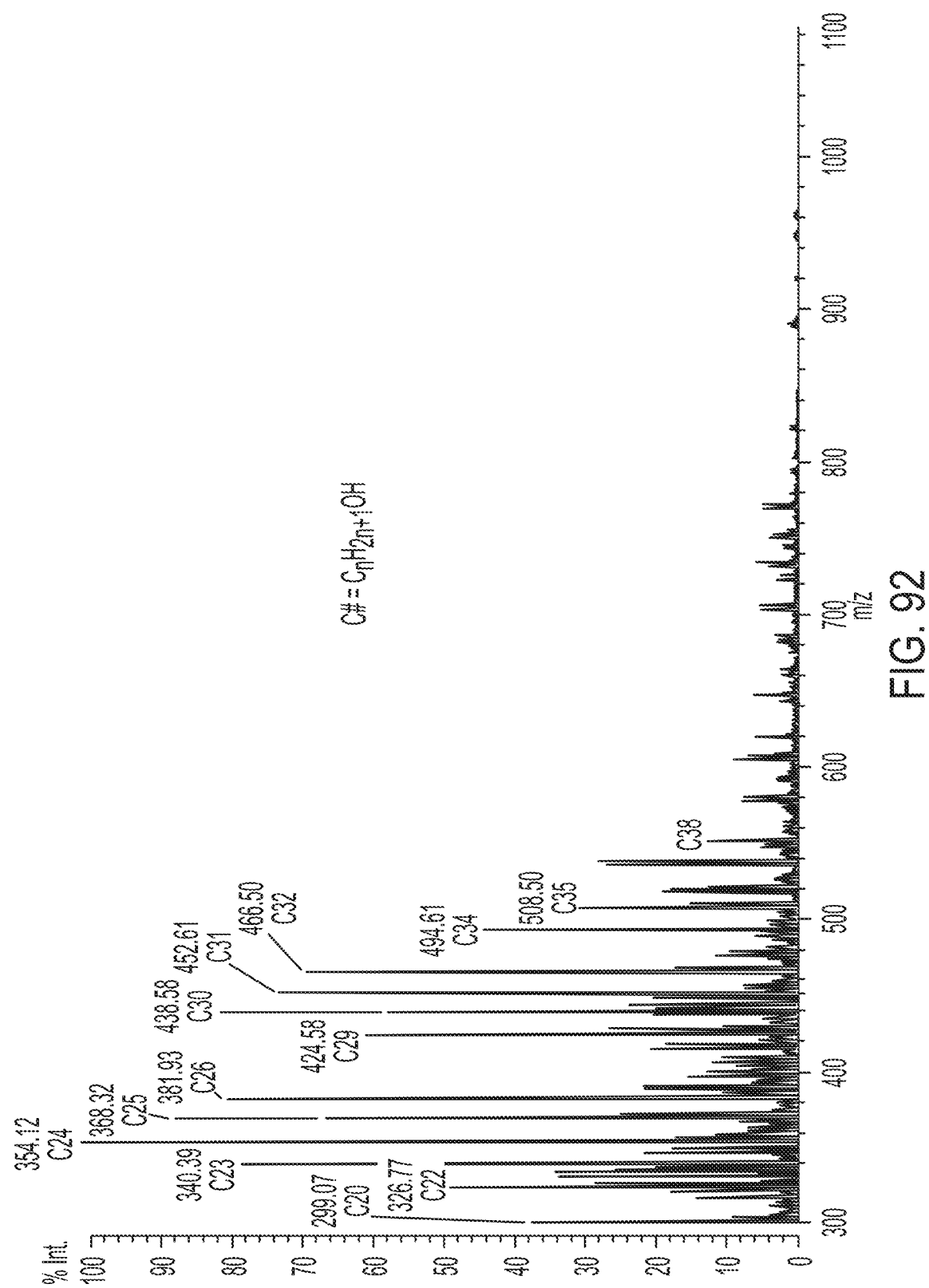

FIG. 92 is the MALDI-TOF-MS spectrum of the oil isolated after reaction of HDPE and AlH$_3$ in the presence of Zr(CH$_2$CMe$_3$)$_2$@SiAlO$_x$ at 200° C. for 12 h under dynamic vacuum, quenched with O$_2$, and extracted with methylene chloride. The spectrum was acquired in linear, positive mode with AgNO$_3$ (salt) and DHB (matrix).

FIGS. 93A-93C are the room temperature DRIFT spectra of samples of Zr(CH$_2$CMe$_3$)$_2$@SiAlO$_x$+AliBu$_3$ treated with different conditions. FIG. 93A is the DRIFT spectrum of Zr(CH$_2$CMe$_3$)$_2$@SiAlO$_x$+AliBu$_3$ heated at 150° C. for 2 h, washed with anhydrous pentane and dried in vacuo. FIG. 93B shows the DRIFT spectrum after D$_2$ gas (1 atm) was passed over the sample at 70° C. for 30 min. FIG. 93C shows the DRIFT spectrum when H$_2$ gas (1 atm) was subsequently passed over the sample at 70° C. for 30 min.

Figure 94:
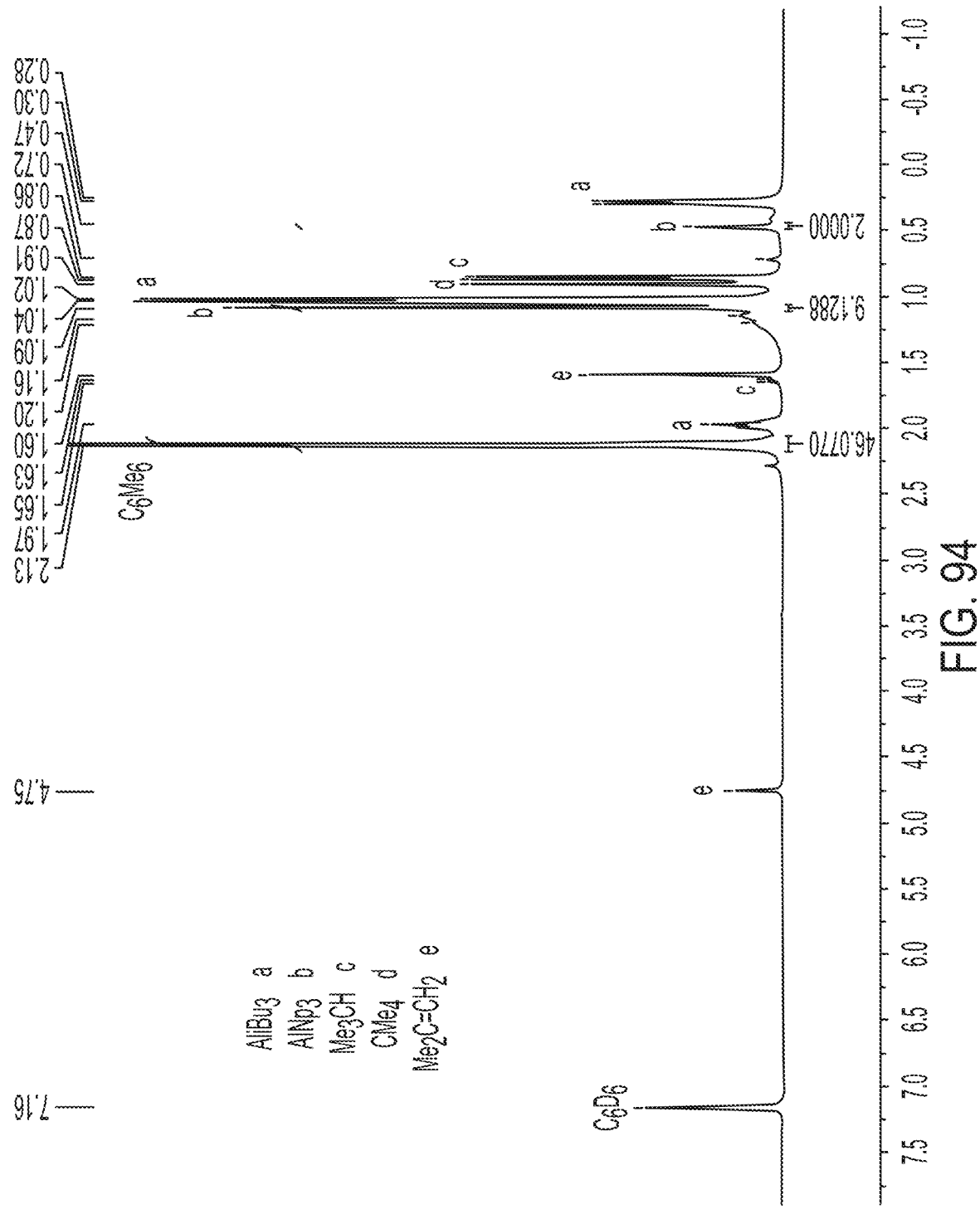

FIG. 94 is the $^1$H NMR spectrum of Zr(CH$_2$CMe$_3$)$_2$@SiAlO$_x$+AliBu$_3$ (3 equiv.) at room temperature in benzene-d$_6$. The presence of AlNp$_3$ (b) is consistent with an alkyl exchange reaction between surface Zr—CH$_2$CMe$_3$ groups and Al—CH$_2$CH(Me)$_2$. About 33% of the total neopentyl groups are transferred to aluminum from zirconium. The presence of isobutylene (e) is consistent with the presence of Zr—H surface species, presumably arising due to alkyl exchange of surface Zr sites with AliBu$_3$ followed by β-hydride eliminations of in-situ formed Zr—CH$_2$—CH(Me)$_2$ groups. Note that AliBu$_3$ by itself is stable in C$_6$D$_6$ at room temperature and no isobutylene is observed. The alkanes isobutane and neopentane are likely formed from the reaction of AliBu$_3$ and AlNp$_3$ with uncapped surface Si—OH groups (~0.08 mmol/g).

Figure 95:
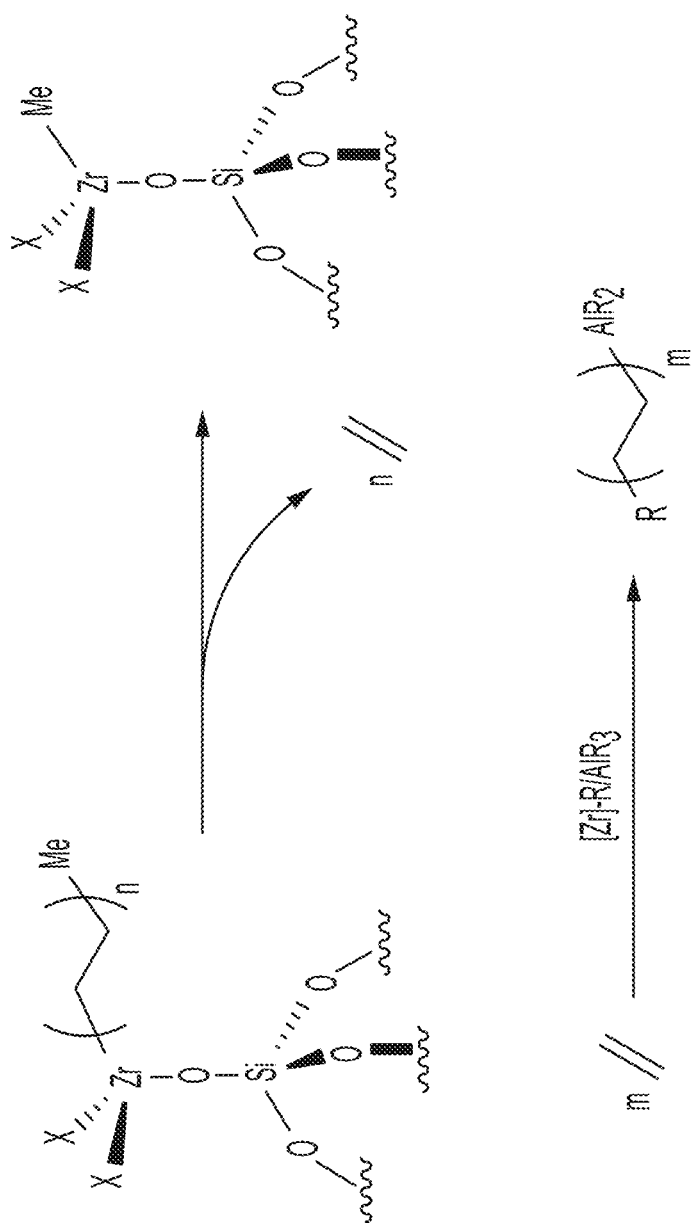

FIG. 95 is a reaction scheme showing depolymerization and re-oligomerization sequence to generate long chain alkylaluminum products is ruled out by attempted ethylene oligomerization under reaction conditions.

Figure 96:
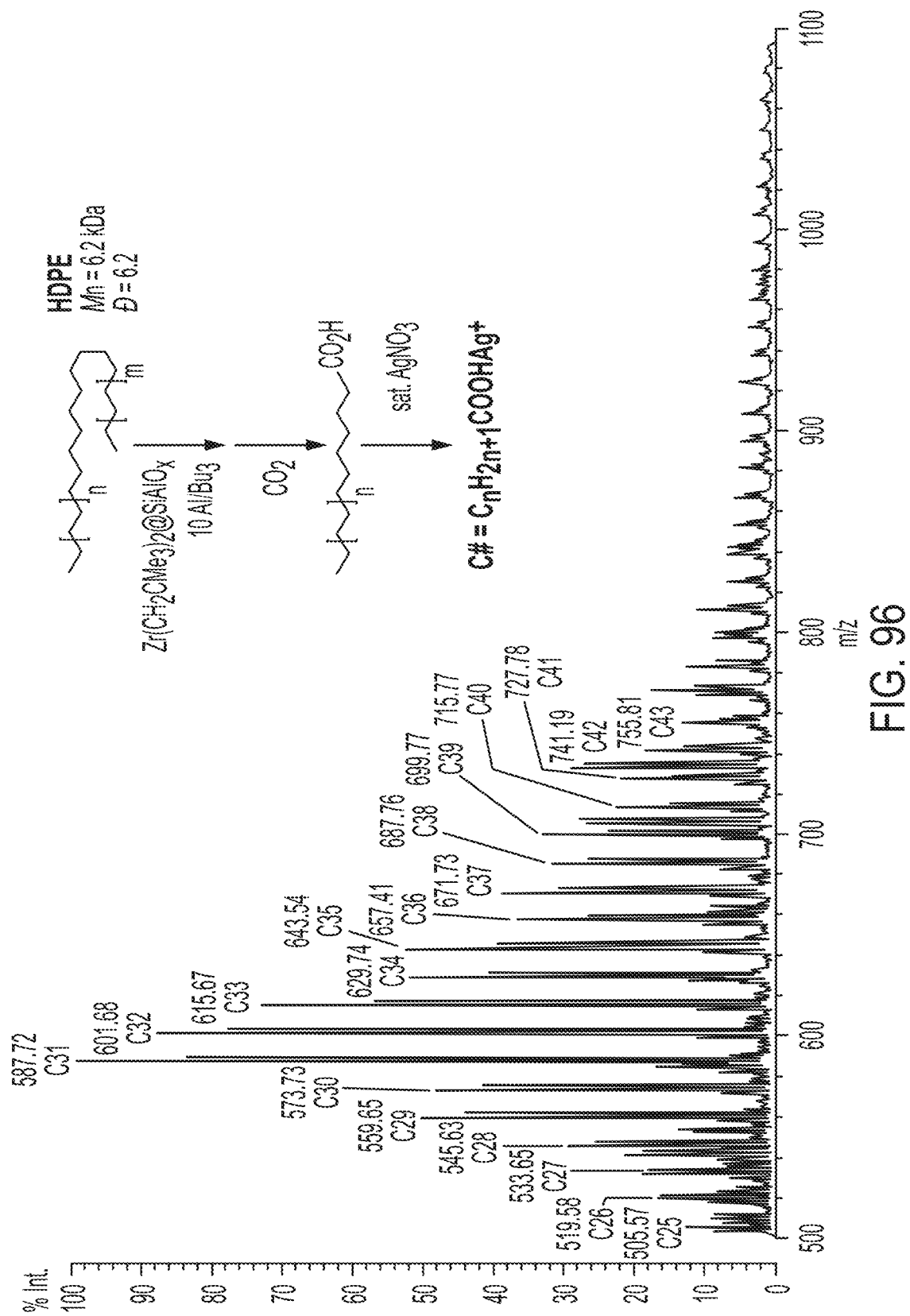

FIG. 96 is the MALDI-TOF-MS showing a distribution of fatty acid chains in oil product as Ag$^+$ adducts obtained from the Zr(CH$_2$CMe$_3$)$_2$@SiAlO$_x$-catalyzed reaction of HDPE and AliBu$_3$ at 200° C. for 12 h, followed by reaction with CO$_2$.

Figure 97:
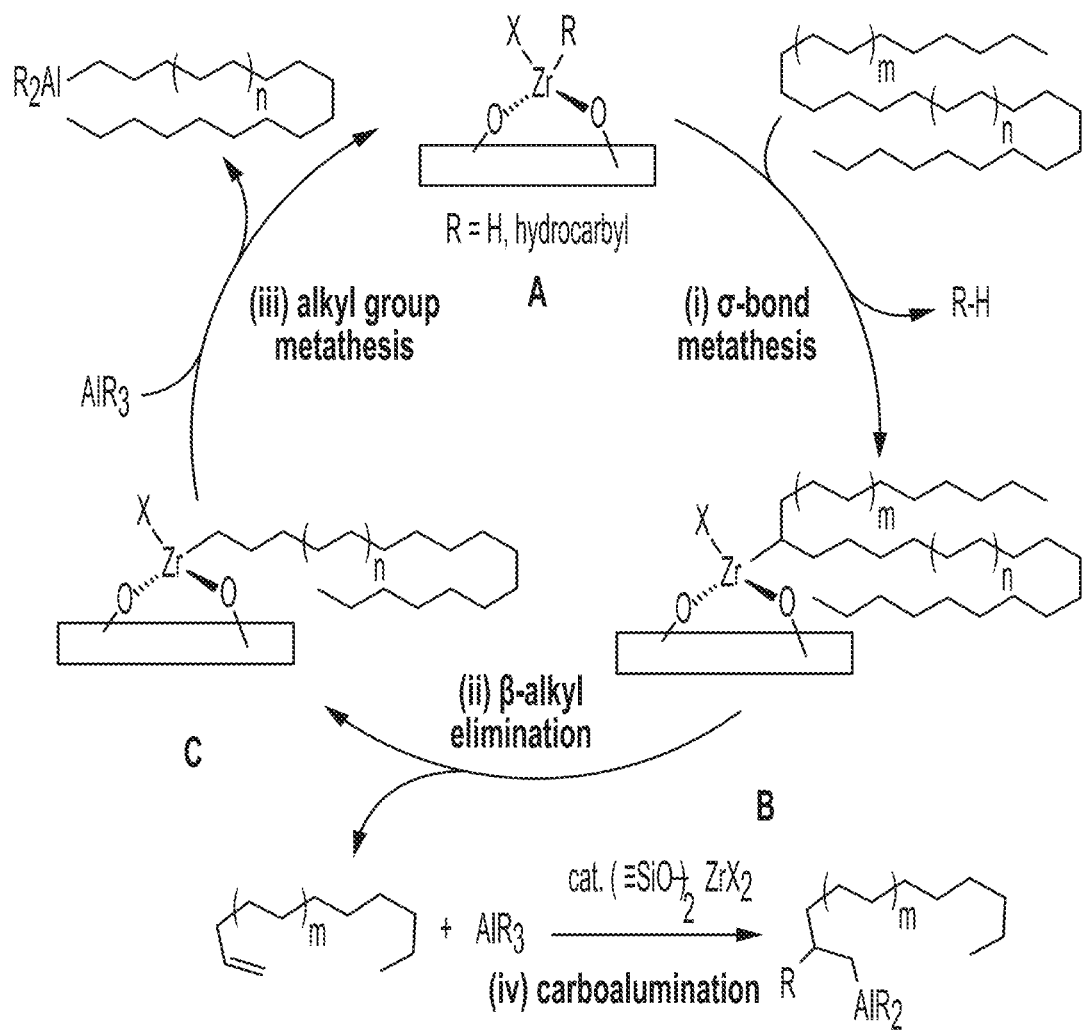

FIG. 97 depicts the possible sequence of elementary steps involved Zr-catalyzed polyethylene deconstruction into long-chain alkylaluminum species, namely (i) metalation of the polymer backbone via C—H bond activation by a grafted alkyl- or hydridozirconium species A, (ii) β-alkyl elimination from a mid-chain polymerylzirconium B resulting in C—C bond cleavage to give a terminal olefin and a new oligomerylzirconium species C, (iii) alkyl group metathesis of the oligomerylzirconium with an alkyl or hydridoaluminum species, and (iv) carboalumination of an in-situ generated olefin by AlR$_3$ resulting in a new C—C bond.

DETAILED DESCRIPTION

One aspect of the present application relates to a process including:
providing one or more polymers, oligomers, or mixtures thereof;
providing a compound of formula (I):

$$Al(R^1)_3 \qquad (I)$$

where
R$^1$ is independently selected at each occurrence thereof from the group consisting of H, aryl, C$_1$-C$_8$ alkyl, and C$_1$-C$_8$ alkoxy;
contacting the polymers, oligomers, or mixtures thereof with the compound of formula (I), as a reaction mixture, in the presence of a catalyst selected from the group consisting of a transition metal catalyst, a lanthanide series metal catalyst, or combinations thereof, under conditions effective to form alkanes, carboxylic acids, alcohols, alkyl halides or aldehydes, which are shorter than the polymers, the oligomers, or the mixtures thereof; and
recovering the formed shorter alkanes, carboxylic acids, alcohols, alkyl halides or aldehydes.

A second aspect of the present application relates to a process including:
providing one or more polymers, oligomers, or mixtures thereof;
providing a compound of formula (I):

$$Al(R^1)_3 \qquad (I)$$

where
R$^1$ is independently selected at each occurrence from the group consisting of H, aryl, C$_1$-C$_8$ alkyl, and C$_1$-C$_8$ alkoxy;
contacting the polymers, oligomers, or mixtures thereof with the compound of formula (I), as a reaction mixture, in the presence of a catalyst selected from the group consisting of a transition metal catalyst, a lanthanide series metal catalyst, or combinations thereof, under conditions effective to form an aluminum alkyl compound of formula (III)

$$Al(R^1)_{3-n}(R^3)_n \qquad (III)$$

where
R$^3$ is independently selected at each occurrence thereof from C$_{12}$-C$_{60}$ alkyls, which are shorter than the polymers, the oligomers, or the mixtures thereof; and
n is an integer ranging from one to three.

As used above, and throughout the description herein, the following terms, unless otherwise indicated, shall be understood to have the following meanings. If not defined otherwise herein, all technical and scientific terms used herein have the same meaning as is commonly understood by one of ordinary skill in the art to which this technology belongs. In the event that there is a plurality of definitions for a term herein, those in this section prevail unless stated otherwise.

The term "alkyl" means an aliphatic hydrocarbon group which may be straight or branched. When not otherwise restricted, the term refers to an alkyl of 20 or fewer carbons. Branched means that one or more lower alkyl groups such as methyl, ethyl, or propyl are attached to a linear alkyl chain. Exemplary alkyl groups include methyl, ethyl, n-propyl, i-propyl, n-butyl, t-butyl, n-pentyl, 3-pentyl, and the like.

The term "aryl" means an aromatic monocyclic or multicyclic (polycyclic) ring system of 6 to about 19 carbon atoms, or of 6 to about 10 carbon atoms, and includes arylalkyl groups. The ring system of the aryl group may be optionally substituted. Representative aryl groups include, but are not limited to, groups such as phenyl, naphthyl, azulenyl, phenanthrenyl, anthracenyl, fluorenyl, pyrenyl, triphenylenyl, chrysenyl, and naphthacenyl.

The term "alkoxy" means groups of from 1 to 6 carbon atoms of a straight, branched, or cyclic configuration and combinations thereof attached to the parent structure through an oxygen. Examples include methoxy, ethoxy, n-propoxy, isopropoxy, n-butoxy, i-butoxy, t-butoxy, phenoxy, cyclopropyloxy, cyclohexyloxy, and the like. Alkoxy also includes methylenedioxy and ethylenedioxy in which each oxygen atom is bonded to the atom, chain, or ring from which the methylenedioxy or ethylenedioxy group is pendant so as to form a ring. Thus, for example, phenyl substituted by alkoxy may be, for example,

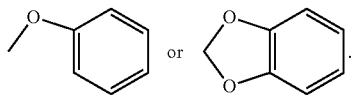

As used herein, "halogen" refers to fluoro, chloro, bromo, or iodo.

Exemplary compounds of formula (I) which may be used in the present application include, but are not limited to AliBu$_3$, AlEt$_3$, AlMe$_3$, AlPh$_3$, Al(C$_8$H$_{17}$)$_3$, and AlH$_3$.

In one embodiment of the process of the present application, the catalyst is formed from a metal selected from the group consisting of zirconium, titanium, hafnium, vanadium, niobium, tantalum, scandium, yttrium, lanthanum, cerium, praseodymium, neodymium, samarium, europium, gadolinium, terbium, dysprosium, holmium, erbium, thulium, ytterbium, and lutetium.

The transition metal catalyst and/or lanthanide-catalyst catalyst may be in the form of formula (II):

where

Met is one or more transition metal or lanthanide series metal selected from the group consisting of zirconium, titanium, hafnium, vanadium, niobium, tantalum, scandium, yttrium, and lanthanum, cerium, praseodymium, neodymium, samarium, europium, gadolinium, terbium, dysprosium, holmium, erbium, thulium, ytterbium, and lutetium;

R$^2$ is independently selected at each occurrence thereof from the group consisting of —H, C$_1$-C$_{10}$ alkyl, C$_1$-C$_{10}$ alkoxy or aryloxy, aryl, —OH, halogen, C$_1$-C$_{10}$ arylalkyl, C$_1$-C$_{10}$ alkylsilylalkyl, siloxy, —BH$_4$, allyl, C$_1$-C$_{10}$ alkylamido, acetylacetonate, acrylate, acetate;

n is an integer ranging from 1 to 3; and support is selected from the group consisting of silica, alumina, silica/alumina, zeolites, metal oxides, mesoporous oxides, natural clays, and mixtures thereof.

As used herein, the term "arylalkyl" refers to aryl groups as described herein in which one or more hydrogen atoms is substituted by alkyl groups, where the radical or point of attachment to the parent molecule is on the alkyl group.

As used herein, the term "alkylsilylalkyl" refers to a silane in which two or more hydrogen atoms are substituted by alkyl groups, where the point of attachment to the parent molecule is on one of the alkyl groups.

As used herein, as "alkylamido" refers to one or more alkyl groups on a nitrogen, attached to the parent molecule through the amido group.

"Unsubstituted" atoms bear all of the hydrogen atoms dictated by their valence.

The term "optionally substituted" is used to indicate that a group may have a substituent at each substitutable atom of the group (including more than one substituent on a single atom), provided that the designated atom's normal valency is not exceeded and the identity of each substituent is independent of the others. Up to three H atoms in each residue are replaced with alkyl, halogen, haloalkyl, hydroxy, lower alkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy. When a substituent is keto (i.e., =O), then two hydrogens on the atom are replaced. Combinations of substituents and/or variables are permissible only if such combinations result in stable compounds. A "stable compound" is meant to be a compound that is sufficiently robust to survive isolation to a useful degree of purity from a reaction mixture, and formulation into an efficacious therapeutic agent.

In some embodiments of catalyst in the form of formula (II),

Met is selected from the group consisting of zirconium, titanium, or hafnium; and R$^2$ is independently selected at each occurrence thereof from the group consisting of —H, -Me, -tBu, -Ph, —OH, —CH$_2$Ph, —CH$_2$SiMe$_3$, —CH$_2$CMe$_3$, —BH$_4$, —Cl, —Br, —I, —NMe$_2$, —NEt$_2$, —NnPr$_2$, —NiBu$_2$, µNC$_5$H$_{10}$, —NC$_6$H$_{12}$, —OMe, —OEt, —OnPr, —OiPr, —OtBu, —OnBu, —OPh, —OSiMe$_3$, —OSiPh$_3$, —OSi(OtBu)$_3$, acetylacetonate, acrylate, acetate, and allyl and substituted derivatives thereof.

Exemplary catalysts of formula (II) useful in the process of the present application include, but are not limited to, Zr(CH$_2$CMe$_3$)$_n$@SiAlO$_x$, Zr(OCH$_2$CMe$_3$)$_n$@SiAlO$_x$, Zr(CH$_2$CMe$_3$)$_n$@SiO$_2$, Zr(OC$_3$H$_7$)$_n$@SiAlO$_x$, Zr(OC$_4$H$_9$)$_n$@SiAlO$_x$, Zr(OC$_4$H$_9$)$_n$@SiO$_2$, Zr(H)$_n$@SiO$_2$, and Zr(H)$_n$@SiAlO$_x$, where n is an integer ranging from 1-3.

Exemplary support materials include, but are not limited to, silica, in amorphous form (e.g., gel, aerosil, or Stöber-type), mesoporous silica (e.g., MCM-41, SBA-15), or crystalline silica (e.g. β-cristobalite); silica-alumina of varying aluminum loadings in amorphous form or crystalline ordered materials; or alumina.

A third aspect of the present application relates to an alkyl aluminum of formula (III):

where

R$^1$ is independently selected at each occurrence thereof from the group consisting of H, aryl, C$_1$-C$_8$ alkyl, and C$_1$-C$_8$ alkoxy;

R$^3$ is independently selected at each occurrence thereof from C$_{12}$-C$_{60}$ alkyls; and n is an integer ranging from one to three.

In some embodiments of the process of the present application, the aluminum alkyl compounds of formula (III) possess an R$^3$ alkyl having anywhere from about 12, 15, 20, 25, 30, 35, 40, 45, 50, or 55 carbons to 20, 25, 30, 35, 40, 45, 50, 55, or 60 carbons. Some examples of the R$^3$ groups include, but are not limited to, C$_{12}$-C$_{45}$ alkyls and C$_{12}$-C$_{38}$ alkyls.

In a further embodiment of the process of the present application, the shorter alkanes, carboxylic acids, alcohols, alkyl halides, or aldehydes formed have 12 to 60 carbons. For example, the shorter alkanes, carboxylic acids, alcohols, alkyl halides, or aldehydes have may have from about 12, 15, 20, 25, 30, 35, 40, 45, 50, or 55 carbons to 20, 25, 30, 35, 40, 45, 50, 55, or 60 carbons. In one embodiment, the number of carbons of the shorter alkanes, carboxylic acids, alcohols, alkyl halides, or aldehydes range from 12 to 45. In a further embodiment, the shorter alkanes, carboxylic acids, alcohols, alkyl halides, or aldehydes have 12 to 38 carbons.

In some embodiments of the process of the present application, when the contacting step is carried out under conditions effective to form shorter alcohols and alkyl halides, the shorter alcohols and alkyl halides formed are primary alcohols and alkyl halides, respectively. The process of making the shorter alcohols involves quenching the alkylaluminum species that forms in the reaction mixture with oxygen. The alkyl halides are formed upon quenching the alkylaluminum species with a halide. These process are discussed further infra.

In a further embodiment of the process of the present application, the polymers, oligomers, or mixtures thereof are polyolefins.

A wide variety of polyolefins (which may or may not have pendant unsaturation) are contemplated for use in the process of the present application. Examples of polyolefins include olefin homopolymers, copolymers, and terpolymers, such as, but not limited to, polyethylene (e.g., high density polyethylene, low density polyethylene, linear low density polyethylene), polyethylene with 1-octene, polypropylene (e.g.,), polyethylene-polypropylene-copolymers, polystyrene, polymers containing two or more monomers, polyisobutene, polymethacrylates, polyalkylstyrenes, partially hydrogenated polyolefins of butadiene and styrene and copolymers of isoprene, such as polymers of styrene and isoprene, and mixtures thereof. EPDM (ethylene/propylene/diene monomer) polymers, ethylene-propylene octene terpolymers and ethylene-propylene ENB terpolymers, are also contemplated for use.

The term "copolymer" refers to a polymer derived from more than one species of monomer.

The term "random copolymer" or "random polymer", also known as "statistical copolymers", refers to a copolymer in which there is no definite order for the sequence of the different building blocks (-M1M2M1M1M2M1M2M2-, wherein M1 and M2 represent different monomers).

The term "block copolymer" or "block polymer" refers to a macromolecule consisting of long sequences of different repeat units. Exemplary block polymers include, but are not limited to, AnBm, AnBmAm, AnBmCk, or AnBmCkAn, wherein A, B, and C represent the different monomers, and n, m, and k are the number of monomers present in each block.

The term "pendant functional group," as used herein refers to a functional group that is a pendant branch from the backbone of a co-polymer. The term "backbone," "backbone chain," or "main chain," as used herein, refers to the linear chain to which all other chains, long or short or both, may be regarded as being pendant. The backbone chain or main chain of a polymer may be the series of covalently bonded atoms that together create the continuous chain of the molecule.

The copolymers useful in the present application may be selected from random copolymers, or block copolymers. The polymers and or oligomers may have pendent functional groups, which may include, for example, branching alkyl chains.

In one embodiment of the process of the present application, the contacting of the polymers, oligomers, or mixtures thereof with the compounds of formula (I) in the presence of a catalyst, forming a reaction mixture, is carried out at a temperature sufficient to melt the polymers, oligomers, or mixtures thereof.

The temperature required to melt the polymers, oligomers, or mixtures thereof is dependent on the polymer, oligomer, or mixture used. The methods for determination of the melting temperature of the polymer, oligomer, or mixture used is known in the art, and common polymeric materials have known melting temperature ranges. Exemplary temperatures that may be used in the method of the present application range from 100° C., 110° C., 120° C., 130° C., 140° C., 150° C., 160° C., 170° C., 180° C., 190° C., 200° C., 210° C., 220° C., 230° C. or 240° C., to 110° C., 120° C., 130° C., 140° C., 150° C., 160° C., 170° C., 180° C., 190° C., 200° C., 210° C., 220° C., 230° C., 240° C. or 250° C. For example, a temperature ranging from 150° C. to 250° C. may be used, however, higher or lower temperatures may also be of use.

In a further embodiment of the process of the present application, the molar ratio of the compound of formula (I) to the catalyst of formula (II) ranges from 3:1 to 20:1. The molar ratio of the polymers, oligomers, or mixtures thereof to the catalyst of formula (II) can range from 1:1 to 1:10.

In a further embodiment of the process of the present application, the contacting of the polymers, oligomers, or mixtures thereof with the compounds of formula (I) in the presence of a catalyst, forming a reaction mixture, is carried out while stirring under inert conditions. The contacting may be carried out under atmospheric pressure, or under a vacuum. Exemplary vacuum ranges include, but are not limited to pressures ranging from 760 mm Hg to 0.0001 mm Hg. Furthermore, the contacting may be carried out for a time period of 1 to 72 hours.

In one embodiment of the process of the present application, the contacting of the polymers, oligomers, or mixtures thereof with the compounds of formula (I) in the presence of a catalyst, forming a reaction mixture, is carried out under conditions effective to form shorter alkanes. These conditions include adding an alcohol or water to the reaction mixture to form the shorter alkanes. Exemplary alcohols that may be used in the formation of the shorter alkanes include, but are not limited to, methanol, ethanol, isopropanol, propanol, butanol, and isobutanol.

In another embodiment of the process of the present application, the contacting of the polymers, oligomers, or mixtures thereof with the compounds of formula (I) in the presence of a catalyst, forming a reaction mixture, is carried out under conditions effective to form shorter carboxylic acids. These conditions include adding carbon dioxide to the reaction mixture to form the shorter carboxylic acids.

The carboxylic acids formed from the process of the present application may be further converted via known reaction conditions to form esters, and amides. For example, in one embodiment of the process of the present application, the shorter carboxylic acids may be reacted with an alcohol and, optionally, an acid to form esters.

The term "ester group" generally refers to a substituent of the general formula —C(O)O—$R^1$, where $R^1$ may be either aliphatic or aromatic.

A proven and widely used method for preparing esters is the condensation of carboxylic acids with alcohols in the presence of catalysts. It is known that esters can be carried out autocatalytically or with catalysis, for example by Brønsted acids or by Lewis acids. Processes of this type are described in Lorz et al., "Phthalic Acid and Derivatives," *Ullmann's Encyclopedia of Industrial Chemistry, p* 131-180 (2007), which is hereby incorporated by reference in its entirety.

In the process of esterification, the reaction mixture of the carboxylic acid and alcohol is usually heated for several hours and the water that is formed is removed. Methods are also known in which the esterification is carried out in a closed system under pressure and high temperatures. For example, WO 2007/126166 discloses a conventionally thermal esterification of fatty acids with alcohols at temperatures of from 200 to 350° C. and pressures of up to 10 bar. During the reaction over several hours, water formed in the reaction is continuously removed with excess alcohol. Some examples of the formation of esters from carboxylic acids are disclosed in U.S. Pat. No. 10,106,486 to Keller et al.; U.S. Pat. No. 7,186,856 to Meng et al.; and U.S. Pat. No. 8,293,935 to Orjueal et al, which are hereby incorporated by reference in their entirety. A further example of esters formed from the condensation reaction of carboxylic acids with alcohols is disclosed in Amore et al., *Macromol. Rapid Commun*, 28(4):473-477 (2007), which is hereby incorporated by reference in its entirety. Amore teaches a microwave-assisted method for producing propionic esters, in which the esterification is completed by water removal.

The carboxylic acid product of the present application may also undergo a condensation reaction with an amine to form an amide. As used herein, an "amine group" has the general formula NRR, where each R is independently a hydrogen, any alkyl or aryl group. The terms "carboxamide" or "amide" as used herein refer to $C(O)NR_aR_b$ wherein $R_a$ and $R_b$ are each independently hydrogen, alkyl, or any other suitable substituent. One embodiment of the process of the present application includes reacting an amine with the shorter carboxylic acids to form amides. Optionally, coupling agents may be added to aid in the formation of the amides.

This reaction is well known in the art. The direct conversion of carboxylic acids and amines to form amides can be difficult due to the basic amine deprotonating the carboxylic acid thus forming a carboxylate. However, heating the ammonium carboxylate and the removing the water that is formed can push the reaction forward to form the amide (Lundberg et al., "Catalytic Amide Formation from Non-activated Carboxylic Acids and Amines," *Chem. Soc. Rev.* 1-29 (2014), which is hereby incorporated by reference in its entirety). More commonly coupling agents are used to activate the carboxylic acid. Some common coupling agent that may be used in the present application include, for example, dicyclohexyl carbodiimide (DCC), N,N'-carbonyldiimidazole (CDI), N-ethyloxycarbonyl-2-ethyloxy-1,2-dihydroquinoline (EEDQ), N-isobutyloxy-carbonyl-2-isobutyloxy-1,2-dihydroquinoline (IIDQ), 1-Ethyl-3-(3-dimethylaminopropyl)carbodiimide (EDC) or benzotriazol-1-yl-oxy-tris-pyrrolidinophosphonium hexafluorophosphate (commercially available as PyBOP® (Novabiochem, a division of Merck KGaA, Darmstadt, Germany)). In some cases the reactions can be conducted in the presence of a base, for example a trialkylamine such as triethylamine or diisopropylethylamine, N-methylmorpholine, N-methylpyrrolidine, 4-DMAP or 1,8-diazabicycle[5.4.0]undec-7-ene (DBU). The coupling reactions preferably are conducted in an inert solvent, such as halogenated hydrocarbons, e.g. dichloromethane, chloroform, dipolar aprotic solvents such as acetonitrile, dimethylformamide, dimethylacetamide, DMSO, HMPT, and ethers such as tetrahydrofuran (THF). Exemplary amide formation reactions are disclosed in U.S. Pat. No. 7,705,025 to Finley et al.; U.S. Pat. No. 9,309,252 to Brian et al.; U.S. Pat. No. 7,820,821 to Mjalli et al.; U.S. Pat. No. 8,012,939 to Simmen et al.; and 9663519 to Charrier at el., which are hereby incorporated by reference in their entirety.

In another embodiment of the process of the present application, the contacting of the polymers, oligomers, or mixtures thereof with the compounds of formula (I) in the presence of a catalyst, forming a reaction mixture, is carried out under conditions effective to form shorter alcohols. These conditions include adding oxygen to the reaction mixture to form the shorter alcohols.

The shorter alcohols (e.g., fatty alcohols) of the present application may be further oxidized to form aldehydes, as is known in the art. In general, alcohol oxidation to an aldehyde is accomplished using a weak oxidizer. Examples of oxidizing agents that may be used for the conversion of the fatty alcohols to fatty aldehydes include, but are not limited to the Swern oxidation (oxalyl chloride, DMSO and trimethylamine), the Collins reagent (complex of chromium(VI) oxide with pyridine), pyridinium chlorochromate (PCC), and Dess-Martin Periodinane (DMP). These reactions are common place in the art and are disclosed in U.S. Pat. No. 7,951,958 to Brodney et al.; U.S. Pat. No. 9,145,410 to Hays et al.; U.S. Pat. No. 8,580,831 to Bur et al.; U.S. Pat. No. 7,915,271 to Ali et al., which are hereby incorporated by reference in their entirety.

In a further embodiment of the process of the present application, the contacting of the polymers, oligomers, or mixtures thereof with the compounds of formula (I) in the presence of a catalyst, forming a reaction mixture, is carried out under conditions effective to form shorter alkyl halides. These conditions include adding a halogen to the reaction mixture to form the shorter alkyl halides. The halogen may be dissolved in a solvent to aid addition. Exemplary solvents useful for halogen addition include, but are not limited to, dichloromethane, chloroform, toluene, and benzene.

The shorter alkyl halides of the present application may be reacted with an alkoxide to form an ether. As used herein, an "ether group" generally refers to a compound in which an oxygen atom is bonded to two alkyl or two aryl groups, or one alkyl and one aryl group.

The formation of an ether from an alkyl halide using an alkoxide is known in the art. The most commonly used method for the preparation of symmetrical and unsymmetrical ethers is the Williamson synthesis, involving a halide and an alkoxide. The reaction involves an $S_N2$ reaction in which an alkoxide ion replaces a halogen, sulfonyl or a sulfate group, however, usually, alkyl halides are used. The alkoxide can be prepared by the reaction of the corresponding alcohol with an active metal such as metallic sodium or a metal hydride like NaH acting upon the alcohol. The resulting alkoxide salt is then reacted with the alkyl halide (sulfonate or sulfate) to produce the ether in an SN2 reaction. These reactions are common place in the art and are disclosed in U.S. Pat. No. 8,143,325 to Bezwada; U.S. Pat. No. 5,446,210 to Hees et al.; 10,111,422 and 6,811,703 to Elliott, which are hereby incorporated by reference in their entirety.

In another embodiment of the process of the present application, the contacting of the polymers, oligomers, or mixtures thereof with the compounds of formula (I) in the presence of a catalyst, forming a reaction mixture, is carried out under conditions effective to form shorter aldehydes. These conditions include adding an orthoester to the reaction mixture to form the shorter aldehydes. As used herein, an "orthoester" refers to compound in which three alkoxy groups are attached to one carbon atom, i.e. having the general formula $RC(OR')_3$.

The environmental, economic, and health impacts of the plastic waste crisis motivate the design and study of new chemistries that enable efficient upcycling of polymers into versatile, value-added intermediates. A new catalytic strategy for transforming single-use polyolefin waste via reactive hydrocarbylaluminum intermediates into functionalized aliphatic chains, such as fatty alcohols and acids is reported herein. Earth-abundant zirconium surface sites catalyze the deconstruction of polyolefins under mild (<200° C.), solvent-free conditions via C—H bond activation, β-alkyl elimination for carbon-carbon bond cleavage, and aluminum-carbon bond formation for functionalization. Catalytic efficiency and selectivity are governed by the activation of surface-supported zirconium precatalysts, which become most effective in the presence of aluminum reagents capable of generating zirconium hydrides.

Intermediate length chain alkylaluminum species are high among desirable targets for polymer deconstruction processes because these organometallics, conventionally synthesized using the Ziegler process, can be converted into fatty alcohols and acids through established methods (Ziegler et al., "Metallorganische Verbindungen, XL Synthese von Alkoholen aus Organoaluminium-Verbindungen," *Liebigs Ann. Chem.* 629:241-250 (1960); Ziegler et al., "Metallorganische Verbindungen, XLI Reaktionen der Aluminiumtrialkyle mit Kohlendioxyd und Schwefeldioxyd," *Liebigs Ann. Chem.* 629:251-256 (1960), which are hereby incorporated by reference in their entirety). The heteroatom-functionalized species are biodegradable and, if produced from discarded polyolefins, would provide an environmentally friendly end-of-life for some plastics. In addition, the hydrido or organoaluminum reagents to be employed in such transformations are further advantaged because aluminum is widely available as the most abundant metal (8.2%, as an oxide) in the earth's crust, and it is readily converted (or recycled) from its oxide to metal to organoaluminum species in atom-economical, optimized processes performed on large scale (Sanders Jr, R. E., "Aluminum and Aluminum Alloys." *Kirk-Othmer Encyclopedia of Chemical Technology*, 1-64 (2012), which is hereby incorporated by reference in its entirety).

The present application discloses that organotransition-metal species, generated as catalytic intermediates by cleavage of C—C bonds in saturated hydrocarbons, could undergo metathetical exchange with organo- or hydridoaluminum species, to create the new intermediate length-chain hydrocarbyl-aluminum species. Such alkyl group metathetical steps are established as part of processes such as carboalumination and hydroalumination of alkenes (Xu and Negishi, "Zirconium-Catalyzed Asymmetric Carboalumination of Unactivated Terminal Alkenes," *Acc. Chem. Res.* 49:2158-2168 (2016); Camara et al, "Zirconium-Catalyzed Carboalumination of α-Olefins and Chain Growth of Aluminum Alkyls: Kinetics and Mechanism," *J. Am. Chem. Soc.* 133:5263-5273 (2011), which are hereby incorporated by reference in their entirety) and as chain-transfer steps in chain-shuttling block co-polymerizations of ethylene and α-olefins (Arriola et al., "Catalytic Production of Olefin Block Copolymers via Chain Shuttling Polymerization,"*Science* 312:714-718 (2006), which is hereby incorporated by reference in its entirety). These processes commonly engage organozirconium catalysts. Moreover, coordinatively unsaturated zirconium sites are known to break C—C bonds by β-alkyl elimination (O'Reilly et al., "β-Alkyl Elimination: Fundamental Principles and Some Applications," *Chem. Rev.* 116:8105-8145 (2016), which is hereby incorporated by reference in its entirety). The related β-allyl elimination and organozirconium/hydridoaluminum exchange are proposed in polybutadiene deconstruction and alumination, catalyzed by Cp$_2$ZrHCl (Schwartz's reagent), which attaches to the chain by hydrozirconation rather than C—H bond metalation (Zheng et al., "Controlled Chain-Scission of Polybutadiene by the Schwartz Hydrozirconation," *Chem. Eur. J.* 19:541-548 (2013), which is hereby incorporated by reference in its entirety).

Herein is reported the catalytic C—C bond alumination of sp$^3$-hybridized carbon in aliphatic hydrocarbons, leveraging C—H bond activation and β-alkyl elimination steps of surface organometallic zirconium chemistry (Corker et al., "Catalytic Cleavage of the C—H and C—C Bonds of Alkanes by Surface Organometallic Chemistry: An EXAFS and IR Characterization of a Zr—H Catalyst,"*Science* 271: 966-969 (1996); Zakharov et al., "Formation of Zirconium Hydrides in Supported Organozirconium Catalysts and Their Role in Ethylene Polymerization," *J Mol. Catal.* 2:421-435 (1977); Yermakovt et al., "Hydride Complexes of Titanium and Zirconium Attached to SiO$_2$ as Hydrogenation Catalysts," *J. Mol. Catal.* 49:121-132 (1989); Schwartz and Ward, "Silica-supported Zirconium Hydrides as Isomerization or Hydrogenation Catalysts for Long-chain Olefins," *J. Mol. Catal.* 8:465-469 (1980); Pasha et al., "C—H and C—C Activation of n-Butane with Zirconium Hydrides Supported on SBA15 Containing N-Donor Ligands: [(≡SiNH—)(≡SiX—)ZrH2], [(≡SiNH—)(≡SiX—)2ZrH], and [(≡SiN═)(≡SiX—)ZrH] (X=—NH—, —O—). A DFT Study," *Organometallics* 33:3320-3327 (2014); Rataboul et al., "Molecular Understanding of the Formation of Surface Zirconium Hydrides upon Thermal Treatment under Hydrogen of [(≡SiO)Zr(CH2tBu)$_3$] by Using Advanced Solid-State NMR Techniques," *J. Am. Chem. Soc.* 126:12541-12550 (2004); Wang et al., "Preparation and Characterization of Zirconium Containing Mesoporous Silicas. II. Grafting Reaction of Tetraneopentyl Zirconium on MCM-41 and Characterization of the Grafted Species and of the Resulting Materials," *Microporous Mesoporous Mater.* 66:169-179 (2003); Quignard et al., "Surface Organometallic Chemistry of Zirconium: Application to the Stoichiometric Activation of the CH Bonds of Alkanes and to the Low-temperature Catalytic Hydrogenolysis of Alkanes," *J. Mol. Catal.* 74:353-363 (1992); Casty et al., "Hydrogen/Deuterium Exchange Kinetics by a Silica-Supported Zirconium Hydride Catalyst: Evidence for a σ-Bond Metathesis Mechanism," *Organometallics* 20:2246-2249 (2001), which are hereby incorporated by reference in their entirety). The studies of the present application have focused on identifying effective catalysts and aluminum reagents, as well as understanding their effects upon the elementary steps involved reactions through conversions of polyethylene into fatty aliphatic alkylaluminum species.

Typical chemical synthesis constructs large, intricate products from smaller building blocks. Yet, naturally occurring resources often contain pre-assembled molecular components, which nonetheless are not directly suitable for conventional routes to desired products. Thus, sustainable conversions would be advanced by efficient catalytic methods that restructure the carbon-based skeletons of molecules and install functional groups.

The present application reports a conversion in which long hydrocarbon chains of polymers are broken into shorter units with the introduction of aluminum end groups. These green organoaluminum species are easily derivatized into biodegradable fatty alcohols, carboxylic acids, or halides, providing high-value, end-of-first-life applications for the catenated chains of single-use polyolefins.

Preferences and options for a given aspect, feature, embodiment, or parameter of the technology described herein should, unless the context indicates otherwise, be regarded as having been disclosed in combination with any and all preferences and options for all other aspects, features, embodiments, and parameters of the technology.

The following Examples are presented to illustrate various aspects of the present application, but are not intended to limit the scope of the claimed application.

EXAMPLES

Materials and Methods
Materials

All manipulations were carried out under inert conditions, either using Schlenk techniques or in a glovebox under a purified nitrogen atmosphere, unless stated otherwise. Dry and degassed solvents were used throughout. Pentane was sparged with nitrogen, passed through activated alumina columns, and stored under nitrogen. Benzene-d6 was degassed via three consecutive freeze-pump-thaw cycles, dried over Na/K alloy, vacuum transferred, and stored over molecular sieves under nitrogen. Tetrakisneopentyl zirconium (Davidson et al., "Silylmethyl and Related Complexes II. Preparation, Spectra, and Thermolysis of the Tetraneopentyls of Titanium, Zirconium, and Hafnium," *J Organomet. Chem.* 57:269-277 (1973), which is hereby incorporated by reference in its entirety), dimethylaluminum hydride (Downs et al., "Dimethylalane, [Me$_2$AlH]n, in the Vapor Phase and in Hydrocarbon Solution: Gas-Phase Electron Diffraction, Spectroscopic, Colligative, and ab Initio Studies," *Organometallics* 19:527-538 (2000), which is hereby incorporated by reference in its entirety), triphenylaluminum (Lehmkuhl and Ziegler, "Metallorganische Verbindungen: Al, Ga, In, Tl," vol. XIII/4, Bahr Eds., Stuttgart: Georg Thieme Verlag, (1970), which is hereby incorporated by reference in its enitrety), and alane (Finholt et al., "Lithium Aluminum Hydride, Aluminum Hydride and Lithium Gallium Hydride, and Some of their Applications in Organic and Inorganic Chemistry," *J. Am. Chem. Soc.* 69:1199-1203 (1947), which is hereby incorporated by reference in its entirety) were synthesized according to literature procedures. Trimethylaluminum, triethylaluminum, triisobutylaluminum, diisobutylaluminum hydride, high density polyethylene (HDPE, $M_n$=6.2 kDa, $M_w$=38.4 kDa, Đ=6.2), isotactic polypropylene (iPP, $M_n$=36.8 kDa, $M_w$=117.6 kDa, Đ=3.2), and Al(NO$_3$)$_3$.9H$_2$O (98%) were purchased from Sigma-Aldrich and used as received. Na$_2$SiO$_3$.9H$_2$O (98%), NH$_4$NO$_3$, and concentrated HCl were purchased from Fisher Scientific, and used as received. Fumed silica (Aerosil) of surface area 300 m$^2$/g was purchased from Evonik, calcined and partially dehydroxylated at 550° C. for 12 h. Titration of the surface silanols in this material with Mg(CH$_2$Ph)$_2$(O$_2$C$_4$H$_8$)$_2$ revealed a surface OH loading of 0.46±0.05 mmol/g.

Methods

1D $^1$H and $^{13}$C{$^1$H}, and 2D $^1$H-$^1$H COSY, TOCSY and $^1$H-$^{13}$C HSQC NMR spectra were acquired on a Brucker NEO 400 MHz spectrometer. Fourier transform infrared (FT-IR) spectra and diffuse reflectance infrared Fourier transform (DRIFT) spectra were recorded on a Bruker VERTEX 80 IR spectrometer. Samples for transmission IR were diluted with KBr and pressed into a pellet using a hydraulic press. DRIFT spectra were collected using a Harrick Praying Mantis accessory and a sealed, ambient-pressure sample chamber consisting of a dome with ZnSe windows. Elemental analysis was performed using a Perkin-Elmer 2400 Series II CHN/S at the Iowa State Chemical Instrumentation Facility. Inductively Coupled Plasma-Optical Emission Spectroscopy (ICP-OES) was performed to measure the amount of zirconium present in the catalytic materials. The samples (2.0-4.0 mg each) were digested for 24 h in aqueous HF and aqua-regia (0.18% and 5% respectively) and analyzed in a Perkin Elmer Optima 2100 DV Inductively Coupled Plasma-Optical Emission Spectroscope.

MALDI-TOF Mass Spectrometry

MALDI-TOF-MS experiments were carried out on a Shimadzu AXIMA Confidence MALDI-TOF mass spectrometer, equipped with an N$_2$ laser (337 nm, 25 Hz repetition rate). The mass spectra were acquired in the linear and positive ion mode. 100 laser pulses were utilized for each measurement.

Stock solutions of products were prepared in tetrahydrofuran at a 0.5 mg/mL concentration, and a stock solution of silver nitrate was prepared in a 1:1 (v:v) mixture of tetrahydrofuran and acetonitrile at a concentration of 10 mg/mL. Final sample solutions for spotting were prepared by mixing equal volumes (0.2 mL) of stock solutions of alkanes and silver nitrate. The matrix (2,5-dihydroxybenzoic acid (DHB)) solution was prepared in a 3:2 (v:v) mixture of tetrahydrofuran and methanol at a 10 mg/mL concentration. The dried-droplet method of sample deposition was employed, where 0.5 μL of the sample solution was deposited on the stainless-steel sample plate, followed by 0.5 μL of the matrix solution. The solvents were allowed to evaporate by air-drying.

General Procedure for Catalytic Alumination of Polyolefins

In the glovebox, the polyolefin reactant, supported catalyst, and aluminum reagent were loaded into a glass tube equipped with a glass-encapsulated magnetic stirrer. The tube was which was sealed with a stainless steel UltraTorr fitting to a closed glass tube with a sidearm containing a re-sealable Teflon-glass valve. The vessel was heated in an aluminum block at the desired temperature (≥150° C. to ensure the polymer was above its melting point) for the required reaction time with mixing. The volatile components of the headspace were sampled and analyzed by GC-MS. After the appropriate time, the contents of the tube were quenched by passing dry air into the vessel through the sidearm for 1 h. The crude reaction mixture was extracted with CH$_2$Cl$_2$ (3×5 mL), and the volatile components were evaporated from the liquid to provide an oil which was further analyzed by spectroscopic and analytical techniques (NMR, IR, GC-MS, MALDI-TOF-MS). Yields of oils are given as a percentage of the starting polyolefin mass. The residual solid was dissolved in hot 1,2-dichlorobenzene and filtered to remove the catalyst. A solid crashed out from the filtrate upon cooling. The supernatant liquid was decanted, and the solid polymer was washed with CH$_2$Cl$_2$ (3×5 mL), dried in vacuo, and analyzed by IR spectroscopy.

Example 1—Preparation of Silica-Alumina (SiAlO$_x$)

Silica-alumina was synthesized by a literature procedure (Yao et al., "A Novel Method to Synthesize Amorphous Silica-Alumina Materials with Mesoporous Distribution without Using Templates and Pore-Regulating Agents," *Chem. Mater.* 14:122-129 (2002), which is hereby incorporated by reference in its entirety).

Example 2—Preparation of Zr(CH$_2$CMe$_3$)$_2$@SiAlO$_x$

Figure 1C:
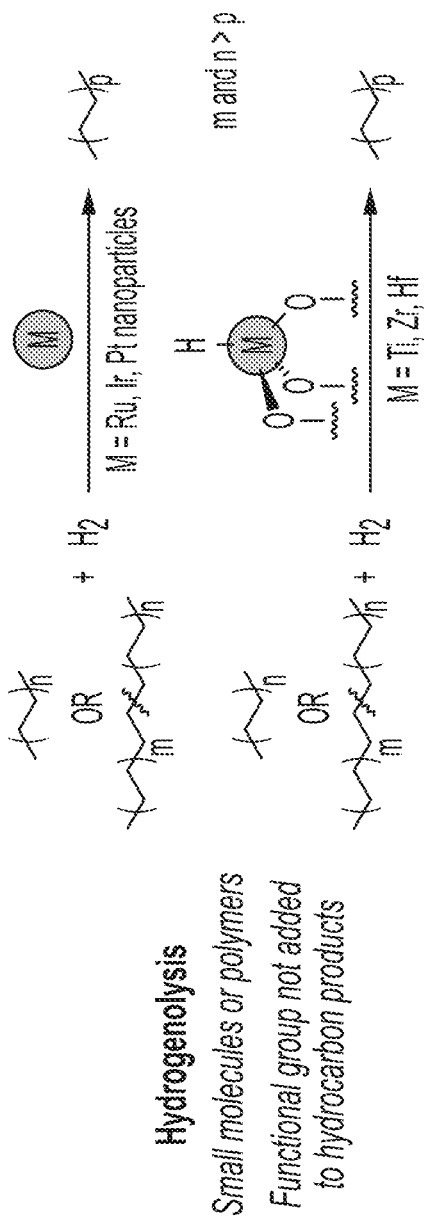
Figure 1D:
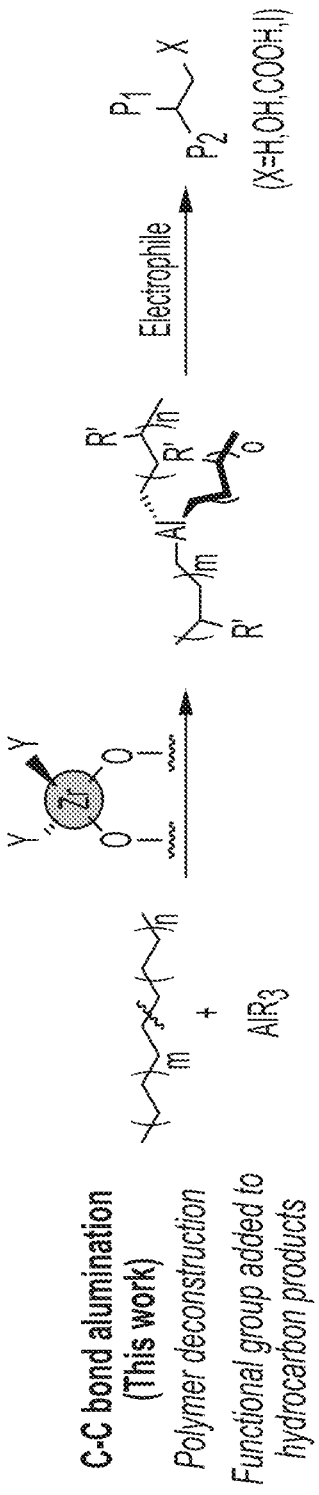
Figure 3:
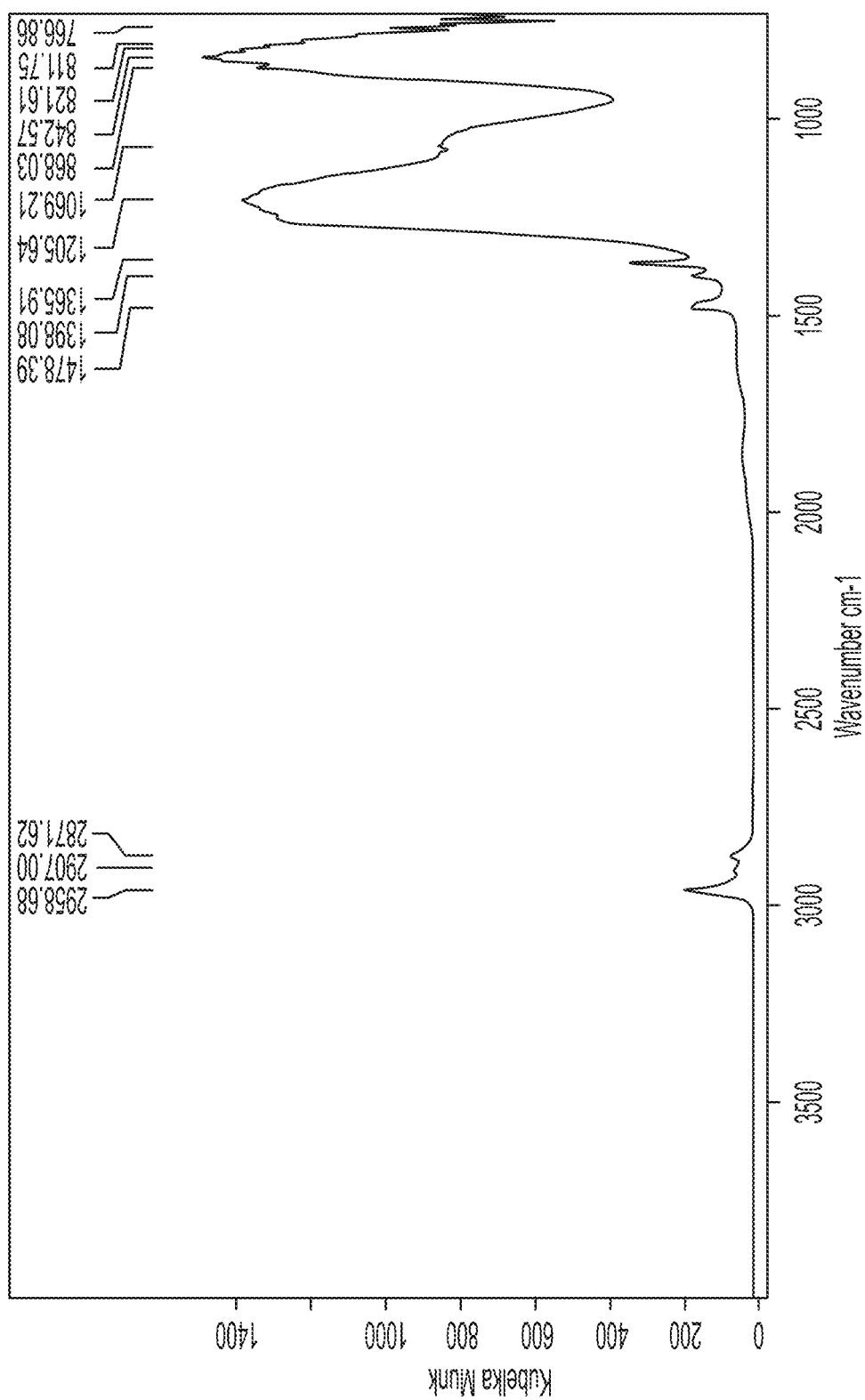
FIG. 3 is the Diffuse Reflectance for Infrared Fourier Transform (DRIFT) spectrum of $Zr(CH_2CMe_3)_2$@$SiAlO_x$ acquired at room temperature.

Zr(CH$_2$CMe$_3$)$_2$@SiAlO$_x$ was synthesized by a procedure adapted from reference (Wang et al., "Preparation and Characterization of Zirconium Containing Mesoporous Silicas. II. Grafting Reaction of Tetraneopentyl Zirconium on MCM-41 and Characterization of the Grafted Species and of the Resulting Materials," *Microporous Mesoporous Mater* 66:169-179 (2003), which is hereby incorporated by reference in its entirety). In the glovebox, 0.30 g of Zr(CH$_2$CMe$_3$)$_4$ (0.8 mmol) was dissolved in anhydrous pentane (7 mL). This solution was added to a suspension of silica-alumina (1.00 g) in pentane (7 mL), and the resulting suspension was stirred at room temperature for 4 h. The suspension was allowed to settle, and the supernatant liquid was decanted. The residual solid was washed with pentane (3×5 mL) and dried overnight in vacuo to afford an off-white powder (0.92 g). This material contains 2.2±0.2 CH$_2$CMe$_3$ groups per Zr center, as determined by titration of Zr(CH$_2$CMe$_3$)$_2$@SiAlO$_x$ with CH$_3$OH and ICP-OES (2.7 wt % Zr, 0.30 mmol Zr/g). Solid-state $^{13}$C NMR spectra and infrared spectra match reported literature values (Eedugurala et al., "Mesoporous Silica-Supported Amidozirconium-Catalyzed Carbonyl Hydroboration," *ACS Catal.* 5:7399-7414 (2015), which is hereby incorporated by reference in its entirety). $^{13}$C NMR (CP-MAS, 400 MHz): δ 94.78 (CH$_2$CMe$_3$), 32.88 (CH$_2$CMe$_3$). IR (DRIFTs, cm$^{-1}$): 2959, 2907, 2872, 1478, 1398, 1366, 1205, 843 (FIG. 3). Elemental analysis for Zr(CH$_2$CMe$_3$)$_2$@SiAlO$_x$: C, 3.30; H, 0.24; Zr, 2.70.

Example 3—Preparation of Zr(CH$_2$CMe$_3$)$_2$@SiO$_2$

Figure 4:
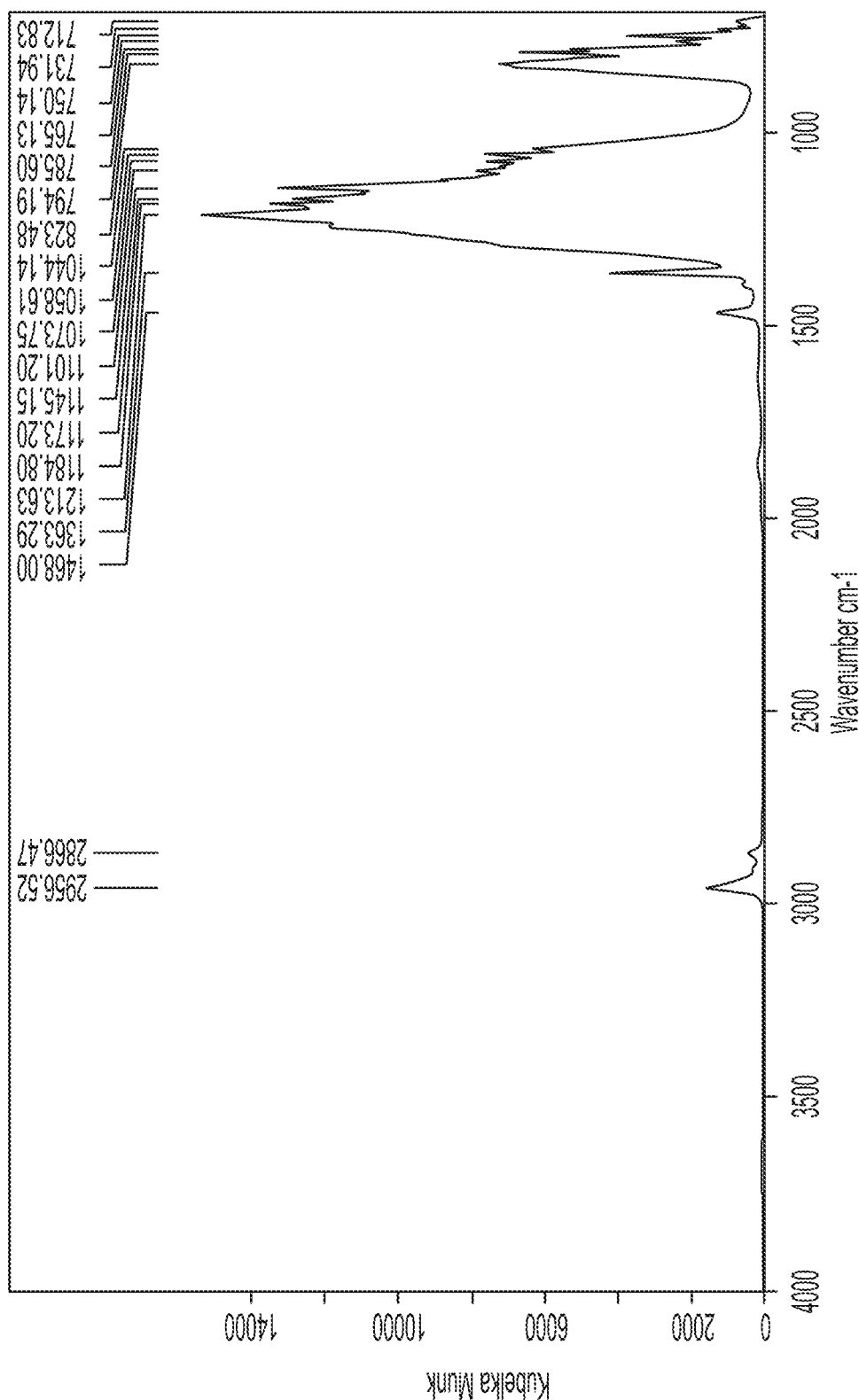
FIG. 4 is the DRIFT spectrum of $Zr(CH_2CMe_3)_2$@$SiO_2$ acquired at room temperature.
Figure 5:
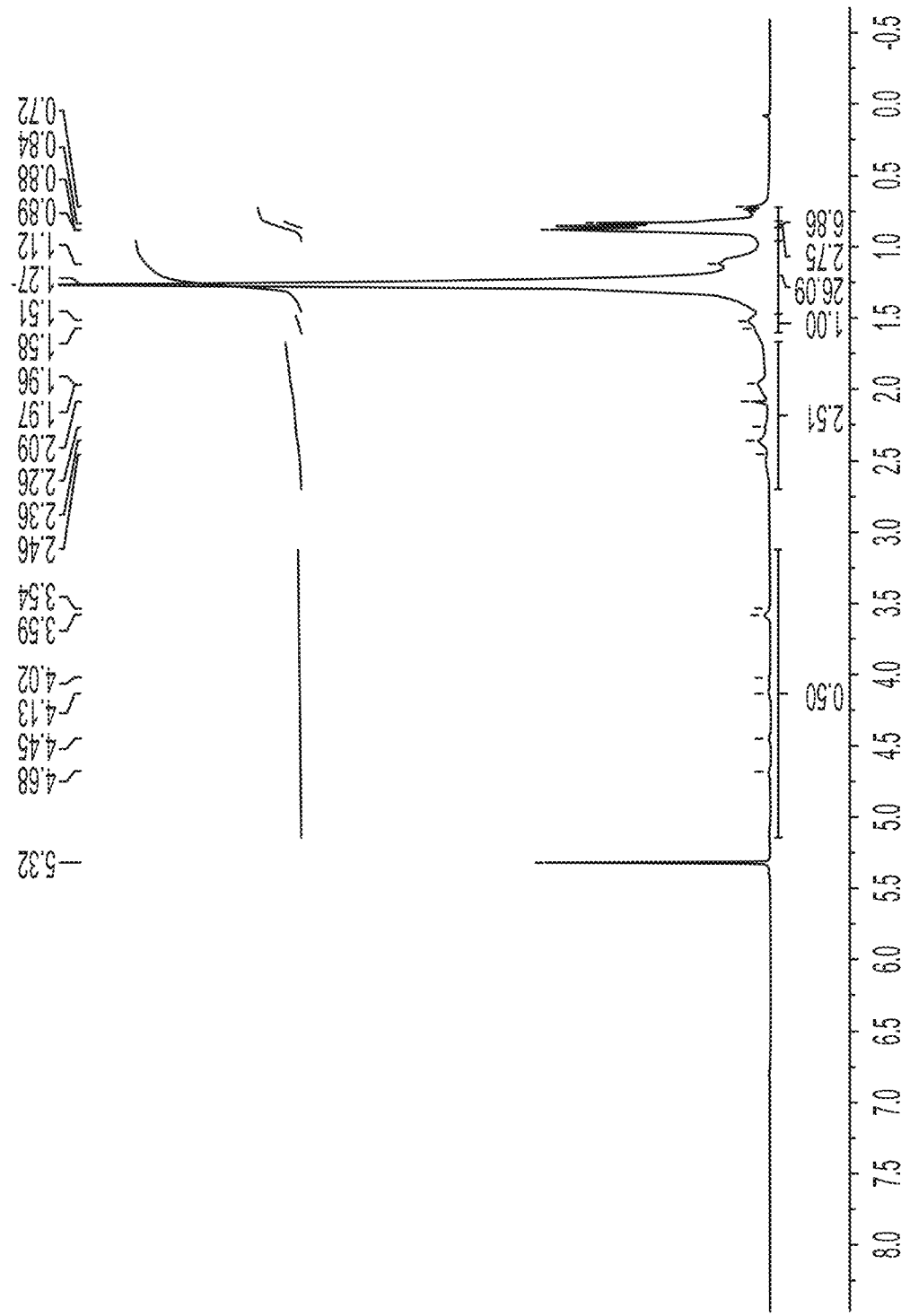
FIG. 5 is the $^1H$ NMR spectrum of the oil isolated after reaction of HDPE and $AliBu_3$ in the presence of $Zr(CH_2CMe_3)_2$@$SiAlO_x$ at 150° C. for 12 h, quenched with $O_2$, and extracted with methylene chloride. The spectrum was acquired at room temperature in methylene chloride-$d_2$ and assigned based on correlation spectroscopy (COSY) and heteronuclear single quantum correlation (HSQC) experiments in FIGS. 7 and 8. Signals at 0.7-0.9 ppm correspond to methyl groups, 1.0-2.7 ppm correspond to methylene groups, and the peak at 1.5 ppm to the methine group. Peaks at 3.5-5.0 ppm have been assigned as $CH_2$—OH species.

Zr(CH$_2$CMe$_3$)$_2$@SiO$_2$ was synthesized by a procedure adapted from reference (Wang et al., "Preparation and Characterization of Zirconium Containing Mesoporous Silicas. II. Grafting Reaction of Tetraneopentyl Zirconium on MCM-41 and Characterization of the Grafted Species and of the Resulting Materials," *Microporous Mesoporous Mater* 66:169-179 (2003), which is hereby incorporated by reference in its entirety) and is compared to the reported material in reference Quignard et al., "Surface Organometallic Chemistry: Synthesis and Characterization of a Tris(neopentyl)zirconium(IV) Complex Grafted to the Surface of a Partially Dehydroxylated Silica," *Inorg. Chem.* 31:928-930 (1992), and Rataboul et al., "Molecular Understanding of the Formation of Surface Zirconium Hydrides upon Thermal Treatment under Hydrogen of [(≡SiO)Zr(CH$_2$tBu)$_3$] by Using Advanced Solid-State NMR Techniques," *J Am. Chem. Soc.* 126:12541-12550 (2004), which are hereby incorporated by reference in their entirety). In the glovebox, 0.30 g of Zr(CH$_2$CMe$_3$)$_4$ (0.8 mmol) was dissolved in anhydrous pentane (7 mL). This solution was added to a suspension of Aerosil (1.00 g) in pentane (7 mL), and the resulting mixture was stirred at room temperature for 4 h. The suspension was allowed to settle, and the supernatant liquid was decanted. The residual solid was washed with pentane (3×5 mL) and dried overnight in vacuo to afford an off-white powder (0.98 g). This material contained 2.1±0.2 CH$_2$CMe$_3$ groups per Zr center, as revealed by titration of Zr(CH$_2$CMe$_3$)$_2$@SiO$_2$ with CH$_3$OH and ICP-OES (3.51 wt % Zr, 0.38 mmol Zr/g). IR (DRIFTs, cm$^{-1}$): 2957, 2866, 1468, 1363, 1214, 1185, 1173, 1145, 823 (FIG. 4). Elemental analysis for Zr(CH$_2$CMe$_3$)$_2$@SiO$_2$: C, 2.32; H, 0.39; Zr, 3.51.

Example 4—HDPE+Zr(CH$_2$CMe$_3$)$_2$@SiAlO$_x$+ AliBu$_3$ (150° C.), (Table 1, Entry 1)

HDPE (0.63 g), Zr(CH$_2$CMe$_3$)$_3$@SiAlO$_x$ (0.10 g, 0.030 mmol Zr) and AliBu$_3$ (60 µL, 0.24 mmol) were allowed to react at 150° C. for 12 h to provide an oil (0.19 g, 31%) which was characterized by NMR, IR, and MALDI, and residual HDPE (0.44 g). MALDI-TOF-MS revealed a bimodal distribution, with maxima at C$_{39}$H$_{79}$OH and C$_{54}$H$_{109}$OH. FIGS. 5-9 show the characterization of the oil isolated after reaction of HDPE and AliBu$_3$ in the presence of Zr(CH$_2$CMe$_3$)$_2$@SiAlO$_x$ at 150° C. for 12 h, quenched with O$_2$, and extracted with methylene chloride.

Example 5—HDPE+Zr(CH$_2$CMe$_3$)$_2$@SiAlO$_x$+ AliBu$_3$ (200° C.), (Table 1, Entry 2)

HDPE (1.00 g), Zr(CH$_2$CMe$_3$)$_3$@SiAlO$_x$ (0.13 g, 0.039 mmol Zr) and AliBu$_3$ (100 µL, 0.40 mmol) were allowed to react at 200° C. for 12 h to provide an oil (0.40 g, 40%) and residual HDPE (0.50 g). Experiments with doubled initial catalyst and AliBu$_3$ loading with respect to polyethylene (10.5 g HDPE/mmol Zr) also gave the oil in 40% yield after 12 h at 200° C. However, two portions of Zr(CH$_2$CMe$_3$)$_3$@SiAlO$_x$ and AliBu$_3$, added initially and after 12 h gave 72% total yield of oil (C$_{32}$~C$_{44}$ alcohol distribution). FIGS. 10-14 show the characterization of the oil isolated after reaction of HDPE and AliBu$_3$ in the presence of Zr(CH$_2$CMe$_3$)$_2$@SiAlO$_x$ at 200° C. for 12 h, quenched with O$_2$, and extracted with methylene chloride.

Example 6—HDPE+Zr(CH$_2$CMe$_3$)$_2$@SiAlO$_x$+ AliBu$_3$ (Zr Catalyst/AliBu$_3$ Added in 3 Portions) (Table 1, Entry 3)

HDPE (1.00 g), Zr(CH$_2$CMe$_3$)$_3$@SiAlO$_x$ (0.11 g, 0.033 mmol Zr) and AliBu$_3$ (120 µL, 0.48 mmol) were allowed to react at 200° C. for 12 h. The reaction tube was cooled to room temperature and additional (same as before) portions of Zr(CH$_2$CMe$_3$)$_2$@SiAlO$_x$ and AliBu$_3$ were added. The mixture was heated at 200° C. for 12 h. This procedure was repeated once more (after a total of 36 h) to provide an oil (0.84 g, 84%), and no visible polyethylene was remaining. FIGS. 15-19 show the characterization of the oil isolated after reaction of HDPE and AliBu$_3$ in the presence of Zr(CH$_2$CMe$_3$)$_2$@SiAlO$_x$ added at 0, 12, and 24 h, at 200° C., quenched with O$_2$, and extracted with methylene chloride.

Example 7—HDPE+Zr(CH$_2$CMe$_3$)$_2$@SiAlO$_x$+ AliBu$_3$ (Quenched with MeOH) (Table 1, Entry 4)

HDPE (1.00 g), Zr(CH$_2$CMe$_3$)$_2$@SiAlO$_x$ (0.11 g, 0.033 mmol Zr) and AliBu$_3$ (100 µL, 0.40 mmol) were allowed to react at 200° C. for 12 h. The reaction tube was cooled to room temperature, and degassed MeOH (3 mL) was added. After 30 min, the solvent was removed under reduced pressure and the residue was extracted with CH$_2$C$_2$ (3×5 mL) to provide an oil (0.38 g, 38%) and residual HDPE (0.64 g). FIGS. 20-25 show the characterization of the oil isolated after reaction of HDPE and AliBu$_3$ in the presence of Zr(CH$_2$CMe$_3$)$_2$@SiAlO$_x$ at 200° C. for 12 h, quenched with MeOH, and extracted with methylene chloride.

Example 8—HDPE+Zr(CH$_2$CMe$_3$)$_2$@SiAlO$_x$+ AliBu$_3$ (Quenched with I2) (Table 1, Entry 5)

HDPE (0.54 g), Zr(CH$_2$CMe$_3$)$_2$@SiAlO$_x$ (0.06 g, 0.019 mmol Zr) and AliBu$_3$ (50 µL, 0.20 mmol) were allowed to react at 200° C. for 12 h. The reaction tube was cooled to room temperature and I$_2$ (0.06 g, 0.23 mmol) in anhydrous and degassed CH$_2$C$_2$ (5 mL) was added. After 30 min, the solvent was removed under reduced pressure, and the residue was extracted with CH$_2$C$_2$ (3×5 mL) to provide an oil (0.23 g, 43%) and residual HDPE (0.32 g). FIGS. 26-30 show the characterization of the oil isolated after reaction of HDPE and AliBu$_3$ in the presence of Zr(CH$_2$CMe$_3$)$_2$@SiAlO$_x$ at 200° C. for 12 h, quenched with I$_2$, and extracted with methylene chloride. Cross-peaks in the $^1$H-$^{13}$C phase sensitive HSQC spectrum of the oil (FIG. 28) corresponding to proton signals at 3.1 ppm and shielded carbon signals at 10 ppm indicated the presence of —CH$_2$—I groups in the product.

Example 9—HDPE+Zr(CH$_2$CMe$_3$)$_2$@SiAlO$_x$+AliBu$_3$ (Quenched with CO$_2$) (Table 1, Entry 6)

HDPE (0.55 g), Zr(CH$_2$CMe$_3$)$_2$@SiAlO$_x$ (0.06 g, 0.019 mmol Zr) and AliBu$_3$ (50 µL, 0.20 mmol) were allowed to react at 200° C. for 12 h. The reaction tube was cooled to room temperature and evacuated. Dry CO$_2$ was introduced into the vessel, which was then heated to 60° C. After 4 h, the reaction mixture was exposed to air, and the residue was extracted with CH$_2$Cl$_2$ (3×5 mL) to provide an oil (0.20 g, 36%) and residual HDPE (0.36 g). FIGS. 31-36 show the characterization of the oil isolated after reaction of HDPE and AliBu$_3$ in the presence of Zr(CH$_2$CMe$_3$)$_2$@SiAlO$_x$ at 200° C. for 12 h, quenched with CO$_2$, and extracted with methylene chloride. Cross-peaks in the $^1$H-$^{13}$C HMBC spectrum of the oil (FIG. 34) corresponding to carbon signals in the range of 170-180 ppm confirmed the presence of —COOH groups in the product.

Example 10—HDPE+Zr(CH$_2$CMe$_3$)$_2$@SiAlO$_x$+AlEt$_3$ (150° C.) (Table 1, Entry 7)

HDPE (0.51 g), Zr(CH$_2$CMe$_3$)$_2$@SiAlO$_x$ (0.10 g, 0.03 mmol Zr) and AlEt$_3$ (50 µL, 0.36 mmol) were allowed to react at 150° C. for 12 h to provide an oil (0.13 g, 25%) and residual HDPE (0.41 g). FIGS. 37-41 show the characterization of the oil isolated after reaction of HDPE and AlEt$_3$ in the presence of Zr(CH$_2$CMe$_3$)$_2$@SiAlO$_x$ at 150° C. for 12 h, quenched with O$_2$, and extracted with methylene chloride.

Example 11—HDPE+Zr(CH$_2$CMe$_3$)$_2$@SiAlO$_x$+AlEt$_3$ (200° C.) (Table 1, Entry 8)

HDPE (0.60 g), Zr(CH$_2$CMe$_3$)$_2$@SiAlO$_x$ (0.10 g, 0.03 mmol Zr) and AlEt$_3$ (50 µL, 0.36 mmol) were allowed to react at 200° C. for 12 h to provide an oil (0.15 g, 24%) and residual HDPE (0.45 g). FIGS. 42-46 show the characterization of the oil isolated after reaction of HDPE and AlEt$_3$ in the presence of Zr(CH$_2$CMe$_3$)$_2$@SiAlO$_x$ at 200° C. for 12 h, quenched with O$_2$, and extracted with methylene chloride.

Example 12—HDPE+Zr(CH$_2$CMe$_3$)$_2$@SiAlO$_x$+AlPh$_3$ (Table 1, Entry 9)

HDPE (0.64 g), Zr(CH$_2$CMe$_3$)$_2$@SiAlO$_x$ (0.07 g, 0.021 mmol Zr) and AlPh$_3$ (66 mg, 0.26 mmol) were allowed to react at 200° C. for 12 h to provide an oil (0.19 g, 29%) and residual HDPE (0.49 g). FIGS. 47-52 show the characterization of the oil isolated after reaction of HDPE and AlPh$_3$ in the presence of Zr(CH$_2$CMe$_3$)$_2$@SiAlO$_x$ at 200° C. for 12 h, quenched with O$_2$, and extracted with methylene chloride.

Example 13—HDPE+Zr(CH$_2$CMe$_3$)$_2$@SiAlO$_x$+AlH$_3$ (Table 1, Entry 10)

HDPE (0.52 g), Zr(CH$_2$CMe$_3$)$_2$@SiAlO$_x$ (0.10 g, 0.03 mmol Zr) and AlH$_3$ (28 mg, 0.93 mmol) were allowed to react at 200° C. for 12 h to provide an oil (0.22 g, 42%) and residual HDPE (0.28 g). FIGS. 53-57 show the characterization of the oil isolated after reaction of HDPE and AlH$_3$ in the presence of Zr(CH$_2$CMe$_3$)$_2$@SiAlO$_x$ at 200° C. for 12 h, quenched with O$_2$, and extracted with methylene chloride.

Example 14—HDPE+Zr(OCH$_2$CMe$_3$)$_2$@SiAlO$_x$+AliBu$_3$ (Table 1, Entry 11)

Zr(CH$_2$CMe$_3$)$_2$@SiAlO$_x$ (0.07 g, 0.021 mmol Zr) was exposed to dry air for 10 min at room temperature to provide Zr(OCH$_2$CMe$_3$)$_2$@SiAlO$_x$. HDPE (0.60 g), Zr(OCH$_2$CMe$_3$)$_2$@SiAlO$_x$, and AliBu$_3$ (100 µL, 0.40 mmol) were allowed to react at 200° C. for 12 h to provide an oil (0.21 g, 34%) and a residual polymeric solid (0.42 g). FIGS. 58-62 show the characterization of the oil isolated after reaction of HDPE and AliBu$_3$ in the presence of Zr(OCH$_2$CMe$_3$)$_2$@SiAlO$_x$ at 200° C. for 12 h, quenched with 02, and extracted with methylene chloride.

Example 15—HDPE+Zr(OCH$_2$CMe$_3$)$_2$@SiAlO$_x$+AlH$_3$ (Table 1, Entry 12)

Zr(CH$_2$CMe$_3$)$_2$@SiAlO$_x$ (0.05 g, 0.015 mmol Zr) was exposed to dry air for 10 min at room temperature to provide Zr(OCH$_2$CMe$_3$)$_2$@SiAlO$_x$. HDPE (0.35 g), Zr(OCH$_2$CMe$_3$)$_2$@SiAlO$_x$ and AlH$_3$ (28 mg, 0.93 mmol) were allowed to react at 200° C. for 12 h to provide an oil (0.17 g, 49%) and a residual polymeric solid (0.18 g). FIGS. 63-67 show the characterization of the oil isolated after reaction of HDPE and AlH$_3$ in the presence of Zr(OCH$_2$CMe$_3$)$_2$@SiAlO$_x$ at 200° C. for 12 h, quenched with O$_2$, and extracted with methylene chloride.

Example 16—HDPE+Zr(CH$_2$CMe$_3$)$_2$@SiO$_2$+AliBu$_3$ (Table 1, Entry 13)

HDPE (1.00 g), Zr(CH$_2$CMe$_3$)$_2$@SiO$_2$ (0.11 g, 0.042 mmol Zr) and AliBu$_3$ (100 µL, 0.40 mmol) were allowed to react at 200° C. for 12 h to provide an oil (0.35 g, 35%) and a residual polymeric solid (0.54 g). Catalytic materials employing SiO$_2$ as the support generated small amounts of alkylsilanes at 200° C., such as iBu$_2$SiH$_2$, Et$_2$SiH$_2$ and Et$_3$SiH, as side products during catalysis, whereas such species were not detected in catalytic reactions of Zr(CH$_2$CMe$_3$)$_2$@SiAlO$_x$. FIGS. 68-72 show the characterization of the oil isolated after reaction of HDPE and AliBu$_3$ in the presence of Zr(CH$_2$CMe$_3$)$_2$@SiO$_2$ at 200° C. for 12 h, quenched with O$_2$, and extracted with methylene chloride Example 17—HDPE+Zr(CH$_2$CMe$_3$)$_2$@SiO$_2$+AlEt$_3$ (Table 1, Entry 14)

HDPE (0.41 g), Zr(CH$_2$CMe$_3$)$_2$@SiO$_2$ (0.05 g, 0.019 mmol Zr) and AlEt$_3$ (50 µL, 0.36 mmol) were allowed to react at 200° C. for 12 h to provide an oil (0.13 g, 33%) and a residual solid (0.29 g). FIGS. 73-77 show the characterization of the oil isolated after reaction of HDPE and AlEt$_3$ in the presence of Zr(CH$_2$CMe$_3$)$_2$@SiO$_2$ at 200° C. for 12 h, quenched with O$_2$, and extracted with methylene chloride.

Example 18—HDPE Grocery Bag+Zr(CH$_2$CMe$_3$)$_2$@SiAlO$_x$+AliBu$_3$ (Table 1, Entry 15)

HDPE from a plastic grocery bag (0.60 g), Zr(CH$_2$CMe$_3$)$_2$@SiAlO$_x$ (0.10 g, 0.03 mmol Zr) and AliBu$_3$ (100 µL, 0.40 mmol) were allowed to react at 200° C. for 12 h to provide an oil (0.19 g, 31%) and a residual polymeric solid (0.41 g). FIGS. 78-82 show the characterization of the oil isolated after reaction of a post-consumer HDPE plastic grocery bag and AliBu$_3$ in the presence of Zr(CH$_2$CMe$_3$)$_2$@SiAlO$_x$ at 200° C. for 12 h, quenched with O$_2$, and extracted with methylene chloride.

Example 19—Isotactic Polypropylene+Zr(CH$_2$CMe$_3$)$_2$@SiAlO$_x$+AliBu$_3$ (Table 1, Entry 16)

Isotactic polypropylene (iPP) (1.00 g), Zr(CH$_2$CMe$_3$)$_2$@SiAlO$_x$ (0.14 g, 0.042 mmol Zr) and AliBu$_3$ (120 μL, 0.48 mmol) were allowed to react at 200° C. for 12 h to provide an oil (0.27 g, 27%) and a residual polymeric solid (0.74 g). FIGS. 83-87 show the characterization of the oil isolated after reaction of isotactic polypropylene and AliBu$_3$ in the presence of Zr(CH$_2$CMe$_3$)$_2$@SiAlO$_x$ at 200° C. for 12 h, quenched with O$_2$, and extracted with methylene chloride.

Example 20—HDPE+Zr(OCH$_2$CMe$_3$)$_2$@SiAlO$_x$+AlH$_3$ (Under Dynamic Vacuum) (Table 1, Entry 17)

Zr(CH$_2$CMe$_3$)$_3$@SiAlO$_x$ (0.12 g, 0.036 mmol Zr) was exposed to dry air for 10 min at room temperature to provide Zr(OCH$_2$CMe$_3$)$_2$@SiAlO$_x$. HDPE (0.85 g), Zr(OCH$_2$CMe$_3$)$_2$@SiAlO$_x$, and AlH$_3$ (29 mg, 0.97 mmol) were allowed to react at 200° C. under dynamic vacuum for 12 h to provide an oil (0.51 g, 60%) and residual HDPE (0.30 g). FIGS. 88-92 show the characterization of the oil isolated after reaction of HDPE and AlH$_3$ in the presence of Zr(CH$_2$CMe$_3$)$_2$@SiAlO$_x$ at 200° C. for 12 h under dynamic vacuum, quenched with O$_2$, and extracted with methylene chloride.

A summary of the experimental results of the Zr-catalyzed deconstruction of polyolefins from Examples 4-20 is presented in Table 1.

Example 21—DRIFT IR Experiments on Putative ZrH Surface Species

Generation of ZrH@SiAlO$_x$ and H/D Exchange Experiments

Zr(CH$_2$CMe$_3$)$_2$@SiAlO$_x$ (0.4 g, 0.12 mmol Zr) and Excess AliBu$_3$ (0.5 mL, 1.98 mmol) were added in a glass tube in the glovebox, which was sealed with an UltraTorr fitting to a closed glass tube adapted with a sidearm containing a re-sealable Teflon-glass valve. The sealed vessel was transferred from the glovebox and attached to a Schlenk line. The reactor inserted into an aluminum block and heated at 150° C. for 2 h. The reactor was then cooled to room temperature, evacuated, taken back into the glovebox, washed with anhydrous pentane (3×2 mL) and dried in vacuo to provide a brown powder, which was sampled and analyzed by DRIFT IR spectroscopy (FIG. 93A). The reactor was reattached to a Schlenk line and evacuated, D$_2$ gas was introduced at atmospheric pressure, and the reactor was sealed. The tube was heated at 70° C. for 30 min, allowed to cool, taken into the glovebox, and a sample was analyzed by DRIFT IR spectroscopy (FIG. 93B). Subsequently, this material was sealed under an atmosphere of H$_2$, heated at 70° C. for 30 min, and analyzed by DRIFT IR spectroscopy (FIG. 93C).

The spectrum in FIG. 93A contained a broad and prominent peak at 1622 cm$^{-1}$, attributed to a Zr—H stretching mode ($v_{ZrH}$) based on related assignments in literature reports. This signal disappeared upon treatment of the material with D$_2$, indicating that the original band at 1622 cm$^{-1}$ was indeed from a hydride species. Alternatively, the signal at 1622 cm$^{-1}$ is reduced by exposure of the material to ambient atmosphere. To rule out adventitious air or moisture in the deuterium exchange experiment, the isotopically labeled material was treated with H$_2$ to regenerate the

TABLE 1

Zr-catalyzed deconstruction of polyolefins into fatty alcohols, acids, iodides, or alkanes.

| entry[a] | Polymer mass[b] (g) | AlR$_3$ | Catalyst | T (° C.) | Oil yield g (%)[c] | Percentage of functionalized molecules |
|---|---|---|---|---|---|---|
| 1 | 0.63 | AliBu$_3$ | Zr(CH$_2$CMe$_3$)$_2$@SiAlO$_x$ | 150 | 0.19 (31%) | 71 |
| 2 | 1.00 | AliBu$_3$ | Zr(CH$_2$CMe$_3$)$_2$@SiAlO$_x$ | 200 | 0.40 (40%) | 68 |
| 3 | 1.00[d] | AliBu$_3$ | Zr(CH$_2$CMe$_3$)$_2$@SiAlO$_x$ | 200 | 0.84 (84%) | 66 |
| 4 | 1.00[e] | AliBu$_3$ | Zr(CH$_2$CMe$_3$)$_2$@SiAlO$_x$ | 200 | 0.38 (38%) | NA |
| 5 | 0.54[f] | AliBu$_3$ | Zr(CH$_2$CMe$_3$)$_2$@SiAlO$_x$ | 200 | 0.23 (43%) | 68 |
| 6 | 0.55[g] | AliBu$_3$ | Zr(CH$_2$CMe$_3$)$_2$@SiAlO$_x$ | 200 | 0.20 (36%) | 75 |
| 7 | 0.51 | AlEt$_3$ | Zr(CH$_2$CMe$_3$)$_2$@SiAlO$_x$ | 150 | 0.13 (25%) | 39 |
| 8 | 0.60 | AlEt$_3$ | Zr(CH$_2$CMe$_3$)$_2$@SiAlO$_x$ | 200 | 0.15 (24%) | 54 |
| 9 | 0.64 | AlPh$_3$ | Zr(CH$_2$CMe$_3$)$_2$@SiAlO$_x$ | 200 | 0.19 (29%) | 66 |
| 10 | 0.52 | AlH$_3$ | Zr(CH$_2$CMe$_3$)$_2$@SiAlO$_x$ | 200 | 0.22 (42%) | 89 |
| 11 | 0.60 | AliBu$_3$ | Zr(OCH$_2$CMe$_3$)$_2$@SiAlO$_x$ | 200 | 0.21 (34%) | 51 |
| 12 | 0.35 | AlH$_3$ | Zr(OCH$_2$CMe$_3$)$_2$@SiAlO$_x$ | 200 | 0.17 (49%) | 62 |
| 13 | 1.00 | AliBu$_3$ | Zr(CH$_2$CMe$_3$)$_2$@SiO$_2$ | 200 | 0.35 (35%) | 85 |
| 14 | 0.41 | AlEt$_3$ | Zr(CH$_2$CMe$_3$)$_2$@SiO$_2$ | 200 | 0.13 (33%) | 82 |
| 15 | 0.60[h] | AliBu$_3$ | Zr(CH$_2$CMe$_3$)$_2$@SiAlO$_x$ | 200 | 0.19 (31%) | 60 |
| 16 | 1.00[i] | AliBu$_3$ | Zr(CH$_2$CMe$_3$)$_2$@SiAlO$_x$ | 200 | 0.27 (27%) | NA |
| 17 | 0.85[j] | AlH$_3$ | Zr(OCH$_2$CMe$_3$)$_2$@SiAlO$_x$ | 200 | 0.51 (60%) | 67 |

[a]Standard conditions: 21 kg HDPE/mol Zr, Al:Zr = 10:1, 150-200° C., 12 h, followed by O$_2$ quench to give fatty alcohols.
[b]HDPE: M$_n$ = 6.2 kDa, M$_w$ = 38.6 kDa, Đ = 6.2.
[c]yield = mass of oil/mass of PO.
[d]3 portions of Zr(CH$_2$CMe$_3$)$_2$@SiAlO$_x$/AliBu$_3$ were added over 36 h.
[e]Quenched with MeOH to give saturated hydrocarbon products.
[f]Quenched with I$_2$ to provide long chain alkyl iodides.
[g]Quenched with CO$_2$ to form fatty acids.
[h]post-consumer HDPE: M$_n$ = 5.3 kDa, M$_w$ = 10.5 kDa, Đ = 19.8.
[i]iPP: M$_n$ = 37.4 kDa, M$_w$ = 117.6 kDa, Đ = 3.2. Quantitative estimation of functional group analysis of the product is not possible due to quaternary carbon centers.
[j]Performed under dynamic vacuum hydride signal at 1622 cm$^{-1}$ and confirm the presence of an active hydride species in the material. Because SiAlO$_x$ and AliBu$_3$ are not catalytically competent for C—C cleavage of HDPE in the absence of surface-supported Zr species, the IR signal at 1622 cm$^{-1}$ was assigned to a catalytically active Zr—H surface species generated from the reaction of zirconium neopentyl and triisobutylaluminum. However, it is not possible to rule out the presence of a bridged bimetallic species containing Zr—H—Al structures, which could also mediate metalation of polyethylene and β-alkyl elimination because the IR bands of this and Zr—H species overlap (Joubert et al., "Synthesis, Characterization, and Catalytic Properties of γ-Al$_2$O$_3$-Supported Zirconium Hydrides through a Combined Use of Surface Organometallic Chemistry and Periodic Calculations," *Organometallics* 26:3329-3335 (2007), which is hereby incorporated by reference in its entirety).

In a second experiment, Zr(CH$_2$CMe$_3$)$_2$@SiAlO$_x$ and 3 equiv. of AliBu$_3$ were allowed to react at room temperature in benzene-d$_6$, and the soluble portion of the reaction mixture was analyzed by $^1$H NMR spectroscopy (FIG. 94). The analysis reveals neopentyl aluminum, isobutylene, neopentane, and isobutane are formed. Neopentyl aluminum species indicate alkyl transfer from neopentyl zirconium to aluminum, either via alkyl group exchange or by alkyl/0-hydride exchange. The former would produce isobutylzirconium species, which could undergo β-hydrogen elimination to form hydridozirconium surface sites and isobutylene, while the latter pathway would produce hydridozirconium surface sites and isobutylene directly.

Experiments Ruling Out Ethylene Oligomerization as Route to Fatty Alcohols

As alternative pathway to fatty aluminum species, terminal polymerylzirconium species, formed by metalation of chain ends or by β-alkyl elimination, could also react by β-alkyl elimination to generate ethylene. This thermodynamically unfavorable step, the microscopic reverse of ethylene insertion during polymerization, could be coupled to an exothermic catalytic ethylene oligomerization that provides the medium length chains of the alkyl aluminum or alkane products (FIG. 95). Independent oligomerization or polymerization experiments involving small amounts of ethylene, Zr(CH$_2$CMe$_3$)$_3$@SiAlO$_x$, and AliBu$_3$ do not give fatty alcohol-range molecular weight species. Thus, a sequence to oils involving HDPE depolymerization to ethylene followed by oligomerization was ruled out, although ethylene formation and re-insertion is not ruled out by this experiment.

Discussion of Examples

The first experiments employed Zr(CH$_2$CMe$_3$)$_2$@SiAlO$_x$ (2.7 wt % Zr, 0.30 mmol Zr/g), which was prepared by grafting Zr(CH$_2$CMe$_3$)$_4$ onto partially dehydroxylated silica-alumina (0.38 mmol SiOH/g, 9.3 wt % Al) in pentane (Quignard et al., "Surface Organometallic Chemistry: Synthesis and Characterization of a Tris(neopentyl)zirconium (IV) Complex Grafted to the Surface of a Partially Dehydroxylated Silica," *Inorg. Chem.* 31:928-930 (1992); Wang et al., "Preparation and Characterization of Zirconium Containing Mesoporous Silicas. II. Grafting Reaction of Tetraneopentyl Zirconium on MCM-41 and Characterization of the Grafted Species and of the Resulting Materials," *Microporous Mesoporous Mater* 66:169-179 (2003); Tosin et al., "Reactivity of Tetraneopentylhafnium, Hf(CH$_2$tBu)$_4$, with Silica Surfaces," *Organometallics* 25:3324-3335 (2006), which are hereby incorporated by reference in their entirety). HDPE and AliBu$_3$ react in the presence of this precatalyst over 12 h at 150° C. to give, after quenching with O$_2$ and workup, an oil containing fatty alcohols and alkanes (31% yield by mass; Scheme 1; Table 1, entry 1).

Scheme 1

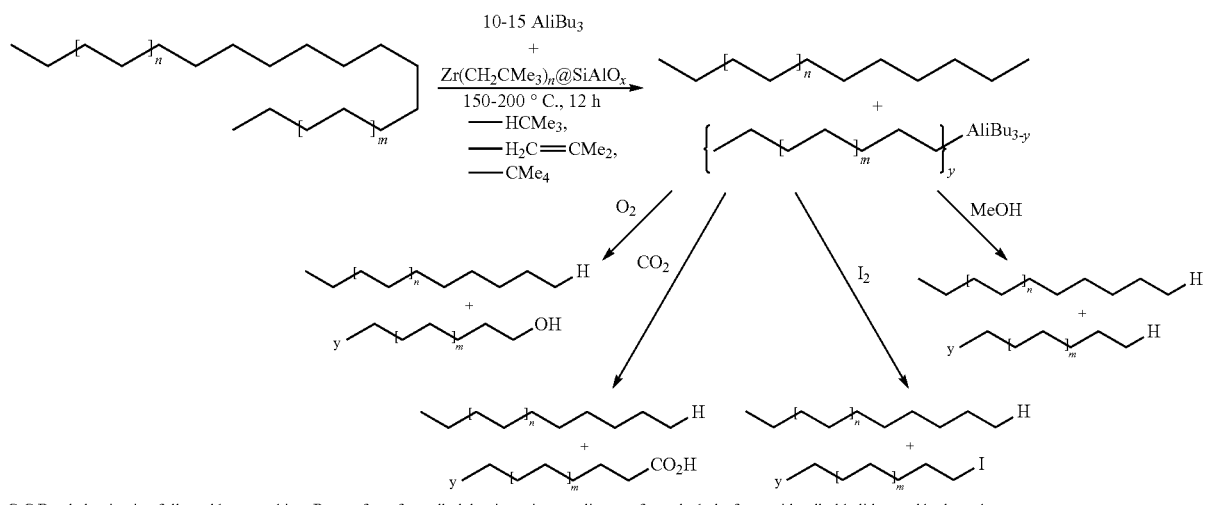

C-C Bond alumination followed by quenching: Routes from fatty alkylaluminum intermediates to fatty alcohols, fatty acids, alkyl halides, and hydrocarbons.

Under the reaction conditions, the HDPE is melted and mixed by magnetic stirring. The isolated reaction products were analyzed by infrared (IR) and NMR spectroscopy, matrix assisted laser desorption ionization-time of flight-mass spectrometry (MALDI-TOF-MS), and gas chromatography (GC)-MS. In the product analysis, detected fatty alcohols correspond to the alkylaluminum species and any active alkylzirconium sites present in the reaction mixture, prior to quenching with O$_2$, whereas functional group-free hydrocarbons are formed prior to quenching.

Figure 6:
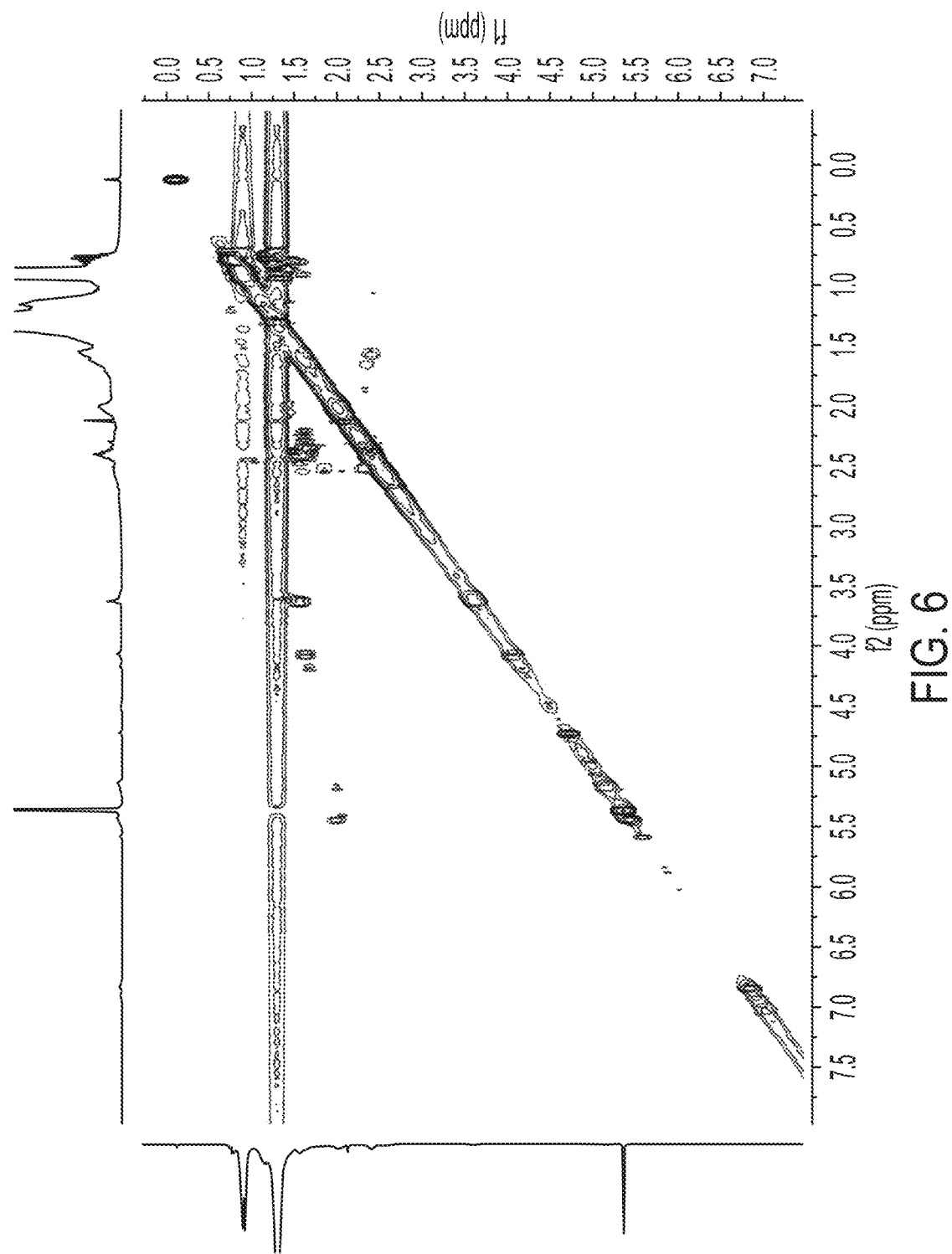
FIG. 6 is the COSY spectrum of the oil isolated after reaction of HDPE and $AliBu_3$ in the presence of $Zr(CH_2CMe_3)_2$@$SiAlO_x$ at 150° C. for 12 h, quenched with $O_2$, and extracted with methylene chloride. The spectrum was acquired at room temperature in methylene chloride-$d_2$. Cross-peaks at 3.5-5.5 ppm correlate with methylene signals at 1.6-2.2 ppm indicative of —$CH_2$—$CH_2$—OH species.
Figure 7:
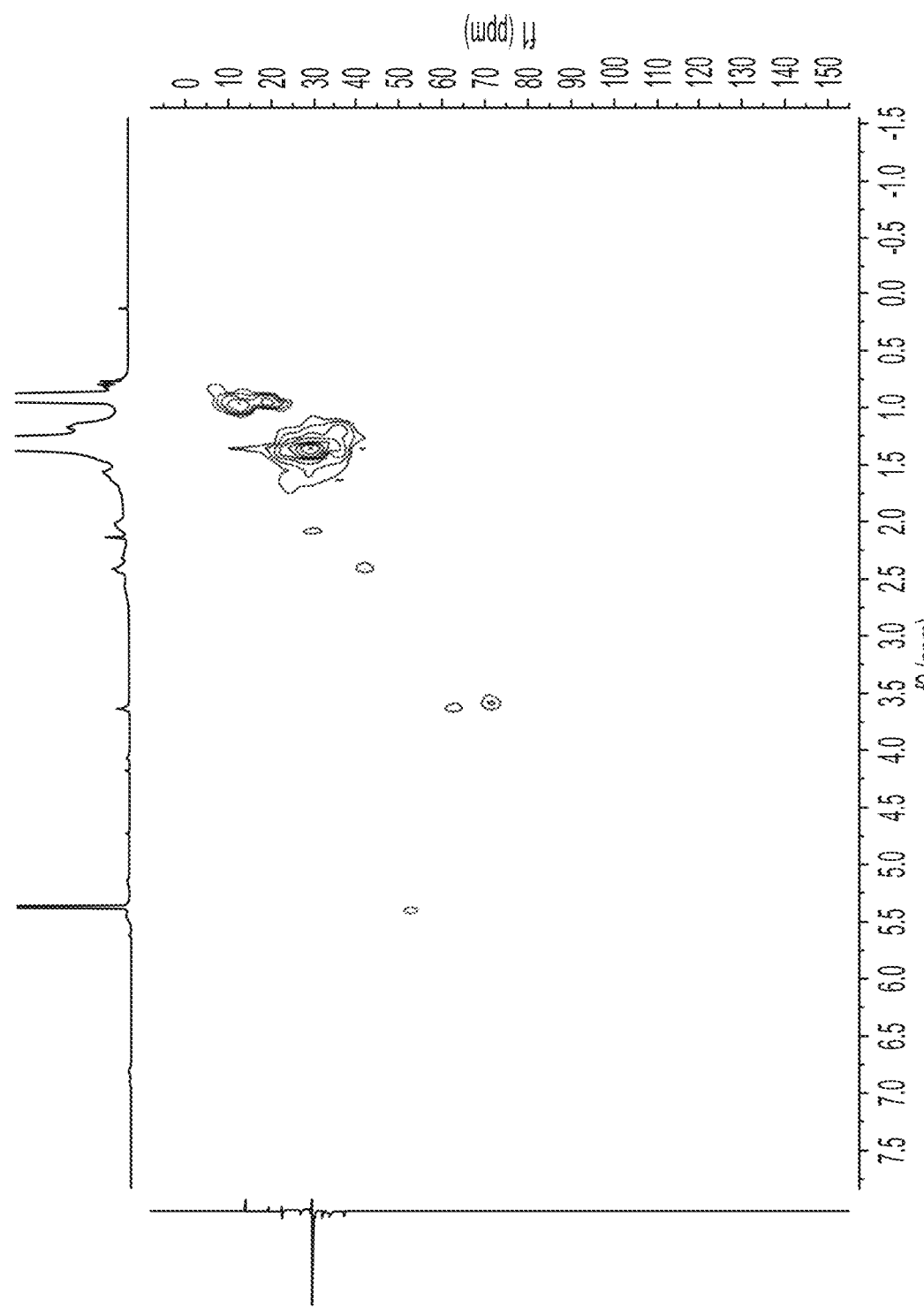
FIG. 7 is the phase sensitive $^1H$-$^{13}C$ HSQC spectrum of the oil isolated after reaction of HDPE and $AliBu_3$ in the presence of $Zr(CH_2CMe_3)_2$@$SiAlO_x$ at 150° C. for 12 h, quenched with $O_2$, and extracted with methylene chloride. The spectrum was acquired at room temperature in methylene chloride-$d_2$. The large polymer chain methylene peaks at $^{13}C$ 30 ppm have the same phase as cross-peaks at $^{13}C$ 60-70 ppm, allowing assignment of the latter to primary alcohols —$CH_2$—OH.
Figure 8:
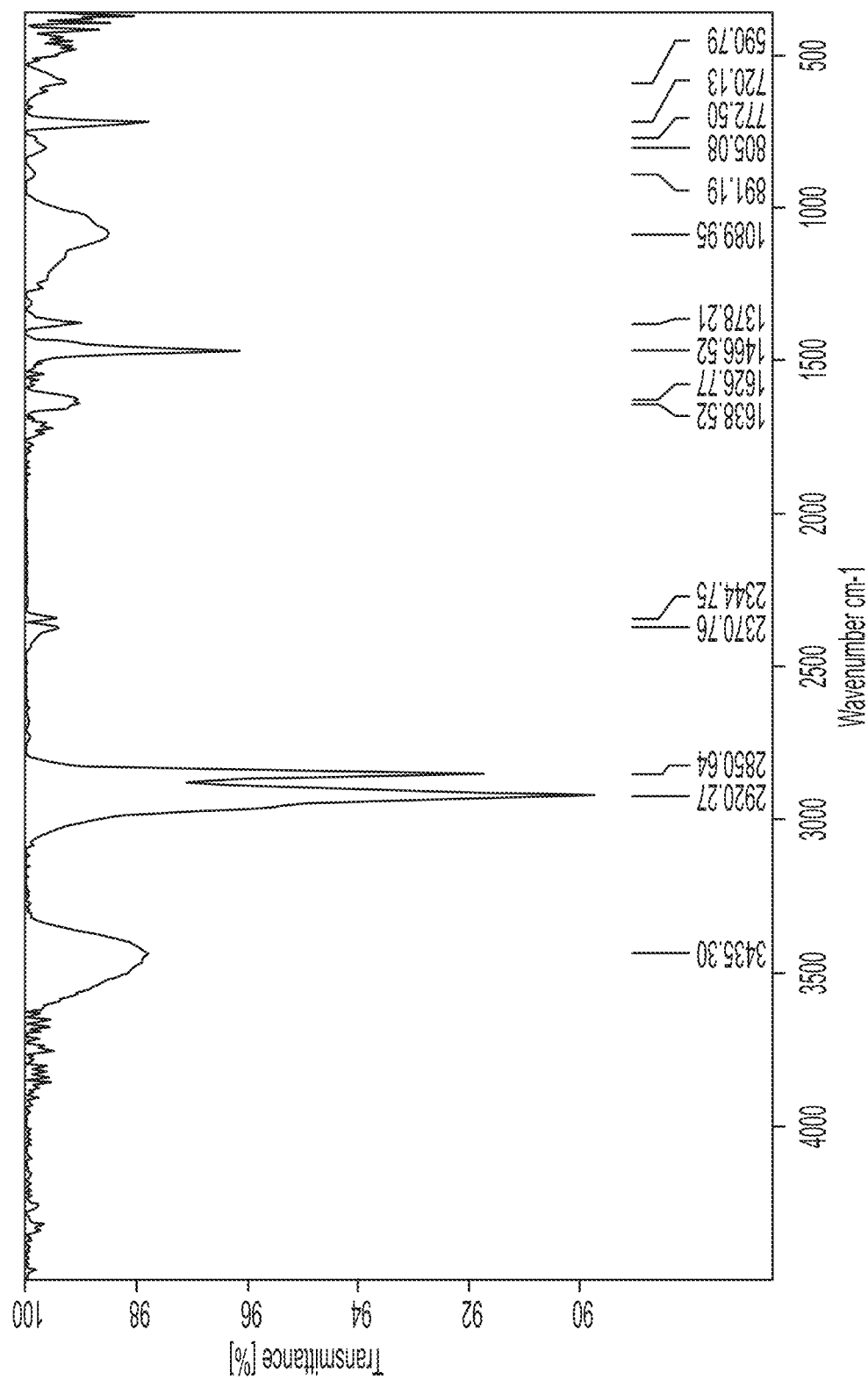
FIG. 8 is the FT-IR spectrum (KBr) of the oil isolated after reaction of HDPE and $AliBu_3$ in the presence of $Zr(CH_2CMe_3)_2$@$SiAlO_x$ at 150° C. for 12 h, quenched with O$_2$, and extracted with methylene chloride. The broad signal at 3435 cm$^{-1}$ corresponds to an O—H stretch.

First, an IR spectrum of the isolated oil revealed broad signals at 3430 and 1090 cm$^{-1}$, characteristic of $v_{O-H}$ and $v_{C-O}$ (FIG. 8). The $^1$H NMR spectrum of the oil contained resonances at ca. 3.6 ppm assigned to $CH_2OH$ in primary alcohols (FIG. 5), which correlated in a COSY experiment with the aliphatic hydrocarbon signals at 1.6 ppm (FIG. 6). The $^1H$ NMR signal at 3.6 ppm also correlated with $^{13}C$ NMR signals at 60-70 ppm in a phase-sensitive $^1H$-$^{13}C$ HSQC experiment, further supporting the —$CH_2OH$ assignment (FIG. 7). These crosspeaks appear with the same phase as those at 30 ppm assigned to the $CH_2$ signals from the polyethylene backbone and opposite phase to cross-peaks at 13 ppm assigned to methyl groups. These data indicate that the alcohols are almost entirely primary. Thus, the direct products of C—C bond cleavage in HDPE are terminal organometallic species. All molecules in the oil are either monoalcohols or alkanes, as shown by MALDI-TOF-MS analysis (see below). Because there is either one or zero OH groups per molecule, the fraction of molecules containing functional groups (in this case, OH) is equal to the fractional number of functional groups per molecule (#FG), which was calculated as the difference between the number of end groups in a chain and the number of methyl chain ends. There are 2 end group in a linear chain, each branch point creates a chain end, and the number of branch points equals the number of methine groups (#CH), giving equation (1):

$$\#FG = 2 + \#CH - \#CH_3 \tag{1}$$

Using integration of the assigned $^1H$ NMR spectrum, the fact that all alcohols are terminal, and assuming that $CMe_2$ groups are insignificant and cyclic species have not formed, this oil contains a mixture 7:3 ratio of monoalcohol:alkane.

Figure 9:
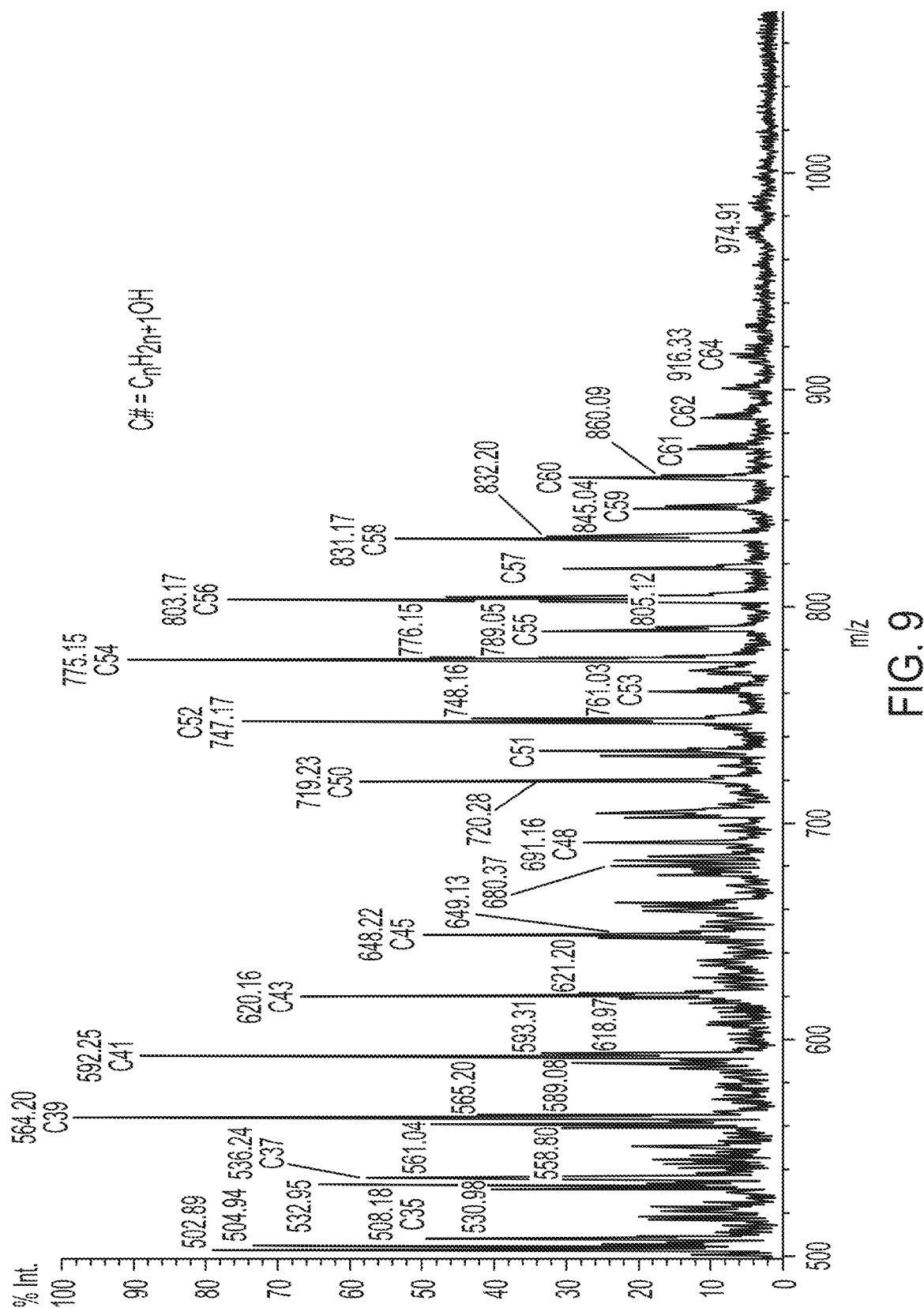
FIG. 9 is the matrix assisted laser desorption ionization-time of flight mass spectrometry (MALDI-TOF-MS) mass spectrum of the oil isolated after reaction of HDPE and AliBu$_3$ in the presence of Zr(CH$_2$CMe$_3$)$_2$@SiAlO$_x$ at 150° C. for 12 h, quenched with O$_2$, and extracted with methylene chloride, acquired in linear, positive mode with AgNO$_3$ (salt) and DHB (matrix).
Figure 10:
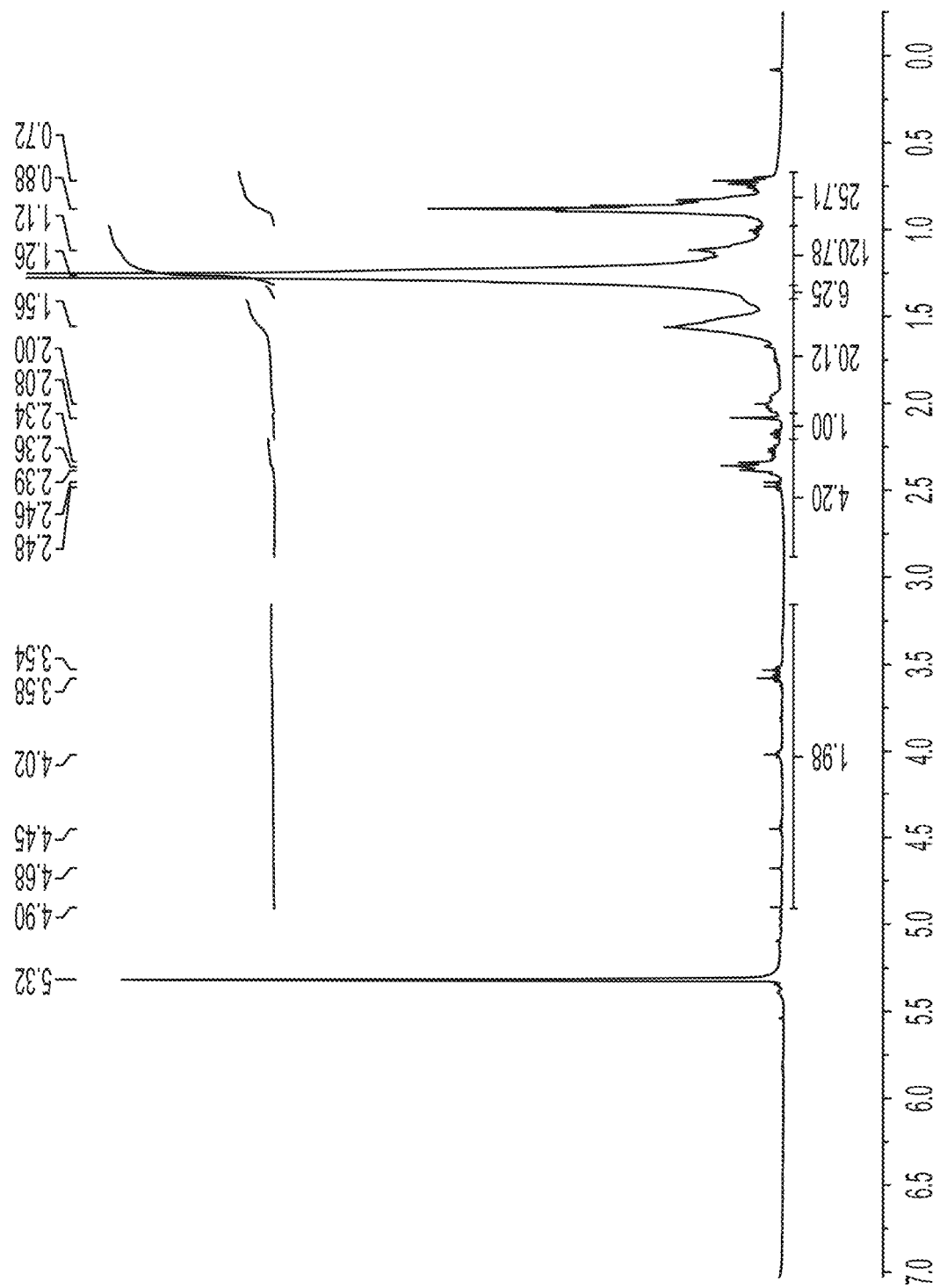
FIG. 10 is the $^1$H NMR spectrum of the oil isolated after reaction of HDPE and AliBu$_3$ in the presence of Zr(CH$_2$CMe$_3$)$_2$@SiAlO$_x$ at 200° C. for 12 h, quenched with O$_2$, and extracted with methylene chloride. The spectrum was acquired at room temperature in methylene chloride-d$_2$ and assigned based on COSY and HSQC experiments in FIGS. 11 and 12. Signals at 0.7-0.9 ppm correspond to methyl groups, peaks at 1.0-2.5 ppm are assigned to methylenes, and those at 1.4 and 2.1 ppm are attributed to methine groups. Peaks at 3.5-5.0 ppm are assigned to —CH$_2$—OH groups.
Figure 11:
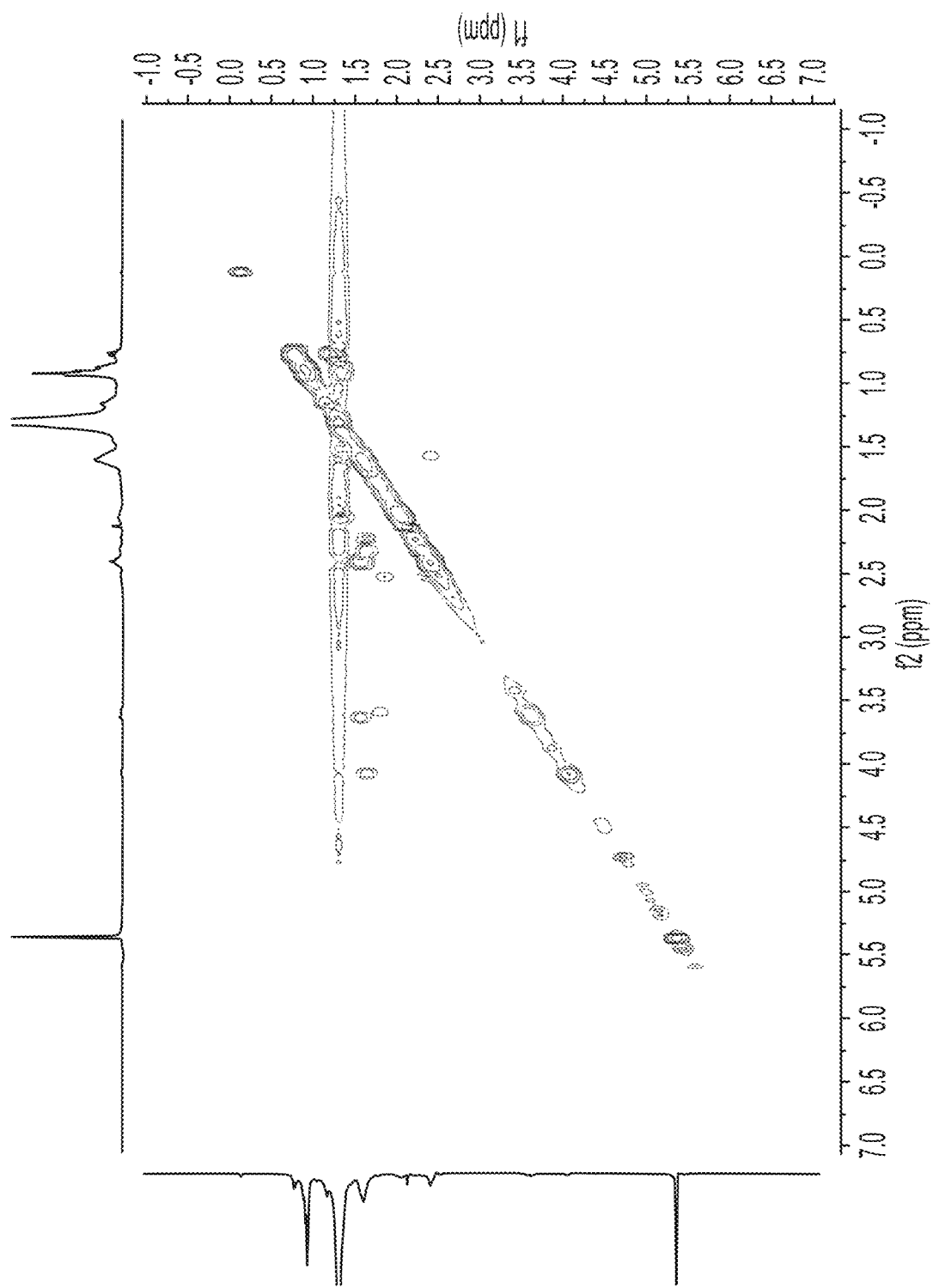
FIG. 11 is the COSY spectrum of the oil isolated after reaction of HDPE and AliBu$_3$ in the presence of Zr(CH$_2$CMe$_3$)$_2$@SiAlO$_x$ at 200° C. for 12 h, quenched with O$_2$, and extracted with methylene chloride. The spectrum was acquired at room temperature in methylene chloride-d$_2$. Cross-peaks at 3.5-4.5 ppm that correspond to methylene peaks at 1.5-2.0 ppm are indicative of —CH$_2$—CH$_2$—OH species.
Figure 12:
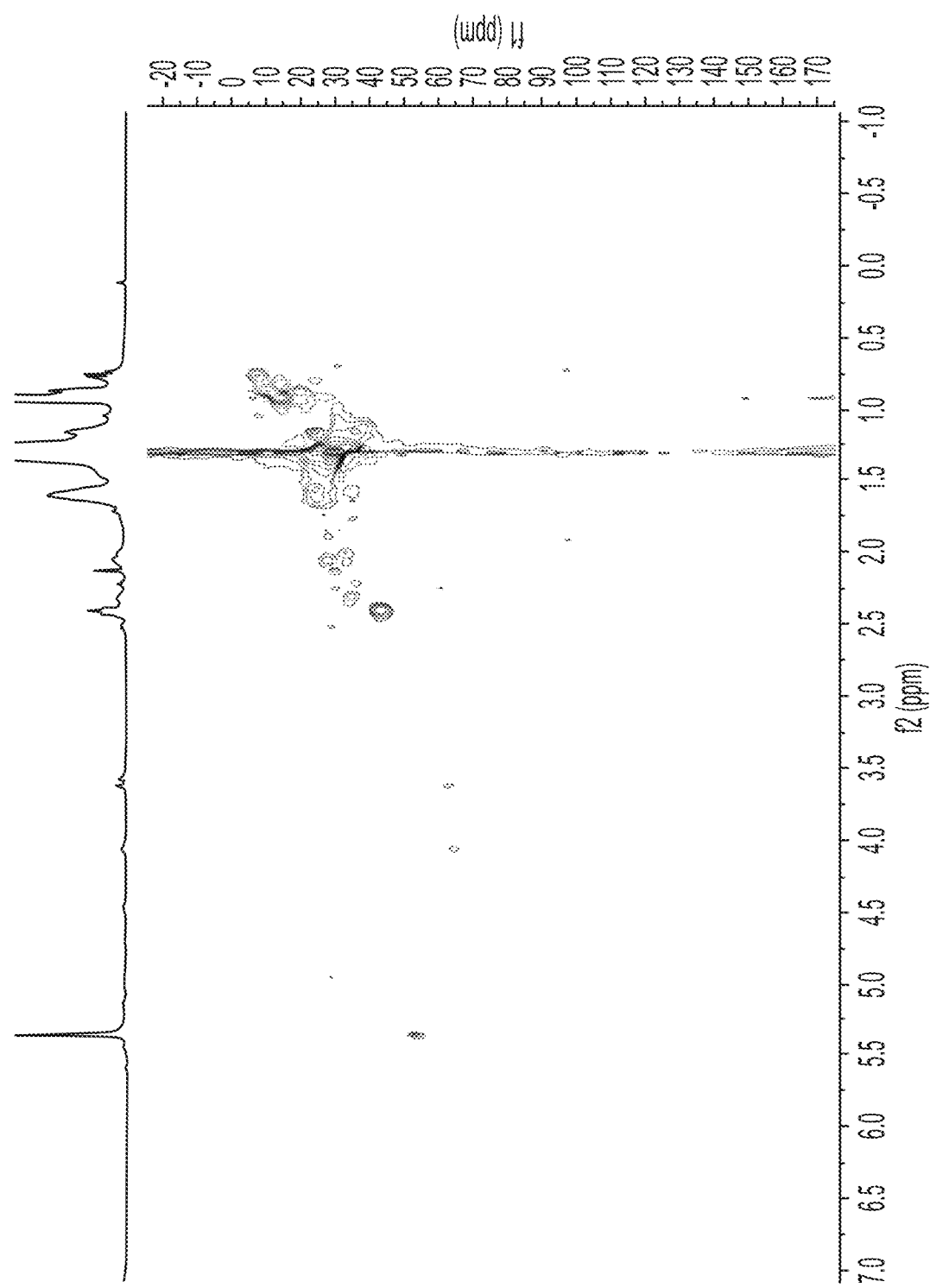
FIG. 12 is the phase sensitive $^1$H-$^{13}$C HSQC spectrum of the oil isolated after reaction of HDPE and AliBu$_3$ in the presence of Zr(CH$_2$CMe$_3$)$_2$@SiAlO$_x$ at 200° C. for 12 h, quenched with O$_2$, and extracted with methylene chloride. The spectrum was acquired at room temperature in methylene chloride-d$_2$. The large peak assigned to polymer methylene CH$_2$ at $^{13}$C 30 ppm has the same phase as cross-peaks at $^{13}$C 60-70 ppm, allowing assignment of the latter to primary alcohols —CH$_2$—OH.
Figure 13:
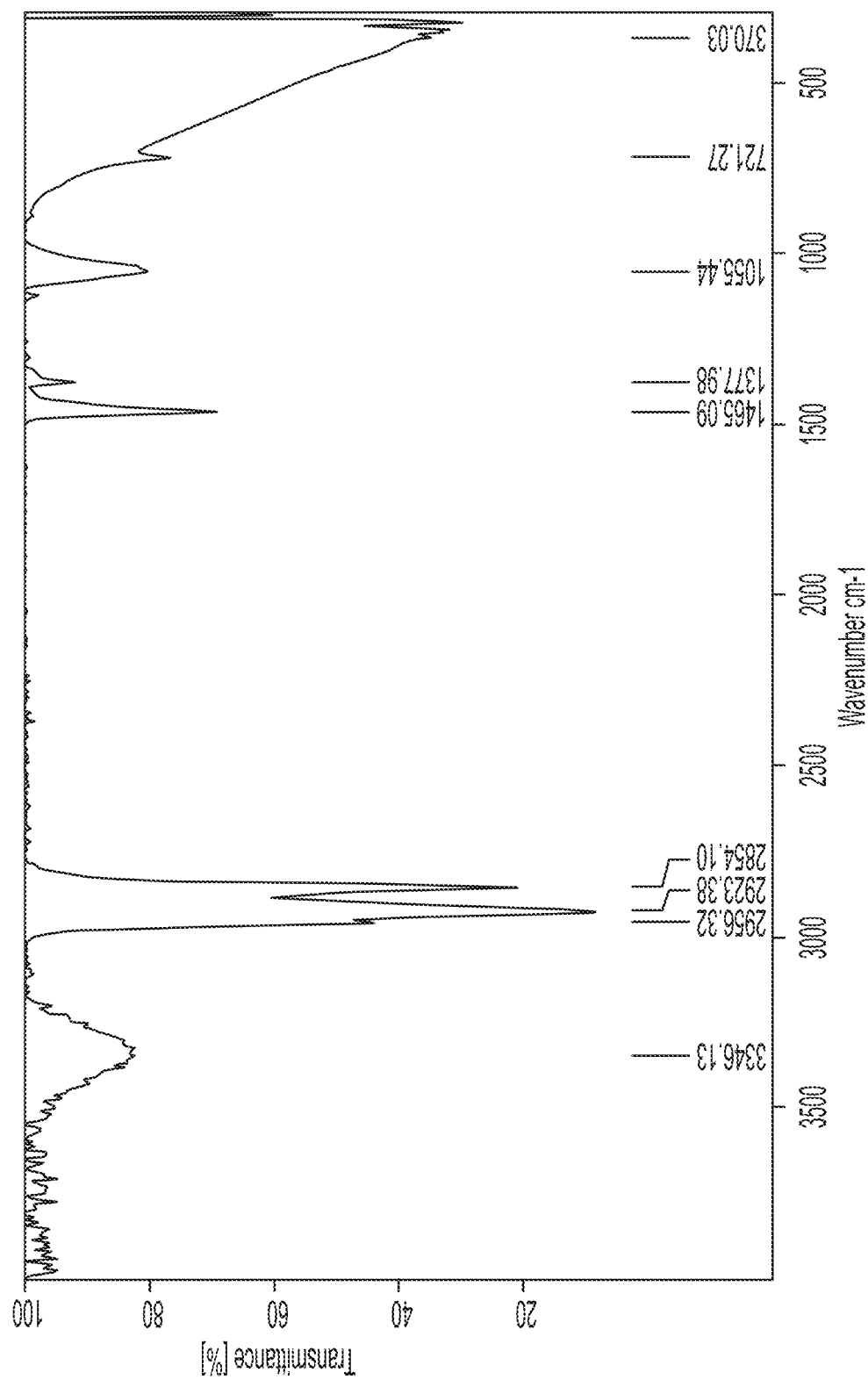
FIG. 13 is the FT-IR spectrum (KBr) of the oil isolated after reaction of HDPE and AliBu$_3$ in the presence of Zr(CH$_2$CMe$_3$)$_2$@SiAlO$_x$ at 200° C. for 12 h, quenched with O$_2$, and extracted with methylene chloride. The broad signal at 3446 cm$^{-1}$ corresponds to the O—H stretching mode.
Figure 14:
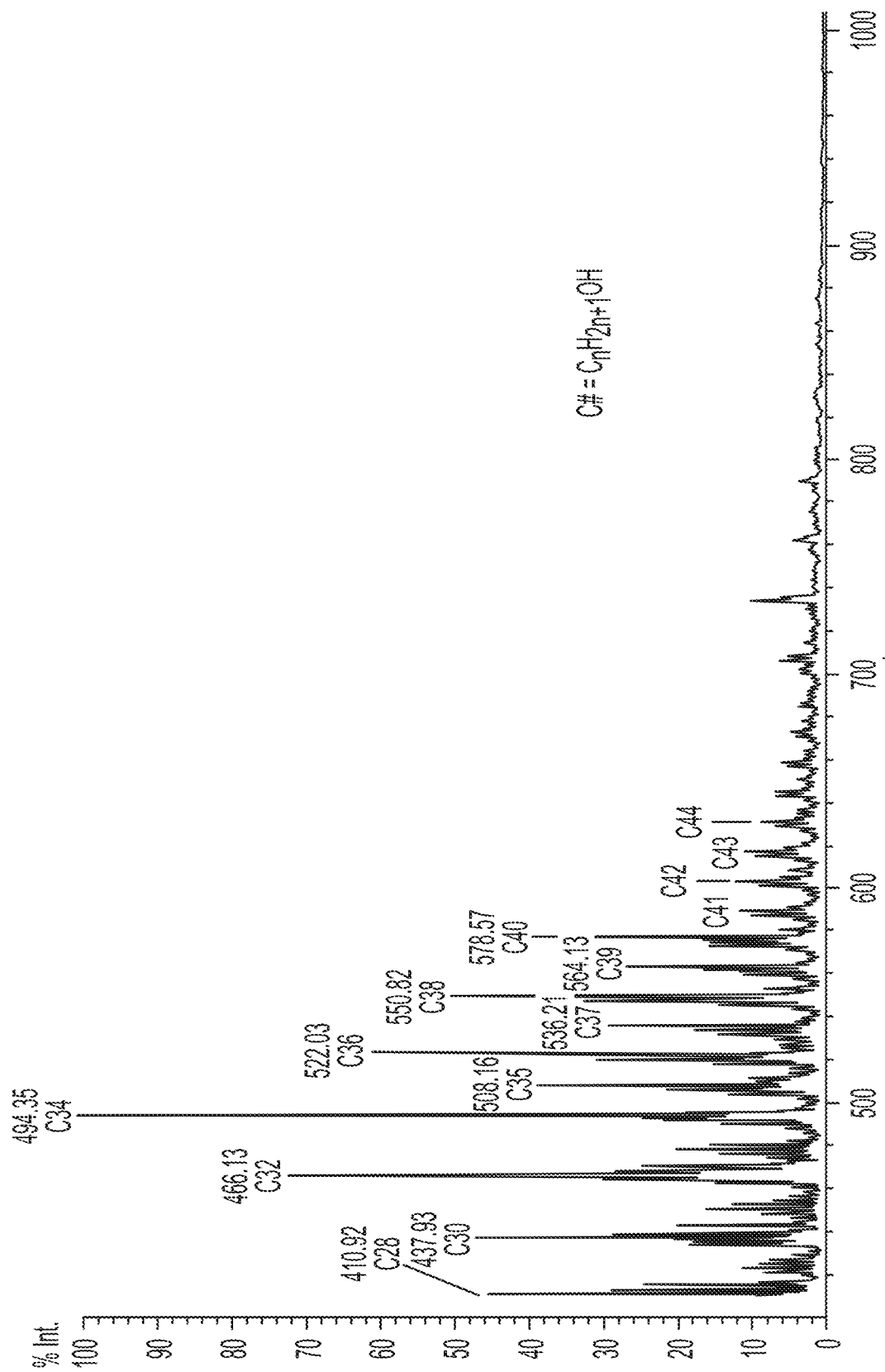
FIG. 14 is the MALDI-TOF-MS of the oil isolated after reaction of HDPE and AliBu$_3$ in the presence of Zr(CH$_2$CMe$_3$)$_2$@SiAlO$_x$ at 200° C. for 12 h, quenched with O$_2$, and extracted with methylene chloride, acquired in linear, positive mode with AgNO$_3$ (salt) and DHB (matrix).
Figure 15:
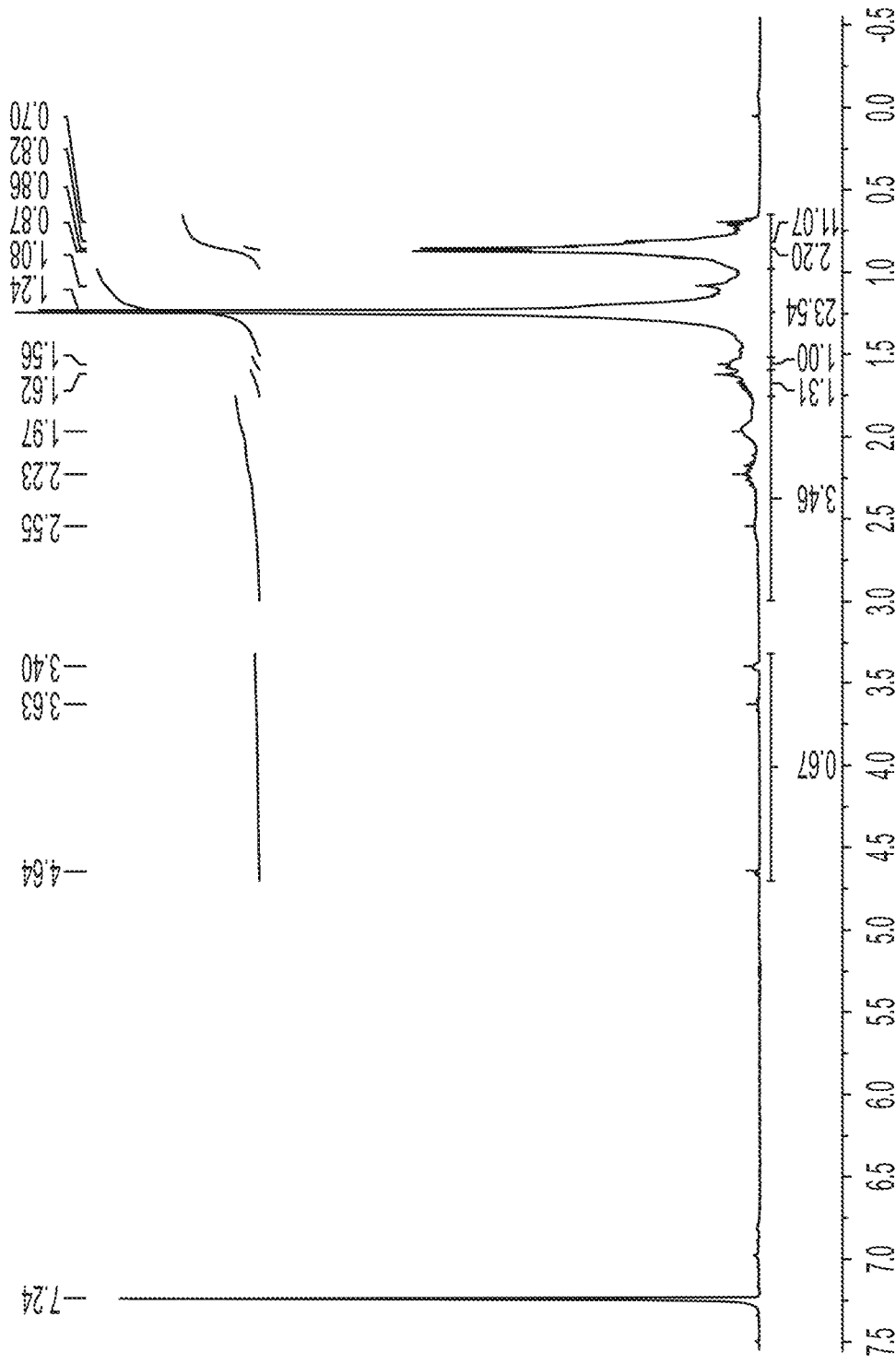
FIG. 15 is the $^1$H NMR spectrum of the oil isolated after reaction of HDPE and AliBu$_3$ in the presence of Zr(CH$_2$CMe$_3$)$_2$@SiAlO$_x$ added at 0, 12, and 24 h, at 200° C., quenched with O$_2$, and extracted with methylene chloride. The spectrum was acquired at room temperature in chloroform-d and assigned based on Total Correlation Spectroscopy (TOCSY) and HSQC experiments in FIGS. 16 and 17. Signals at 0.7-1.0 ppm are attributed to methyl groups, signals at 1.0-1.4 and 1.8-3.0 ppm are assigned to methylene groups, and the peak at 1.8 ppm corresponds to methine species. Peaks at 3.3-4.7 ppm are assigned to —CH$_2$—OH groups.
Figure 16:
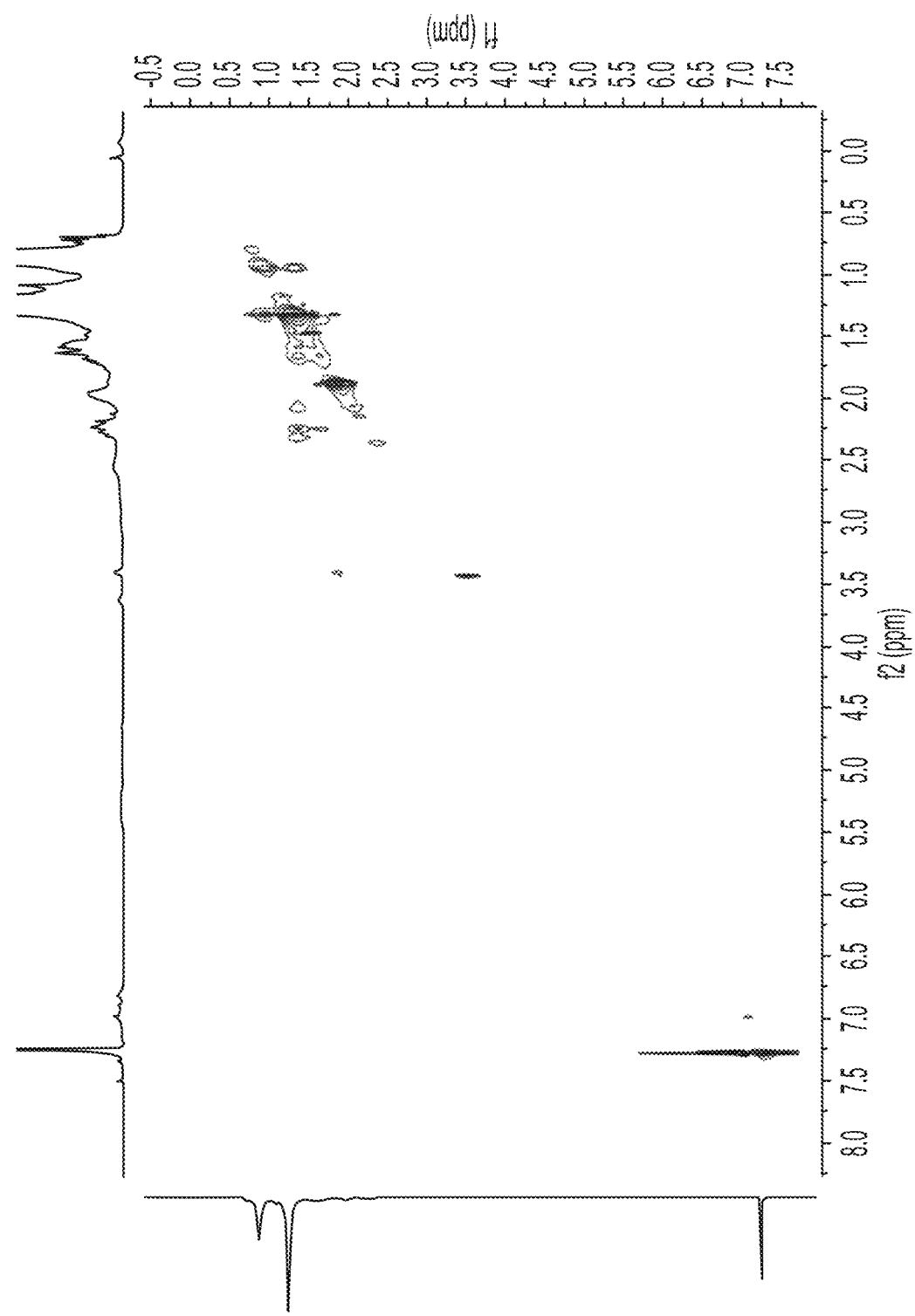
FIG. 16 is the TOCSY spectrum of the oil isolated after reaction of HDPE and AliBu$_3$ in the presence of Zr(CH$_2$CMe$_3$)$_2$@SiAlO$_x$ added at 0, 12, and 24 h, at 200° C., quenched with O$_2$, and extracted with methylene chloride. The spectrum was acquired at room temperature in chloroform-d. Cross-peaks at 3.5 ppm correlate with methylene peaks at 2.0 ppm, which is indicative of —CH$_2$—CH$_2$—OH species.
Figure 17:
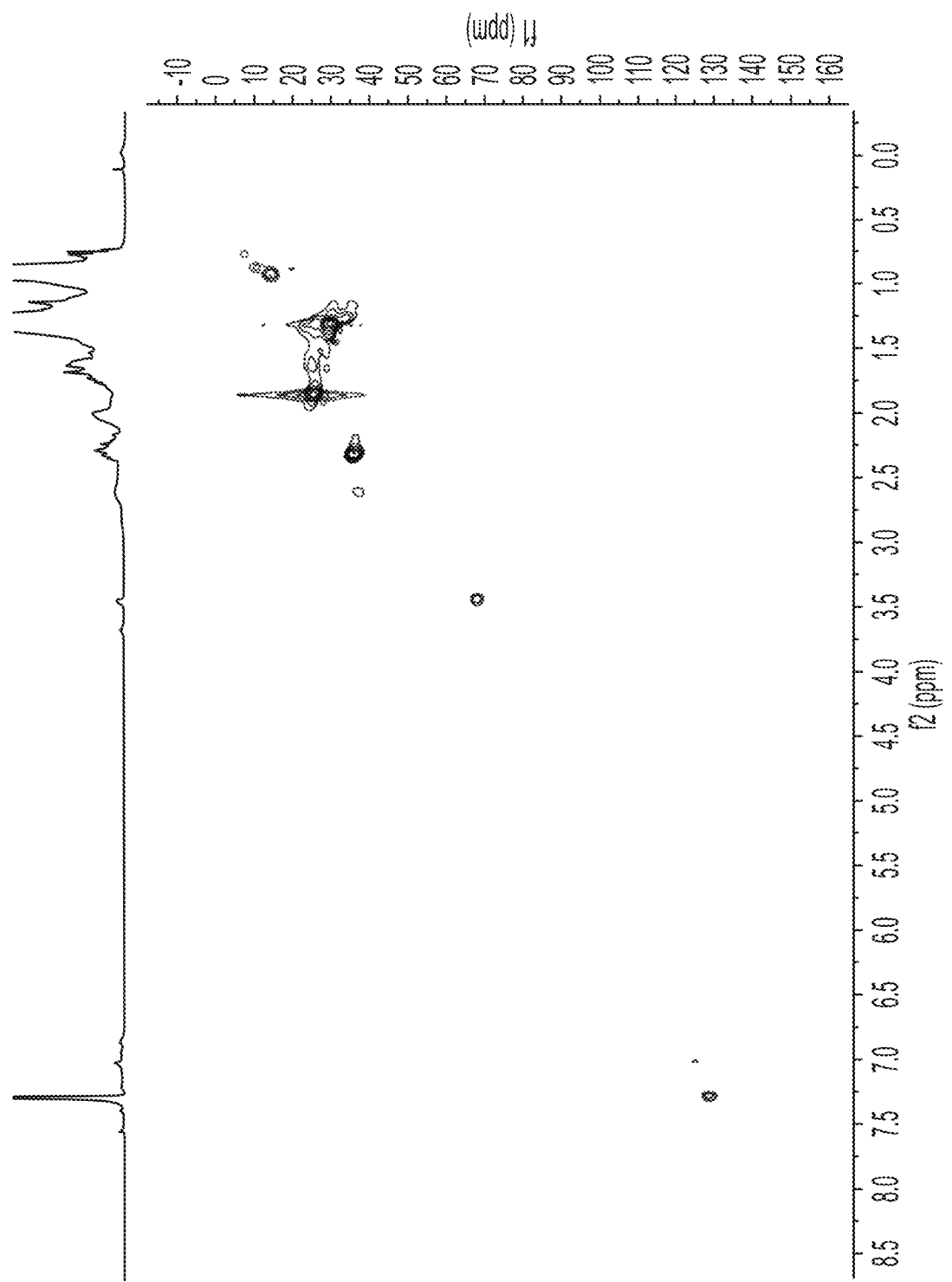
FIG. 17 is the phase sensitive $^1$H-$^{13}$C HSQC spectrum of the oil isolated after reaction of HDPE and AliBu$_3$ in the presence of Zr(CH$_2$CMe$_3$)$_2$@SiAlO$_x$ added at 0, 12, and 24 h, at 200° C., quenched with O$_2$, and extracted with methylene chloride. The spectrum was acquired at room temperature in chloroform-d. The large peak assigned to polymer methylene CH$_2$ at $^{13}$C 30 ppm have the same phase as cross-peaks at $^{13}$C 60-70 ppm, allowing assignment of the latter to primary alcohols —CH$_2$—OH.
Figure 18:
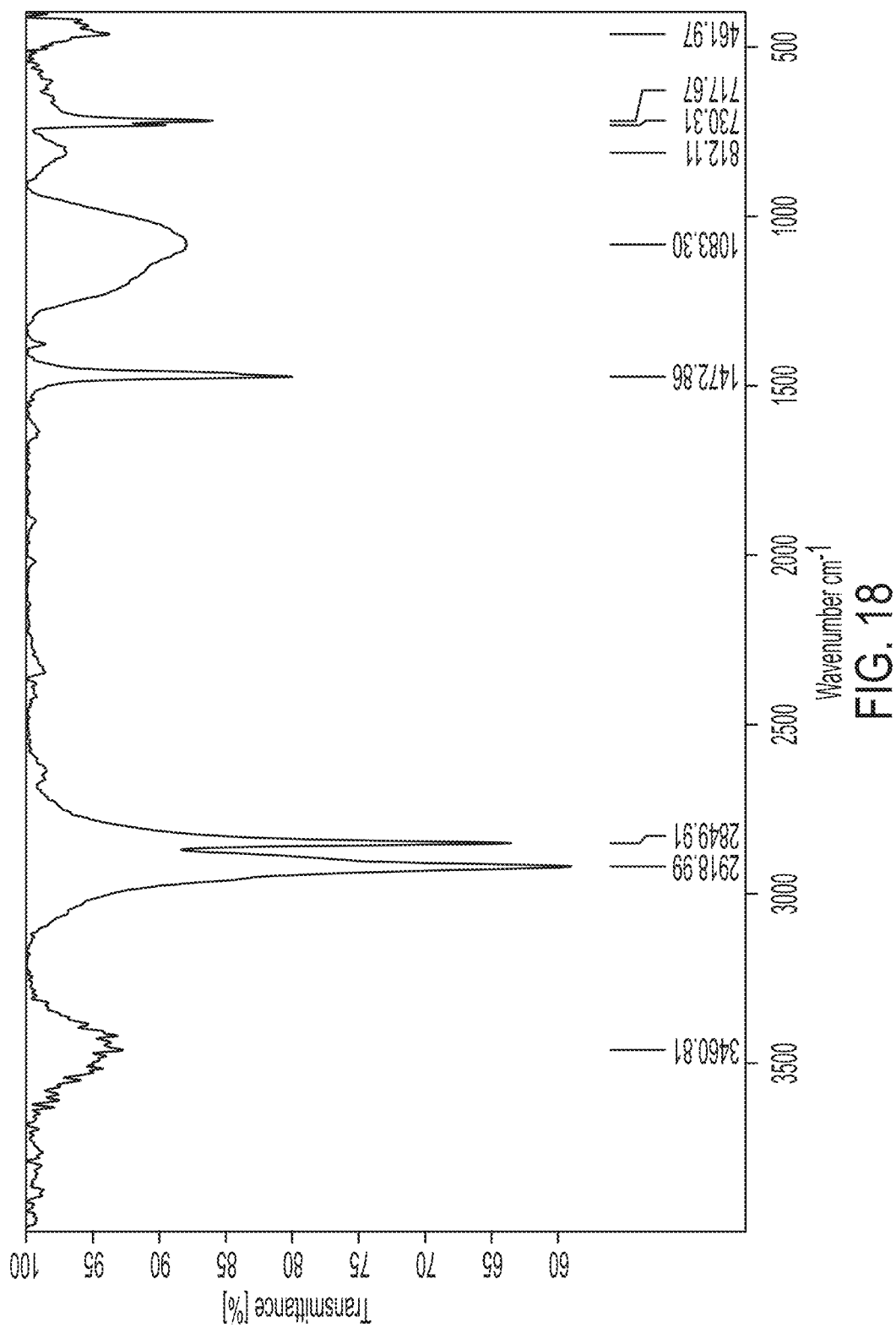
FIG. 18 is the FT-IR spectrum (KBr) of oil isolated after reaction of HDPE and AliBu$_3$ in the presence of Zr(CH$_2$CMe$_3$)$_2$@SiAlO$_x$ added at 0, 12, and 24 h, at 200° C., quenched with O$_2$ and extracted with methylene chloride. The broad signal at 3460 cm$^{-1}$ corresponds to an O—H stretch.
Figure 19:
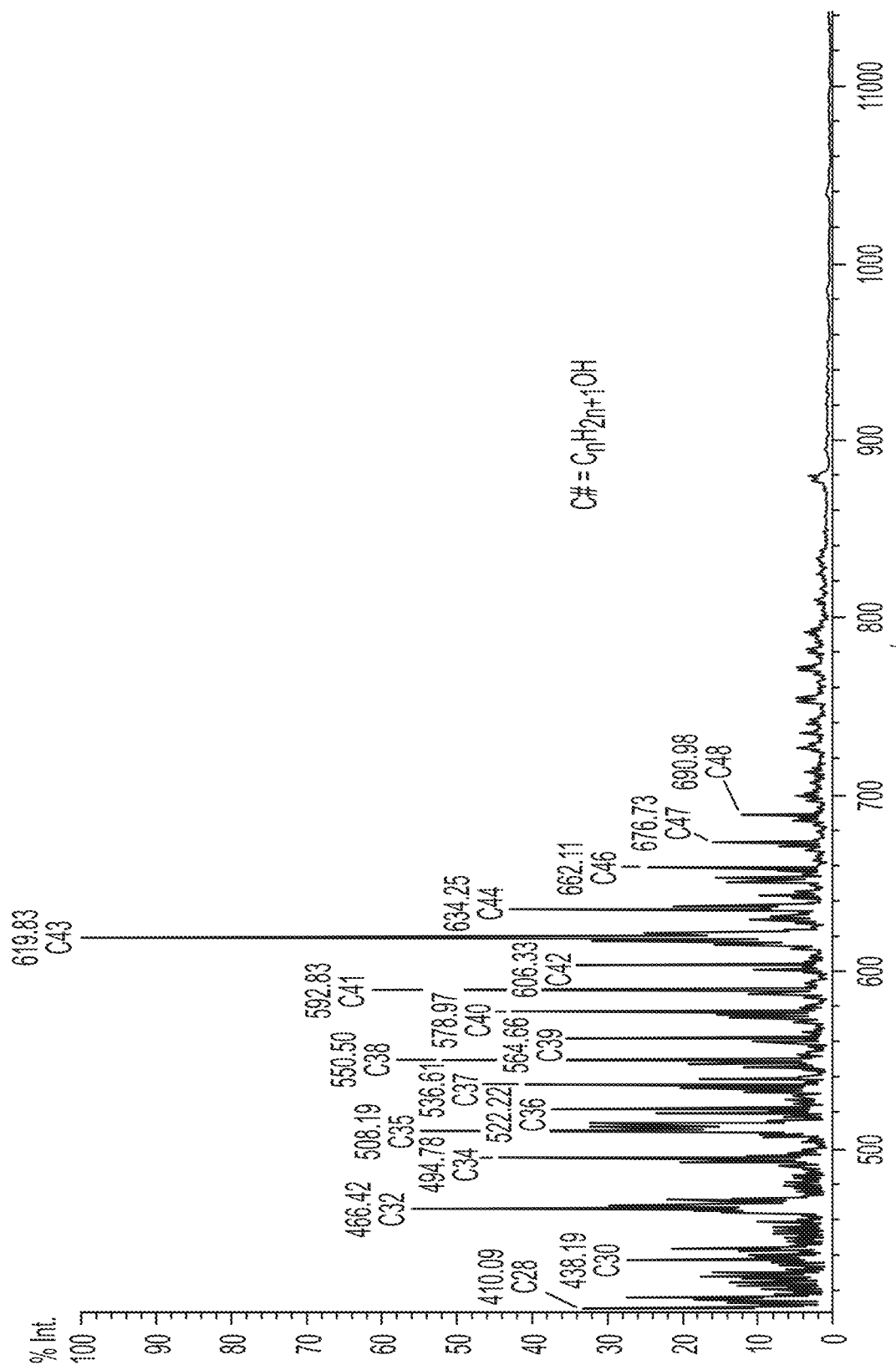
FIG. 19 is the MALDI-TOF-MS of the oil isolated after reaction of HDPE and AliBu$_3$ in the presence of Zr(CH$_2$CMe$_3$)$_2$@SiAlO$_x$ added at 0, 12, and 24 h, at 200° C., quenched with O$_2$, and extracted with methylene chloride. The spectrum was acquired in linear, positive mode with AgNO$_3$ (salt) and DHB (matrix), and alcohols self-ionize readily.
Figure 20:
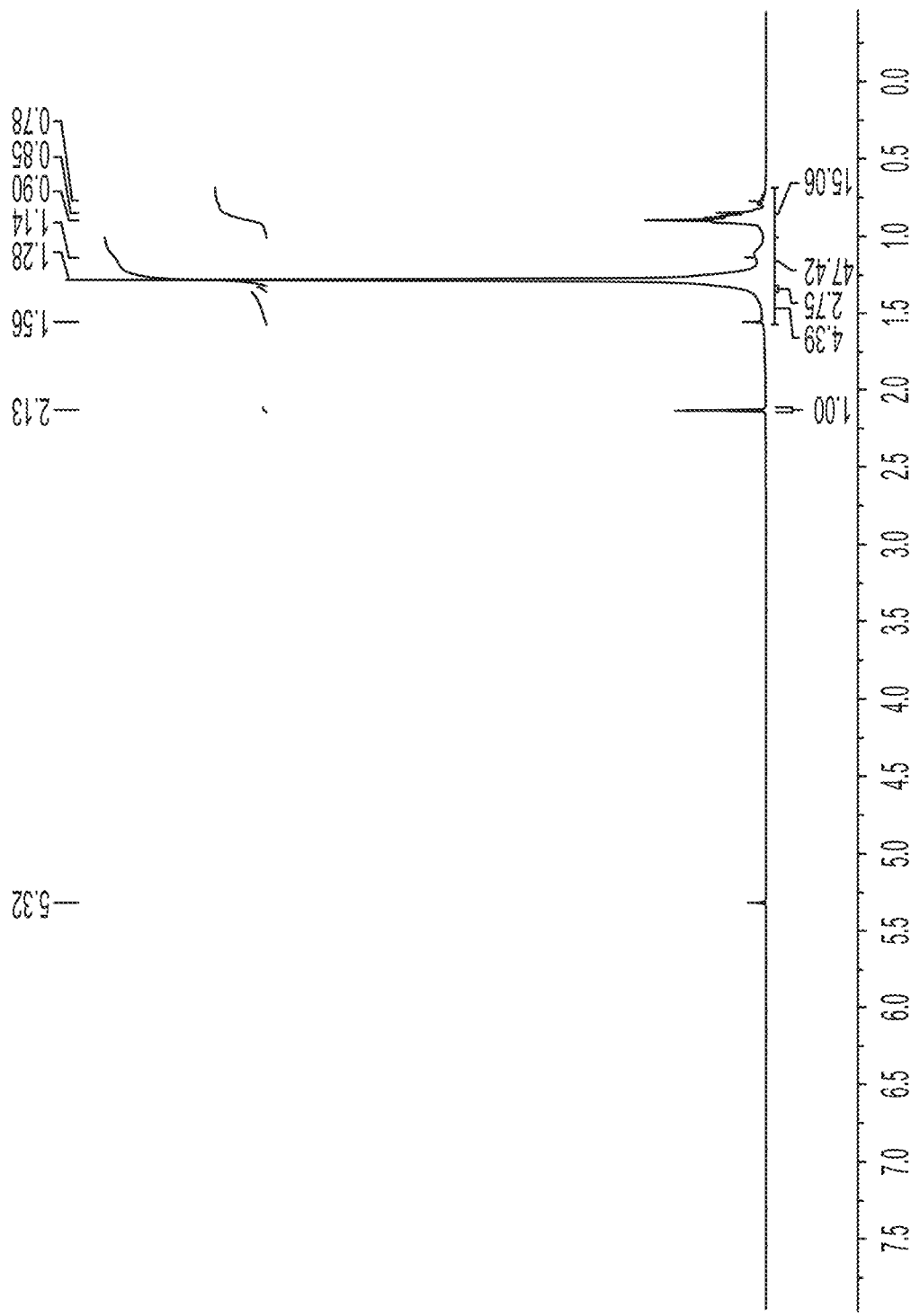
FIG. 20 is the $^1$H NMR spectrum of the oil isolated after reaction of HDPE and AliBu$_3$ in the presence of Zr(CH$_2$CMe$_3$)$_2$@SiAlO$_x$ at 200° C. for 12 h, quenched with degassed MeOH, and extracted with methylene chloride. The spectrum was acquired at room temperature in methylene chloride-d$_2$ and assigned based on COSY and HSQC experiments in FIGS. 21 and 22. Signals at 0.7-1.0 ppm correspond to methyl groups, those at 1.0-1.6 ppm correspond to methylene moieties, and those at 2.13 ppm corresponds to methine groups. Note that signals from ca 5 to 3 ppm were not detected, in contrast to spectra quenched with O$_2$, which contained signal in that region assigned to CH$_2$OH.
Figure 21:
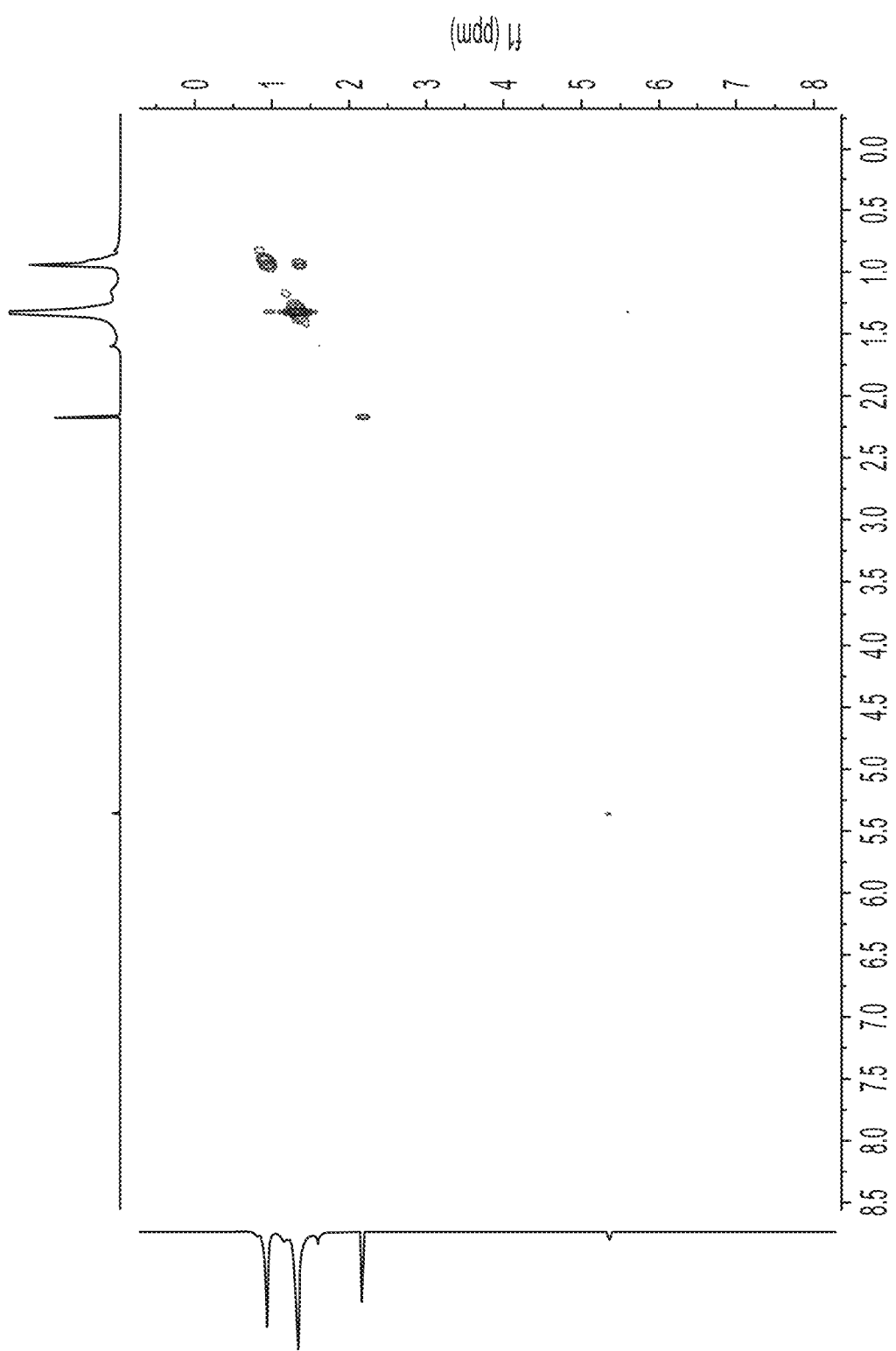
FIG. 21 is the COSY spectrum of the oil isolated after reaction of HDPE and AliBu$_3$ in the presence of Zr(CH$_2$CMe$_3$)$_2$@SiAlO$_x$ at 200° C. for 12 h, quenched with MeOH, and extracted with methylene chloride. The spectrum was acquired at room temperature in methylene chloride-d$_2$.
Figure 22:
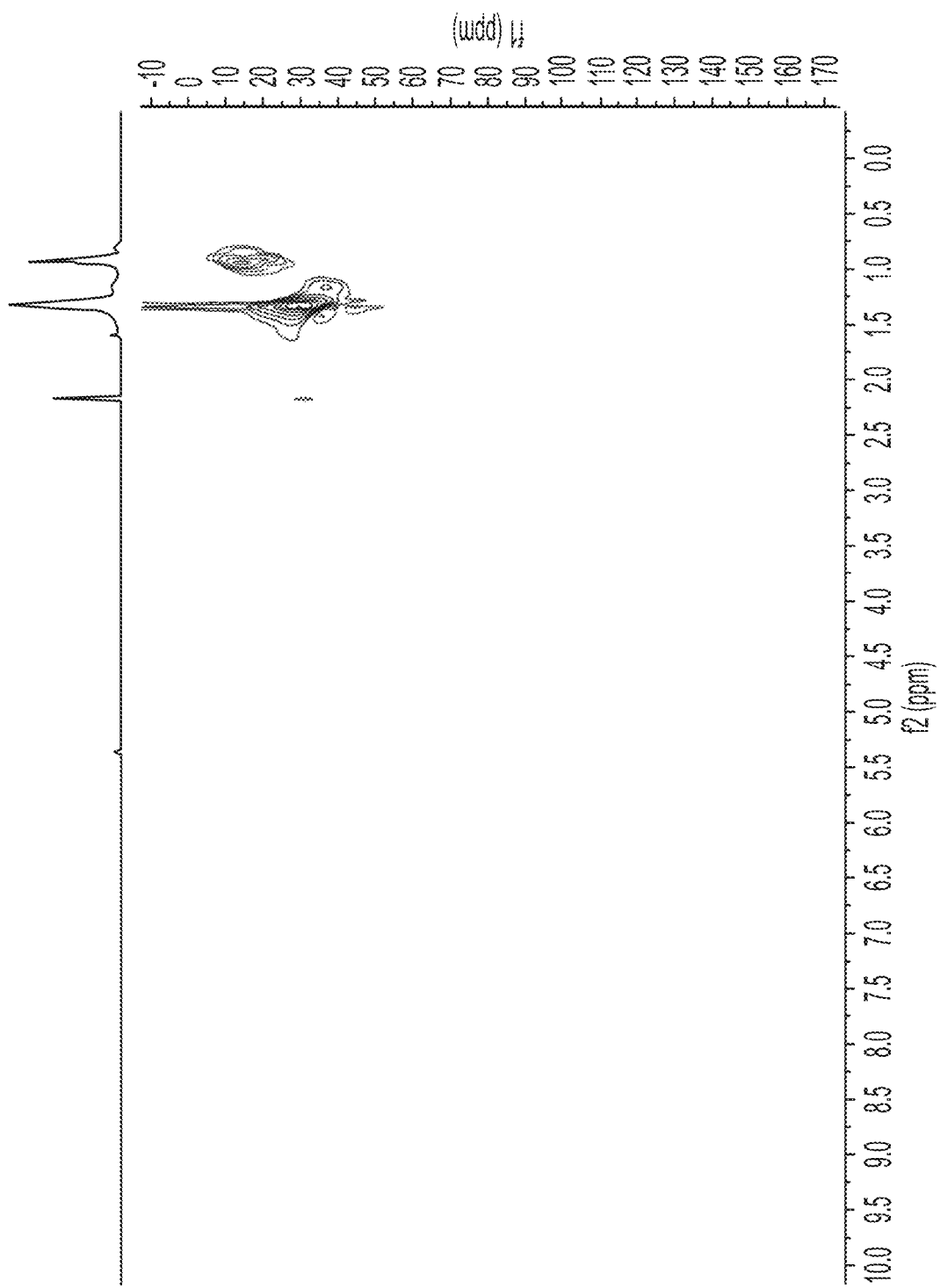
FIG. 22 is the phase sensitive $^1$H-$^{13}$C HSQC spectrum of the oil isolated after reaction of HDPE and AliBu$_3$ in the presence of Zr(CH$_2$CMe$_3$)$_2$@SiAlO$_x$ at 200° C. for 12 h, quenched with MeOH and extracted with methylene chloride. The spectrum was acquired at room temperature in methylene chloride-d$_2$. The cross-peak at 32 ppm, which is opposite in phase with that of the prominent methylene signal, is assigned to methine groups.
Figure 23:
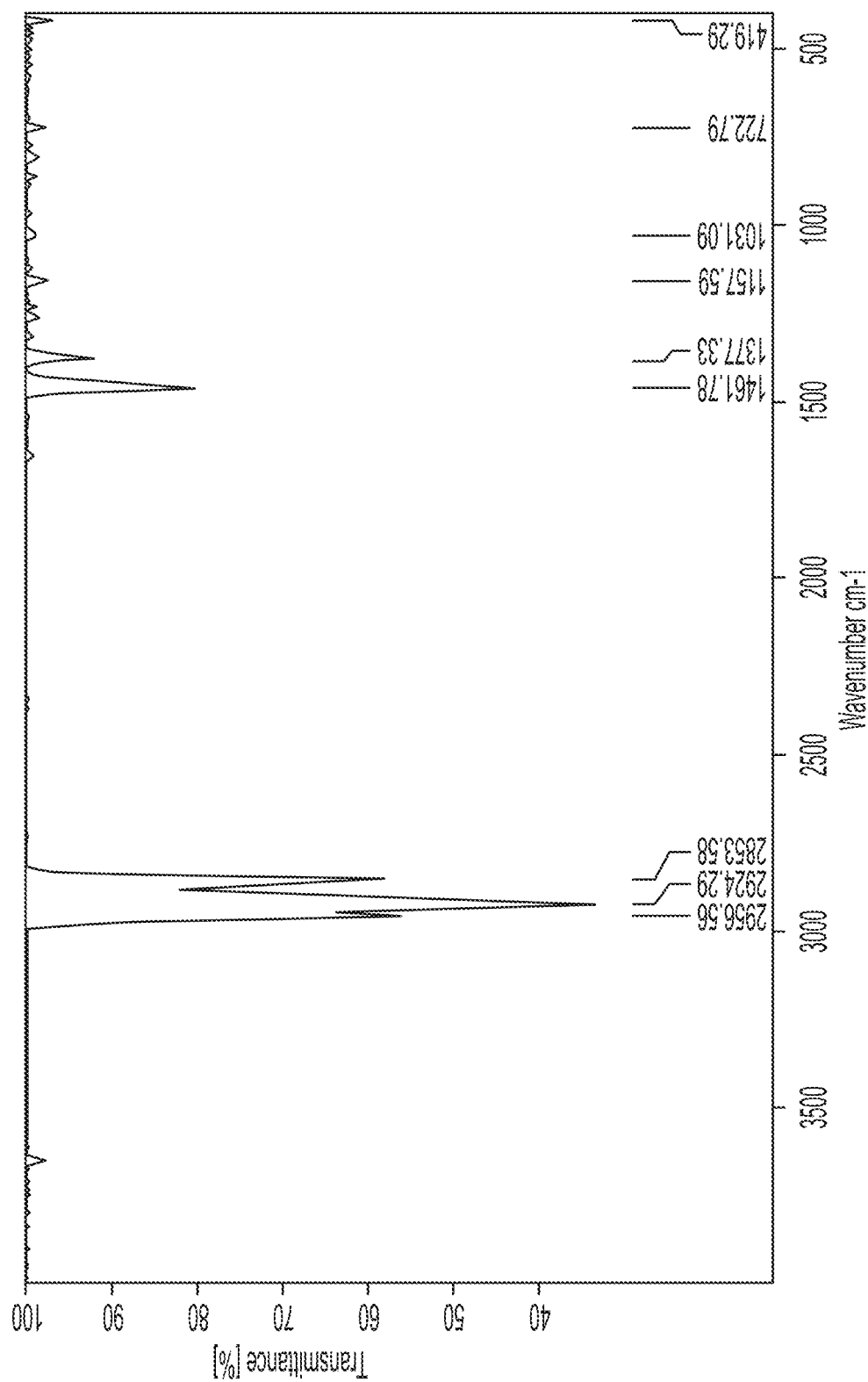
FIG. 23 is the FT-IR spectrum (KBr) of the oil isolated after reaction of HDPE and AliBu$_3$ in the presence of Zr(CH$_2$CMe$_3$)$_2$@SiAlO$_x$ at 200° C. for 12 h, quenched with MeOH, and extracted with methylene chloride. Note that the diagnostic OH signal in O$_2$-quenched reactions is not detected in this material.
Figure 24:
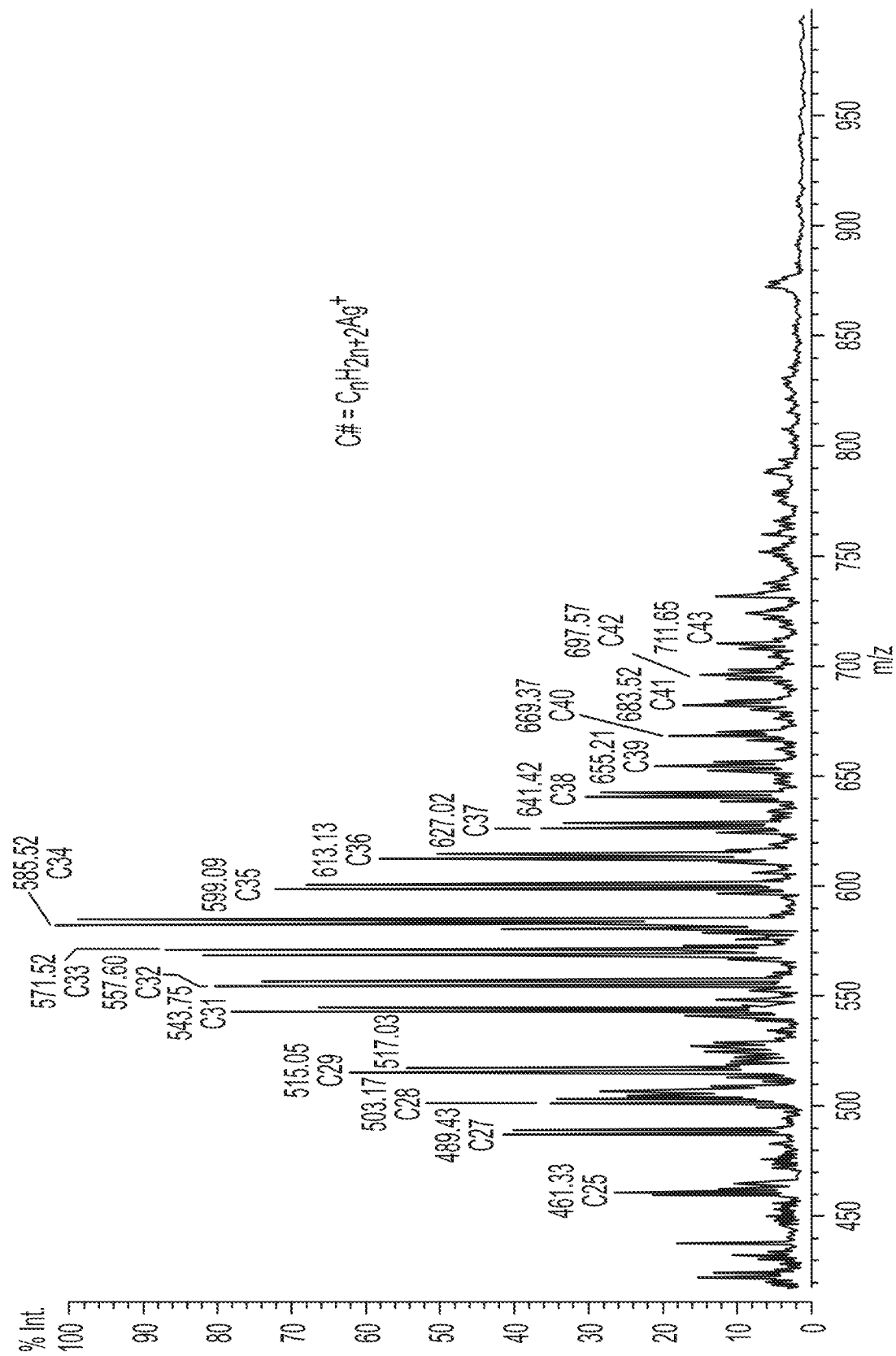
FIG. 24 is the MALDI-TOF-MS of oil isolated after reaction of HDPE and AliBu$_3$ in the presence of Zr(CH$_2$CMe$_3$)$_2$@SiAlO$_x$ at 200° C. for 12 h, quenched with MeOH, and extracted with methylene chloride. The spectrum was acquired in linear, positive mode with AgNO$_3$ (salt) and DHB (matrix), and species appear as pairs of signals due to detection of $^{107}$Ag and $^{109}$Ag adducts.
Figure 25:
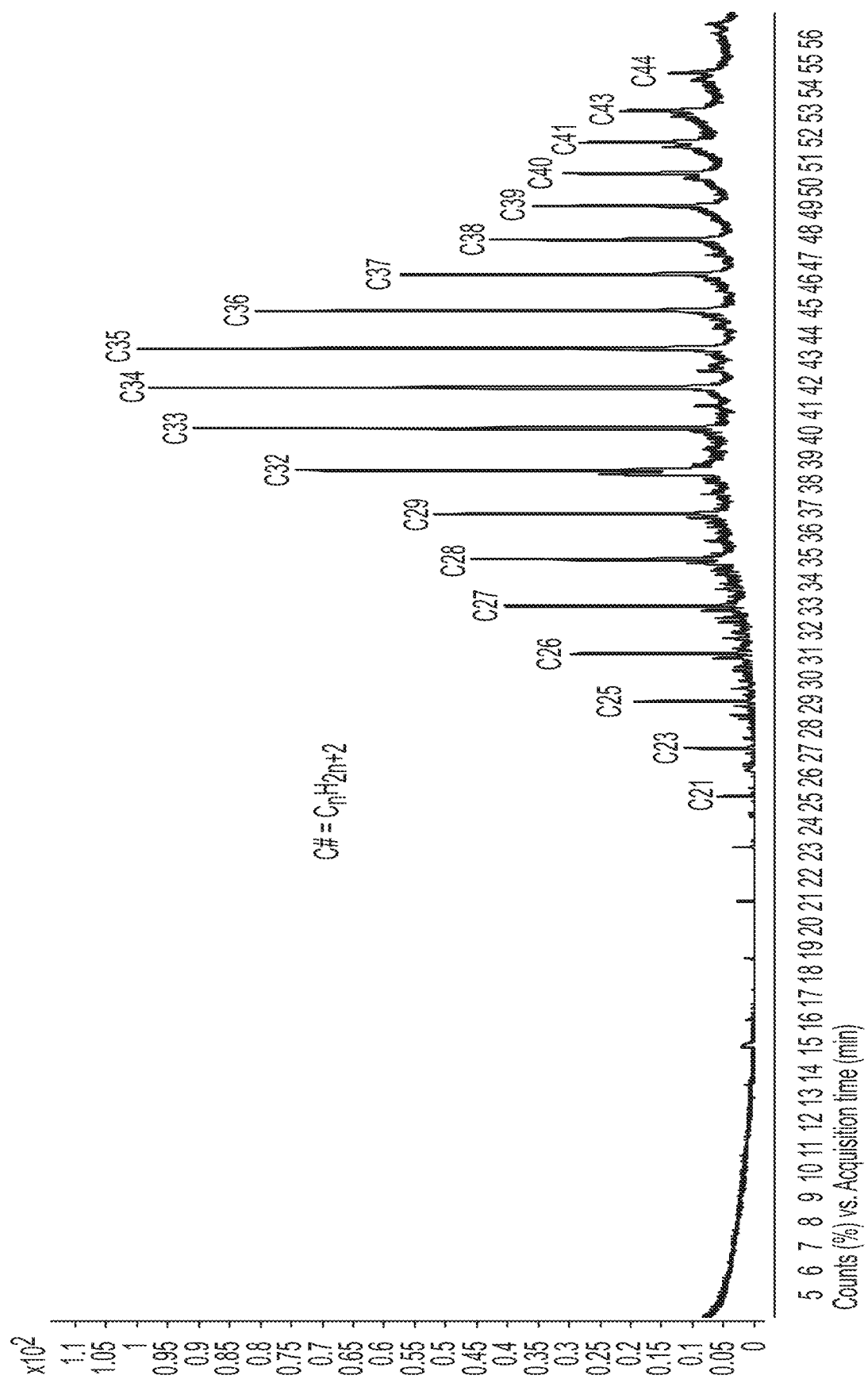
FIG. 25 is the GC-MS of the oil isolated after reaction of HDPE and AliBu$_3$ in the presence of Zr(CH$_2$CMe$_3$)$_2$@SiAlO$_x$ at 200° C. for 12 h, quenched with MeOH, and extracted with methylene chloride. The spectrum was acquired by dissolving the sample in methylene chloride. The GC-MS spectrum corroborates the distribution of hydrocarbon species detected in the MALDI-TOF-MS spectrum (FIG. 24), as well as the distributions of $O_2$, $I_2$, and $CO_2$-quenched reactions performed with $Zr(CH_2CMe_3)_2$@$SiAlO_x$ at 200° C. for 12 h. Hence, the MALDI-TOF-MS spectra are confirmed as representative of the samples compositions.
Figure 26:
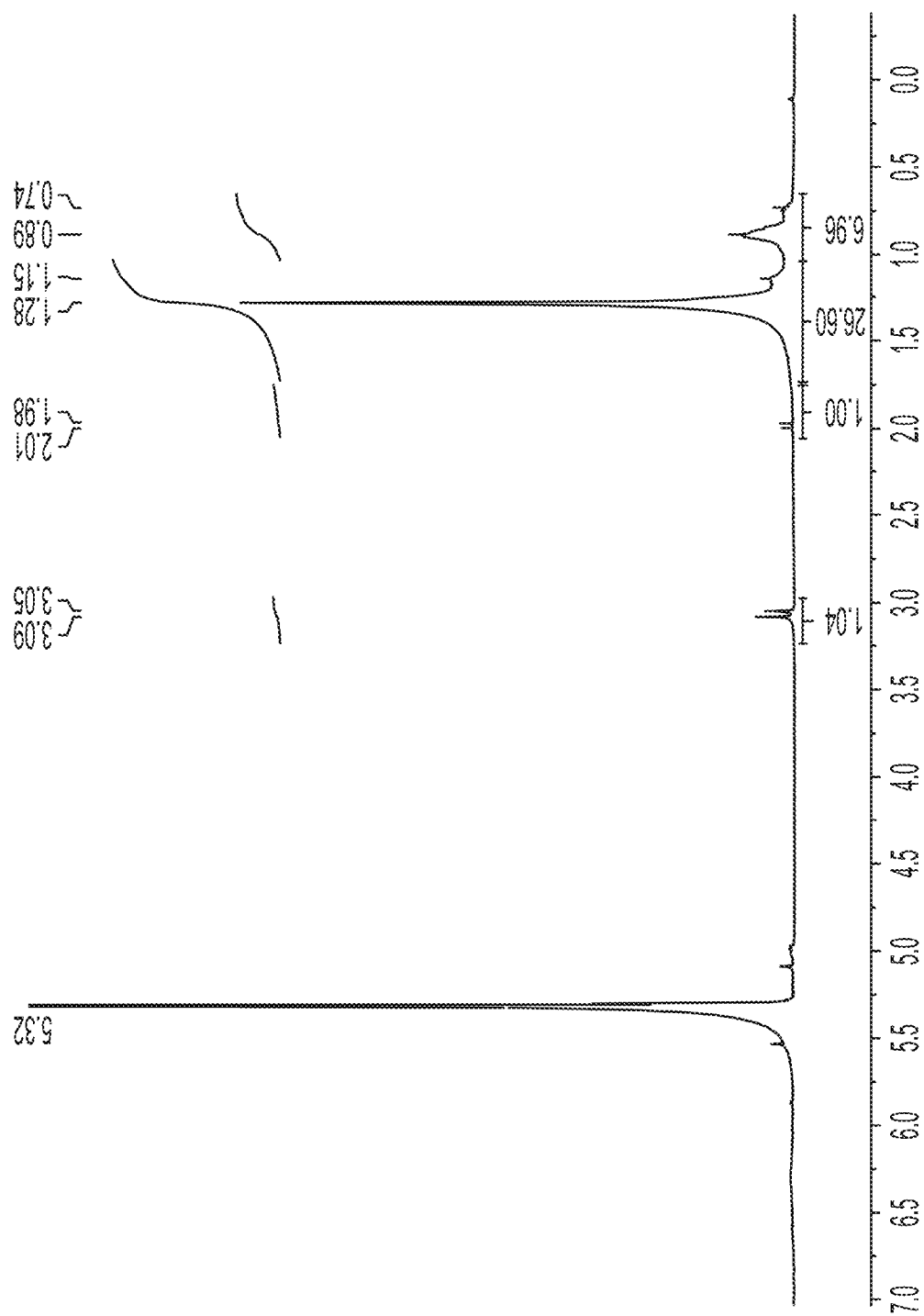
FIG. 26 is the $^1H$ NMR spectrum of the oil isolated after reaction of HDPE and $AliBu_3$ in the presence of $Zr(CH_2CMe_3)_2$@$SiAlO_x$ at 200° C. for 12 h, quenched with $I_2$, and extracted with methylene chloride. The spectrum was acquired at room temperature in methylene chloride-$d_2$ and assigned based on COSY and HSQC experiments in FIGS. 27 and 28. Signals at 0.7-1.0 ppm are assigned to methyls, those at 1.0-1.7 ppm correspond to methylene units, and those at 1.7-2.1 ppm are attributed to methine groups. Peaks at 3.0-3.2 ppm are assigned as —$CH_2$—I groups.
Figure 27:
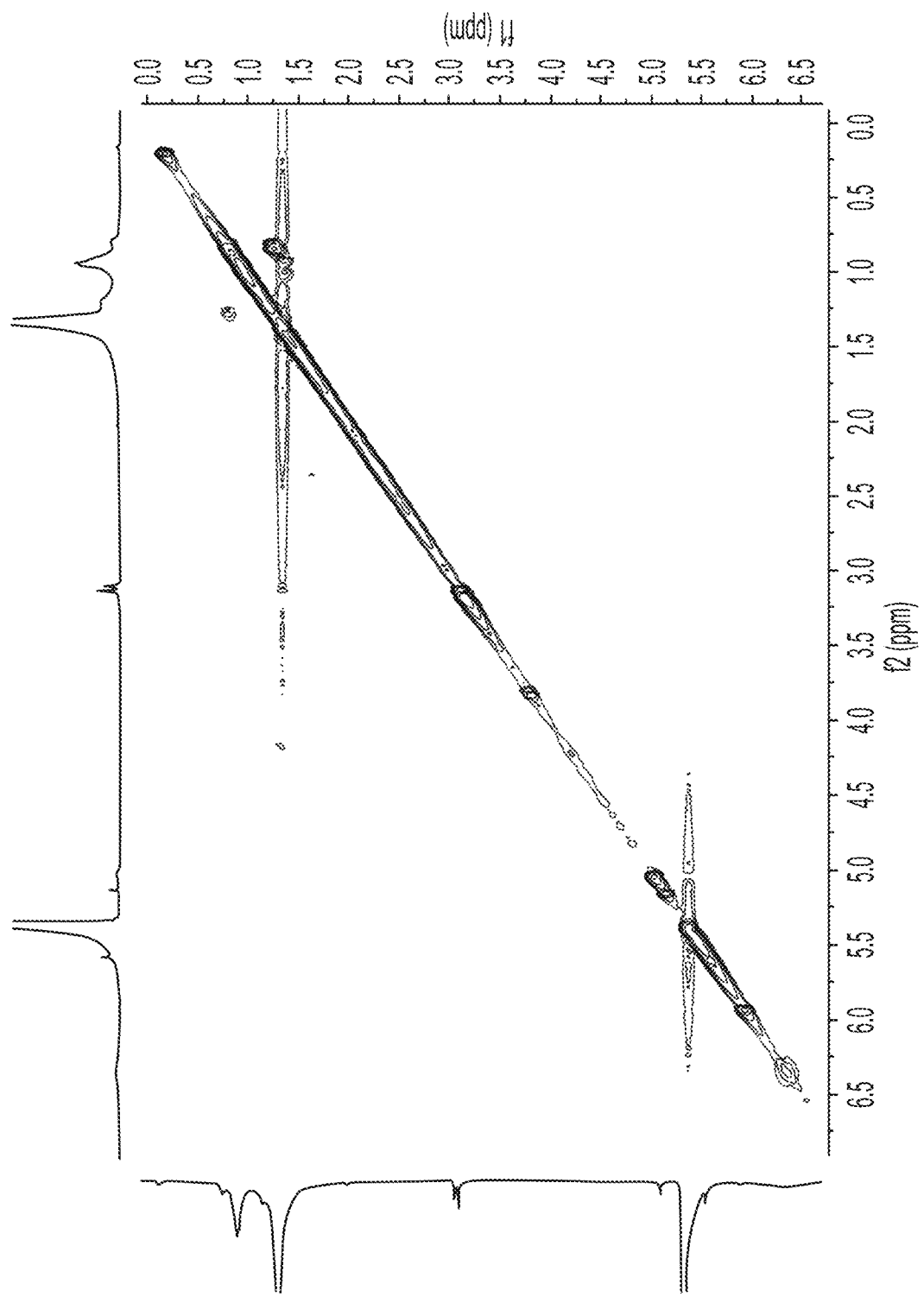
FIG. 27 is the COSY spectrum of the oil isolated after reaction of HDPE and $AliBu_3$ in the presence of $Zr(CH_2CMe_3)_2$@$SiAlO_x$ at 200° C. for 12 h, quenched with $I_2$, and extracted with methylene chloride. The spectrum was acquired at room temperature in methylene chloride-$d_2$. The weak cross-peak at 3.1 ppm correlated with methylene signals at 1.3 ppm indicates —$CH_2$—$CH_2$—I species.
Figure 28:
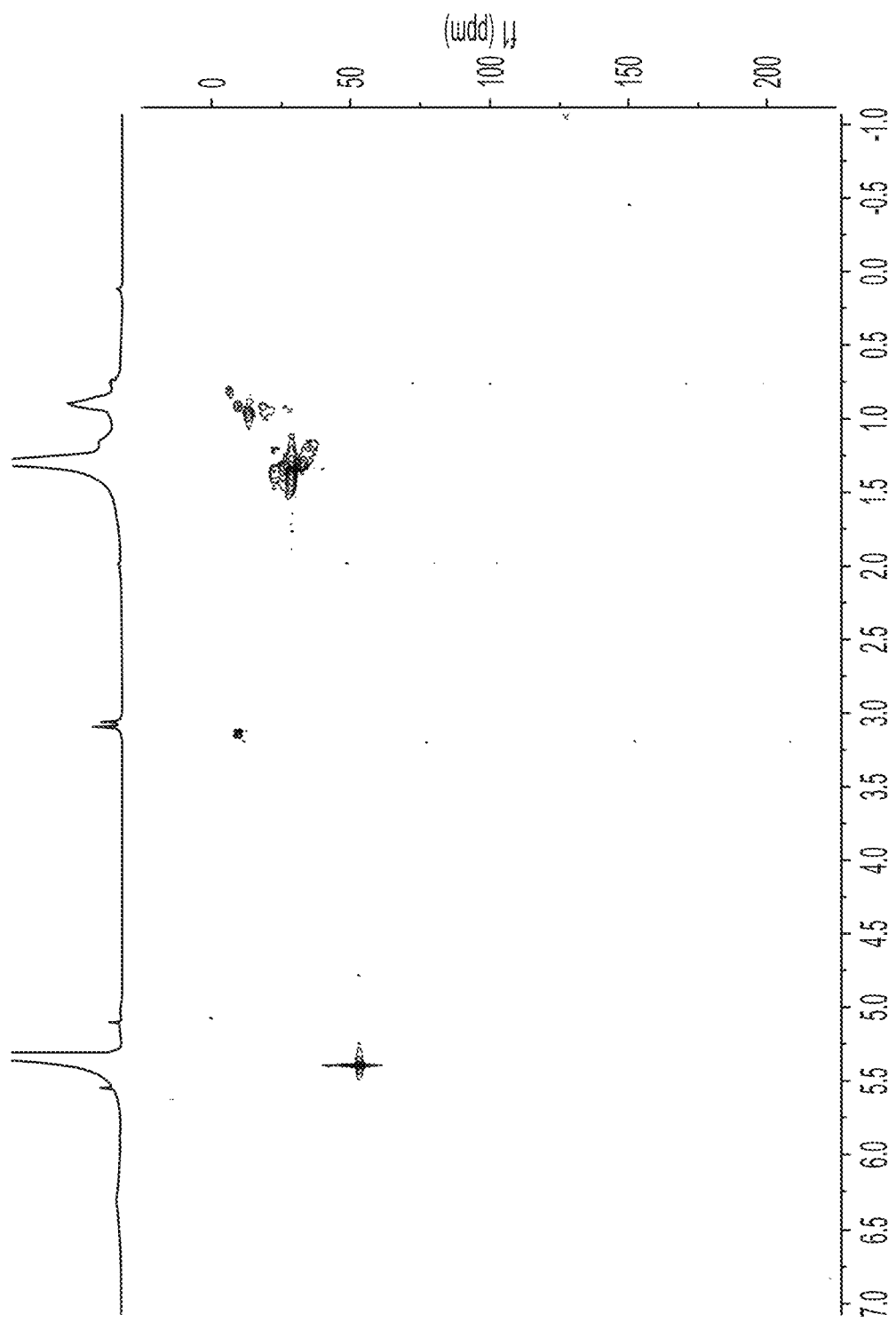
FIG. 28 is the $^1H$-$^{13}C$ phase sensitive HSQC spectrum of the oil isolated after reaction of HDPE and $AliBu_3$ in the presence of $Zr(CH_2CMe_3)_2$@$SiAlO_x$ at 200° C. for 12 h, quenched with $I_2$, and extracted with methylene chloride. The spectrum was acquired at room temperature in methylene chloride-$d_2$. The large peak assigned to polymer methylene $CH_2$ at $^{13}C$ 30 ppm has the same phase as cross-peaks at $^{13}C$ 10 ppm, allowing assignment of the latter to primary —$CH_2$—I.
Figure 29:
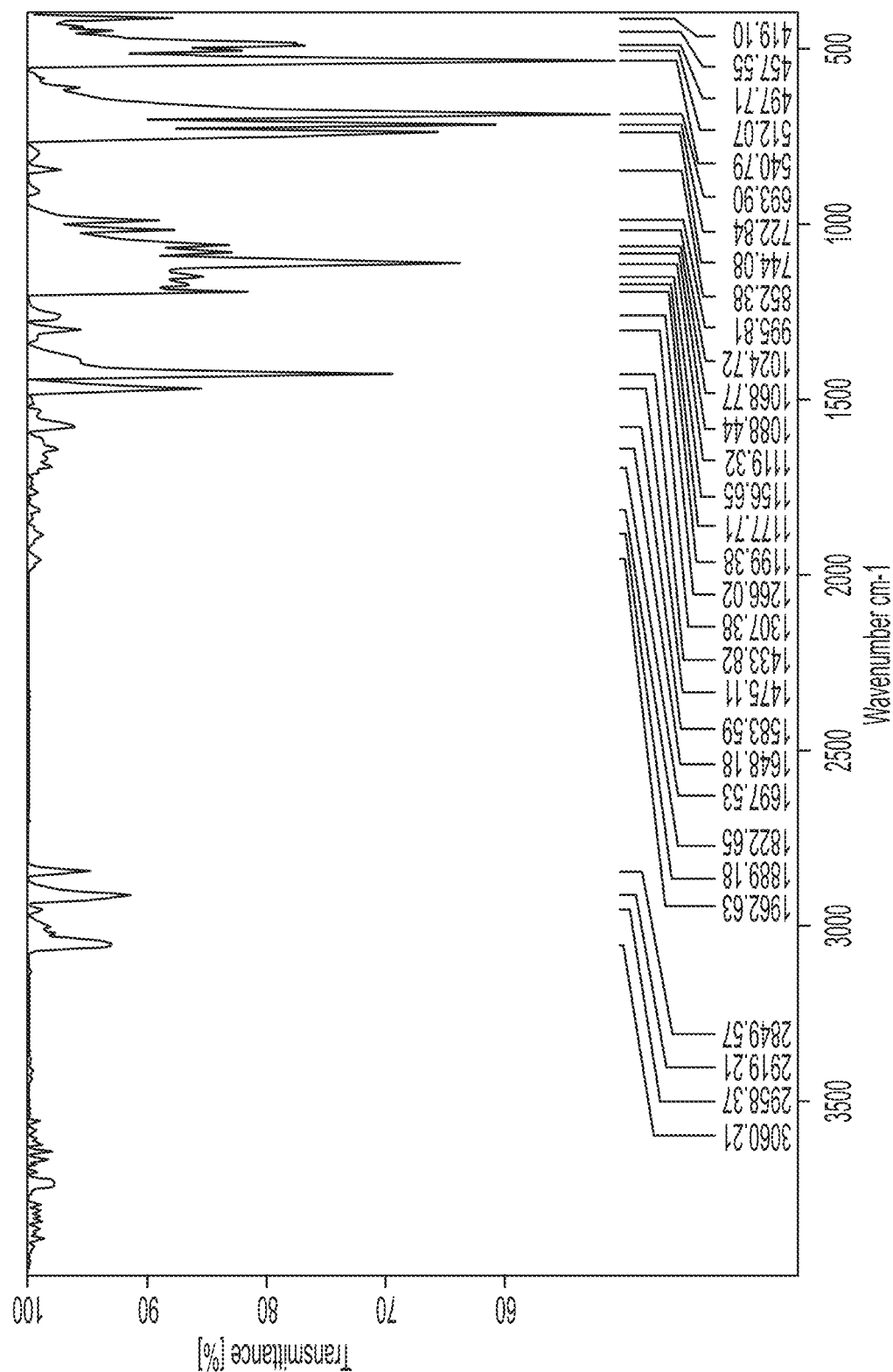
FIG. 29 is the FT-IR spectrum (KBr) of the oil isolated after reaction of HDPE and $AliBu_3$ in the presence of $Zr(CH_2CMe_3)_2$@$SiAlO_x$ at 200° C. for 12 h, quenched with $I_2$, and extracted with methylene chloride. Signals between 490-515 $cm^{-1}$ are assigned to C—I stretching modes.
Figure 30:
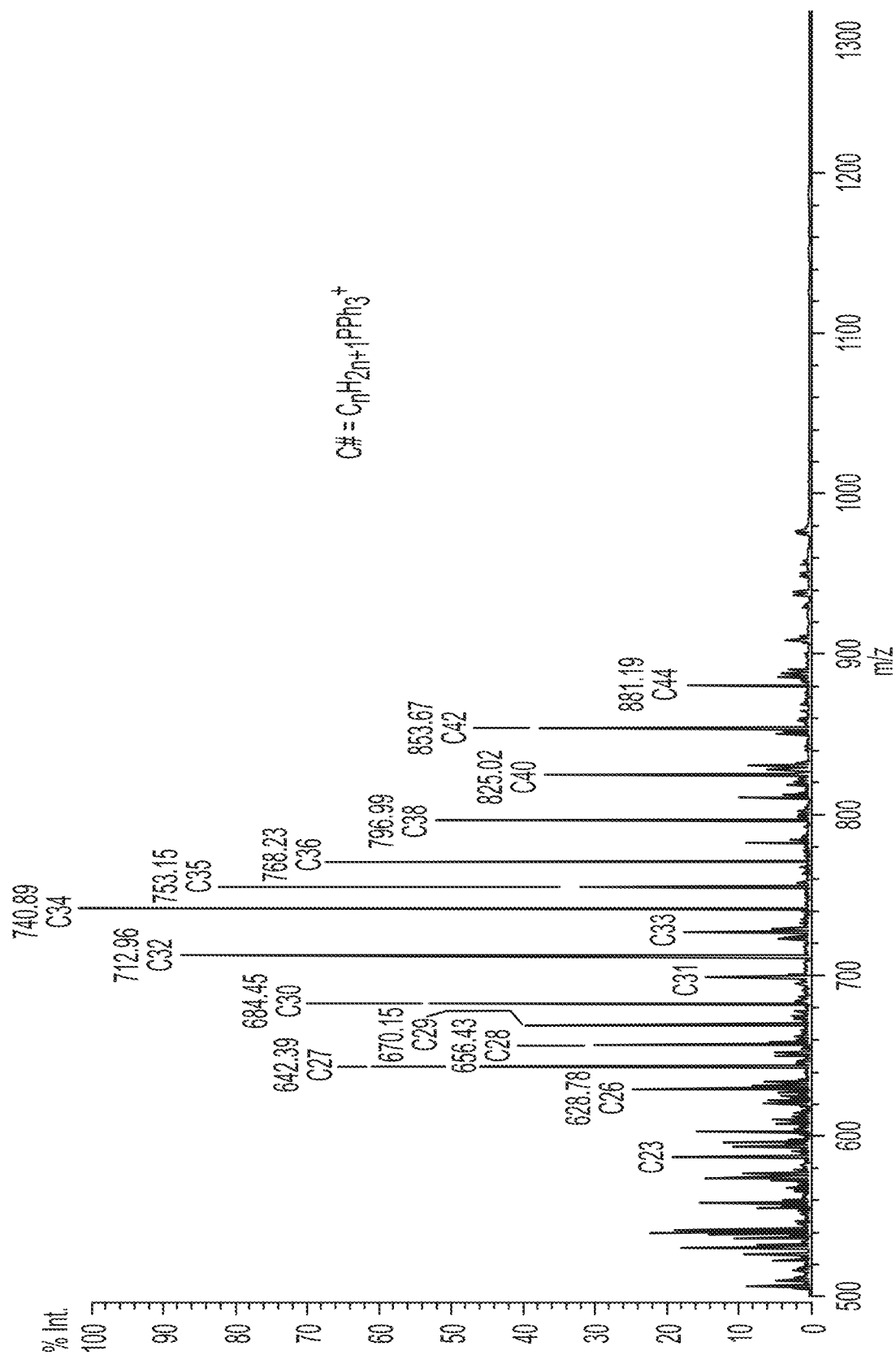
FIG. 30 is the MALDI-TOF-MS spectrum of the oil isolated after reaction of HDPE and $AliBu_3$ in the presence of $Zr(CH_2CMe_3)_2$@$SiAlO_x$ at 200° C. for 12 h, quenched with $I_2$, and extracted with methylene chloride. The isolated sample was dissolved in methylene chloride and $PPh_3$ and heated at 50° C. for 4 h. The spectrum was acquired in linear, positive mode with DHB (matrix). Major peaks correspond to alkyl phosphonium species.
Figure 31:
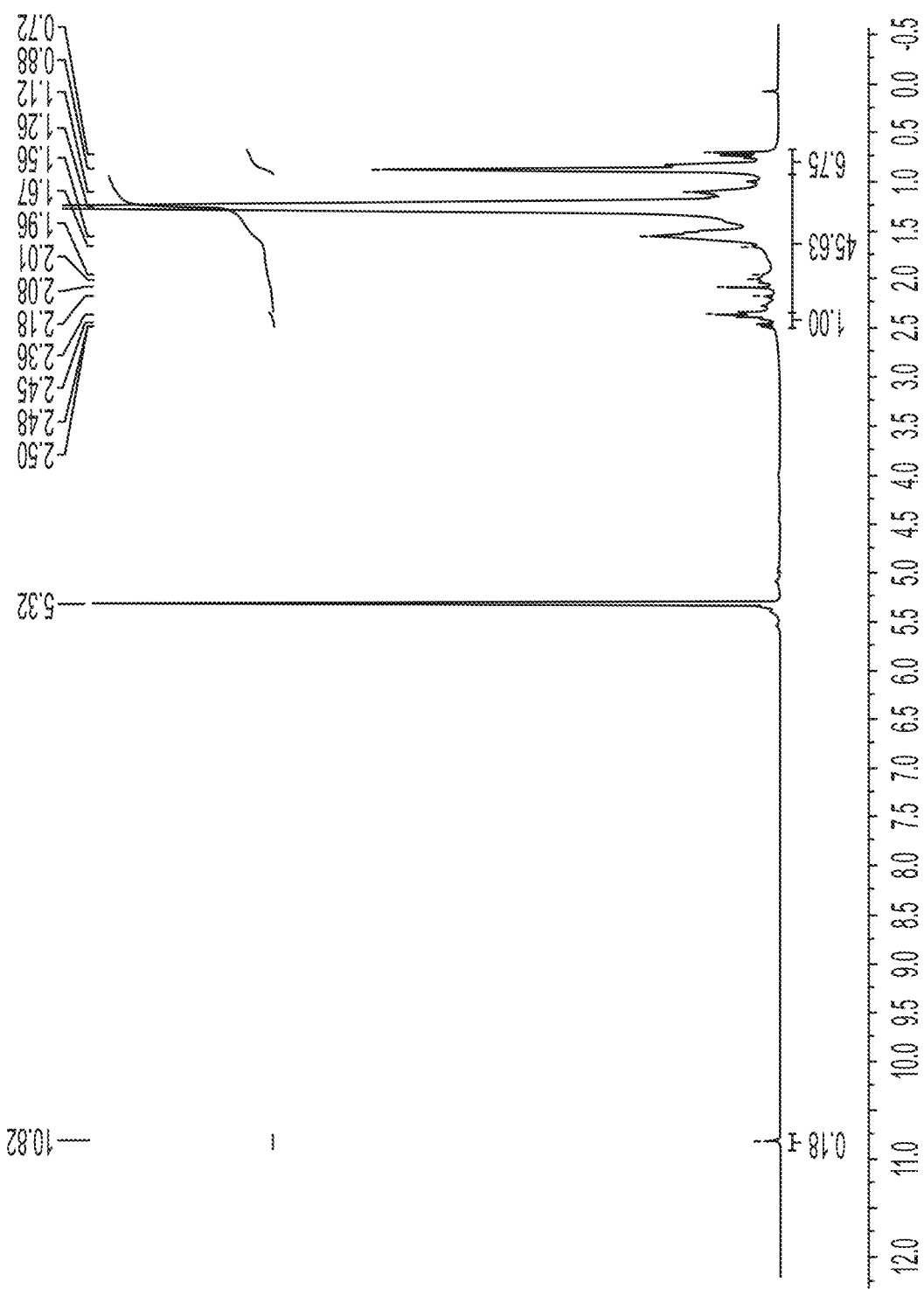
FIG. 31 is the $^1H$ NMR spectrum of the oil isolated after reaction of HDPE and $AliBu_3$ in the presence of $Zr(CH_2CMe_3)_2$@$SiAlO_x$ at 200° C. for 12 h, quenched with $CO_2$, and extracted with methylene chloride. The spectrum was acquired at room temperature in methylene chloride-$d_2$ and assigned based on COSY, HSQC and heteronuclear multiple bond correlation (HMBC) experiments shown in FIGS. 32, 33, and 34. Signals at 0.7-0.9 ppm are assigned to methyl groups, 1.0-2.3 ppm correspond to methylene groups, and 2.3-2.5 ppm are attributed to methine groups. The peak at 10.8 ppm is assigned to a —COOH group.
Figure 32:
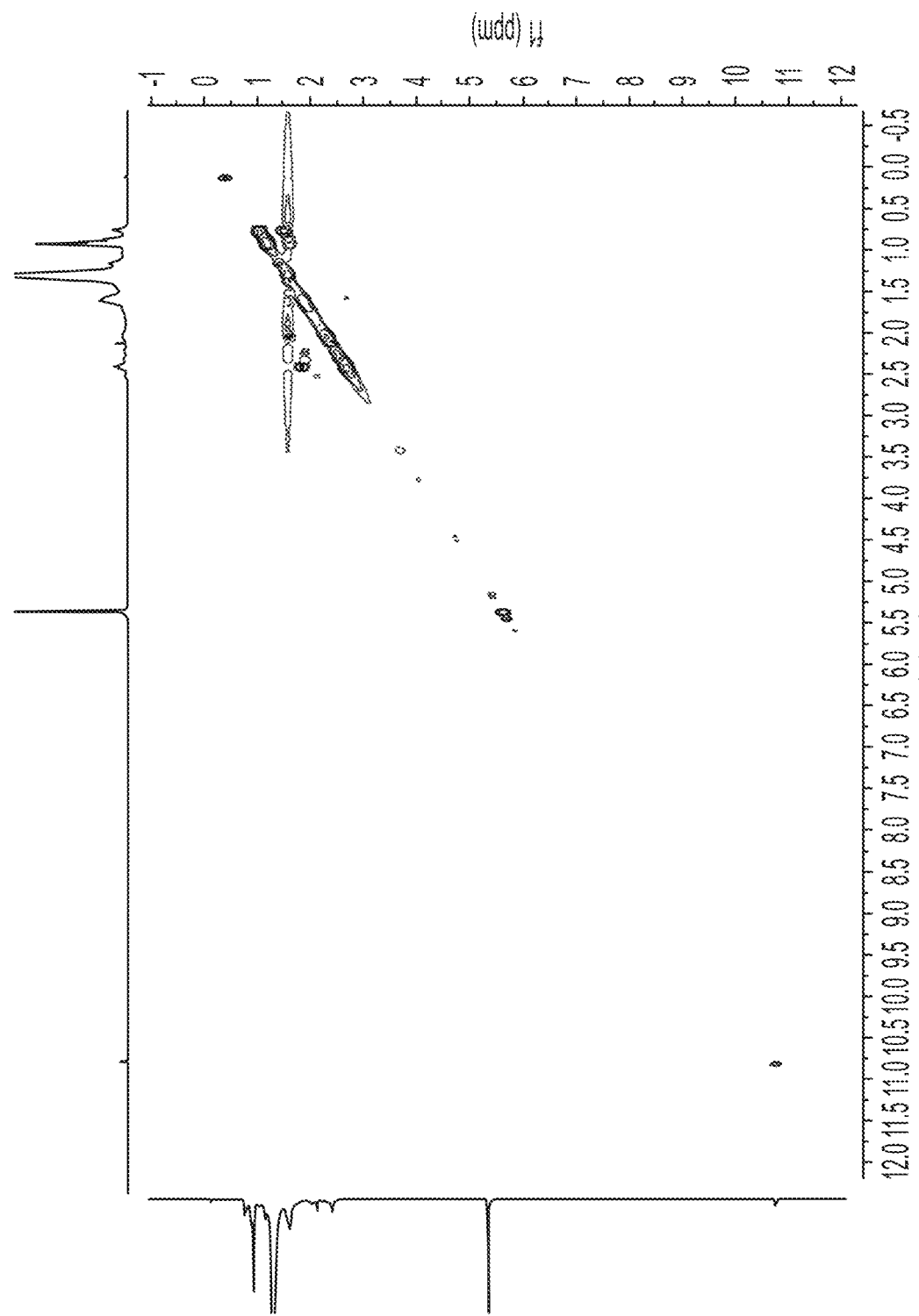
FIG. 32 is the COSY spectrum of the oil isolated after reaction of HDPE and $AliBu_3$ in the presence of $Zr(CH_2CMe_3)_2$@$SiAlO_x$ at 200° C. for 12 h, quenched with $CO_2$, and extracted with methylene chloride. The spectrum was acquired at room temperature in methylene chloride-$d_2$.
Figure 33:
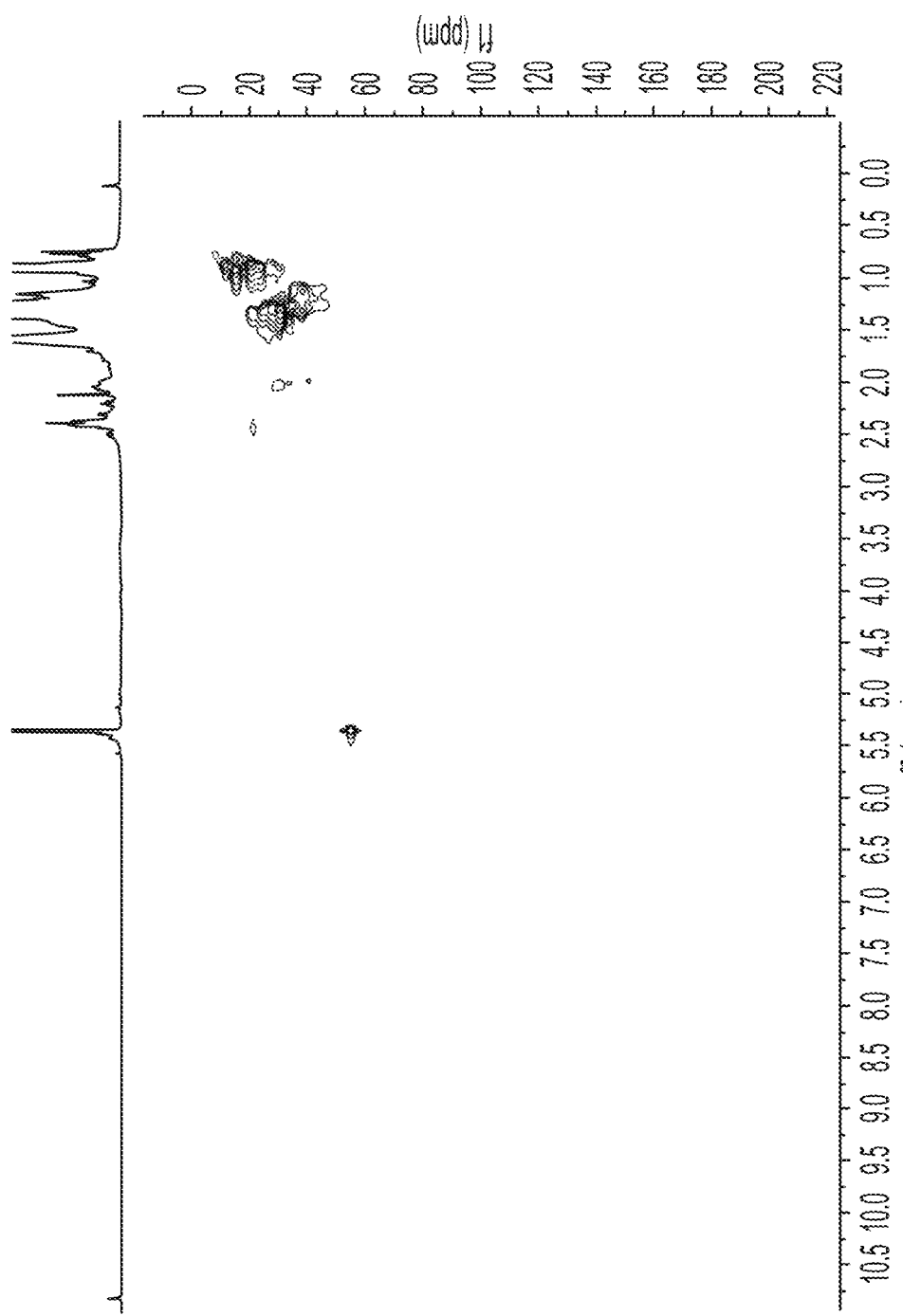
FIG. 33 is the phase sensitive $^1H$-$^{13}C$ HSQC spectrum of the oil isolated after reaction of HDPE and $AliBu_3$ in the presence of $Zr(CH_2CMe_3)_2$@$SiAlO_x$ at 200° C. for 12 h, quenched with $CO_2$, and extracted with methylene chloride. The spectrum was acquired at room temperature in methylene chloride-$d_2$.
Figure 34:
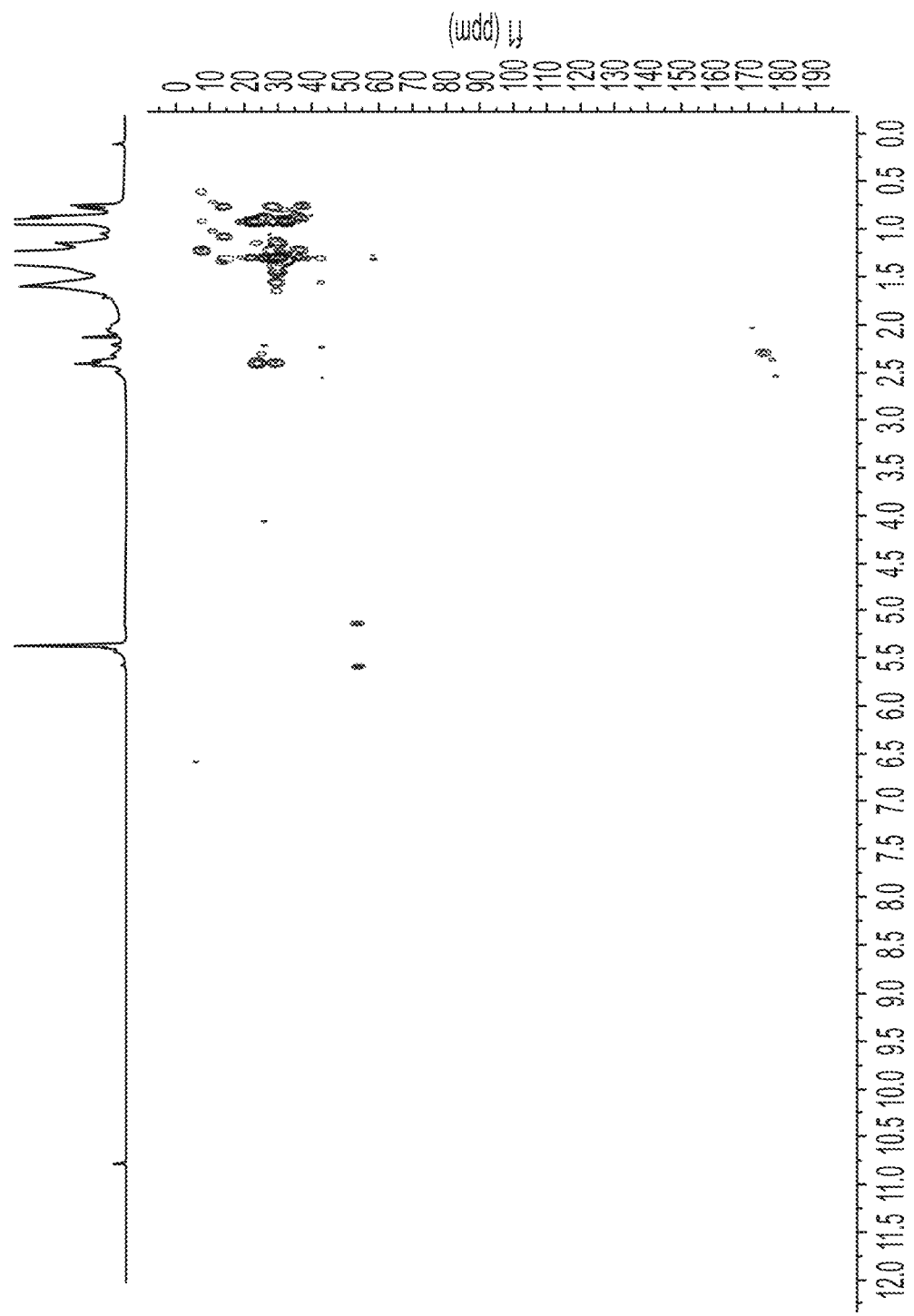
FIG. 34 is the $^1H$-$^{13}C$ HMBC spectrum of the oil isolated after reaction of HDPE and $AliBu_3$ in the presence of $Zr(CH_2CMe_3)_2$@$SiAlO_x$ at 200° C. for 12 h, quenched with $CO_2$, and extracted with methylene chloride. The spectrum was acquired at room temperature in methylene chloride-$d_2$. Cross-peaks at $^{13}C$ 170-180 ppm reveal long-range correlations with methylene and methine signals in the $^1H$ dimension at 2.0-2.5 ppm, consistent with —$CH_2$—$CH_2$—COOH and —(R)CH—$CH_2$—COOH chain ends.
Figure 35:
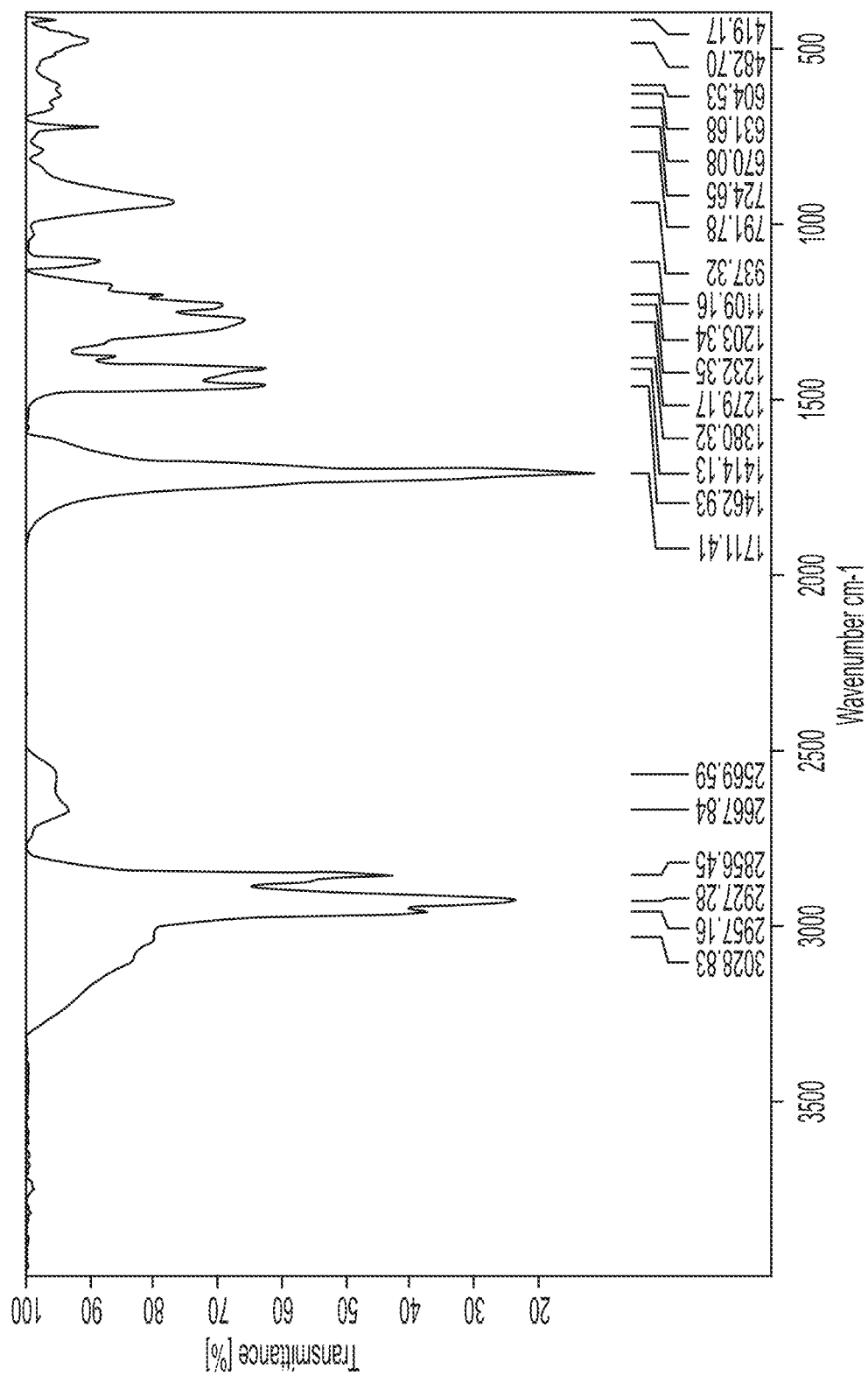
FIG. 35 is the FT-IR spectrum (KBr) of the oil isolated after reaction of HDPE and $AliBu_3$ in the presence of $Zr(CH_2CMe_3)_2$@$SiAlO_x$ at 200° C. for 12 h, quenched with $CO_2$, and extracted with methylene chloride. The broad signal between 2800-3400 $cm^{-1}$ corresponds to an O—H stretch and the intense signal at 1711 $cm^{-1}$ corresponds to a C=O stretch typical of R—COOH species.
Figure 36:
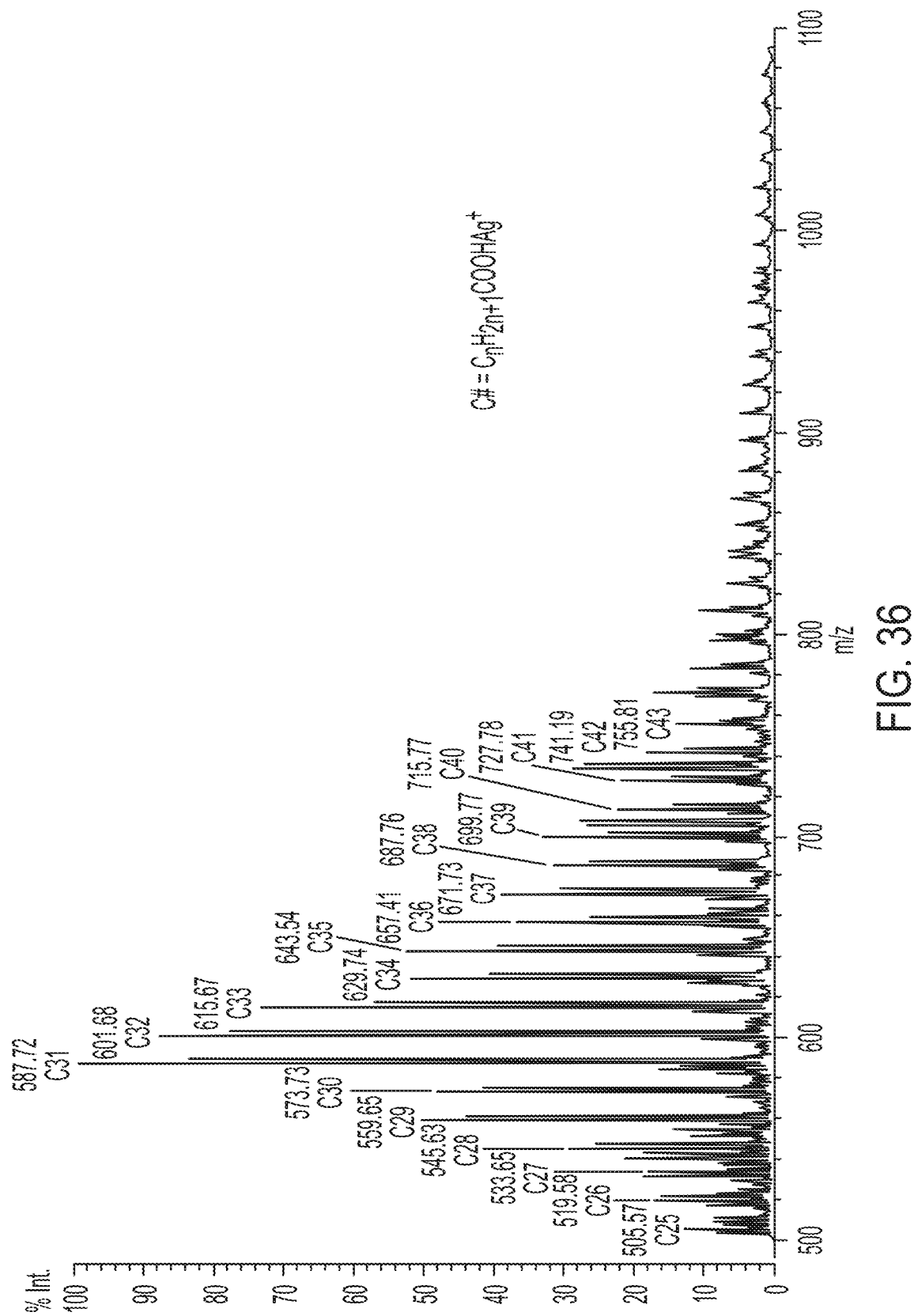
FIG. 36 is the MALDI-TOF-MS spectrum of oil isolated after reaction of HDPE and $AliBu_3$ in the presence of $Zr(CH_2CMe_3)_2$@$SiAlO_x$ at 200° C. for 12 h, quenched with $CO_2$, and extracted with methylene chloride. The spectrum was acquired in linear, positive mode with $AgNO_3$ (salt) and DHB (matrix), and species appear as pairs due to $^{107}Ag$ and $^{109}Ag$ adducts.
Figure 37:
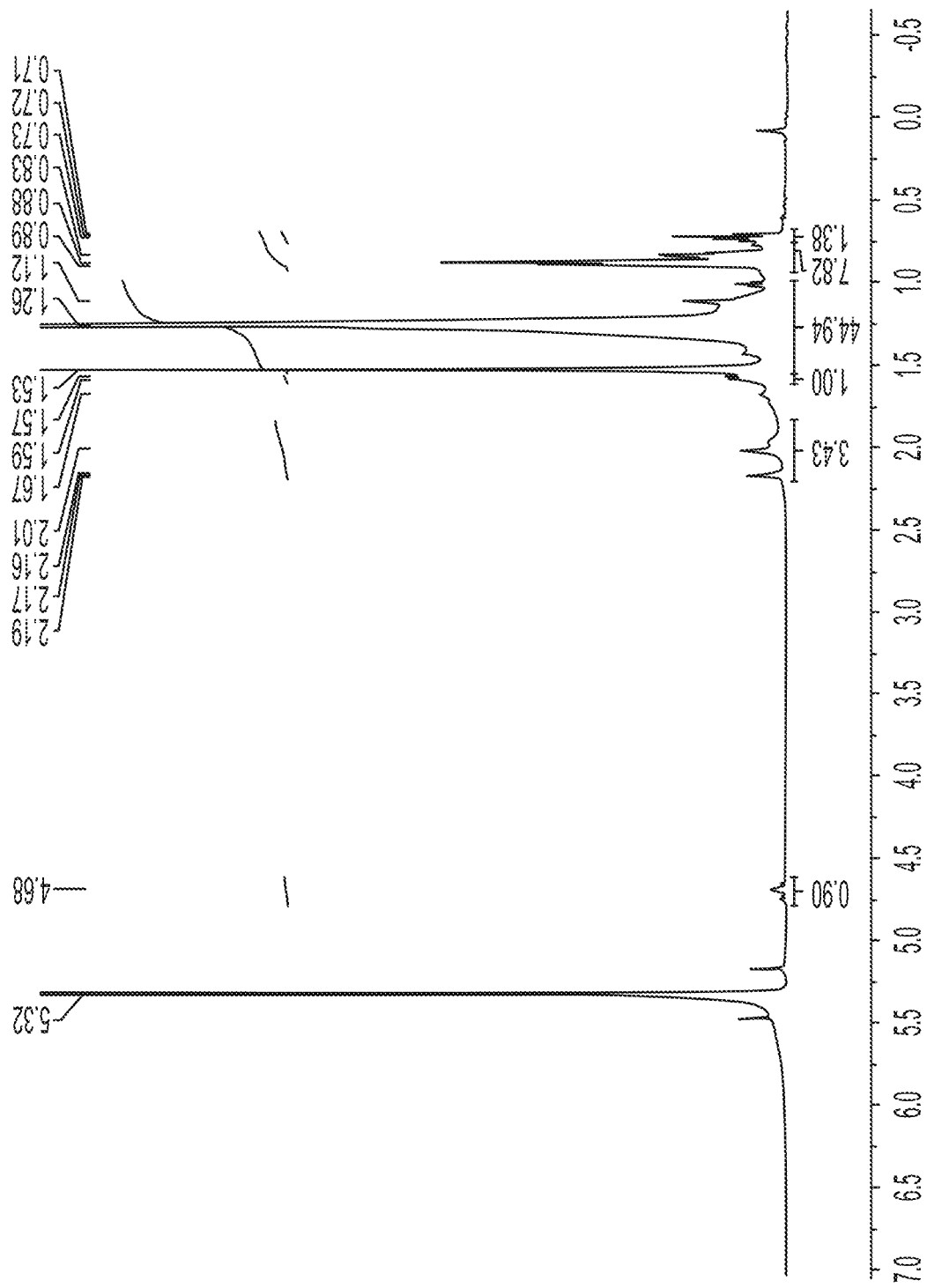
FIG. 37 is the $^1H$ NMR spectrum of the oil isolated after reaction of HDPE and $AlEt_3$ in the presence of $Zr(CH_2CMe_3)_2$@$SiAlO_x$ at 150° C. for 12 h, quenched with $O_2$, and extracted with methylene chloride. The spectrum was acquired at room temperature in methylene chloride-$d_2$ and assigned based on COSY and HSQC experiments in FIGS. 38 and 39. Signals at 0.7-0.9 ppm correspond to methyl groups, peaks at 1.0-1.6 and 1.7-2.2 ppm are attributed to the methylene groups, and those at 1.6-1.7 ppm correspond to methine groups. Peaks at 4.6-4.8 ppm are assigned to —$CH_2$—OH moieties.
Figure 38:
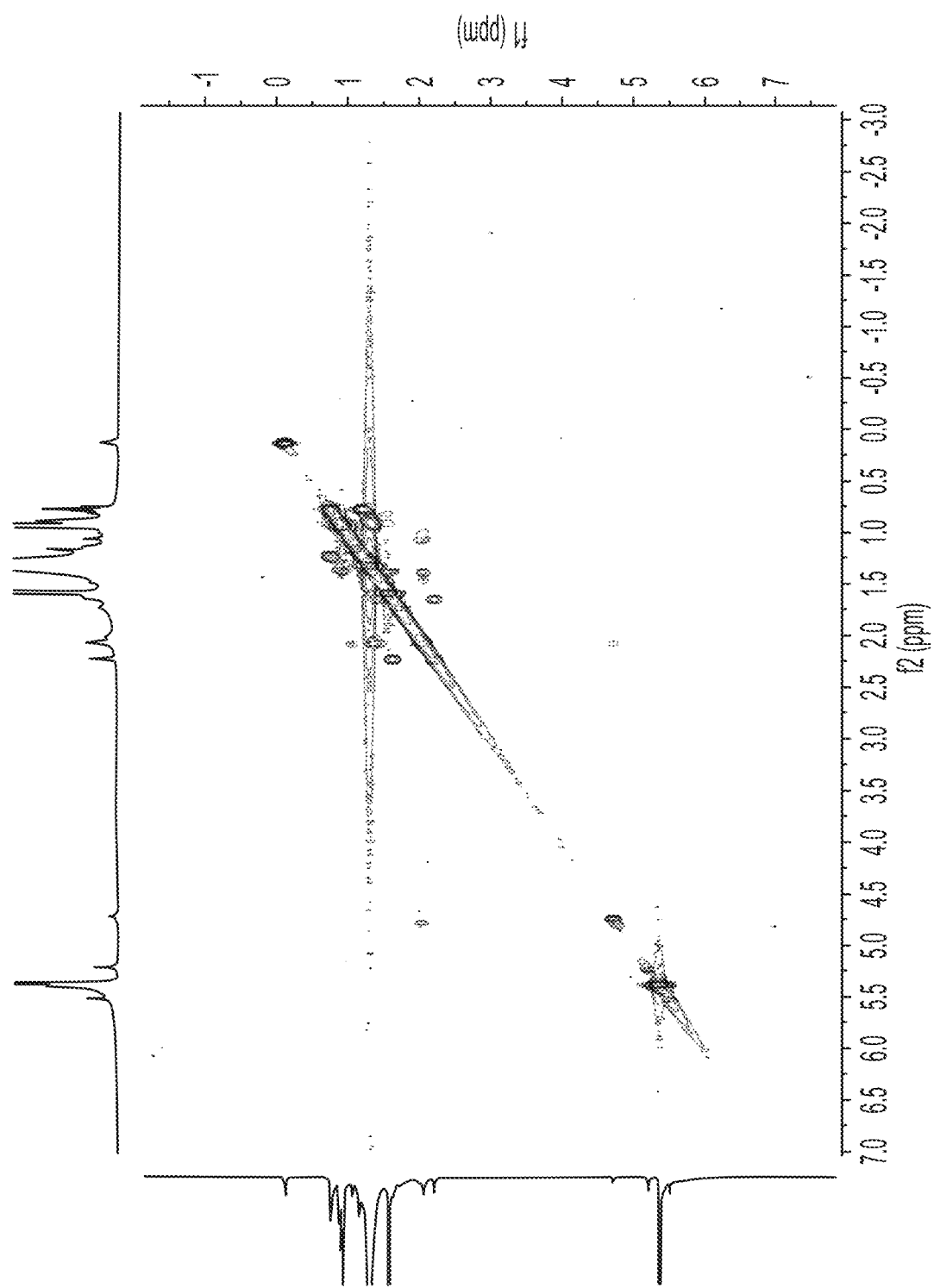
FIG. 38 is the COSY spectrum of the oil isolated after reaction of HDPE and $AlEt_3$ in the presence of $Zr(CH_2CMe_3)_2$@$SiAlO_x$ at 150° C. for 12 h, quenched with $O_2$, and extracted with methylene chloride. The spectrum was acquired at room temperature in methylene chloride-$d_2$. The cross-peak at 4.7 ppm correlates to the methylene signal at 2.0 ppm, consistent with the —$CH_2$—$CH_2$—OH end group structure.
Figure 39:
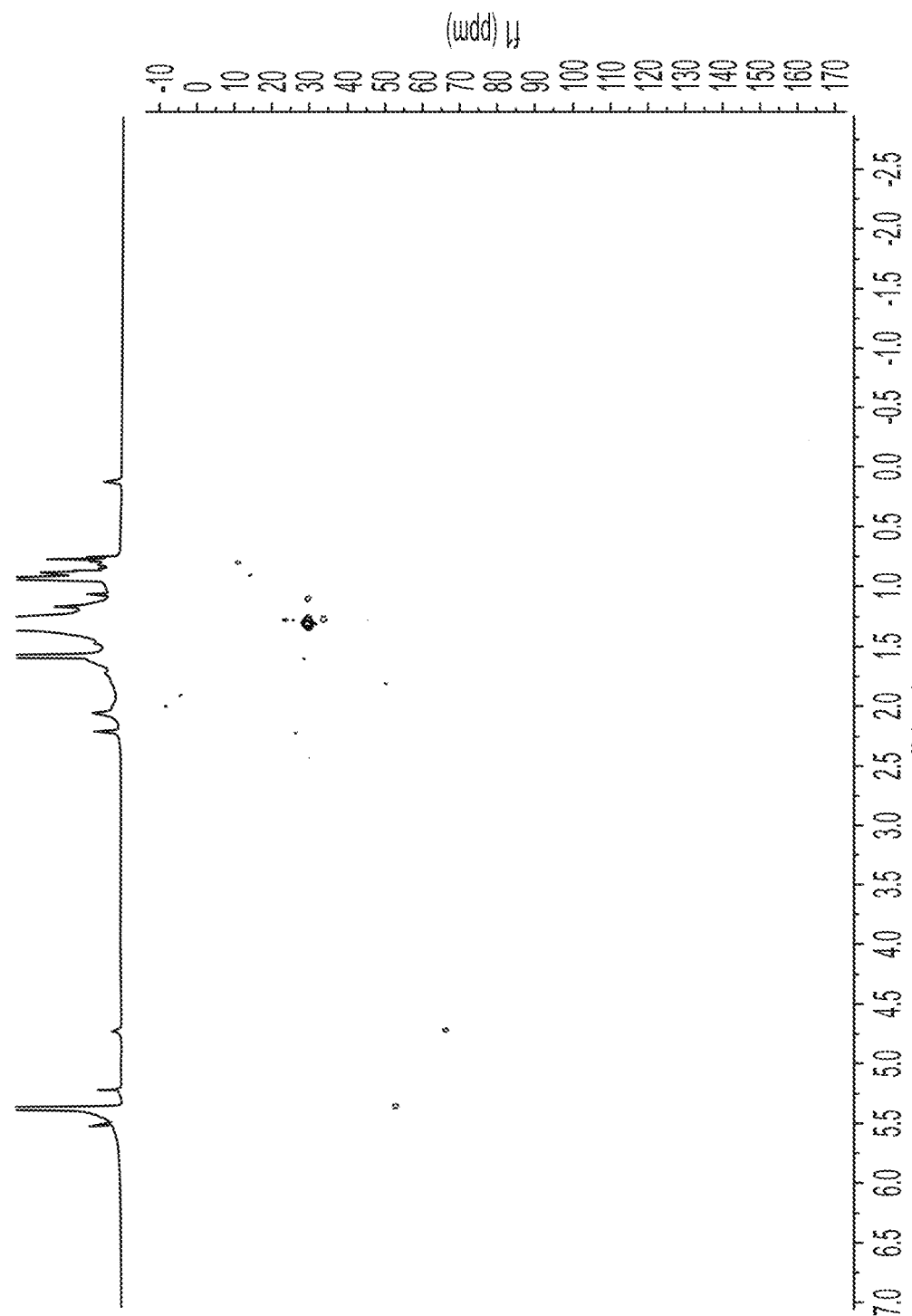
FIG. 39 is the phase sensitive $^1H$-$^{13}C$ HSQC spectrum of the oil isolated after reaction of HDPE and $AlEt_3$ in the presence of $Zr(CH_2CMe_3)_2$@$SiAlO_x$ at 150° C. for 12 h, quenched with $O_2$, and extracted with methylene chloride. The spectrum was acquired at room temperature in methylene chloride-$d_2$. Cross-peaks at $^{13}C$ 60-70 ppm have the same phase as the methylene peaks at 30 ppm, which is indicative of —$CH_2$—OH species (i.e., the alcohols are primary).
Figure 40:
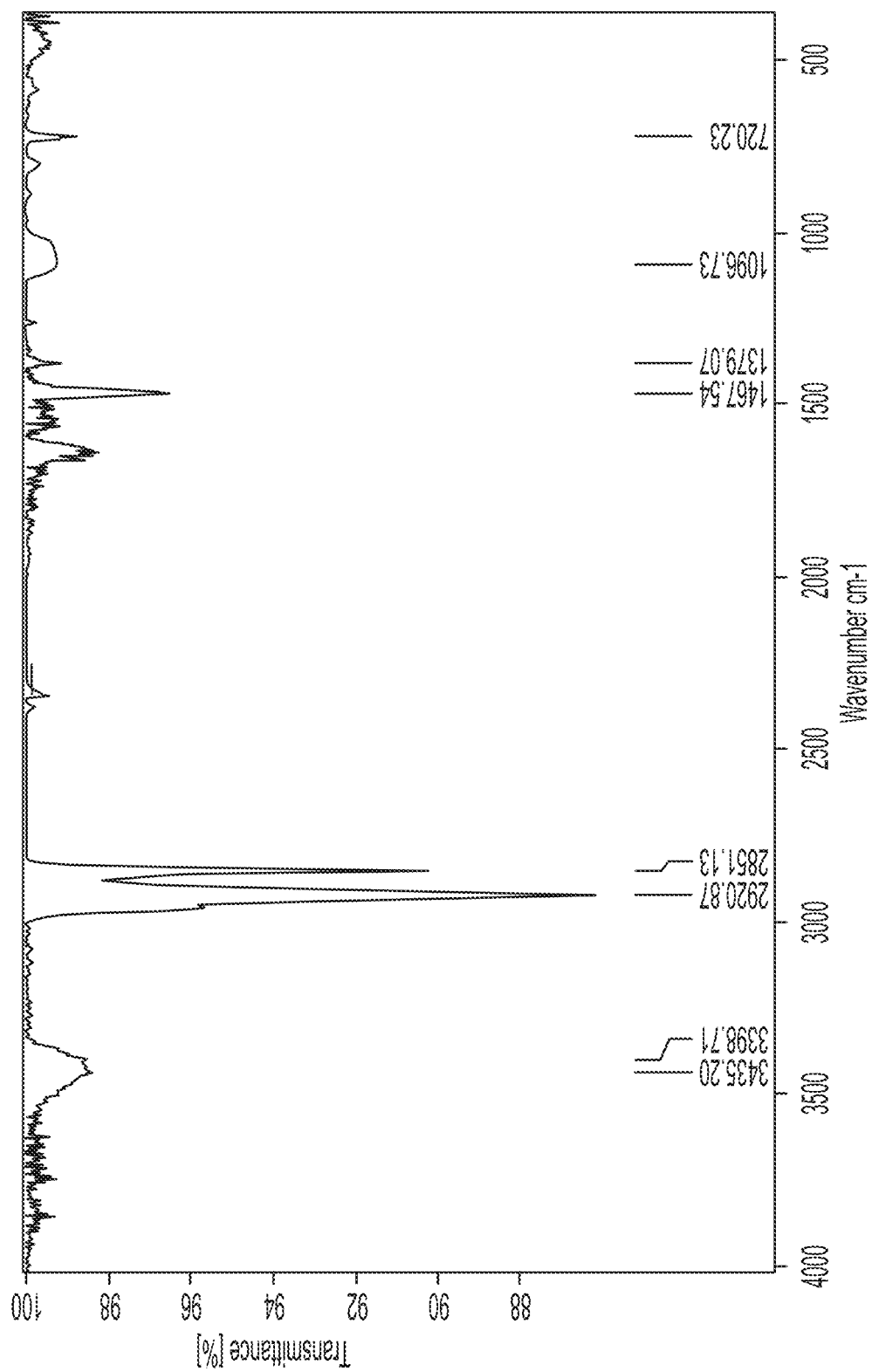
FIG. 40 is the FT-IR spectrum (KBr) of the oil isolated after reaction of HDPE and $AlEt_3$ in the presence of $Zr(CH_2CMe_3)_2$@$SiAlO_x$ at 150° C. for 12 h, quenched with $O_2$, and extracted with methylene chloride. The broad signal at 3435 $cm^{-1}$ corresponds to an O—H stretching mode.
Figure 41:
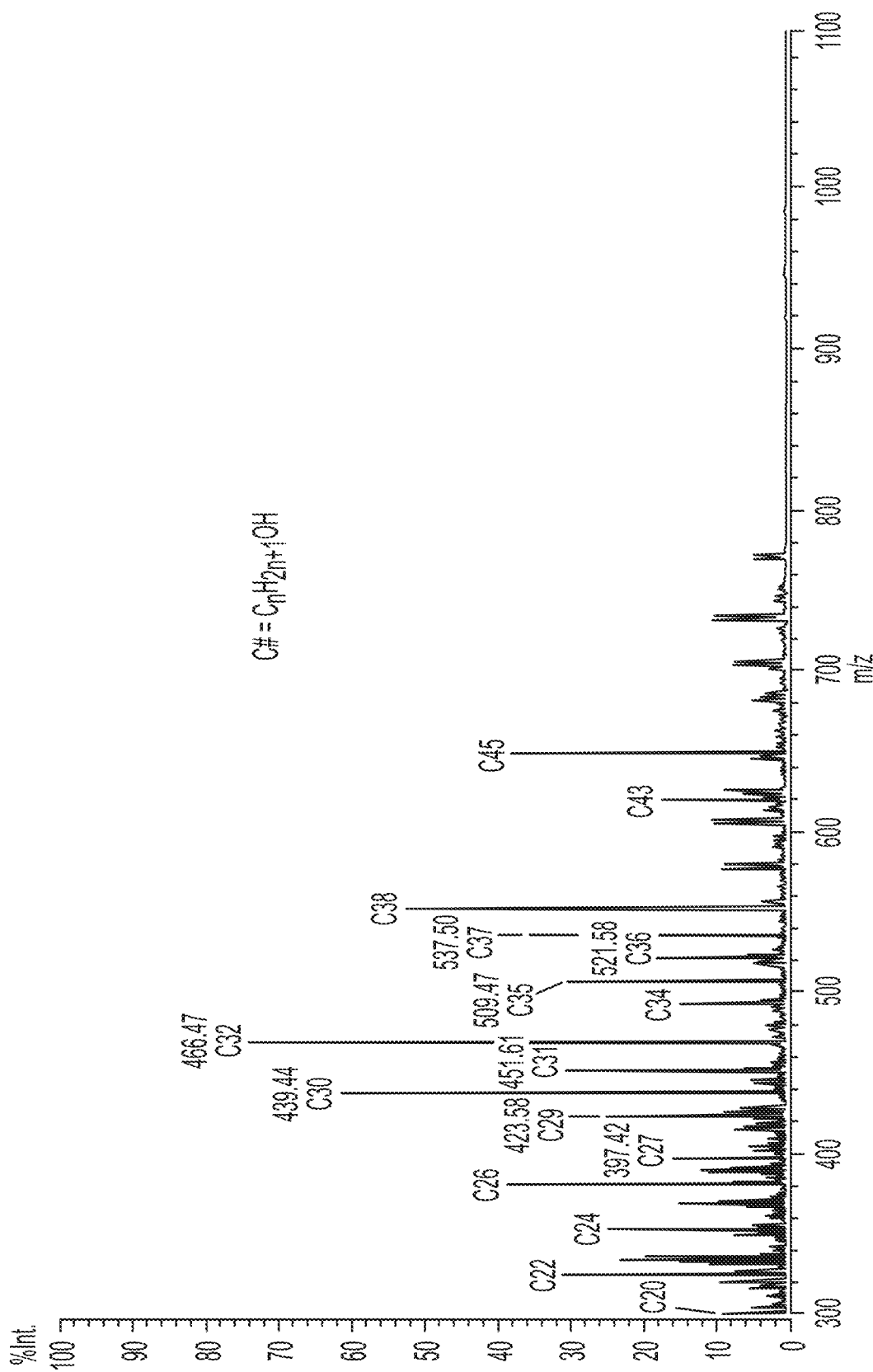
FIG. 41 is the MALDI-TOF-MS spectrum of the oil isolated after reaction of HDPE and $AlEt_3$ in the presence of $Zr(CH_2CMe_3)_2$@$SiAlO_x$ at 150° C. for 12 h, quenched with $O_2$, and extracted with methylene chloride. The spectrum was acquired in linear, positive mode with $AgNO_3$ (salt) and DHB (matrix).
Figure 42:
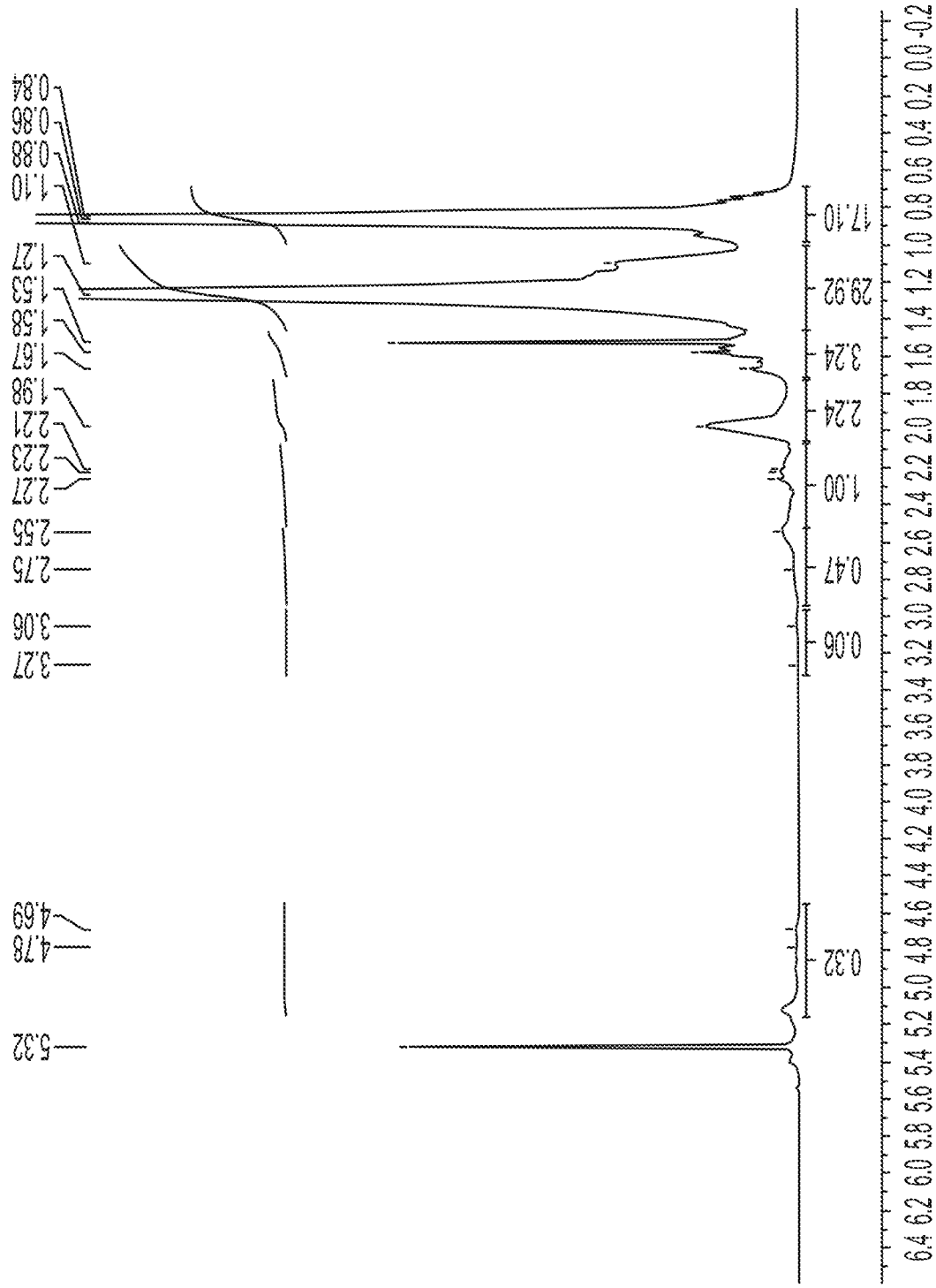
FIG. 42 is the $^1H$ NMR spectrum of the oil isolated after reaction of HDPE and $AlEt_3$ in the presence of $Zr(CH_2CMe_3)_2$@$SiAlO_x$ at 200° C. for 12 h, quenched with $O_2$, and extracted with methylene chloride. The spectrum was acquired at room temperature in methylene chloride-$d_2$ and assigned based on total correlation spectroscopy (TOCSY) and HSQC experiments in FIGS. 43 and 44. Signals at 0.7-0.9 ppm correspond to methyl, peaks at 1.0-1.5, 1.7-2.1, and 2.6-3.3 ppm are attributed to methylene moieties, and those at 1.5-1.7, 2.1-2.6 ppm correspond to methine groups. Peaks at 4.6-5.2 ppm are assigned to —$CH_2$—OH groups.
Figure 43:
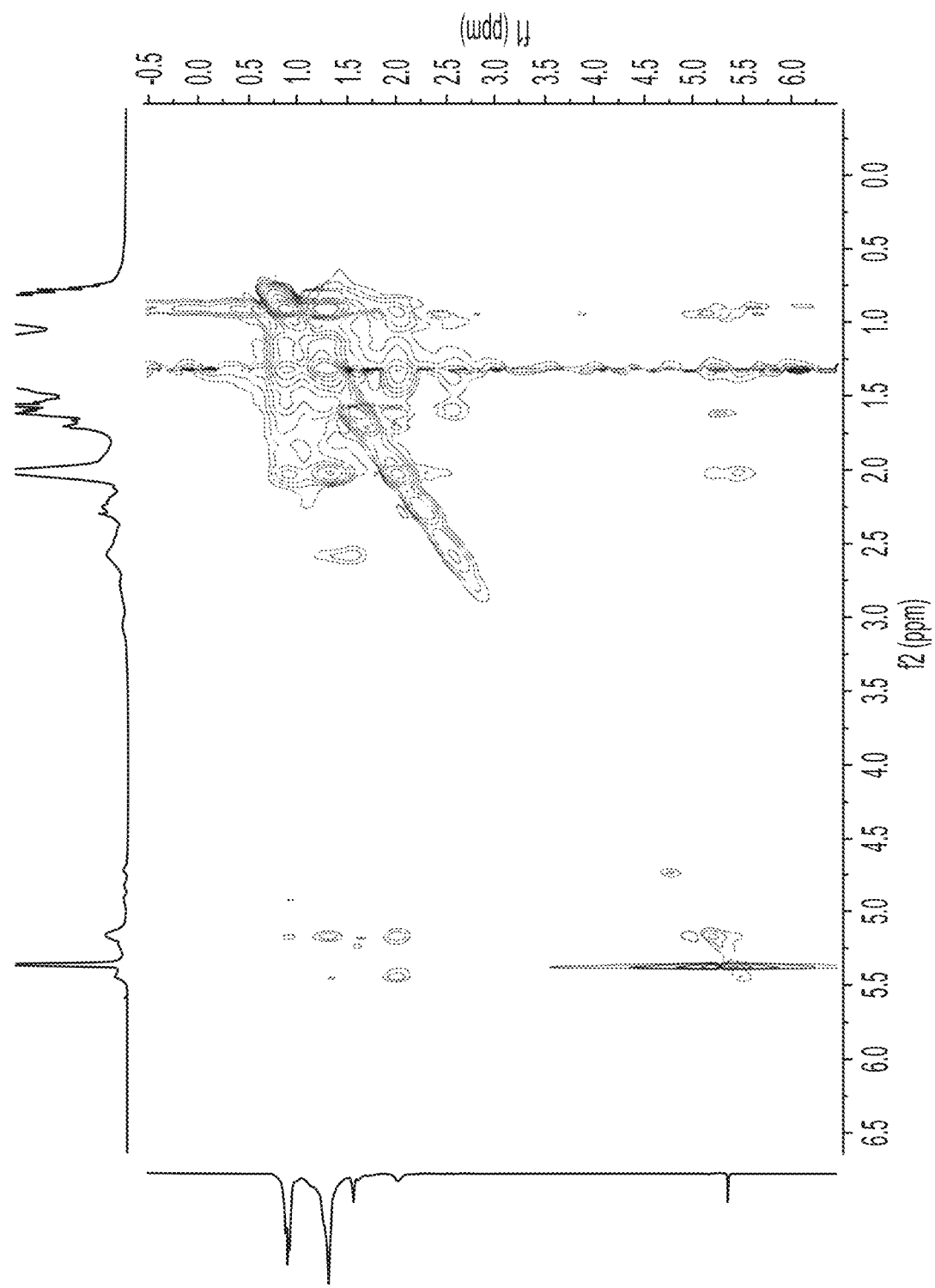
FIG. 43 is the TOCSY spectrum of the oil isolated after reaction of HDPE and $AlEt_3$ in the presence of $Zr(CH_2CMe_3)_2$@$SiAlO_x$ at 200° C. for 12 h, quenched with $O_2$, and extracted with methylene chloride. The spectrum was acquired at room temperature in methylene chloride-$d_2$. Cross-peaks at 4.7-5.3 ppm correlating to methylene signals at 1.3 and 2.1 ppm are indicative of —$CH_2$—$CH_2$—OH structures.
Figure 44:
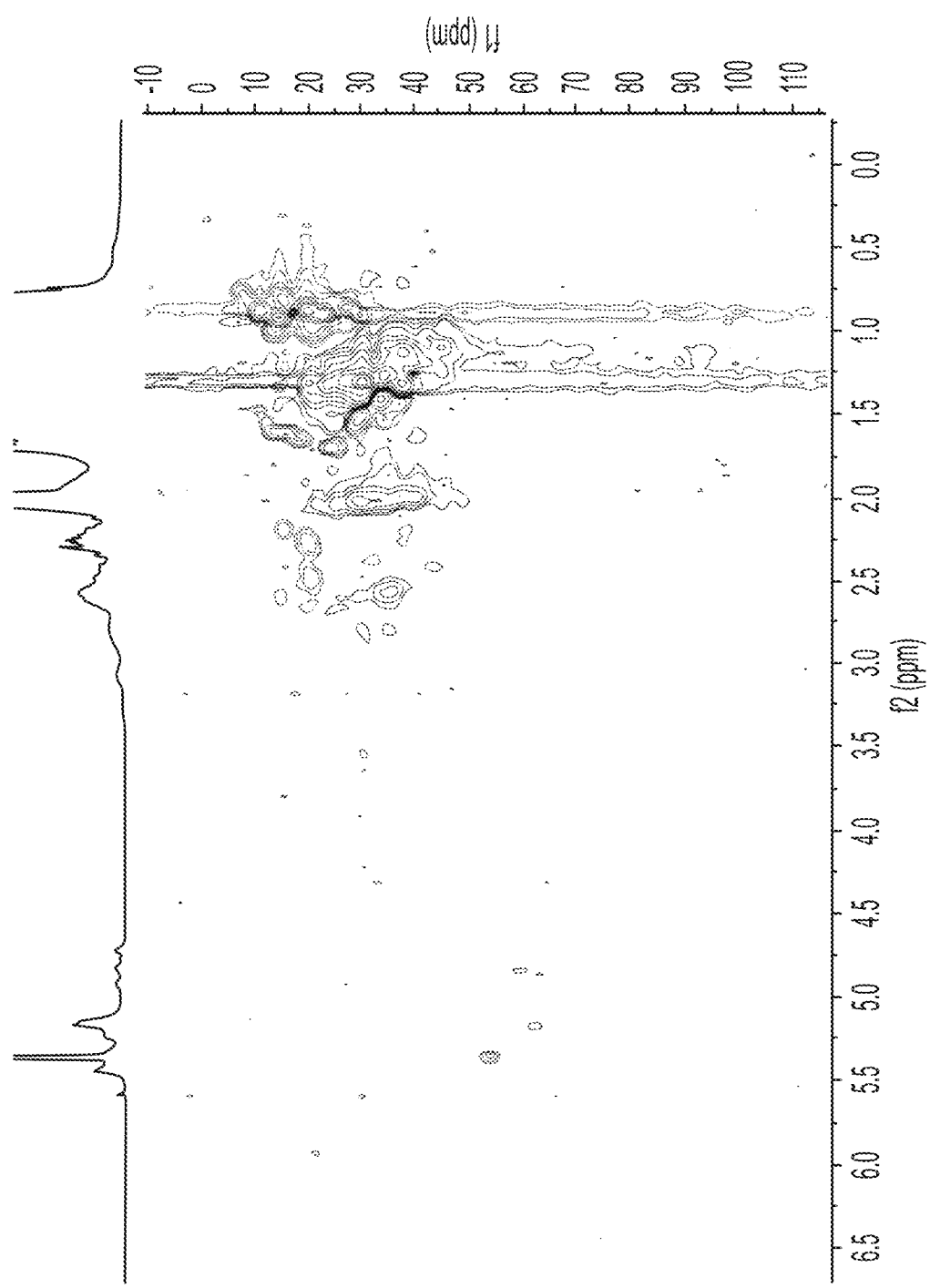
FIG. 44 is the phase sensitive $^1H$-$^{13}C$ HSQC spectrum of the oil isolated after reaction of HDPE and $AlEt_3$ in the presence of $Zr(CH_2CMe_3)_2$@$SiAlO_x$ at 200° C. for 12 h, quenched with $O_2$, and extracted with methylene chloride. The spectrum was acquired at room temperature in methylene chloride-$d_2$. Cross-peaks at $^{13}C$ 60-65 ppm have the same phase as methylene peaks at 30 ppm, indicative of —$CH_2$—OH end groups (i.e., alcohols are primary).
Figure 45:
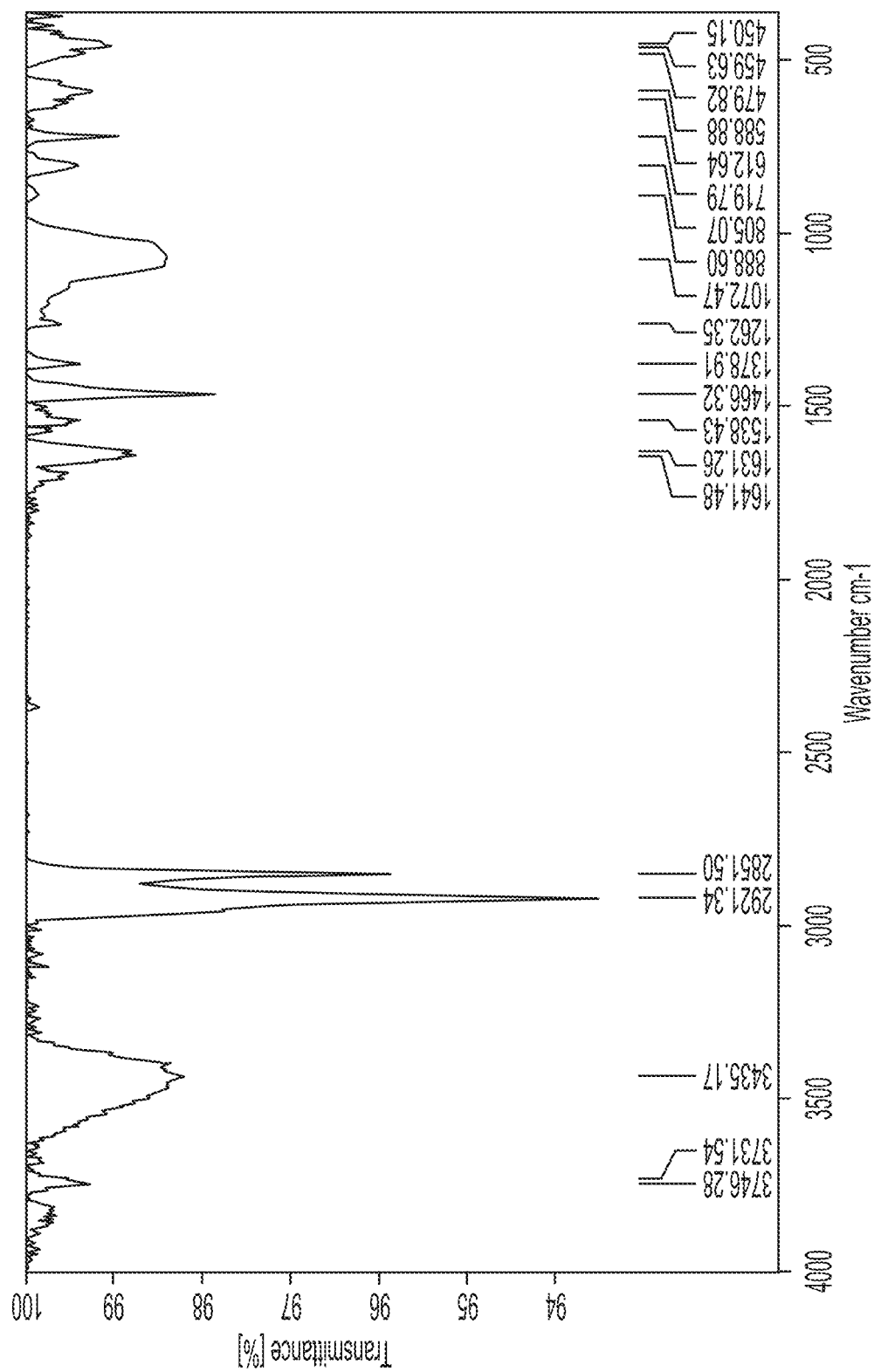
FIG. 45 is the FT-IR spectrum (KBr) of the oil isolated after reaction of HDPE and $AlEt_3$ in the presence of $Zr(CH_2CMe_3)_2$@$SiAlO_x$ at 200° C. for 12 h, quenched with $O_2$, and extracted with methylene chloride. The broad signal at 3435 $cm^{-1}$ corresponds to an O—H stretch.
Figure 46:
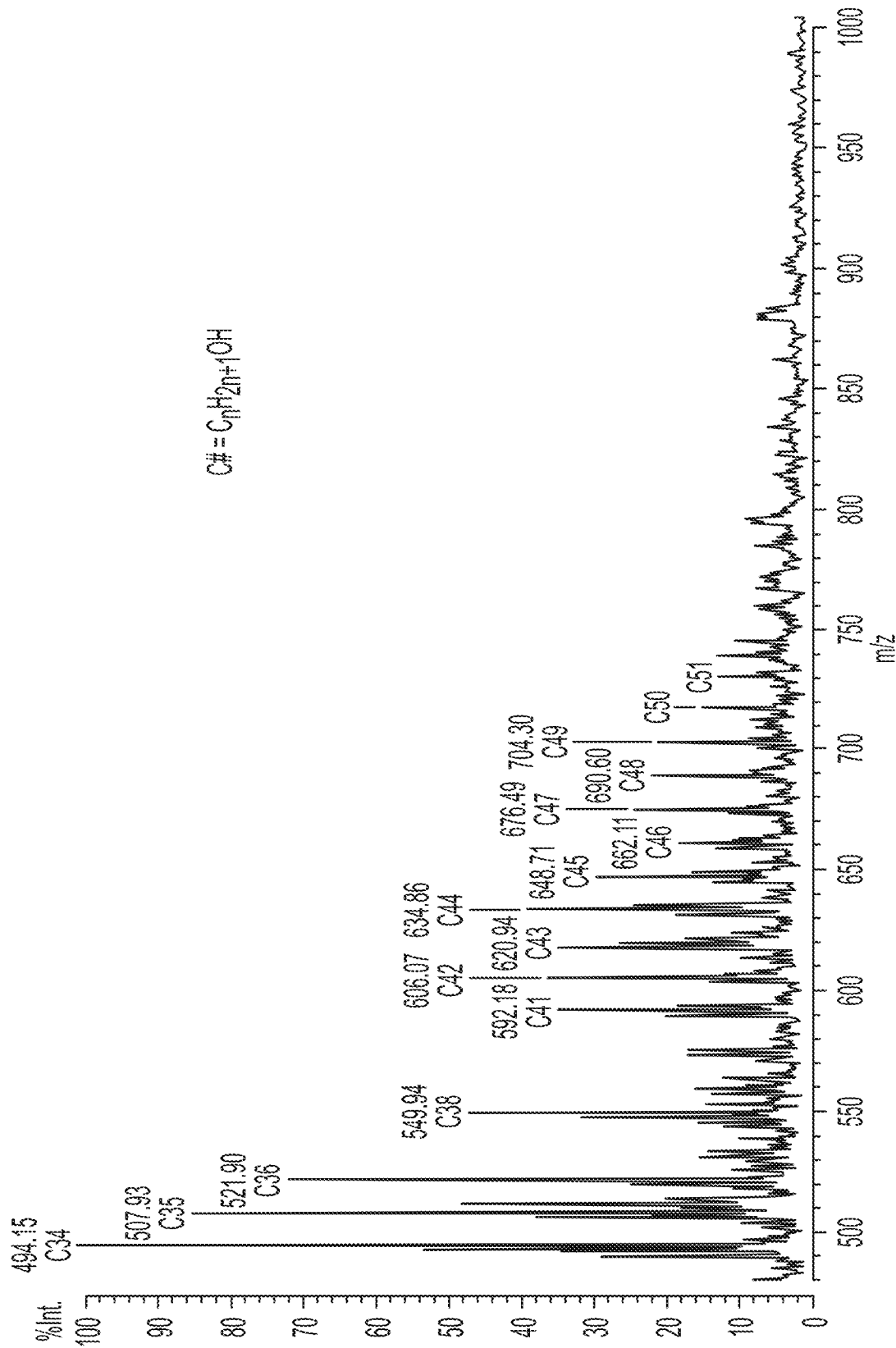
FIG. 46 is the MALDI-TOF-MS spectrum of the oil isolated after reaction of HDPE and $AlEt_3$ in the presence of $Zr(CH_2CMe_3)_2$@$SiAlO_x$ at 200° C. for 12 h, quenched with $O_2$, and extracted with methylene chloride. The spectrum was acquired in linear, positive mode with $AgNO_3$ (salt) and DHB (matrix).
Figure 47:
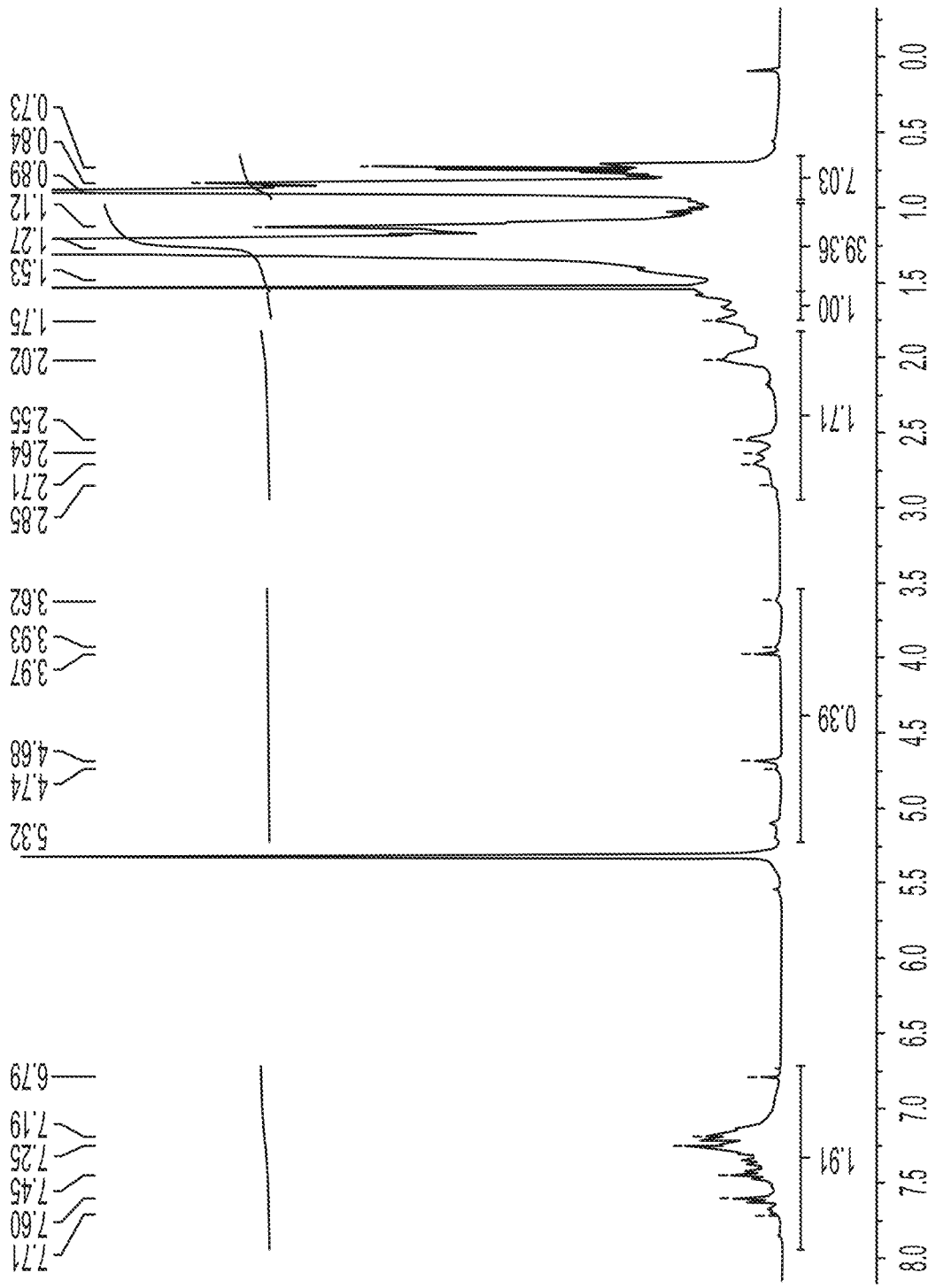
FIG. 47 is the $^1H$ NMR spectrum of the oil isolated after reaction of HDPE and $AlPh_3$ in the presence of $Zr(CH_2CMe_3)_2$@$SiAlO_x$ at 200° C. for 12 h, quenched with $O_2$, and extracted with methylene chloride. The spectrum was acquired at room temperature in methylene chloride-$d_2$ and assigned based on COSY and HSQC experiments in FIGS. 48 and 49. Signals at 0.7-0.9 ppm correspond to methyl groups, peaks at 1.0-1.6 and 1.8-3.0 ppm are attributed to methylenes, and those at 1.6-1.8 ppm are assigned to methine groups. Incorporation of phenyl groups in the product is evident from the aromatic signals between 6.8-8.0 ppm. Signals at 3.5-4.8 ppm are assigned to —$CH_2$—OH groups.
Figure 48:
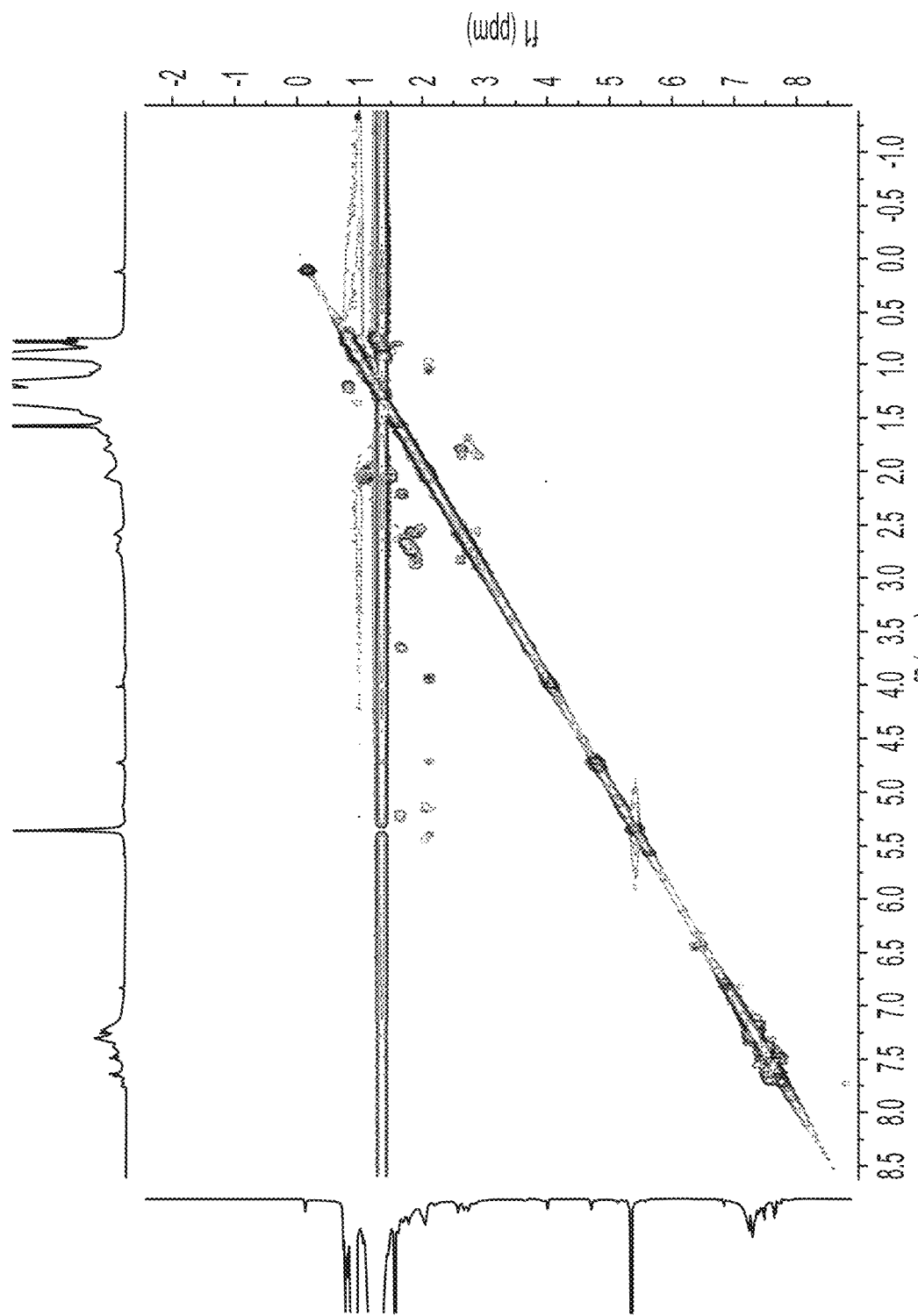
FIG. 48 is the COSY spectrum of the oil isolated after reaction of HDPE and $AlPh_3$ in the presence of $Zr(CH_2CMe_3)_2$@$SiAlO_x$ at 200° C. for 12 h, quenched with $O_2$, and extracted with methylene chloride. The spectrum was acquired at room temperature in methylene chloride-$d_2$. Cross-peaks at 4.0, 4.7, and 5.1 ppm correlate with the methylene signals at 2.1 ppm, and cross-peaks at 3.6 and 5.2 ppm correlate with methine signals at 1.6 ppm, indicative of both —$CH_2$—$CH_2$—OH and —(R)CH—$CH_2$—OH structures (R=phenyl or alkyl, as shown in the HMBC below).
Figure 49:
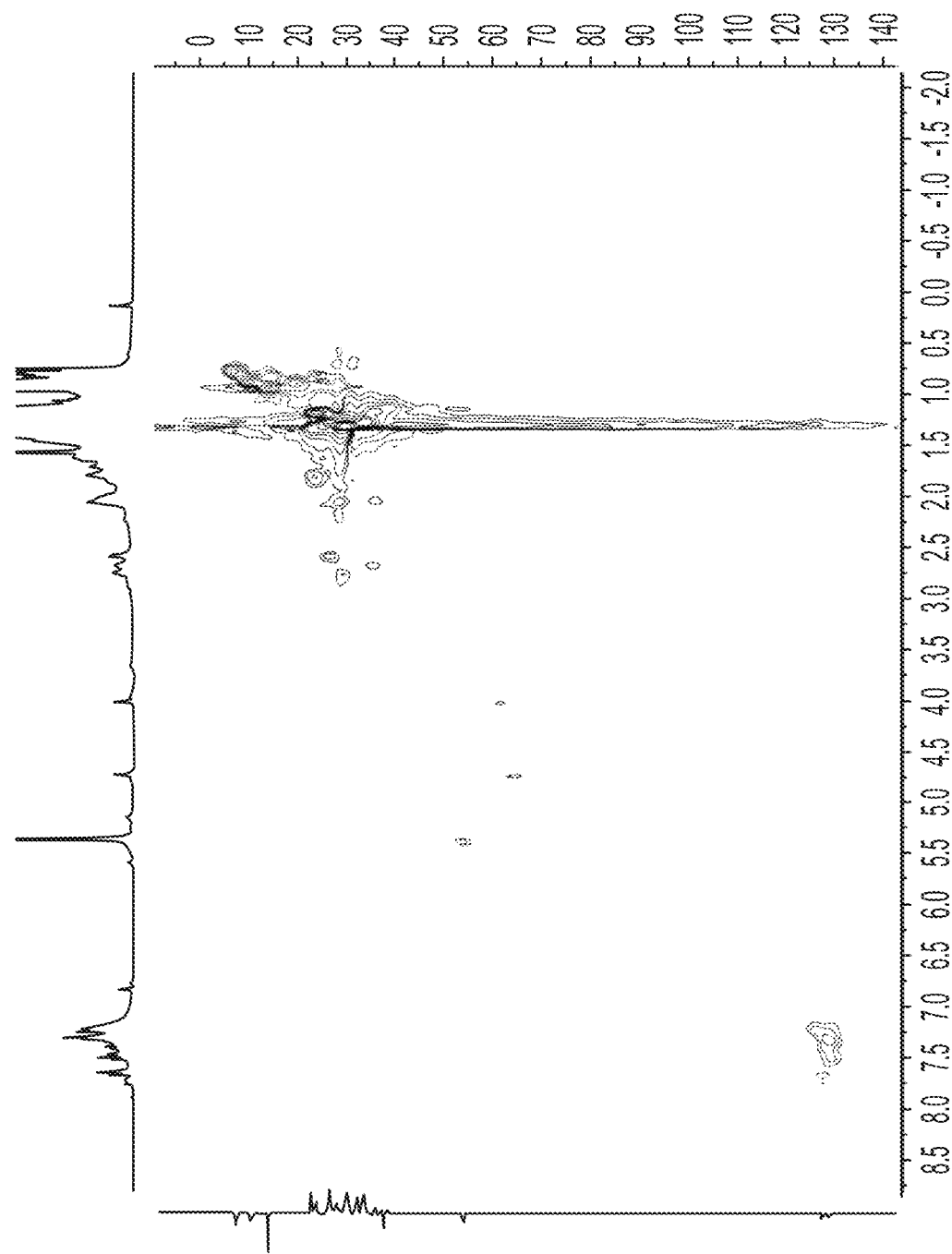
FIG. 49 is the phase sensitive $^1H$-$^{13}C$ HSQC spectrum of the oil isolated after reaction of HDPE and $AlPh_3$ in the presence of $Zr(CH_2CMe_3)_2$@$SiAlO_x$ at 200° C. for 12 h, quenched with $O_2$, and extracted with methylene chloride. The spectrum was acquired at room temperature in methylene chloride-$d_2$. Cross-peaks at $^{13}C$ 60-70 ppm have the same phase as methylene peaks at 30 ppm, revealing the —$CH_2$—OH structure. Cross-peaks at $^{13}C$ 125-135 ppm correspond to aromatic C—H groups and have the opposite phase as methylene peaks at 30 ppm.
Figure 50:
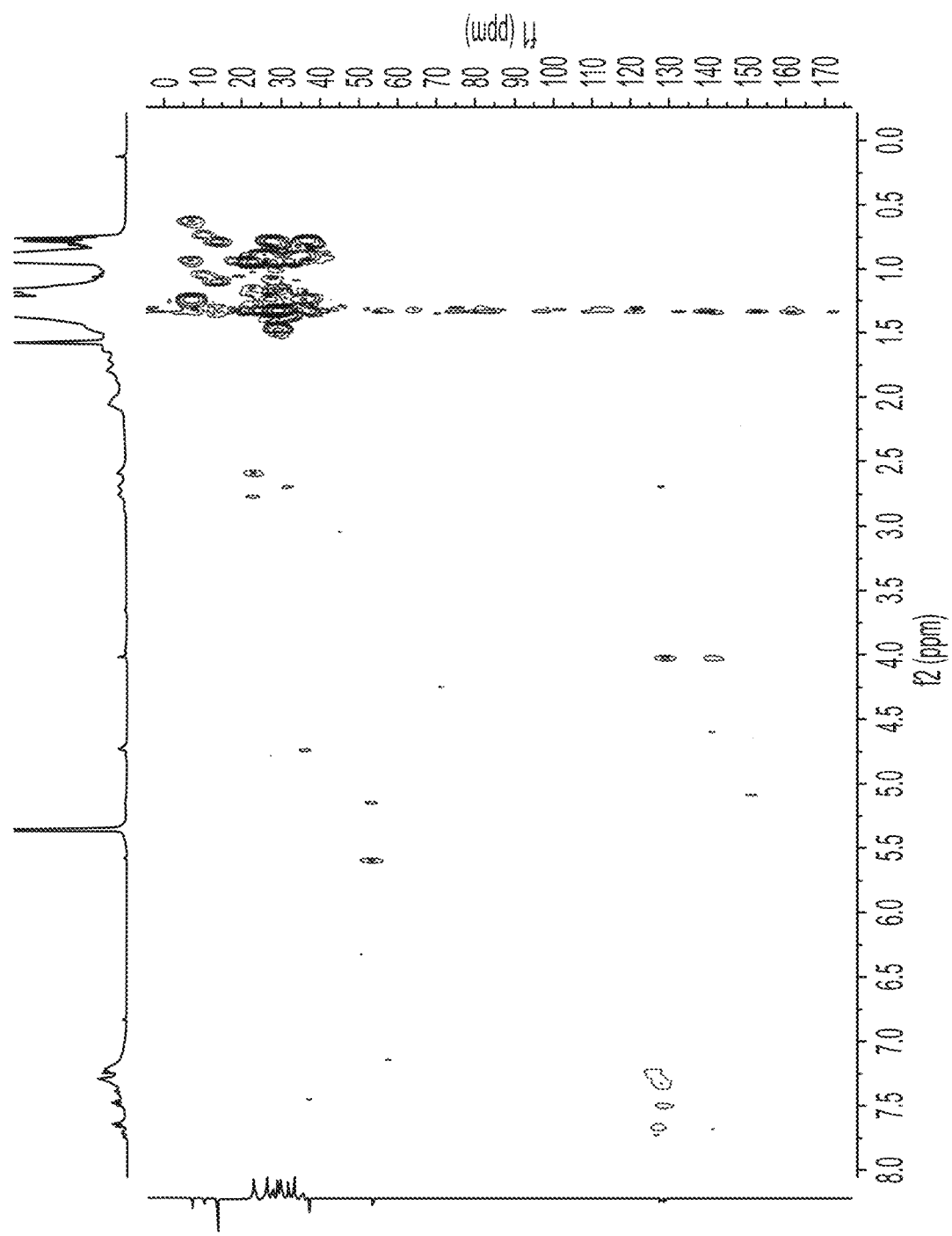
FIG. 50 is the $^1H$-$^{13}C$ HMBC spectrum of the oil isolated after reaction of HDPE and $AlPh_3$ in the presence of $Zr(CH_2CMe_3)_2$@$SiAlO_x$ at 200° C. for 12 h, quenched with $O_2$, and extracted with methylene chloride. The spectrum was acquired at room temperature in methylene chloride-$d_2$. Cross-peaks at $^{13}C$ 130-140 ppm correlate with $^1H$ NMR signals at 4.1 ppm assigned to $CH_2OH$, and $^1H$ NMR signals at 7.5 ppm assigned to aromatic protons correlate with $^{13}C$ signals at 40 ppm assigned to methines. These observations indicate that -Ph(CH)—$CH_2$—OH species are formed, which would arise from phenylalumination of in-situ generated olefins (e.g., by β-alkyl or hydrogen elimination), followed by quenching with $O_2$. Note that the MALDI-TOF-MS shown below also indicates aromatic alkylalcohols are formed during deconstruction.
Figure 51:
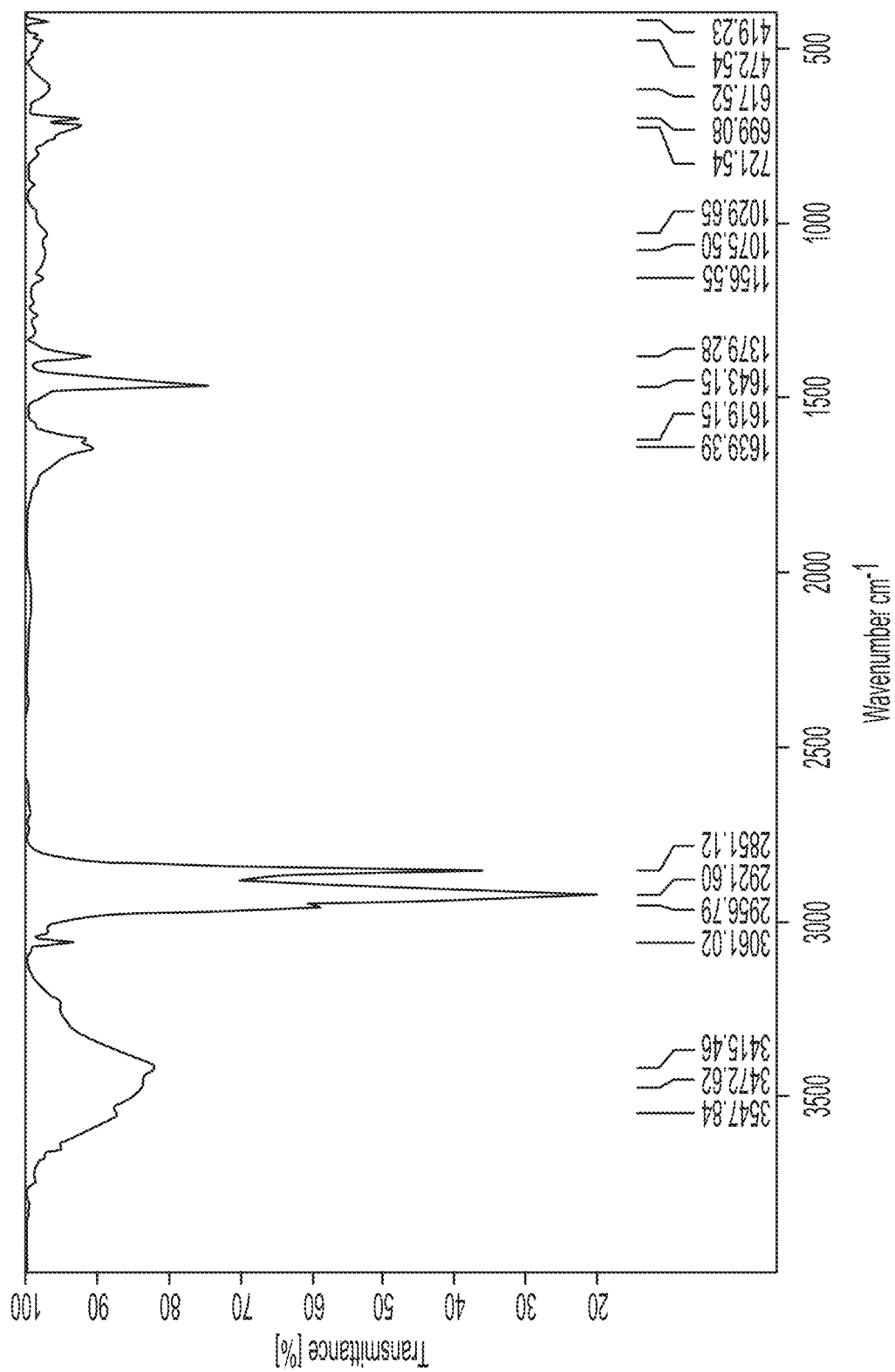
FIG. 51 is the FT-IR spectrum (KBr) of the oil isolated after reaction of HDPE and $AlPh_3$ in the presence of $Zr(CH_2CMe_3)_2$@$SiAlO_x$ at 200° C. for 12 h, quenched with $O_2$, and extracted with methylene chloride. Broad signals between 3100-3700 $cm^{-1}$ correspond to an O—H stretching modes. Signals at 3061 $cm^{-1}$ and 1619-1639 $cm^{-1}$ correspond to C—H and C=C stretching modes of aromatic groups.
Figure 52:
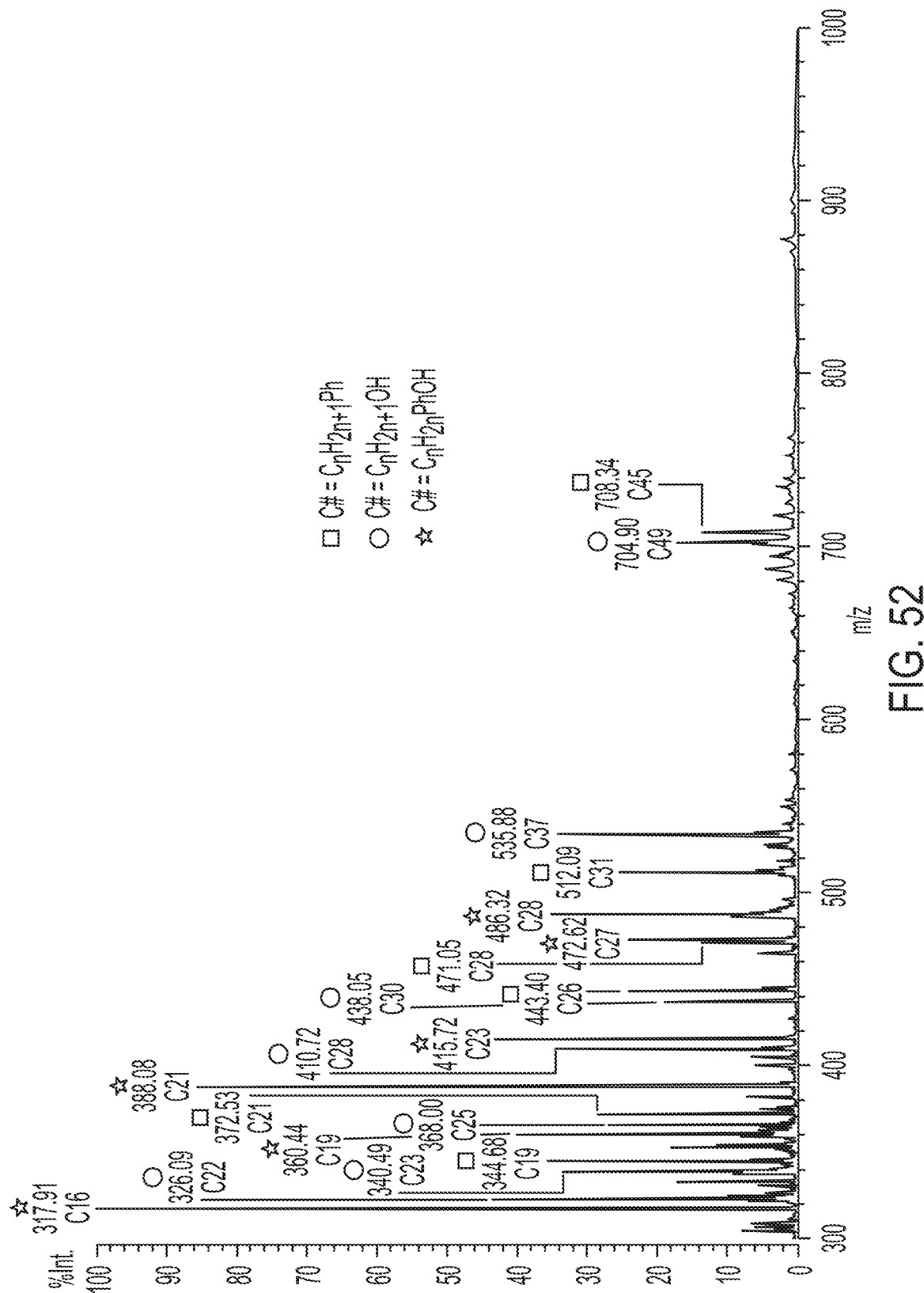
FIG. 52 is the MALDI-TOF-MS spectrum of oil isolated after reaction of HDPE and $AlPh_3$ in the presence of $Zr(CH_2CMe_3)_2$@$SiAlO_x$ at 200° C. for 12 h, quenched with $O_2$, and extracted with methylene chloride. The spectrum was acquired in linear, positive mode with DHB (matrix). Three distinct types of species were identified, namely (1) alkyl benzenes, (2) fatty alcohols, and (3) fatty alcohols containing a single phenyl group as a result of phenylalumination.
Figure 53:
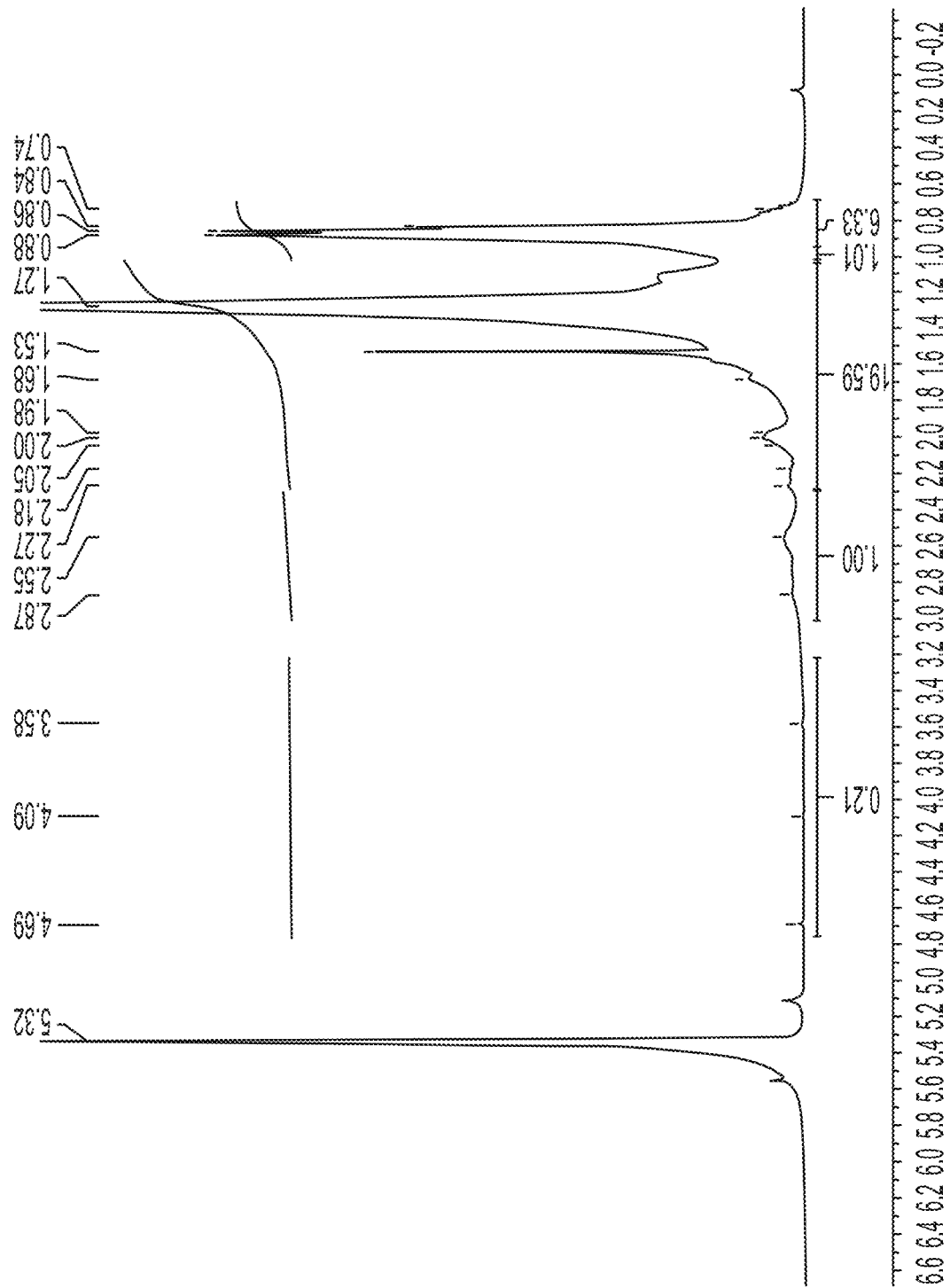
FIG. 53 is the $^1H$ NMR spectrum of the oil isolated after reaction of HDPE and $AlH_3$ in the presence of $Zr(CH_2CMe_3)_2$@$SiAlO_x$ at 200° C. for 12 h, quenched with $O_2$, and extracted with methylene chloride. The spectrum was acquired at room temperature in methylene chloride-$d_2$ and assigned based on COSY and HSQC experiments in FIGS. 54 and 55. Signals at 0.7-1.0 ppm are assigned to methyls, those at 1.0-2.3 ppm correspond to methylenes, and those at 2.3-3.0 ppm are attributed to methine groups. Peaks at 3.6-4.8 ppm are assigned to —$CH_2$—OH groups.
Figure 54:
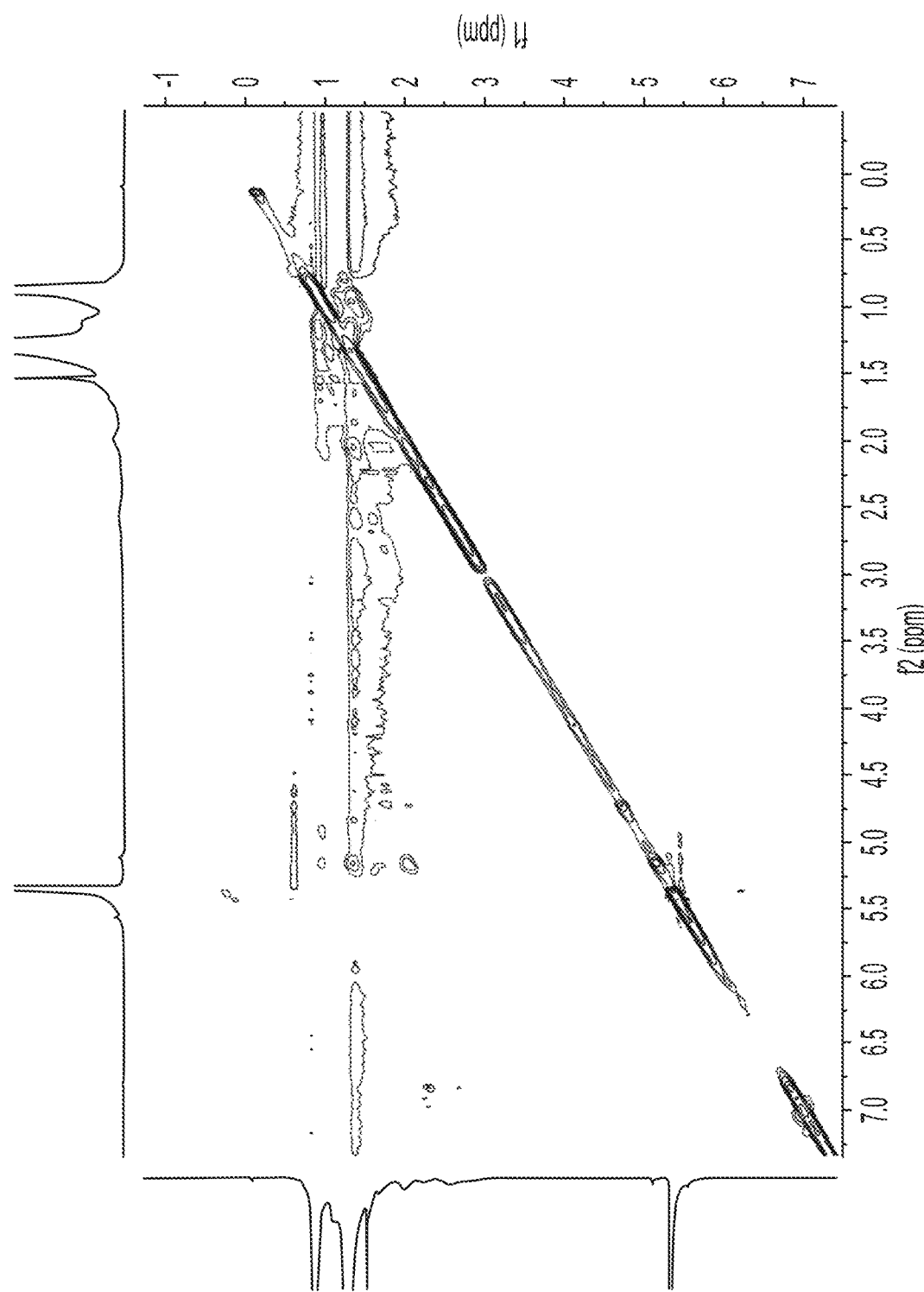
FIG. 54 is the TOCSY spectrum of the oil isolated after reaction of HDPE and $AlH_3$ in the presence of $Zr(CH_2CMe_3)_2$@$SiAlO_x$ at 200° C. for 12 h, quenched with $O_2$, and extracted with methylene chloride. The spectrum was acquired at room temperature in methylene chloride-$d_2$. Cross-peaks at 4.5-4.7 ppm correlate with methylene signals at 1.6 ppm, indicative of —$CH_2CH_2$—OH species.
Figure 55:
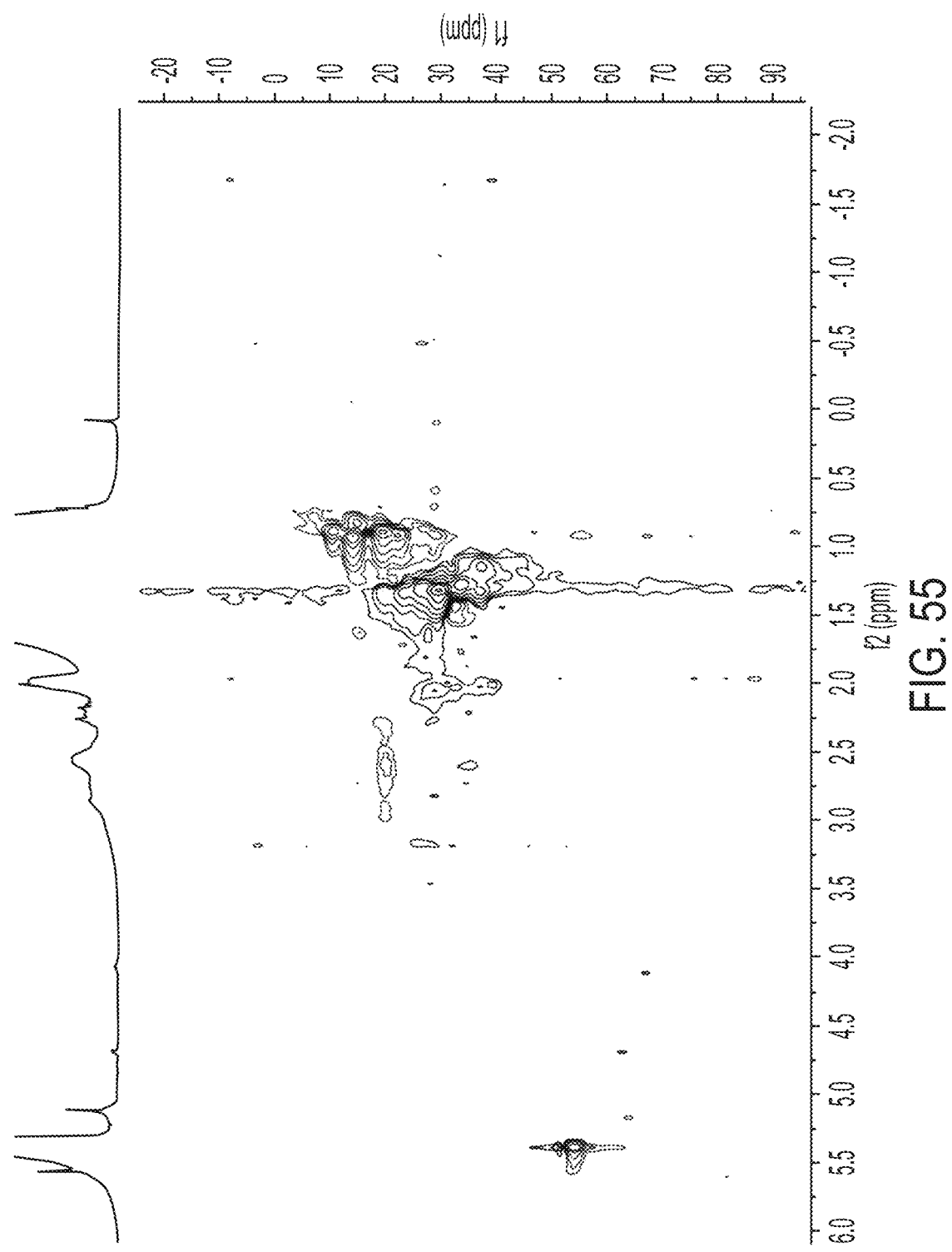
FIG. 55 is the Phase sensitive $^1H$-$^{13}C$ HSQC spectrum of the oil isolated after reaction of HDPE and $AlH_3$ in the presence of $Zr(CH_2CMe_3)_2$@$SiAlO_x$ at 200° C. for 12 h, quenched with $O_2$, and extracted with methylene chloride. The spectrum was acquired at room temperature in methylene chloride-$d_2$. Cross-peaks at $^{13}C$ 60-70 ppm have the same phase as methylene peaks at 30 ppm, revealing the former are —$CH_2$—OH moieties (primary alcohols).
Figure 56:
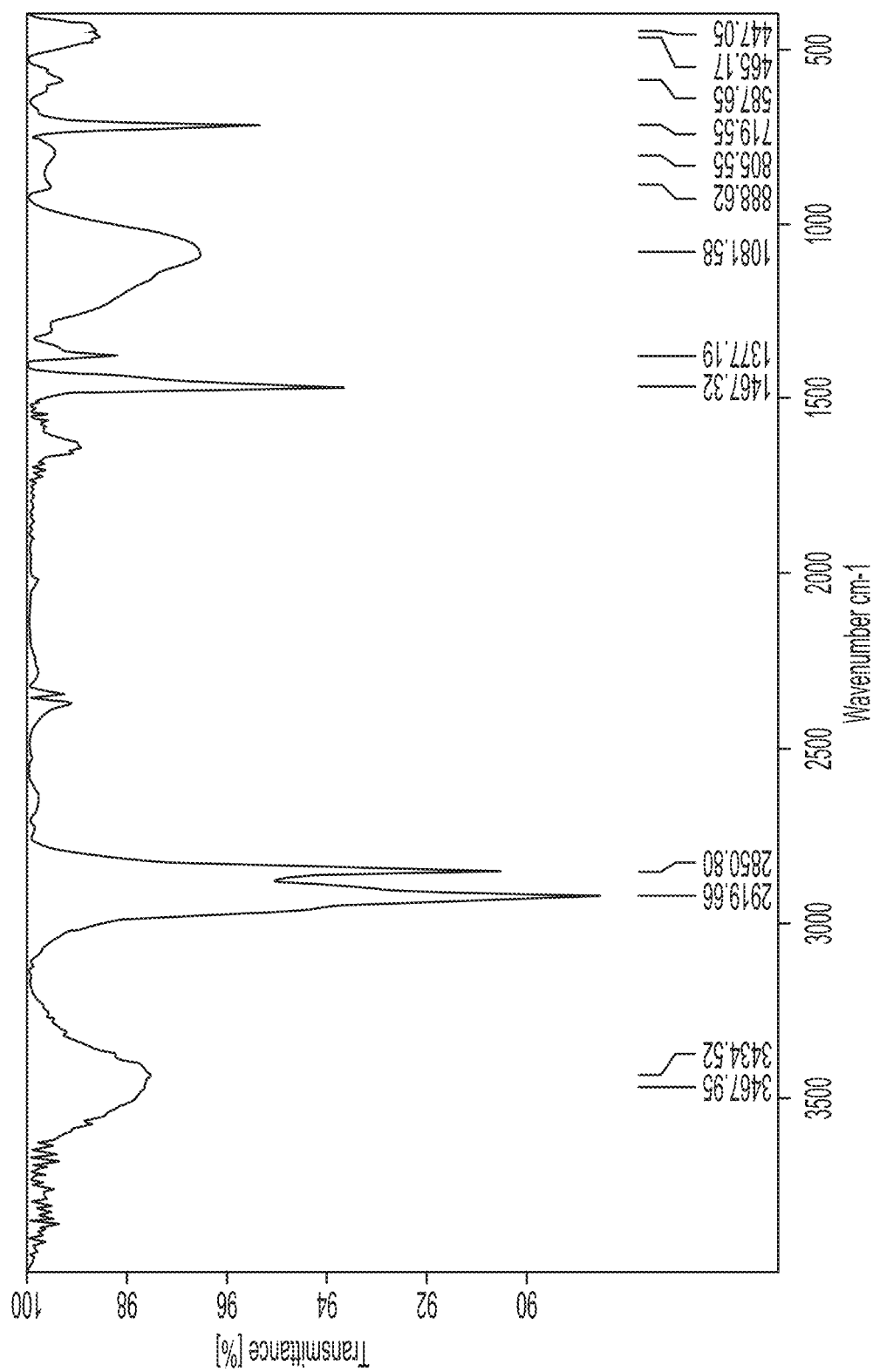
FIG. 56 is the FT-IR spectrum (KBr) of oil isolated after reaction of HDPE and $AlH_3$ in the presence of $Zr(CH_2CMe_3)_2$@$SiAlO_x$ at 200° C. for 12 h, quenched with $O_2$, and extracted with methylene chloride. The broad signal at 3435 $cm^{-1}$ corresponds to an O—H stretch.
Figure 57:
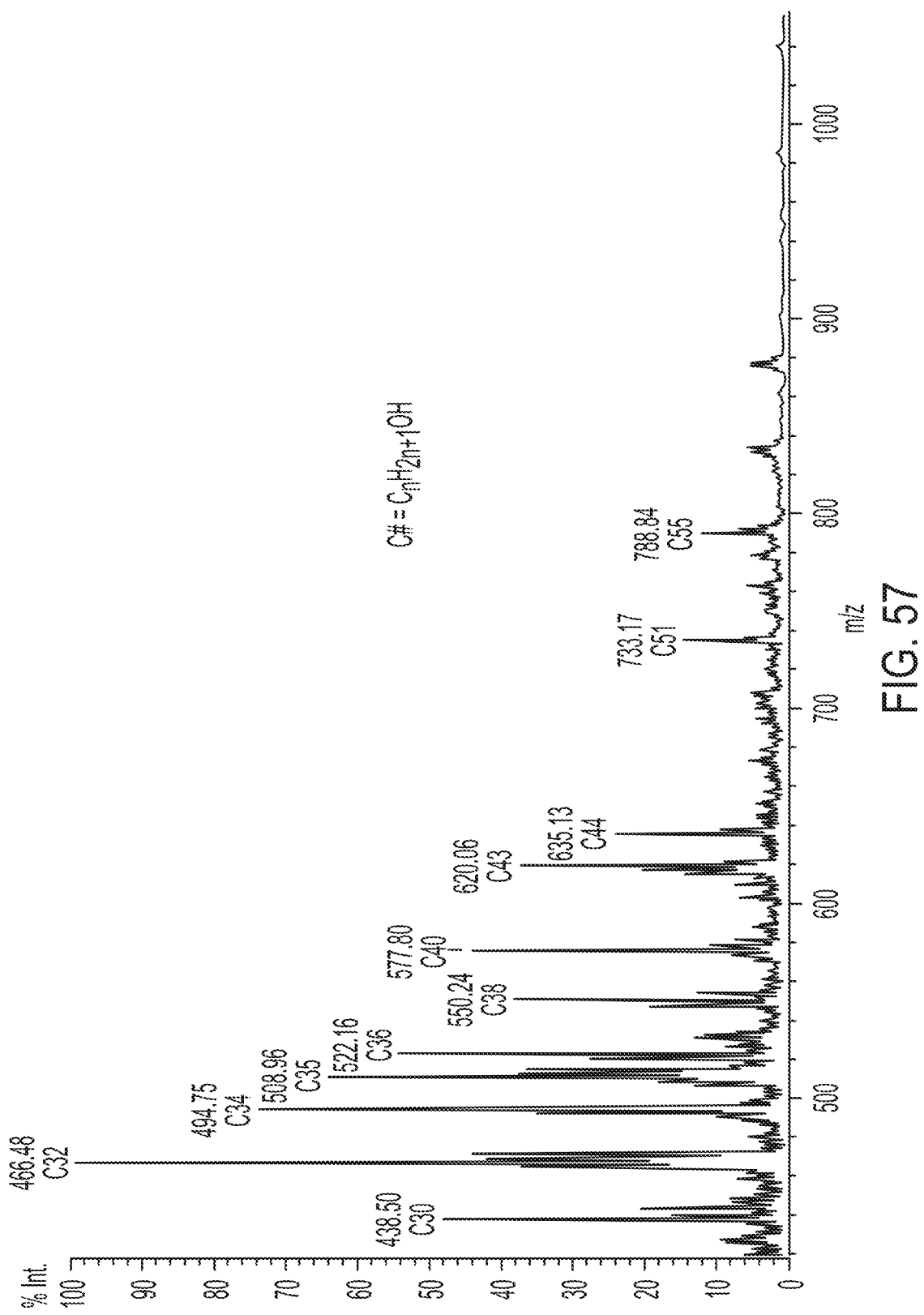
FIG. 57 is the MALDI-TOF-MS spectrum of oil isolated after reaction of HDPE and $AlH_3$ in the presence of $Zr(CH_2CMe_3)_2$@$SiAlO_x$ at 200° C. for 12 h, quenched with $O_2$, and extracted with methylene chloride. The spectrum was acquired in linear, positive mode with $AgNO_3$ (salt) and DHB (matrix).
Figure 58:
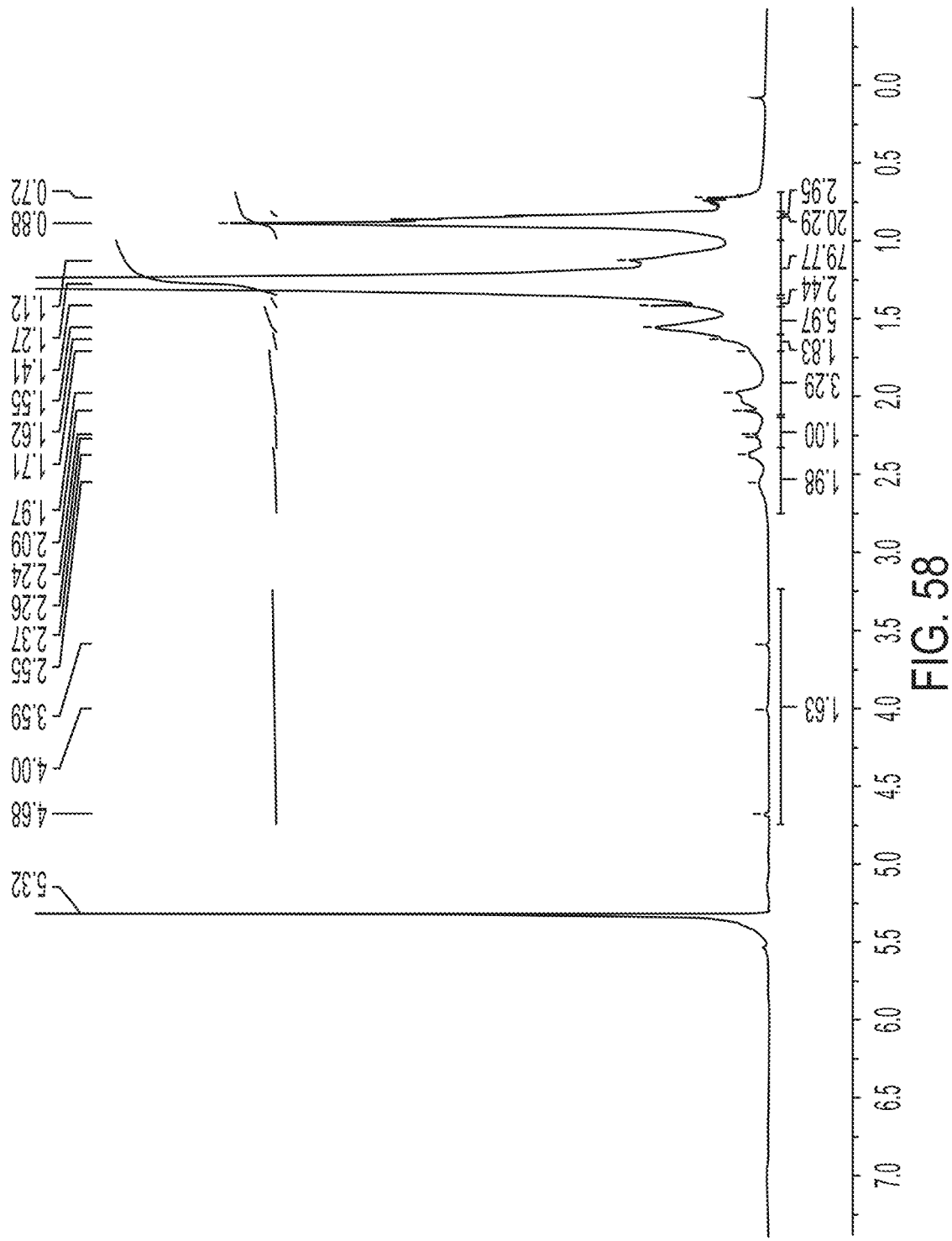
FIG. 58 is the $^1H$ NMR spectrum of the oil isolated after reaction of HDPE and $AliBu_3$ in the presence of $Zr(OCH_2CMe_3)_2@SiAlO_x$ at 200° C. for 12 h, quenched with $O_2$, and extracted with methylene chloride. The spectrum was acquired at room temperature in methylene chloride-$d_2$ and assigned based on COSY and HSQC experiments in FIGS. 59 and 60. Signals at 0.7-1.0 ppm are assigned to methyls, the peaks at 1.0-1.3, 1.4-1.6, 1.7-2.1, and 2.3-2.7 ppm correspond to methylene groups, and those at 1.3-1.4, 1.6-1.7, and 2.1-2.3 ppm are attributed to methine groups. Peaks at 3.5-4.7 ppm are assigned to $CH_2$—OH groups.
Figure 59:
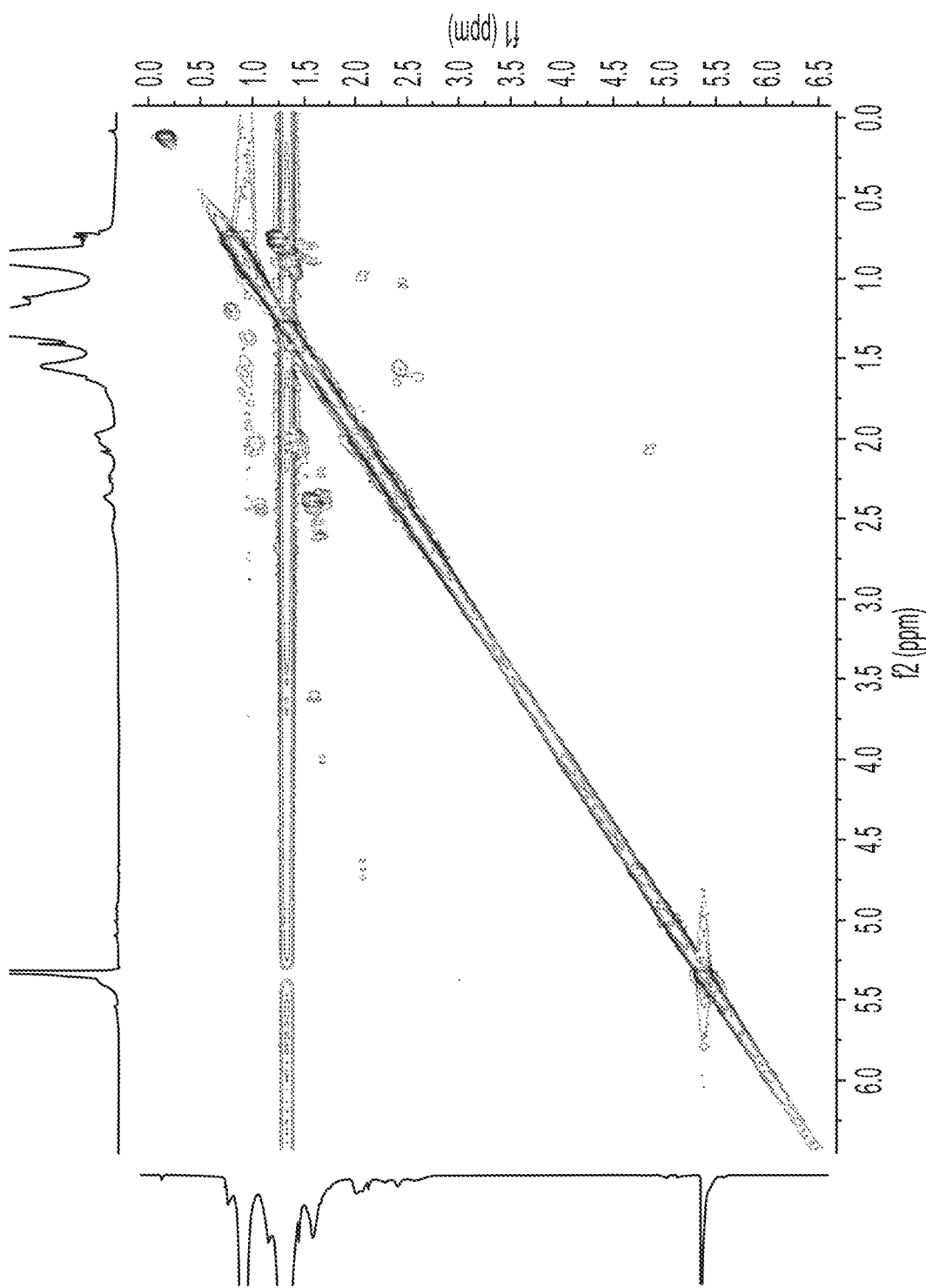
FIG. 59 is the COSY spectrum of the oil isolated after reaction of HDPE and $AliBu_3$ in the presence of $Zr(OCH_2CMe_3)_2@SiAlO_x$ at 200° C. for 12 h, quenched with $O_2$, and extracted with methylene chloride. The spectrum was acquired at room temperature in methylene chloride-$d_2$. Cross-peaks at 3.6-4.8 ppm correlate with methylene signals at 1.5-2.0 ppm, which is indicative of $CH_2$—$CH_2$—OH moieties.
Figure 60:
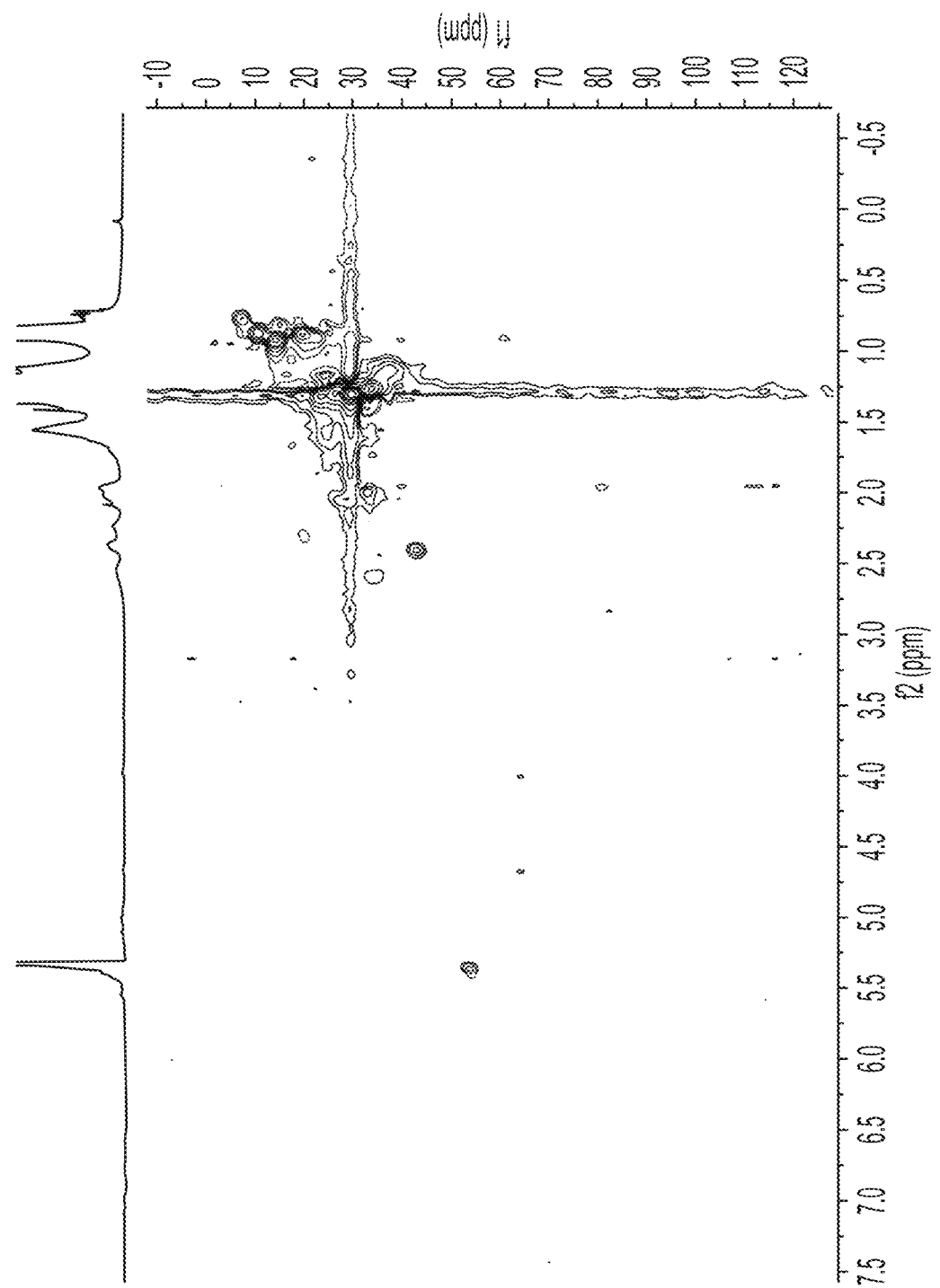
FIG. 60 is the phase sensitive $^1H$-$^{13}C$ HSQC spectrum of the oil isolated after reaction of HDPE and $AliBu_3$ in the presence of $Zr(OCH_2CMe_3)_2@SiAlO_x$ at 200° C. for 12 h, quenched with $O_2$, and extracted with methylene chloride. The spectrum was acquired at room temperature in methylene chloride-$d_2$. Cross-peaks at $^{13}C$ 60-70 ppm that have the same phase as methylene peaks at 30 ppm revealing the former are —$CH_2$—OH moieties.
Figure 61:
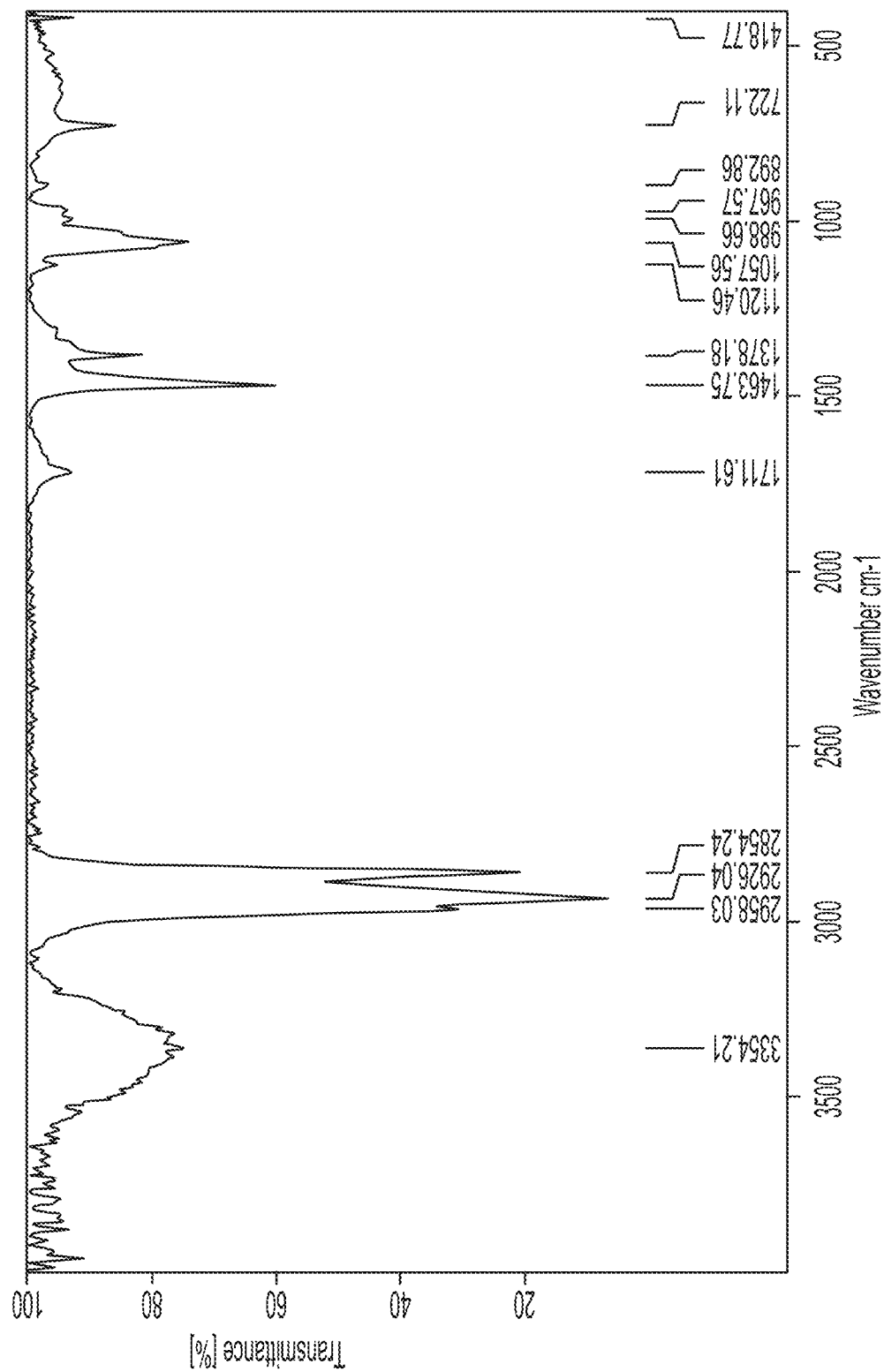
FIG. 61 is the FT-IR spectrum (KBr) of the oil isolated after reaction of HDPE and $AliBu_3$ in the presence of $Zr(OCH_2CMe_3)_2@SiAlO_x$ at 200° C. for 12 h, quenched with $O_2$, and extracted with methylene chloride. The broad signal at 3354 $cm^1$ corresponds to an O—H stretch.
Figure 62:
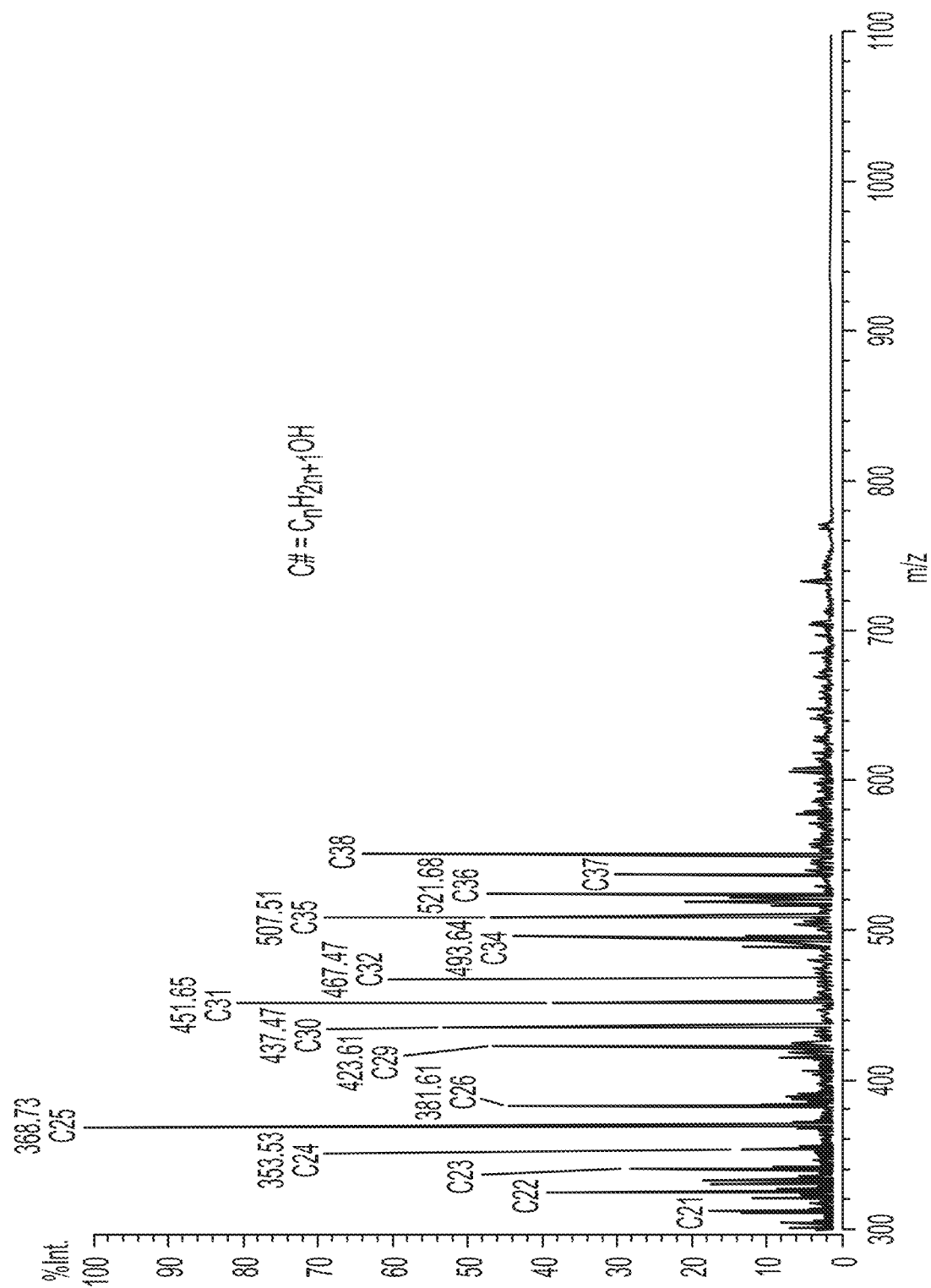
FIG. 62 is the MALDI-TOF-MS spectrum of the oil isolated after reaction of HDPE and $AliBu_3$ in the presence of $Zr(OCH_2CMe_3)_2@SiAlO_x$ at 200° C. for 12 h, quenched with $O_2$, and extracted with methylene chloride. The spectrum was acquired in linear, positive mode with $AgNO_3$ (salt) and DHB (matrix).
Figure 63:
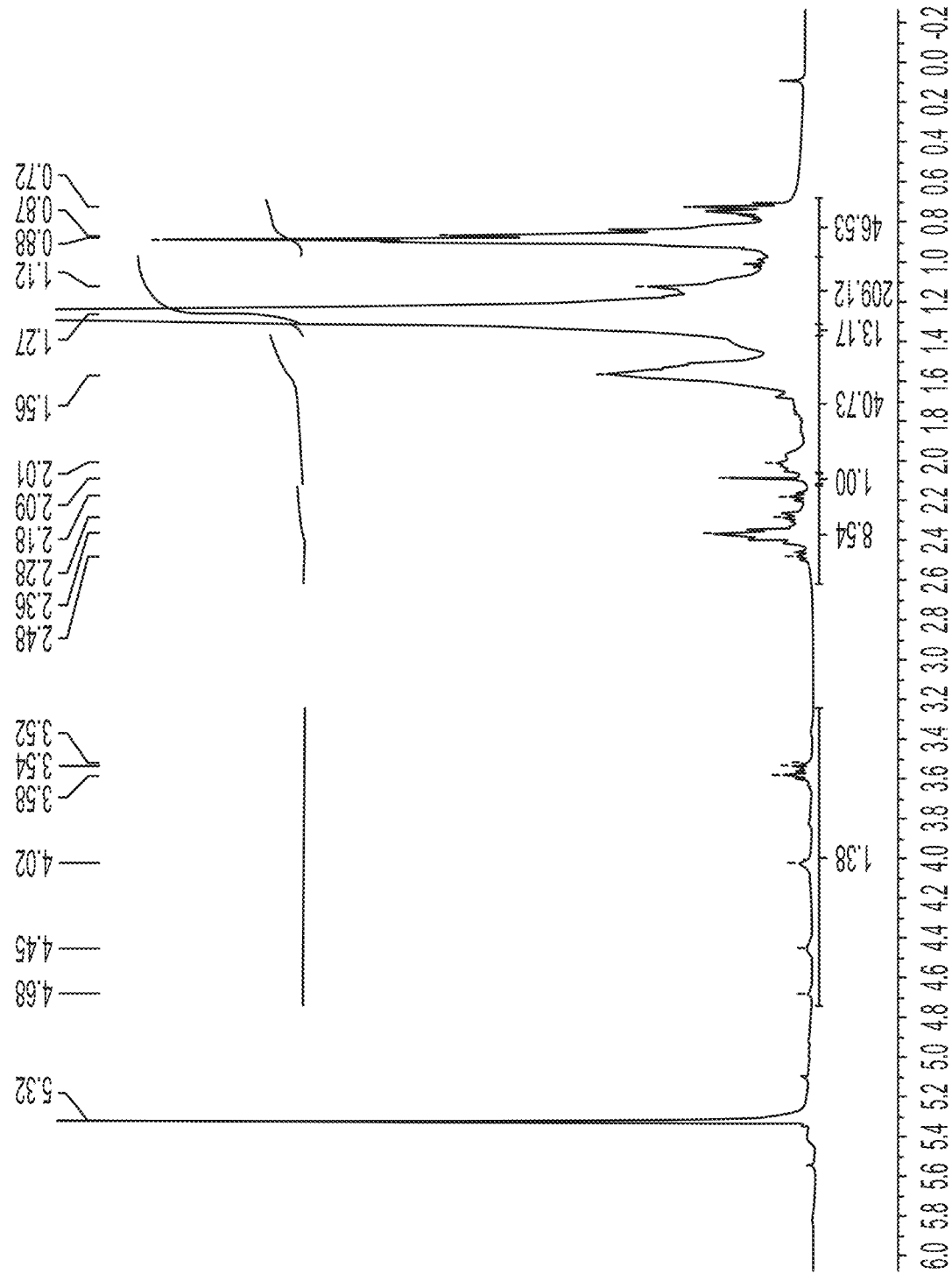
FIG. 63 is the $^1H$ NMR spectrum of the oil isolated after reaction of HDPE and $AlH_3$ in the presence of $Zr(OCH_2CMe_3)_2@SiAlO_x$ at 200° C. for 12 h, quenched with $O_2$, and extracted with methylene chloride. The spectrum was acquired at room temperature in methylene chloride-$d_2$ and assigned based on COSY and HSQC experiments in FIGS. 64 and 65. Signals at 0.7-1.0 ppm are assigned to methyl groups, peaks at 1.0-1.3, 1.4-2.1, and 2.2-2.7 ppm correspond to methylene groups, and those at 1.3-1.4 and 2.1-2.2 ppm are attributed to methine groups. Peaks at 3.3-4.8 ppm are assigned to —$CH_2$—OH groups.
Figure 64:
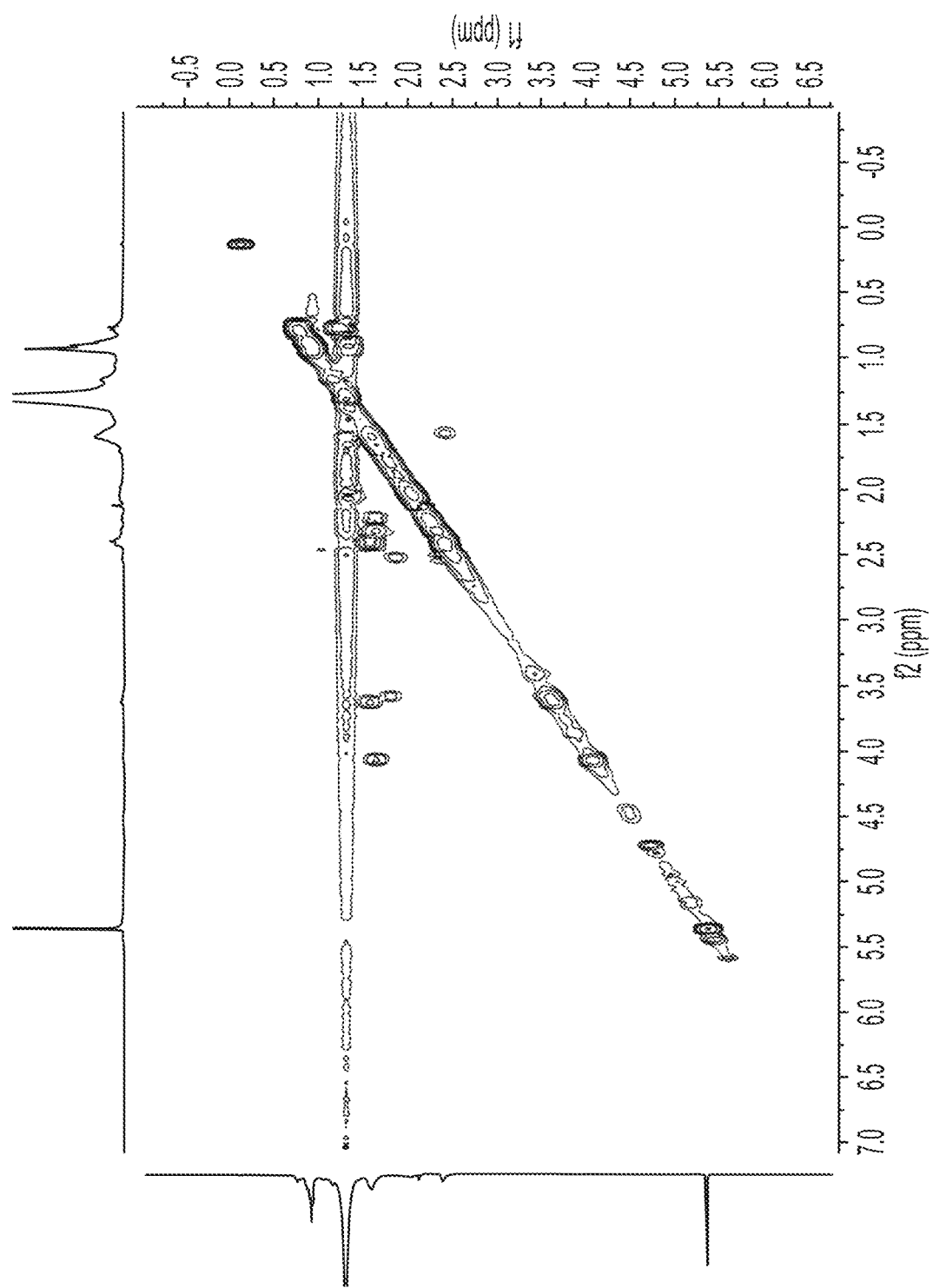
FIG. 64 is the COSY spectrum of the oil isolated after reaction of HDPE and $AlH_3$ in the presence of $Zr(OCH_2CMe_3)_2@SiAlO_x$ at 200° C. for 12 h, quenched with $O_2$, and extracted with methylene chloride. The spectrum was acquired at room temperature in methylene chloride-$d_2$. Cross-peaks at 3.5-4.1 ppm correlate with methylene signals at 1.5-1.8 ppm, indicative of —$CH_2$—$CH_2$—OH moieties.
Figure 65:
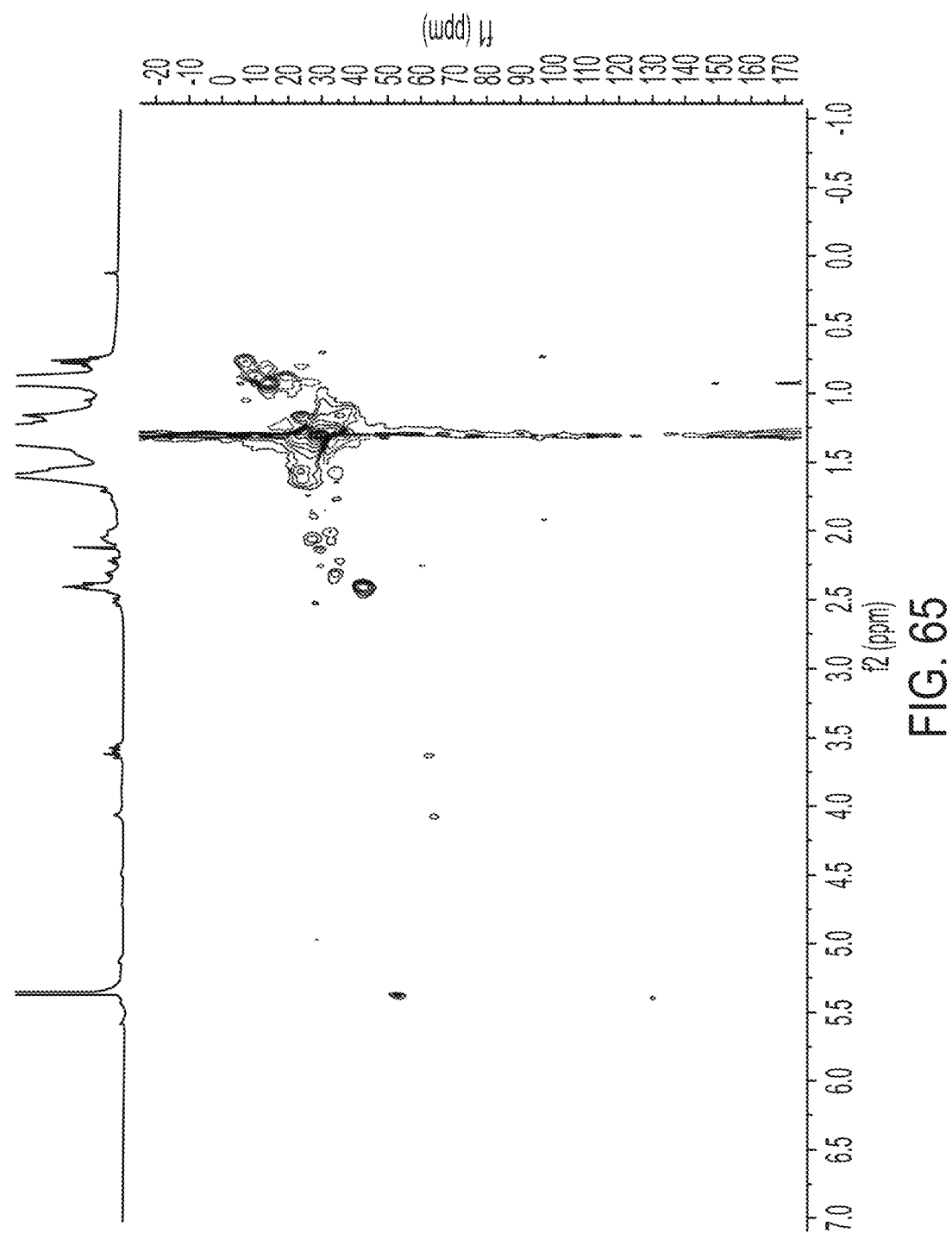
FIG. 65 is the phase sensitive $^1H$-$^{13}C$ HSQC spectrum of the oil isolated after reaction of HDPE and $AlH_3$ in the presence of $Zr(OCH_2CMe_3)_2@SiAlO_x$ at 200° C. for 12 h, quenched with $O_2$, and extracted with methylene chloride. The spectrum was acquired at room temperature in methylene chloride-$d_2$. Cross-peaks at $^{13}C$ 60-70 ppm have the same phase as methylene peaks at 30 ppm, revealing the former are —$CH_2$—OH moieties.
Figure 66:
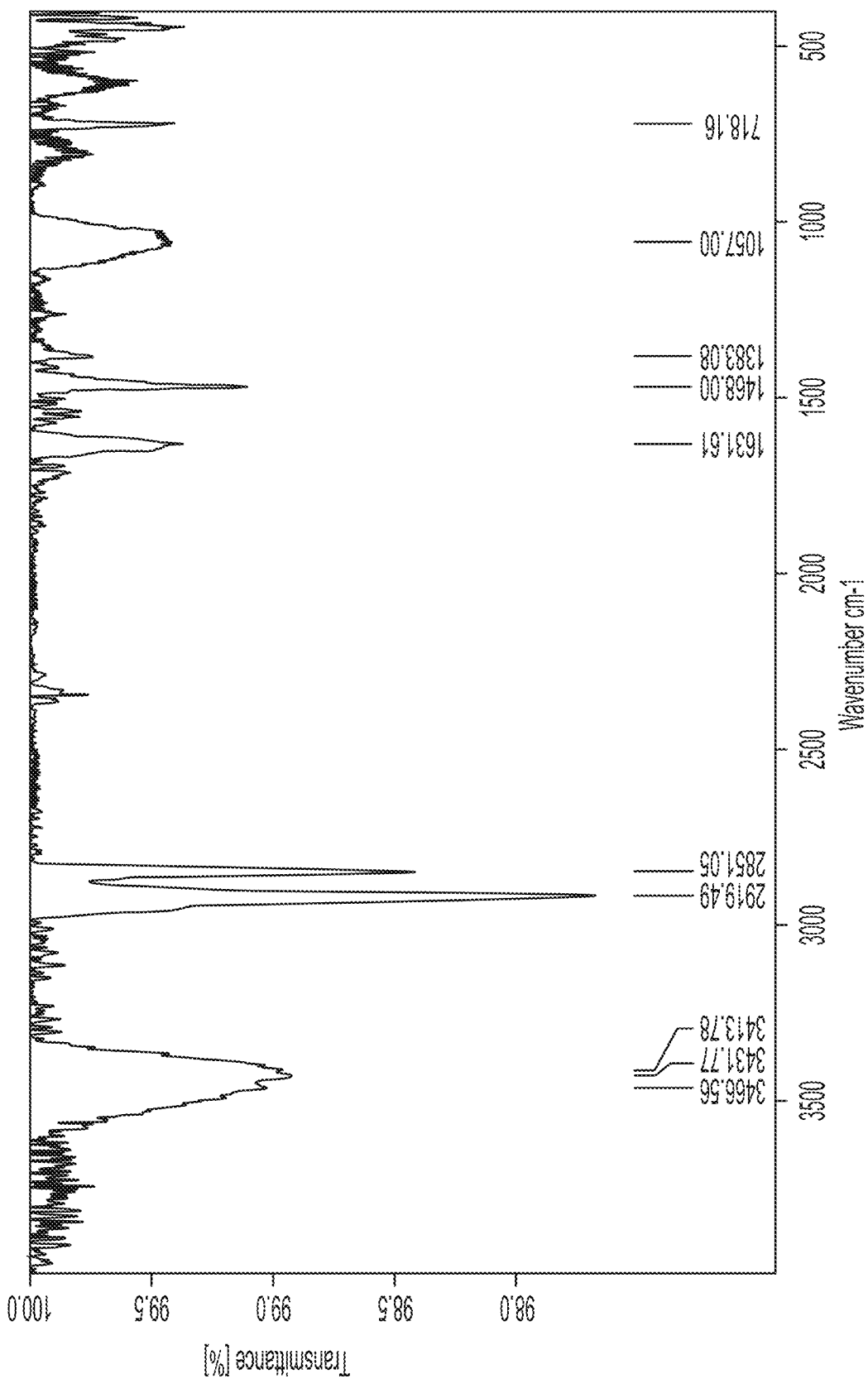
FIG. 66 is the FT-IR spectrum (KBr) of the oil isolated after reaction of HDPE and $AlH_3$ in the presence of $Zr(OCH_2CMe_3)_2@SiAlO_x$ at 200° C. for 12 h, quenched with $O_2$, and extracted with methylene chloride. Broad signals between 3300-3600 $cm^{-1}$ correspond to 0-H stretches.
Figure 67:
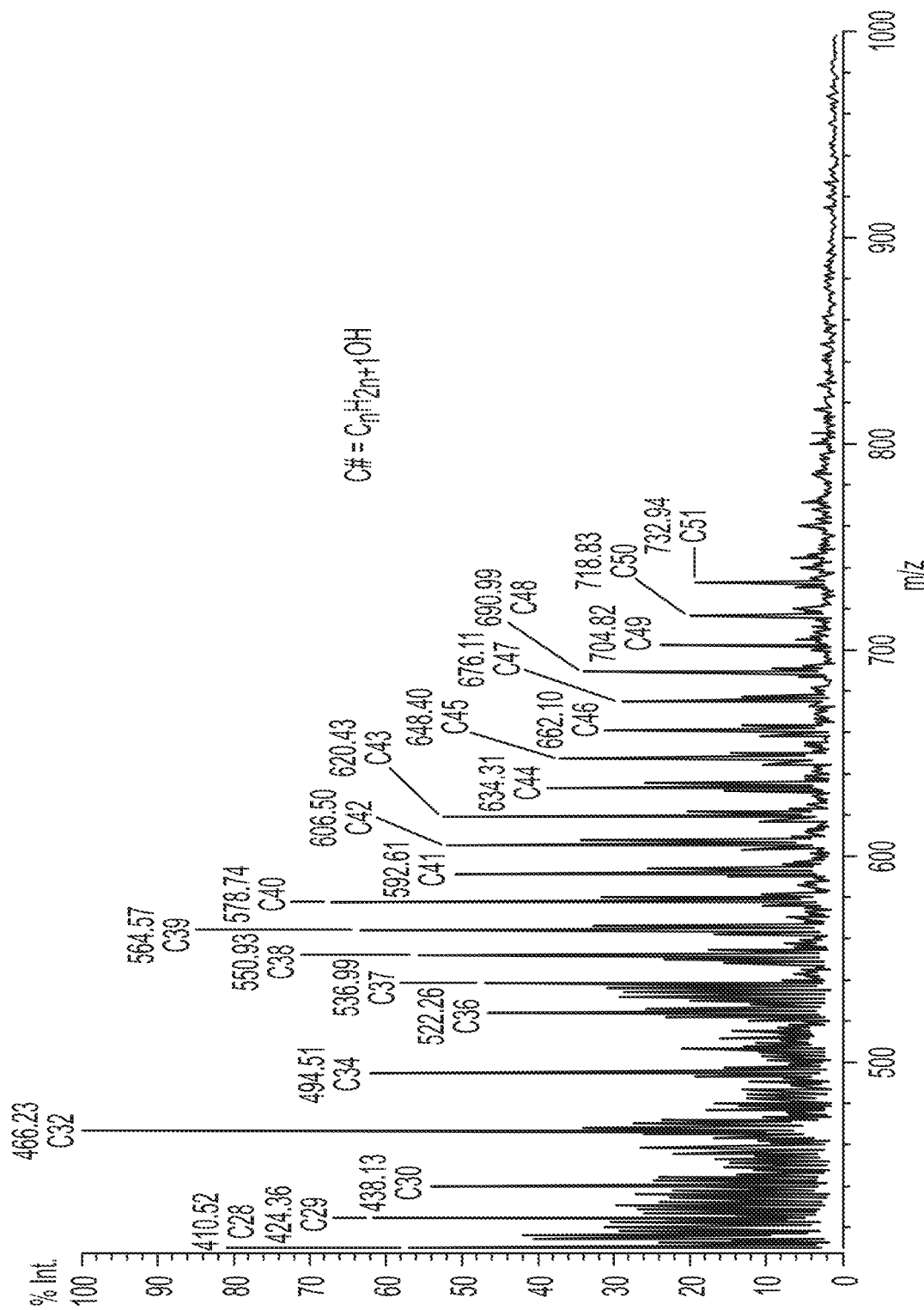
FIG. 67 is the MALDI-TOF-MS spectrum of the oil isolated after reaction of HDPE and $AlH_3$ in the presence of $Zr(OCH_2CMe_3)_2@SiAlO_x$ at 200° C. for 12 h, quenched with $O_2$, and extracted with methylene chloride. The spectrum was acquired in linear, positive mode with $AgNO_3$ (salt) and DHB (matrix).
Figure 68:
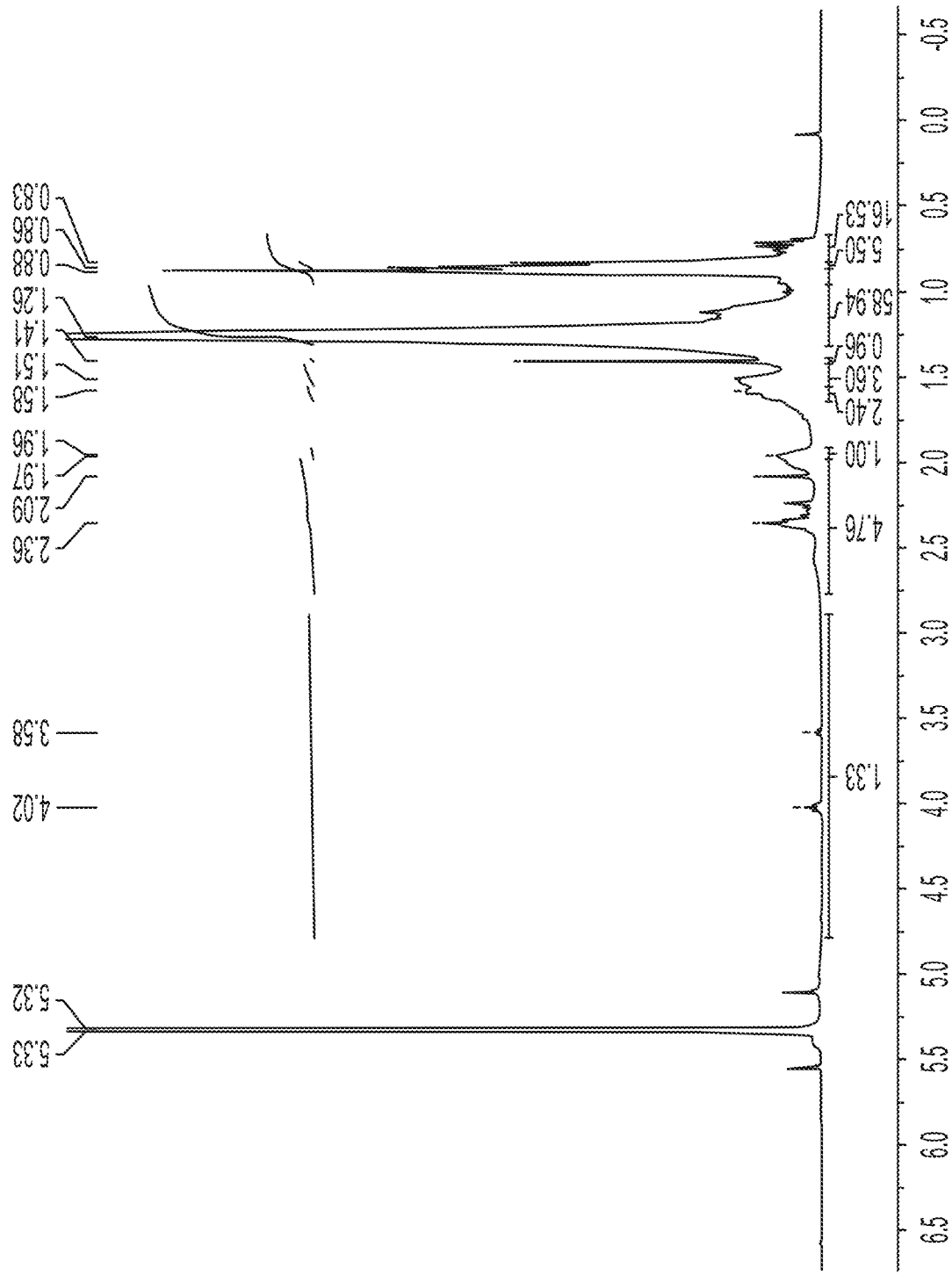
FIG. 68 is the $^1H$ NMR spectrum of the oil isolated after reaction of HDPE and $AliBu_3$ in the presence of $Zr(CH_2CMe_3)_2@SiO_2$ at 200° C. for 12 h, quenched with $O_2$, and extracted with methylene chloride. The spectrum was acquired at room temperature in methylene chloride-$d_2$ and assigned based on COSY and HSQC experiments in FIGS. 69 and 70. Signals at 0.7-1.0 ppm are assigned to methyl groups, peaks at 1.0-1.3, 1.4-1.6, and 2.0-2.7 ppm correspond to methylene groups, and those at 1.3-1.4, 1.6-1.7, and 1.8-2.0 ppm are attributed to methine groups. Peaks at 3.3-4.7 ppm are assigned to —$CH_2$—OH groups.
Figure 69:
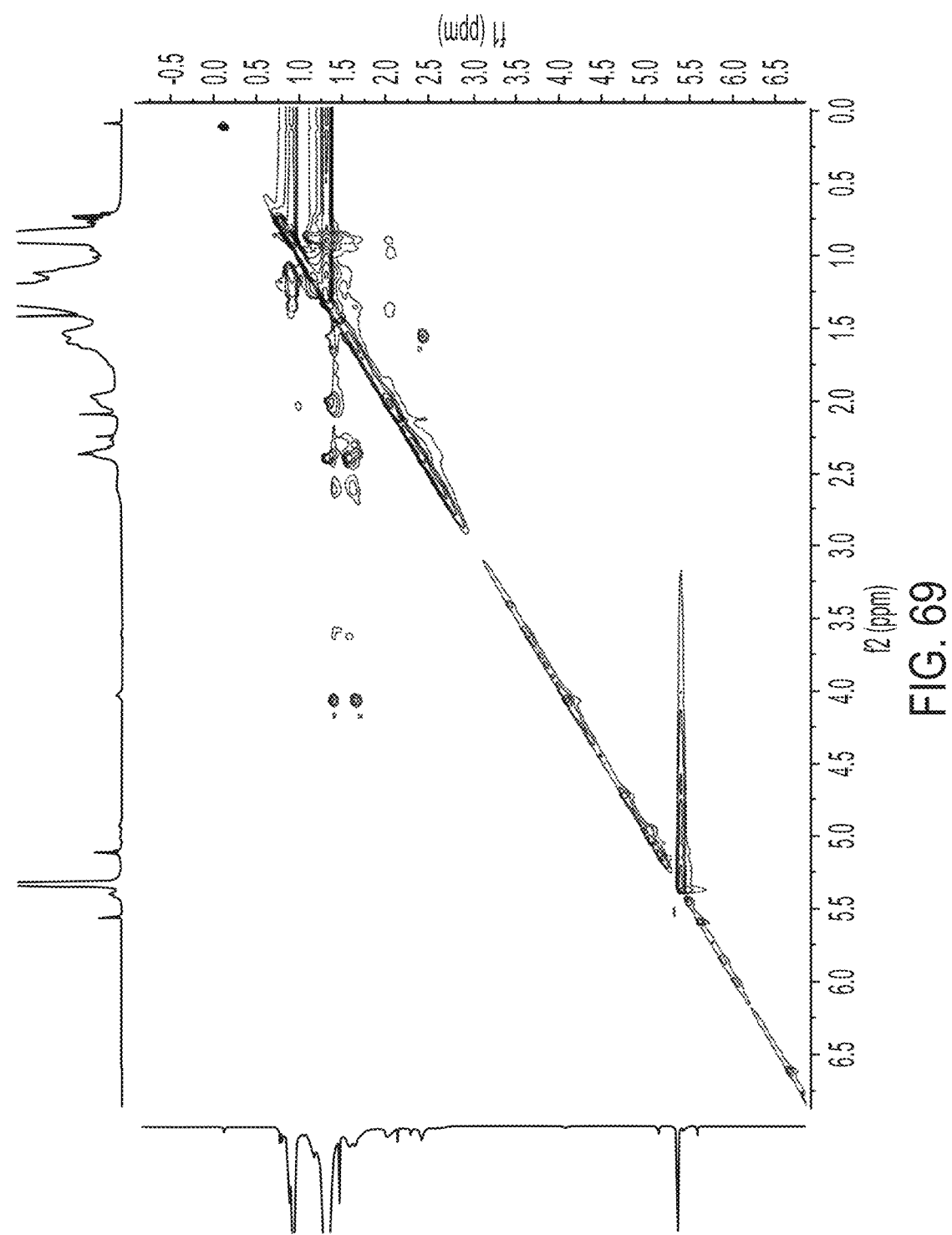
FIG. 69 is the COSY spectrum of the oil isolated after reaction of HDPE and $AliBu_3$ in the presence of $Zr(CH_2CMe_3)_2@SiO_2$ at 200° C. for 12 h, quenched with $O_2$, and extracted with methylene chloride. The spectrum was acquired at room temperature in methylene chloride-$d_2$. Cross-peaks at 3.6-4.0 ppm correlate with methylene signals at 1.4-1.6 ppm, indicative of —$CH_2$—$CH_2$—OH species.
Figure 70:
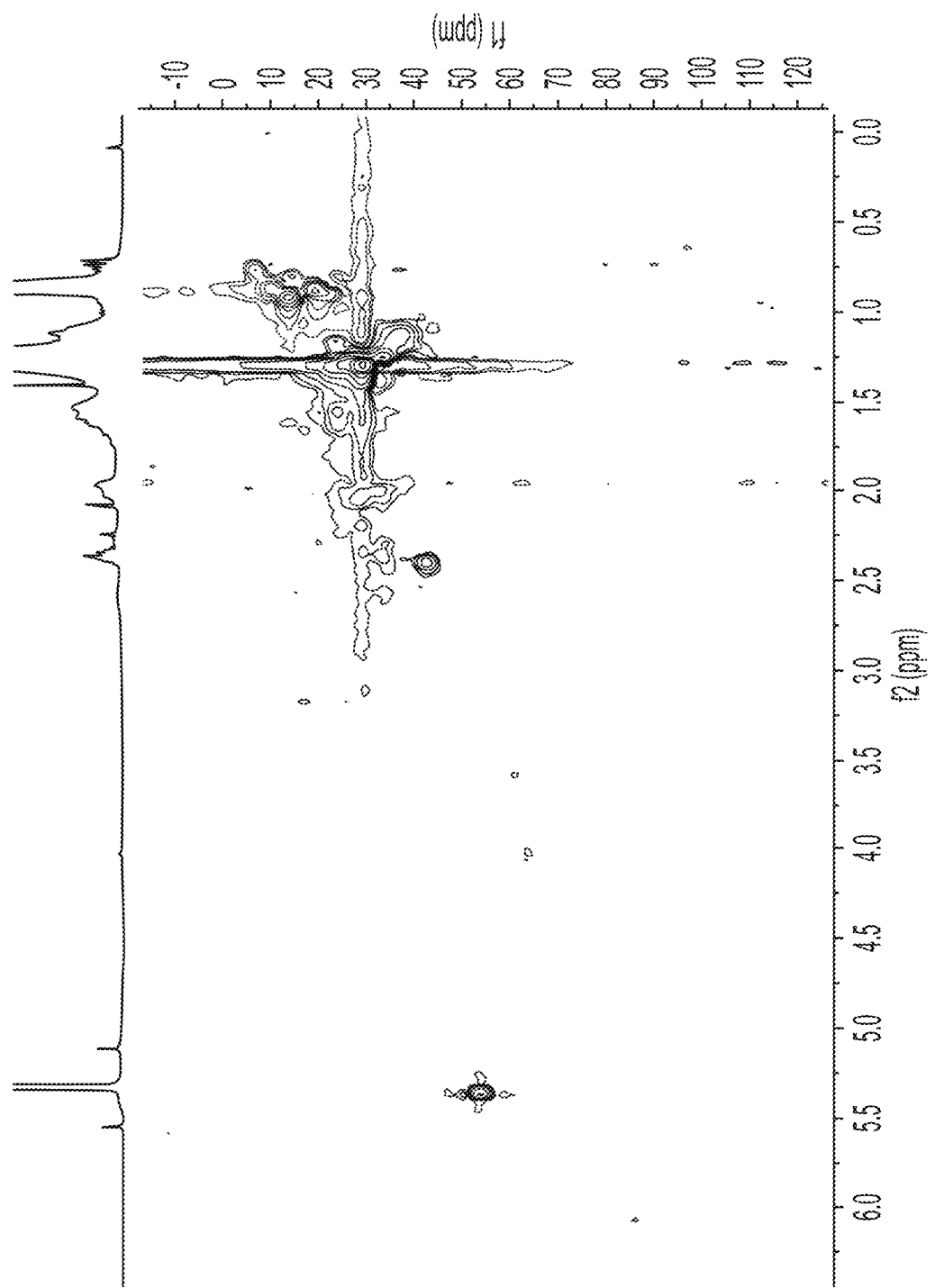
FIG. 70 is the phase sensitive $^1H$-$^{13}C$ HSQC spectrum of the oil isolated after reaction of HDPE and $AliBu_3$ in the presence of $Zr(CH_2CMe_3)_2@SiO_2$ at 200° C. for 12 h, quenched with $O_2$, and extracted with methylene chloride. The spectrum was acquired at room temperature in methylene chloride-$d_2$. Cross-peaks at $^{13}C$ 60-70 ppm have the same phase as methylene peaks at 30 ppm, revealing the former are —$CH_2$—OH moieties.
Figure 71:
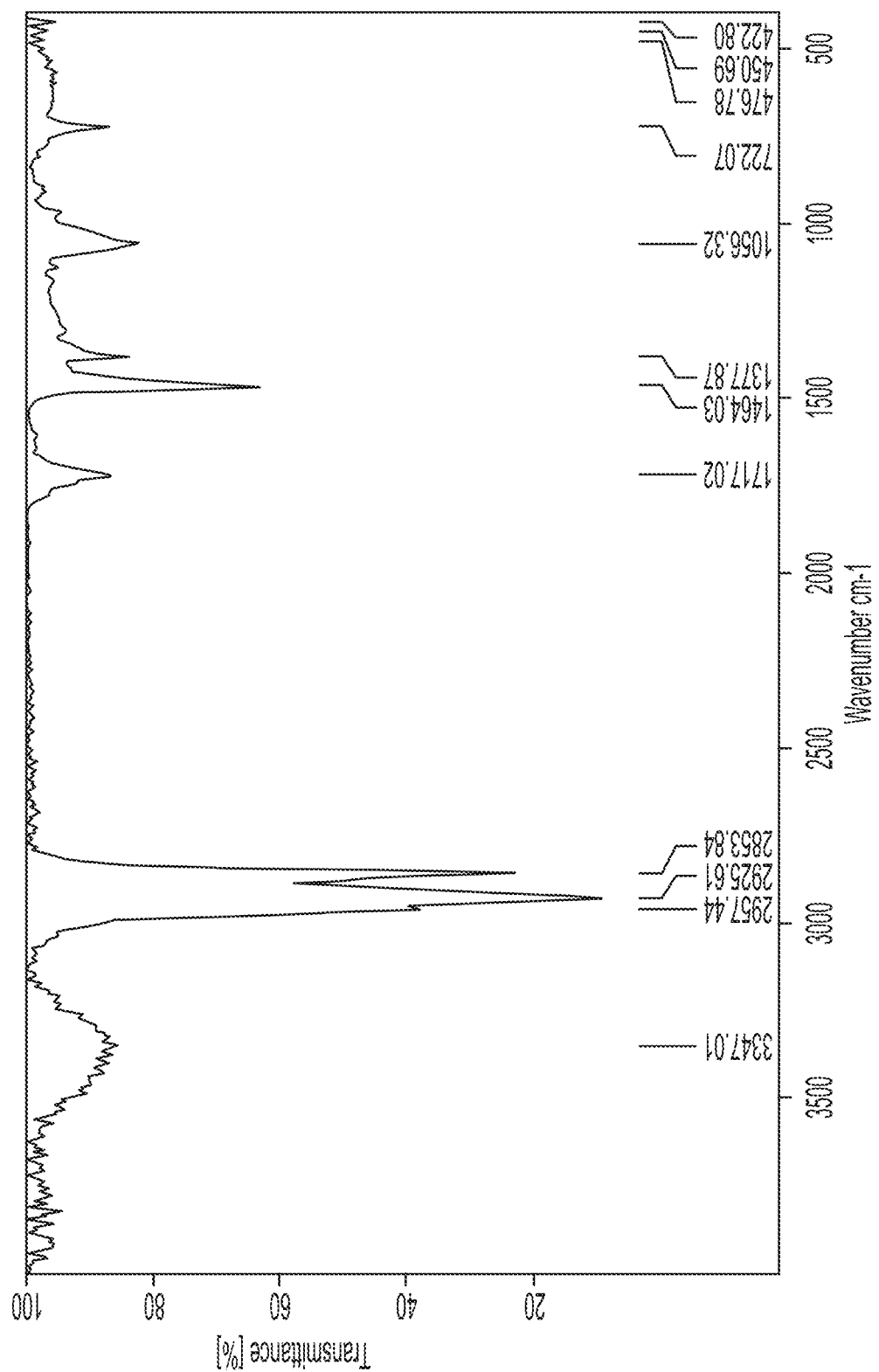
FIG. 71 is the FT-IR spectrum (KBr) of the oil isolated after reaction of HDPE and $AliBu_3$ in the presence of $Zr(CH_2CMe_3)_2@SiO_2$ at 200° C. for 12 h, quenched with $O_2$, and extracted with methylene chloride. The broad signal at 3347 $cm^{-1}$ corresponds to an O—H stretch.

The oil was further analyzed by MALDI-TOF-MS, which detected functionalized chains from $C_{35}H_{71}OH$ up to $C_{64}H_{129}OH$ directly and aliphatic hydrocarbons as $Ag^+$ adducts (see FIG. 9). Alcohols and alkanes were easily distinguished in MALDI-TOF-MS, because alcohols self-ionize with high efficiency to give signal patterns corresponding to their natural isotopic distribution (Grace et al., "An in situ Silver Cationization Method for Hydrocarbon Mass Spectrometry," *J. Am. Soc. Mass Spectrom.* 16:437-440 (2005), which is hereby incorporated by reference in its entirety), whereas alkanes appeared as characteristic pairs due to $^{107}Ag$ and $^{109}Ag$ adducts. In addition, GC-MS detected fatty alcohols from $C_{12}$-$C_{20}$ and long-chain hydrocarbons $C_{19}$-$C_{30}$ in the product oil; quantification of these species indicated they compose only 6% of the oil, by mass. Neopentanol or isobutanol, expected from $O_2$ quench of neopentyl or isobutyl metal species, were not detected by GC-MS, suggesting these species are insignificant. Instead, neopentane and isobutylene were observed by GC-MS analysis as >95% of the gases in the reactor headspace.

At 200° C., the $Zr(CH_2CMe_3)_2@SiAlO_x$-catalyzed reaction of HDPE and 10 equiv. of $AliBu_3$ gives a higher yield of oils (40%, Table 1, entry 2) after 12 h. A MALDI-TOF-MS revealed shorter chains (a $C_{34}$-centered distribution) compared to the products from the experiment at 150° C. Essentially identical yields are obtained after 24 h of continuous heating or upon addition of a second portion of $AliBu_3$ after 12 h, suggesting that the zirconium catalyst deactivates during the first portion of the reaction. Experiments with more $AliBu_3$ (50 equiv. relative to Zr) give only minimal amounts of oil (3%). Instead, improved conversion of HDPE is accomplished by adding portions of $Zr(CH_2CMe_3)_2@SiAlO_x$ and $AliBu_3$ every 12 h. Polymer was not observed after three reaction cycles with 84% total oil yield. In addition, the synthetic versatility of the alkyl-aluminum products was demonstrated in HDPE deconstruction reactions quenched with methanol, $I_2$, or $CO_2$ (Table 1, entries 4-6; MALDI-TOF-MS shown in FIG. 96) that gave hydrocarbons, or mixtures containing alkyl iodides or fatty acids, respectively, with similar $C_{32}$ to $C_{34}$-centered distributions of chains. This catalytic system is also able to transform post-consumer HDPE from a supermarket bag, which was otherwise untreated, as well as isotactic polypropylene (Table 1, entries 15-16).

Mixtures of partially dehydroxylated zirconium-free $SiAlO_x$, $AliBu_3$, and HDPE heated at 200° C. for 12 h return the polymer with little change to its molecular weight ($M_n$=5.8 kDa) and trace amounts of oil (<2%) containing trimerized isobutylene resulting from $AliBu_3$ thermolysis (Ziegler et al., "Metallorganische Verbindungen, XXXII Zerfalls-und Austauschreaktionen der Aluminiumtrialkyle," *Liebigs Ann. Chem.* 629:53-89 (1960), which is hereby incorporated by reference in its entirety). Thus, the catalytic species derived from (—$SiO)_2Zr(CH_2CMe_3)_2$ is the active site for carbon-carbon bond cleavage of polyethylene, and oligomeryl and polymeryl aluminum species are the primary products. Although acid sites on $SiAlO_x$ (or even weaker acid sites on $SiO_2$) would mediate detectable degradation of HDPE at 200° C. (Yanik and Karayildirim, *Feedstock Recycling and Pyrolysis of Waste Plastics*, Scheirs Eds. Sussex, UK John Wiley & Sons, p 209-224 (2006), which is hereby incorporated by reference in its entirety), $AliBu_3$ reacts to cap the few surface silanol sites (Werghi et al., "Well-defined Silica Supported Aluminum Hydride: Another Step Towards the Utopian Single Site Dream?" *Chem. Sci.* 6:5456-5465 (2015); Kermagoret et al., "Triisobutylaluminum: Bulkier and Yet More Reactive Towards Silica Surfaces Than Triethyl or Trimethylaluminum," *Dalton Trans.* 42:12681-12687 (2013), which are hereby incorporated by reference in their entirety) and blocks acid-promoted thermolysis to favor zirconium-catalyzed pathways.

Main group alkyl and hydride reagents influence catalytic alkene polymerizations and could also affect these deconstruction reactions. The trend of reactivity of a series of main group compounds in this $Zr(CH_2CMe_3)_2@SiAlO_x$-catalyzed polyethylene upcycling process, in terms of yields of oils, is $AlH_3 \sim AliBu_3 > AlPh_3 \sim AlEt_3 >> AlMe_3 \sim HAliBu_2$ (DIBAL-H)~$HAlMe_2 \sim ZnEt_2$. Several of these experiments are also mechanistically informative and provide evidence for metalation and carboalumination steps that are part of the processes.

The most effective co-reactant for Zr-catalyzed deconstruction of HDPE is $AlH_3$, the reaction of which at 200° C. for 12 h provides an oil in comparable yield (42%) as with $AliBu_3$ and significantly higher amounts of alcohol chains (89%) compared to alkanes (11%). Similar ranges of $C_nH_{2n+1}OH$ species were observed in the MALDI-TOF-MS spectra of oils obtained in otherwise equivalent reactions using $AlH_3$ and $AliBu_3$ at 200° C., although the spectra were not identical. $AlEt_3$ is less effective for carbon-carbon bond cleavage than $AliBu_3$ or $AlH_3$, affording oils in 23% yield after 12 h at both 150 and 200° C. The structure HO—$CH_2$—$CH(CH_2CH_3)$—R (R=aliphatic polymer chain), identified from a $^1H$-$^1H$ COSY experiment, was the dominant alcoholic species, based on the 1.53 ratio of integrated signals of (CH)—$CH_2$—$CH_3$ to $CH_2$—OH. The fraction of molecules containing OH, calculated as described above, was 0.39. Thus, $AlEt_3$ was less active and also less effective than $AliBu_3$ for introducing aluminum into the products, giving the highest percentage of alkanes of all reactive aluminum reagents. A higher yield of oil product (29% by mass after workup with $O_2$) from the catalyzed reaction of HDPE and $AlPh_3$ at 200° C., compared to $AlEt_3$, is partially affected by the formation of aromatic-containing species, identified by $^1$H and $^{13}$C NMR spectroscopy, GC-MS, and MALDI-TOF-MS (see Supplementary).

Figure 72:
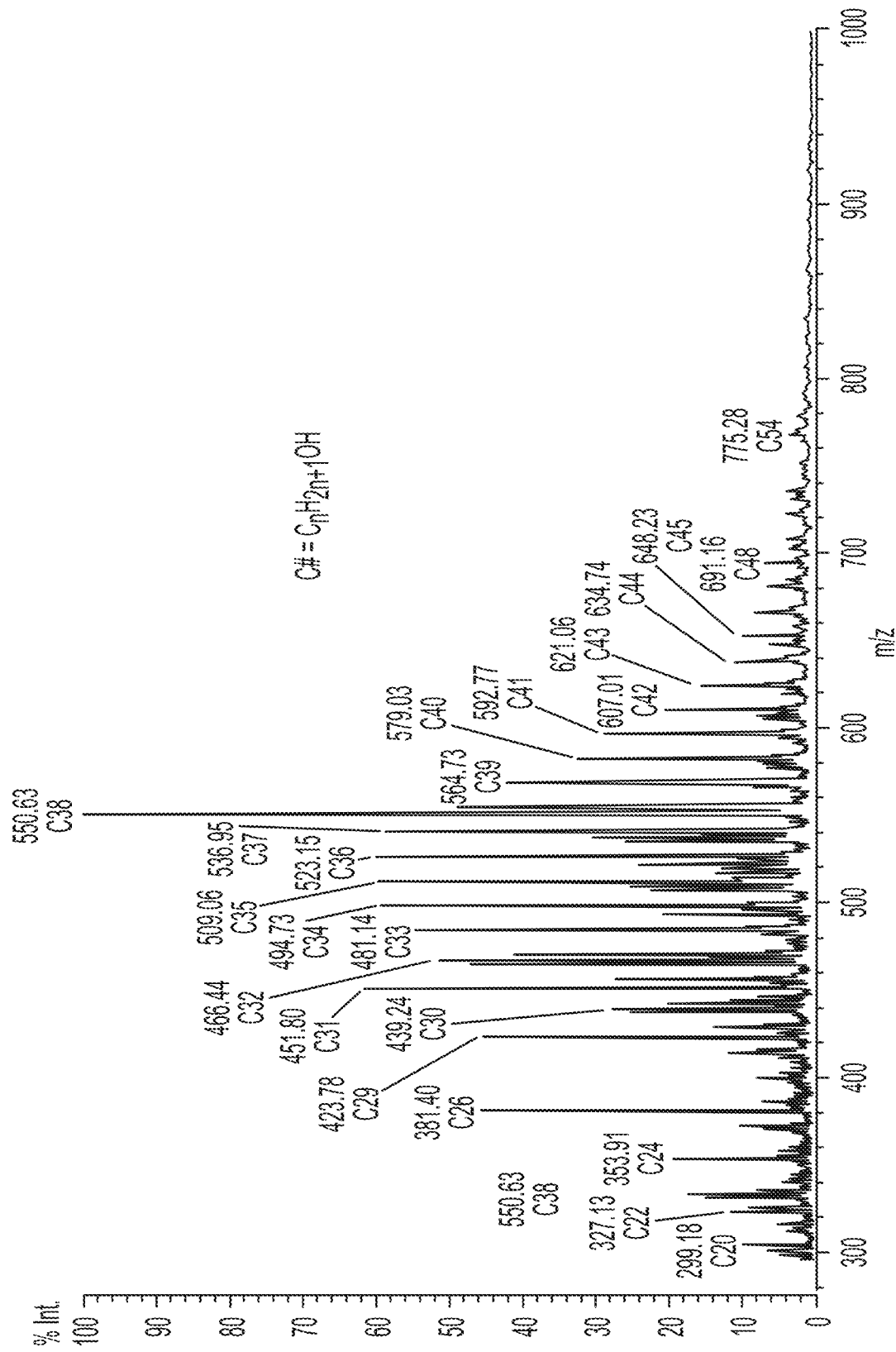
FIG. 72 is the MALDI-TOF-MS spectrum of the oil isolated after reaction of HDPE and $AliBu_3$ in the presence of $Zr(CH_2CMe_3)_2@SiO_2$ at 200° C. for 12 h, quenched with $O_2$, and extracted with methylene chloride. The spectrum was acquired in linear, positive mode with $AgNO_3$ (salt) and DHB (matrix).
Figure 73:
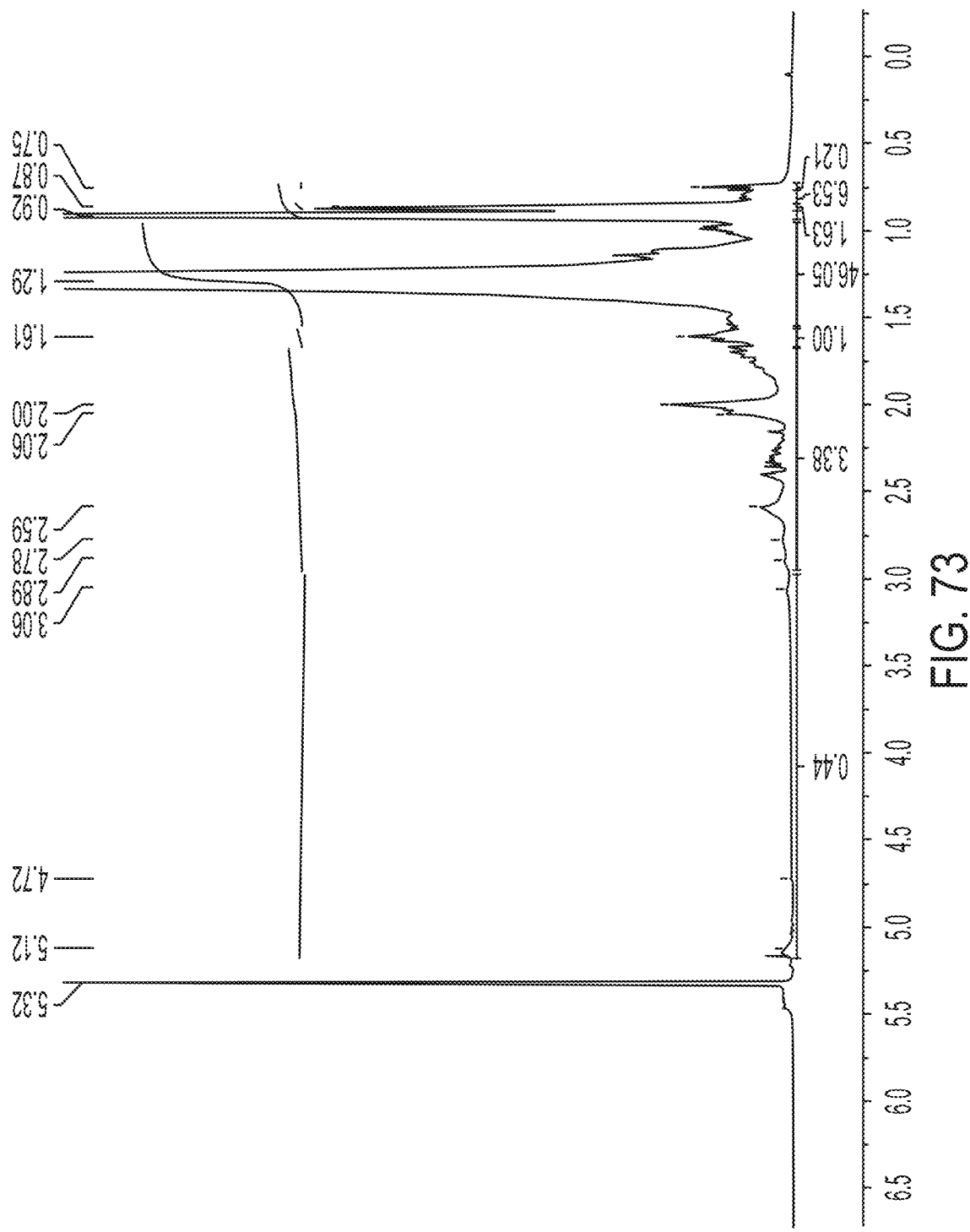
FIG. 73 is the $^1H$ NMR spectrum of the oil isolated after reaction of HDPE and $AlEt_3$ in the presence of $Zr(CH_2CMe_3)_2@SiO_2$ at 200° C. for 12 h, quenched with $O_2$, and extracted with methylene chloride. The spectrum was acquired at room temperature in methylene chloride-$d_2$ and assigned based on COSY and HSQC experiments in FIGS. 74 and 75. Signals at 0.7-1.0 ppm are assigned to methyl groups, peaks at 1.0-1.6 and 1.7-3.0 ppm correspond to methylene groups, and those at 1.6-1.7 ppm are attributed to methine groups. Peaks at 3.0-5.2 ppm are assigned to —$CH_2$—OH groups.
Figure 74:
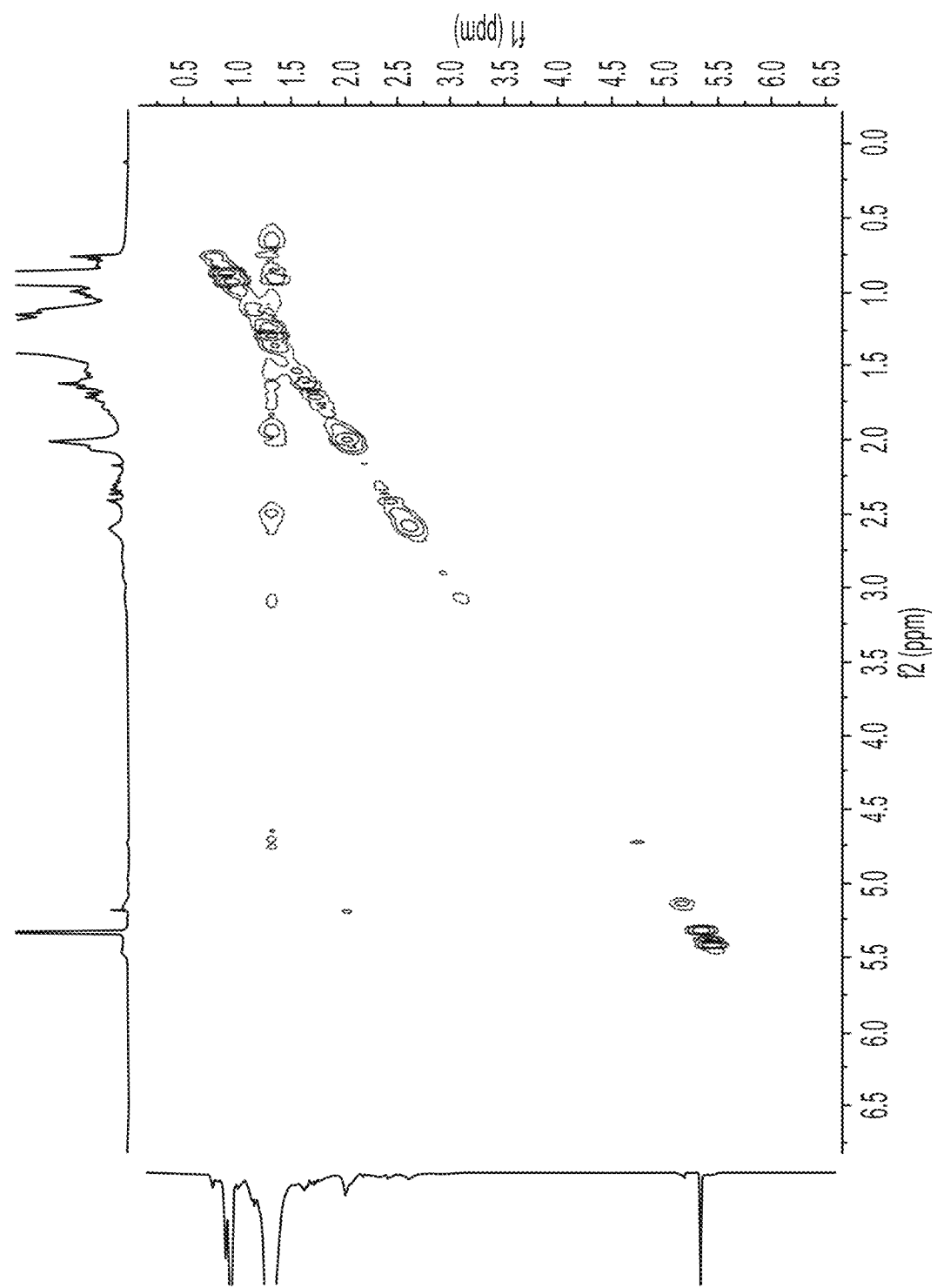
FIG. 74 is the COSY spectrum of the oil isolated after reaction of HDPE and $AlEt_3$ in the presence of $Zr(CH_2CMe_3)_2@SiO_2$ at 200° C. for 12 h, quenched with $O_2$, and extracted with methylene chloride. The spectrum was acquired at room temperature in methylene chloride-$d_2$.

Zr(CH$_2$CMe$_3$)$_2$@SiAlO$_x$ was initially tested because its surface hydrides are reported to be more active for propane metathesis and polyolefin hydrogenolysis than the silica-supported analogues (Dufaud and Basset, "Catalytic Hydrogenolysis at Low Temperature and Pressure of Polyethylene and Polypropylene to Diesels or Lower Alkanes by a Zirconium Hydride Supported on Silica-Alumina: A Step Toward Polyolefin Degradation by the Microscopic Reverse of Ziegler-Natta Polymerization," *Angew. Chem. Int. Ed.* 37:806-810 (1998); Thieuleux et al., "Homologation of Propane Catalyzed by Oxide-Supported Zirconium Dihydride and Dialkyl Complexes," *Angew. Chem. Int. Ed* 46:2288-2290 (2007), which are hereby incorporated by reference in their entirety). In addition, aluminum is known to incorporate into silica framework sites in reactions of excess AliBu$_3$ and SiO$_2$ (Kermagoret et al., "Triisobutylaluminum: Bulkier and Yet More Reactive Towards Silica Surfaces Than Triethyl or Trimethylaluminum," *Dalton Trans.* 42:12681-12687 (2013), which is hereby incorporated by reference in its entirety), and this in situ support modification also could influence catalytic activity. In fact, an aerosil silica-supported zirconium catalyst, Zr(CH$_2$CMe$_3$)$_2$@SiO$_2$, provides an alcohol-containing oil in nearly equivalent yield (35%) after heating HDPE and AliBu$_3$ for 12 h at 200° C. Moreover, the oil is approximately 85% alcohols and only 15% alkanes. The Zr(CH$_2$CMe$_3$)$_2$@SiO$_2$-catalyzed reaction with AlEt$_3$ provided the oil product in similar single-pass yield (32%) and high alcohol content (82%), as a notable contrast with the silica-alumina supported catalyst. These reactions afforded alcohol species with a normal, ca. C$_{35}$-centered distribution of monoalcohols, as detected by MALDI-TOF-MS (FIGS. 72 and 77, respectively). The similarly high reactivity of catalysts supported on silica and silica-alumina may be attributed to the known surface alumination and subsequent incorporation of aluminum centers into silica framework sites in reactions of excess AliBu$_3$ and SiO$_2$ (Kermagoret et al., "Triisobutylaluminum: Bulkier and Yet More Reactive Towards Silica Surfaces Than Triethyl or Trimethylaluminum," *Dalton Trans.* 42:12681-12687 (2013), which is hereby incorporated by reference in its entirety). In fact, trace amounts of ethylsilane species were detected in GC-MS and NMR spectra of the reaction products, which was consistent with aluminum substitutions for silicon occurring in the silica support framework during the catalytic reaction. This in situ alumination of the silica support could influence the reactivity of the active species generated from the Zr(CH$_2$CMe$_3$)$_2$@SiO$_2$ precatalyst. Such an effect would not be available in alkylaluminum-free hydrogenolysis reactions catalyzed by surface-supported hydridozirconium, leading to distinct activity for zirconium supported on the two oxides.

The silica- or silica-alumina-supported neopentylzirconium, as well as the (≡SiO)$_3$ZrH catalyst for polyethylene hydrogenolysis, are exceedingly sensitive to irreversible reactions with air and moisture to give deactivated materials. Thus, small amounts of protic or oxidative impurities in the polyethylene reactant could have an outsized effect upon catalytic performance. Because the alkylaluminum reactant can serve as an alkylating agent for converting alkoxyzirconium into alkylzirconium sites, some poisoned sites could also be re-activated under catalytic conditions. In this context, the polyolefin reactants used in this study, although clean and dry, were essentially used as received and did not undergo exhaustive purification prior to use. More convenient precatalysts would be tolerant of ambient air, prior to treatment with alkylaluminum reagents for HDPE deconstruction. In fact, ≡SiO—Zr(CH$_2$CMe$_3$)$_3$ and O$_2$ react to provide ≡SiO—Zr(OCH$_2$CMe$_3$)$_3$ (Quignard et al., "Surface Organometallic Chemistry of Zirconium: Application to the Stoichiometric Activation of the CH Bonds of Alkanes and to the Low-temperature Catalytic Hydrogenolysis of Alkanes," *J. Mol. Catal.* 74:353-363 (1992), which is hereby incorporated by reference in its entirety), as does (≡SiO)$_2$Zr(CH$_2$CMe$_3$)$_2$. This air-exposed material, upon combination with AliBu$_3$, generates a catalytically active species for HDPE deconstruction to an oil in 34% yield, approximately half of which are alcohols. The oil product contains less alcohol functionality (ca. 50% of molecules are monoalcohols) than the oil from Zr(CH$_2$CMe$_3$)$_2$@SiAlO$_x$. The headspace of the reaction vessel is >98% isobutylene, with very little isobutane. Air-stable Zr(OCH$_2$CMe$_3$)$_2$@SiAlO$_x$ can also be activated by AlH$_3$, and the reaction with HDPE affords an oil (49% yield) containing a lower percentage of alcohols (62%). The MALDI-TOF-MS spectrum of this oil revealed a distribution of alcohols from C$_{28}$H$_{57}$OH to C$_{51}$H$_{103}$OH, which is similar to the product range of the analogous reaction with the air-sensitive catalyst.

The deconstruction of HDPE into long chain alkylaluminum species likely involves the sequence shown in FIG. 97, comprising (i) metalation of the polymer backbone via C—H bond activation by a grafted zirconium alkyl or hydride species A, (ii) β-alkyl elimination from a mid-chain polymerylzirconium B resulting in C—C bond cleavage to give a terminal olefin and a new alkylzirconium species C, (iii) transmetalation of the alkylzirconium with an alkylaluminum species (chain transfer to aluminum) and (iv) carboalumination of an in-situ generated olefin by AlR$_3$ resulting in a new C—C bond.

First, evidence for metalation in step i is provided by the reaction by-products. Neopentane (CMe$_4$) is detected in the headspace within the first 15 min. of reactions catalyzed by Zr(CH$_2$CMe$_3$)$_2$@SiAlO$_x$, regardless of the organoaluminum reagent, suggesting that the polymer is metalated by a Zr—CH$_2$CMe$_3$ species. Likewise, benzene is observed in reactions involving AlPh$_3$ prior to workup with O$_2$, supporting the idea that phenylzirconium species react with hydrocarbons by metalation. In addition, a plausible pathway to long chain hydrocarbon side products involves the reaction of polyethylene chains and short polymerylzirconium intermediates. Finally, in the reaction of HDPE with Zr(OCH$_2$CMe$_3$)$_2$@SiAlO$_x$ and AliBu$_3$, CMe$_4$ was not detected, further indicating that CMe$_4$ formation is associated with metalation by neopentylzirconium rather than resulting from reaction of neopentylaluminum species and/or polymer hydrogenolysis.

Surface zirconium hydride species, formed by ligand exchange reactions of aluminum hydride and zirconium alkyls, also likely are involved in metalations. In support of this idea, hydridoaluminum species are formed from AliBu$_3$ at high temperatures (Ziegler et al., "Metallorganische Verbindungen, XXXII Zerfalls-und Austauschreaktionen der Aluminiumtrialkyle," *Liebigs Ann. Chem.* 629:53-89 (1960), which is hereby incorporated by reference in its entirety). During the catalytic HDPE deconstruction and alumination reactions involving AliBu$_3$, isobutylene formation (major, along with a minor amount of isobutane) is consistent with the generation of hydridozirconium species. Furthermore, DRIFT analysis of the surface species revealed a band at 1623 cm$^{-1}$ assigned to $v_{ZrH}$ in the material obtained by reaction of Zr(CH$_2$CMe$_3$)$_2$@SiAlO$_x$ and AliBu$_3$ at 150° C. for 4 h (34, 35). This signal disappeared upon treatment with $D_2$ (the signal for presumed $v_{ZrD}$ is not resolved from Si/Al—O bands) and reappeared upon treatment with $H_2$ (FIG. 93). The DRIFT spectra of SiAlO$_x$ treated with AliBu$_3$, in contrast, are unchanged by reaction with $D_2$. The effective catalytic combination of Zr(OCH$_2$CMe$_3$)$_2$@SiAlO$_x$ and AlH$_3$ also likely provide hydridozirconium surface sites for metalation. Thus, zirconium alkyl or hydride species react with long-chain polyethylene to give polymerylzirconium and alkane or hydrogen as the byproduct. Interestingly, hydride-generating aluminum reagents (AlH$_3$ and AliBu$_3$) provide higher yields of oils than reactions with alkyl (AlEt$_3$) or aryl (AlPh$_3$) transfer reagents, which may reflect increased rate of mid-chain metalation by hydridozirconium compared to alkyl or arylzirconium.

Mid-chain polymerylzirconium species B are cleaved into a shorter terminal polymerylzirconium C and vinyl-terminated chain fragments via 3-alkyl elimination. This step is responsible for chain cleavage leading to polymer deconstruction. The newly shortened polymerylzirconium can react with AlR$_3$ via alkyl group exchange or hydride transfer to form [Zr]—R or [Zr]—H and polymerylAlR$_2$, step iii in FIG. 97. Catalytic hydroalumination or carboalumination of the vinyl-termination polymer fragment, via insertion into [Zr]—R or [Zr]—H and chain transfer, will also generate β-branched (R$_2$Al—CH$_2$CHR—) or linear (R$_2$Al—CH$_2$CH$_2$—) aluminum terminated chains (step iv). Thus, all functional groups terminate the chains as a consequence of the β-alkyl and chain transfer mechanistic sequence.

Other sequences of elementary steps could account for the observed structure of the products. For example, the polymerylzirconium intermediates C can react with small molecules, such as H$_2$ or benzene. Accordingly, high alkane content was observed with the catalytic systems Zr(CH$_2$CMe$_3$)$_2$@SiAlO$_x$/AlPh$_3$ (~55%) and Zr(OCH$_2$CMe$_3$)$_2$@SiAlO$_x$/AliBu$_3$ (~50%). This influence of small molecules was further tested by reacting HDPE and AlH$_3$ in the presence of Zr(OCH$_2$CMe$_3$)$_2$@SiAlO$_x$ under vacuum (Table 1, entry 17). Under these single-pass, dynamic low-pressure conditions, the mass of the reaction mixture decreased by 21% and a high yield (60%) was obtained. MALDI-TOF-MS analysis of this oil revealed significantly lower molecular weight alcohols, from C$_{20}$H$_{41}$OH to C$_{38}$H$_{77}$OH than that from the analogous reaction carried out in a sealed vessel. This oil contained comparable fraction of alcohol molecules (~67%, by $^1$H NMR analysis) as the experiment under N$_2$. Clearly, the dynamic removal of small molecules from the reaction mixture allows chain cleavage by β-alkyl elimination to be kinetically more competitive compared to chain transfer processes; however, relative rates of chain transfer involving alumination and alkane production are not affected by dynamic vacuum.

In conclusion, these new polyolefin deconstruction/heterofunctionalization reactions will enable the development of incipient plastic upcycling efforts that contribute to efforts addressing the rapidly growing global plastic waste catastrophe. These methods could complement oxidative transformations, which typically provide diacids through radical pathways (Pifer and Sen, "Chemical Recycling of Plastics to Useful Organic Compounds by Oxidative Degradation," Angew. Chem. Int. Ed. 37:3306-3308 (1998), which is hereby incorporated by reference in its entirety). Advantageously, the early-metal catalyst and alkylaluminum reagent influence the structure, size, and distribution of products by favoring unique combinations and influencing rates of elementary steps. That is, advances in catalyst design though organometallic chemistry promote desirable specific upcycling outcomes. Even though early metal alkyl and hydride reagents are notoriously sensitive to air and moisture compared to noble metal hydrogenolysis catalysts (Celik et al., "Upcycling Single-Use Polyethylene into High-Quality Liquid Products," ACS Cent. Sci. 5:1795-1803 (2019); Watson and Roe, "β-Alkyl Transfer in a Lanthanide Model for Chain Termination," J. Am. Chem. Soc. 104:6471-6473 (1982), which are hereby incorporated by reference in their entirety), the activation of air-stable and earth abundant zirconium catalyst precursors in situ by aluminum reagents allows techniques from polymerization to be applied to polymer upcycling. The aluminum reagents even protect the sensitive active site to allow the deconstruction/alumination of untreated post-consumer HDPE. Although hydrogen for upcycling by hydrogenolysis is less expensive than aluminum regents, the production of long chain alkylaluminum species from waste polyolefins should be compared to the traditional Ziegler synthesis (Ziegler, "A Forty Years' Stroll Through the Realms of Organometallic Chemistry" Advances in Organometallic Chemistry vol 6, Stone and West Eds. New York, NY: Academic Press, p. 1-17 (1968), which is hereby incorporated by reference in its entirety). In fact, the abundance, accessibility (from aluminum, hydrogen, and alkenes), and large-scale industrial application of alkylaluminum reagents contribute to the potential of this new transformation in upcycling.

The combination of β-alkyl elimination and heterobimetallic alkyl group metathetical exchange at surface-immobilized organozirconium sites provides a valuable method to install reactive groups and reconstruct the carbon-skeleton of organic molecules, without the need for prior activation or directing groups. The alkylaluminum reagent can activate air-stable alkoxyzirconium species to generate highly air sensitive hydridozirconium active sites, which are also innoculated by the alkylaluminums against poisoning. Both AliBu$_3$ and AlH$_3$ react with alkyl and alkoxyzirconium species to generate surface zirconium hydrides. Moreover, both the catalysts and reactants are based upon earth-abundant, readily available, and non-toxic metal centers. In this regard, these catalytic reactions, as applied to polyolefins, are viable to compete with conventional syntheses of fatty alcohols. This new process could motivate recovery of discarded polyolefins from the environment, produce value-added chemical products, and offer an environmentally friendly end-of-life for materials currently destined for landfills.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:
1. A process comprising:
providing one or more polymers, oligomers, or mixtures thereof;
providing a compound of formula (I):

$$Al(R^1)_3 \qquad (I),$$

wherein
R$^1$ is independently selected at each occurrence thereof from the group consisting of H, aryl, C$_1$-C$_8$ alkyl, and C$_1$-C$_8$ alkoxy;

contacting the polymers, oligomers, or mixtures thereof with the compound of formula (I), as a reaction mixture, in the presence of a catalyst having a formula (II):

$$\text{Met}(R^2)_n@\text{support} \quad (II),$$

wherein
Met is a metal selected from the group consisting of zirconium, titanium, hafnium, scandium, yttrium, lanthanum, and lutetium;
$R^2$ is independently selected at each occurrence thereof from the group consisting of H, $C_1$-$C_{10}$ alkyl, $C_5$-$C_{10}$ alkoxy, and $BH_4$;
n is an integer ranging from 1 to 3; and
support is selected from the group consisting of silica, silica/alumina, and zeolites, under conditions effective to form alkanes, carboxylic acids, alcohols, alkyl halides, or aldehydes, which are shorter than the polymers, the oligomers, or the mixtures thereof; and
recovering the formed shorter alkanes, carboxylic acids, alcohols, alkyl halides, or aldehydes.

2. The process of claim 1, wherein the catalyst of formula (II) is selected from the group consisting of $Zr(CH_2CMe_3)_n@SiAlO_x$, $Zr(OCH_2CMe_3)_n@SiAlO_x$, $Zr(CH_2CMe_3)_n@SiO_2$, $Zr(H)_n@SiO_2$, and $Zr(H)_n@SiAlO_x$, wherein n is an integer ranging from 1-3.

3. The process of claim 1, wherein the compound of formula (I) is selected from the group consisting of $AliBu_3$, $AlEt_3$, $AlMe_3$, $AlPh_3$, $Al(C_8H_{17})_3$, and $AlH_3$.

4. The process of claim 1, wherein the polymers, oligomers, or mixtures thereof are polyolefins and wherein said polyolefins are selected from the group consisting of high density polyethylene, low density polyethylene, polypropylene, linear low density polyethylene, polyethylene-polypropylene-copolymers, polystyrene, and mixtures thereof.

5. The process of claim 1, wherein said contacting is carried out at a temperature sufficient to melt the polymers, oligomers, or mixtures thereof.

6. The process of claim 1, wherein said contacting is carried out under atmospheric pressure or under a vacuum.

7. The process of claim 1, wherein said contacting is carried out under conditions effective to form the shorter alkanes and comprises:
adding an alcohol or water to the reaction mixture to form the shorter alkanes.

8. The process of claim 1, wherein said contacting is carried out under conditions effective to form shorter carboxylic acids and comprises:
adding carbon dioxide to the reaction mixture under conditions effective to form the shorter carboxylic acids.

9. The process of claim 1, wherein said contacting is carried out under conditions effective to form the shorter alcohols and comprises:
adding oxygen to the reaction mixture to form the shorter alcohols.

10. The process of claim 1, wherein said contacting is carried out under conditions effective to form shorter alkyl halides and comprises:
adding a halogen to the reaction mixture to form the shorter alkyl halides.

11. The process of claim 1, wherein said contacting is carried out under conditions effective to form the shorter aldehydes and comprises:
adding an orthoester to the reaction mixture to form the shorter aldehydes.

12. The process of claim 1, wherein the molar ratio of the compound of formula (I) to the catalyst of formula (II) ranges from 3:1 to 20:1.

13. A process comprising:
providing one or more polymers, oligomers, or mixtures thereof;
providing a compound of formula (I):

$$Al(R^1)_3 \quad (I),$$

wherein
$R^1$ is independently selected at each occurrence thereof from the group consisting of H, aryl, $C_1$-$C_8$ alkyl, and $C_1$-$C_8$ alkoxy;
contacting the polymers, oligomers, or mixtures thereof with the compound of formula (I), as a reaction mixture, in the presence of a catalyst having a formula (II):

$$\text{Met}(R^2)_n@\text{support} \quad (II),$$

wherein
Met is a metal selected from the group consisting of zirconium, titanium, hafnium, scandium, yttrium, lanthanum, and lutetium;
$R^2$ is independently selected at each occurrence thereof from the group consisting of H, $C_1$-$C_{10}$ alkyl, $C_5$-$C_{10}$ alkoxy, and $BH_4$;
n is an integer ranging from 1 to 3; and
support is selected from the group consisting of silica, silica/alumina, and zeolites;
under conditions effective to form an aluminum alkyl compound of formula (III):

$$Al(R^1)_{3-n}(R^3)_n \quad (III),$$

wherein
$R^3$ is independently selected at each occurrence thereof from $C_{12}$-$C_{60}$ alkyls, which are shorter than the polymers, the oligomers, or the mixtures thereof; and
n is an integer ranging from one to three.

14. The process of claim 13, wherein the catalyst of formula (II) is selected from the group consisting of $Zr(CH_2CMe_3)_n@SiAlO_x$, $Zr(OCH_2CMe_3)_n@SiAlO_x$, $Zr(CH_2CMe_3)_n@SiO_2$, $Zr(H)_n@SiO_2$, and $Zr(H)_n@SiAlO_x$, wherein n is an integer ranging from 1-3.

15. The process of claim 13, wherein the compound of formula (I) is selected from the group consisting of $AliBu_3$, $AlEt_3$, $AlMe_3$, $AlPh_3$, $Al(C_8H_{17})_3$, and $AlH_3$.

16. The process of claim 13, wherein the polymers, oligomers, or mixtures thereof are polyolefins and wherein said polyolefins are selected from the group consisting of high density polyethylene, low density polyethylene, polypropylene, linear low density polyethylene, polyethylene-polypropylene-copolymers, polystyrene, and mixtures thereof.

17. The process of claim 13, wherein said contacting is carried out at a temperature sufficient to melt the polymers, oligomers, or mixtures thereof.

18. The process of claim 13, wherein said contacting is carried out under atmospheric pressure or under a vacuum.

19. The process according to claim 1, wherein Met is a metal selected from the group consisting of zirconium, titanium, yttrium, lanthanum, and lutetium.

20. The process according to claim 13, wherein Met is a metal selected from the group consisting of zirconium, titanium, yttrium, lanthanum, and lutetium.

* * * * *